(12) United States Patent
Ast et al.

(10) Patent No.: US 10,611,841 B2
(45) Date of Patent: Apr. 7, 2020

(54) BISPECIFIC T CELL ACTIVATING ANTIGEN BINDING MOLECULES

(71) Applicant: Hoffmann-La Roche Inc., Little Falls, NJ (US)

(72) Inventors: Oliver Ast, Bassersdorf (CH); Marina Bacac, Zurich (CH); Sabine Imhof-Jung, Planegg (DE); Christiane Neumann, Niederweningen (CH); Christian Klein, Bonstetten (CH); Stefan Klostermann, Neuried (DE); Michael Molhoj, Munich (DE); Joerg Thomas Regula, Munich (DE); Wolfgang Schaefer, Mannheim (DE); Pablo Umana, Wollerau (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/879,260

(22) Filed: Jan. 24, 2018

(65) Prior Publication Data

US 2018/0222981 A1  Aug. 9, 2018

Related U.S. Application Data

(62) Division of application No. 14/816,252, filed on Aug. 3, 2015, now Pat. No. 9,914,776.

(30) Foreign Application Priority Data

Aug. 4, 2014 (EP) .................................... 14179764
Jun. 5, 2015 (EP) .................................... 15170866

(51) Int. Cl.
| | | |
|---|---|---|
| *A61K 39/395* | (2006.01) | |
| *C07K 16/28* | (2006.01) | |
| *C07K 16/30* | (2006.01) | |
| *C07K 16/32* | (2006.01) | |

(52) U.S. Cl.
CPC ...... *C07K 16/2809* (2013.01); *C07K 16/2878* (2013.01); *C07K 16/2887* (2013.01); *C07K 16/3053* (2013.01); *C07K 16/32* (2013.01); *C07K 2317/14* (2013.01); *C07K 2317/21* (2013.01); *C07K 2317/31* (2013.01); *C07K 2317/33* (2013.01); *C07K 2317/51* (2013.01); *C07K 2317/515* (2013.01); *C07K 2317/526* (2013.01); *C07K 2317/54* (2013.01); *C07K 2317/55* (2013.01); *C07K 2317/64* (2013.01); *C07K 2317/66* (2013.01); *C07K 2317/732* (2013.01); *C07K 2317/92* (2013.01); *C07K 2317/94* (2013.01)

(58) Field of Classification Search
CPC ............ C07K 16/2809; C07K 16/2887; C07K 2317/51; C07K 2317/515; C07K 2317/64; C07K 2317/31; C07K 2317/55; C07K 2317/21; C07K 2317/732; C07K 2317/33; C07K 2317/92; C07K 2317/60; A61K 39/395; A61K 2039/505
See application file for complete search history.

(56) References Cited

U.S. PATENT DOCUMENTS

| | | |
|---|---|---|
| 5,571,894 A | 11/1996 | Wels et al. |
| 5,587,458 A | 12/1996 | King et al. |
| 5,591,828 A | 1/1997 | Bosslet et al. |
| 5,731,168 A | 3/1998 | Carter et al. |
| 5,821,337 A | 10/1998 | Carter et al. |
| 5,869,046 A | 2/1999 | Presta et al. |
| 6,248,516 B1 | 6/2001 | Winter et al. |
| 6,737,056 B1 | 5/2004 | Presta |
| 6,809,185 B1 | 10/2004 | Schoonjans et al. |
| 7,332,581 B2 | 2/2008 | Presta |
| 7,695,936 B2 | 4/2010 | Carter et al. |
| 8,227,577 B2 | 7/2012 | Klein et al. |
| 8,236,308 B2 | 8/2012 | Kischel et al. |
| 8,242,247 B2 | 8/2012 | Klein et al. |
| 8,642,742 B2 | 2/2014 | Hofer et al. |
| 8,703,132 B2 | 4/2014 | Imhof-Jung et al. |
| 8,709,421 B2 | 4/2014 | Heiss et al. |
| 8,796,424 B2 | 8/2014 | Croasdale et al. |
| 8,846,042 B2 | 9/2014 | Zhou |
| 8,969,526 B2 | 3/2015 | Baehner et al. |

(Continued)

FOREIGN PATENT DOCUMENTS

| | | |
|---|---|---|
| EP | 0404097 B1 | 9/1996 |
| EP | 1870459 A1 | 12/2007 |

(Continued)

OTHER PUBLICATIONS

Lloyd et al., Protein Engineering, Design & Selection 22:159-168 (Year: 2009).*
Edwards et al., J Mol Biol. 334(1): 103-118 (Year: 2003).*
Rudnick et al., Cancer. Biotherp. & Radiopharm. 24: 155-162 (Year: 2009).*
Yu et al (Investigative Ophthalmology & Visual Science 49(2): 522-527 (Year: 2008).*
Dernier et al., Bio/Technology 12:320 (Year: 1994).*
Beckman et al., Cancer. 109:170-179 (Year: 2007).*
Atwell et al., "Stable heterodimers from remodeling the domain interface of a homodimer using a phage display library," J Mol Biol. 270(1):26-35 (1997).

(Continued)

*Primary Examiner* — Phuong Huynh
(74) *Attorney, Agent, or Firm* — Clark & Elbing LLP; Karen L. Elbing

(57) ABSTRACT

The present invention generally relates to novel bispecific antigen binding molecules for T cell activation and re-direction to specific target cells. In addition, the present invention relates to polynucleotides encoding such bispecific antigen binding molecules, and vectors and host cells comprising such polynucleotides. The invention further relates to methods for producing the bispecific antigen binding molecules of the invention, and to methods of using these bispecific antigen binding molecules in the treatment of disease.

41 Claims, 73 Drawing Sheets

Specification includes a Sequence Listing.

(56) References Cited

U.S. PATENT DOCUMENTS

| | | |
|---|---|---|
| 9,068,008 B2 | 6/2015 | Mossner et al. |
| 9,206,260 B2 | 12/2015 | Hofer et al. |
| 9,266,938 B2 | 2/2016 | Ast et al. |
| 9,266,967 B2 | 2/2016 | Klein et al. |
| 9,382,323 B2 | 7/2016 | Brinkmann et al. |
| 9,447,159 B2 | 9/2016 | Ast et al. |
| 9,526,797 B2 | 12/2016 | Gerdes et al. |
| 9,914,776 B2 | 3/2018 | Ast et al. |
| 2002/0004587 A1 | 1/2002 | Miller et al. |
| 2007/0071675 A1 | 3/2007 | Wu et al. |
| 2007/0111281 A1 | 5/2007 | Sondermann et al. |
| 2007/0219133 A1 | 9/2007 | Lazar et al. |
| 2008/0241152 A1 | 10/2008 | Alitalo et al. |
| 2009/0252683 A1 | 10/2009 | Kischel et al. |
| 2010/0015133 A1 | 1/2010 | Igawa et al. |
| 2010/0150918 A1 | 6/2010 | Kufer et al. |
| 2010/0316645 A1 | 12/2010 | Imhof-Jung et al. |
| 2011/0293613 A1 | 12/2011 | Brinkmann et al. |
| 2012/0225071 A1 | 9/2012 | Klein et al. |
| 2012/0276125 A1 | 11/2012 | Ast et al. |
| 2013/0022601 A1 | 1/2013 | Brinkmann et al. |
| 2013/0058936 A1 | 3/2013 | Bruenker et al. |
| 2013/0058937 A1 | 3/2013 | Auer et al. |
| 2013/0060011 A1 | 3/2013 | Bruenker et al. |
| 2013/0078249 A1 | 3/2013 | Ast et al. |
| 2013/0171095 A1 | 7/2013 | Bernett et al. |
| 2014/0088295 A1 | 3/2014 | Smith et al. |
| 2014/0112914 A1 | 4/2014 | Nezu et al. |
| 2014/0154254 A1 | 6/2014 | Kannan et al. |
| 2014/0242079 A1 | 8/2014 | Bacac et al. |
| 2014/0242080 A1 | 8/2014 | Jaeger et al. |
| 2014/0288275 A1 | 9/2014 | Moore et al. |
| 2014/0294823 A1 | 10/2014 | Moore et al. |
| 2014/0294833 A1 | 10/2014 | Desjarlais et al. |
| 2014/0302064 A1 | 10/2014 | Moore |
| 2014/0322217 A1 | 10/2014 | Moore et al. |
| 2014/0363426 A1 | 12/2014 | Moore et al. |
| 2014/0370013 A1 | 12/2014 | Desjarlais et al. |
| 2014/0377270 A1 | 12/2014 | Moore et al. |
| 2015/0166661 A1 | 6/2015 | Chen et al. |
| 2015/0274845 A1 | 10/2015 | Bruenker et al. |
| 2015/0315296 A1 | 11/2015 | Schaefer et al. |
| 2015/0368351 A1 | 12/2015 | Vu et al. |
| 2015/0376287 A1 | 12/2015 | Vu et al. |
| 2016/0075785 A1 | 3/2016 | Ast et al. |
| 2016/0130347 A1 | 5/2016 | Bruenker et al. |
| 2016/0145354 A1 | 5/2016 | Bacac et al. |
| 2016/0175397 A1 | 6/2016 | Umana et al. |
| 2016/0208017 A1 | 7/2016 | Ast et al. |
| 2016/0208019 A1 | 7/2016 | Bacac et al. |
| 2016/0263240 A1 | 9/2016 | Ast et al. |
| 2016/0297881 A1 | 10/2016 | Vu et al. |
| 2016/0368985 A1 | 12/2016 | Hotzel et al. |
| 2017/0008971 A1 | 1/2017 | Dennis et al. |
| 2017/0096485 A1 | 4/2017 | Bacac et al. |
| 2017/0096495 A1 | 4/2017 | Bacac et al. |
| 2017/0114146 A1 | 4/2017 | Klein et al. |
| 2017/0174786 A1 | 6/2017 | Bacac et al. |
| 2017/0190783 A1 | 7/2017 | Bacac et al. |
| 2017/0209573 A1 | 7/2017 | Bacac et al. |
| 2017/0253670 A1 | 9/2017 | Klein et al. |
| 2017/0267783 A1 | 9/2017 | Nezu et al. |
| 2017/0306018 A1 | 10/2017 | Vu et al. |
| 2017/0306036 A1 | 10/2017 | Vu et al. |
| 2017/0306044 A1 | 10/2017 | Vu et al. |
| 2017/0327579 A1 | 11/2017 | Vu et al. |
| 2017/0327580 A1 | 11/2017 | Vu et al. |

FOREIGN PATENT DOCUMENTS

| | | | |
|---|---|---|---|
| EP | 1870459 | A4 | 9/2010 |
| EP | 2578230 | A1 | 4/2013 |
| EP | 2647707 | A1 | 10/2013 |
| EP | 2647707 | A4 | 4/2014 |
| EP | 1870459 | B1 | 6/2016 |
| WO | WO-91/03493 | A1 | 3/1991 |
| WO | WO-93/01161 | A1 | 1/1993 |
| WO | WO-93/16185 | A2 | 8/1993 |
| WO | WO-96/01126 | A1 | 1/1996 |
| WO | WO-96/27011 | A1 | 9/1996 |
| WO | WO-96/40210 | A1 | 12/1996 |
| WO | WO-98/50431 | A2 | 11/1998 |
| WO | WO-98/50431 | A3 | 1/1999 |
| WO | WO-02/09573 | A2 | 2/2002 |
| WO | WO-03/074679 | A2 | 9/2003 |
| WO | WO-2005/044859 | A2 | 5/2005 |
| WO | WO-2006/082515 | A2 | 8/2006 |
| WO | WO-2007/024715 | A2 | 3/2007 |
| WO | WO-2007/042261 | A2 | 4/2007 |
| WO | WO-2007/075270 | A2 | 7/2007 |
| WO | WO-2007/110205 | A2 | 10/2007 |
| WO | WO-2007/146968 | A2 | 12/2007 |
| WO | WO-2007/147901 | A1 | 12/2007 |
| WO | WO-2007/024715 | A3 | 10/2008 |
| WO | WO-2008/119566 | A2 | 10/2008 |
| WO | WO-2008/119567 | A2 | 10/2008 |
| WO | WO-2007/024715 | A9 | 4/2009 |
| WO | WO-2009/070642 | A1 | 6/2009 |
| WO | WO-2009/080251 | A1 | 7/2009 |
| WO | WO-2009/080252 | A1 | 7/2009 |
| WO | WO-2009/080253 | A1 | 7/2009 |
| WO | WO-2009/080254 | A1 | 7/2009 |
| WO | WO-2009/089004 | A1 | 7/2009 |
| WO | WO-2010/115589 | A1 | 10/2010 |
| WO | WO-2010/129304 | A2 | 11/2010 |
| WO | WO-2010/136172 | A1 | 12/2010 |
| WO | WO-2010/145792 | A1 | 12/2010 |
| WO | WO-2010/145793 | A1 | 12/2010 |
| WO | WO-2010/129304 | A3 | 2/2011 |
| WO | WO-2011/028952 | A1 | 3/2011 |
| WO | WO-2011/090754 | A1 | 7/2011 |
| WO | WO-2011/090762 | A1 | 7/2011 |
| WO | WO-2011/143545 | A1 | 11/2011 |
| WO | WO-2012/058768 | A1 | 5/2012 |
| WO | WO-2012/058768 | A8 | 6/2012 |
| WO | WO-2012/073985 | A1 | 6/2012 |
| WO | WO-2012/117002 | A1 | 9/2012 |
| WO | WO-2012/130831 | A1 | 10/2012 |
| WO | WO-2012/143524 | A2 | 10/2012 |
| WO | WO-2012/158818 | A2 | 11/2012 |
| WO | WO-2012/162067 | A2 | 11/2012 |
| WO | WO-2013/012414 | A1 | 1/2013 |
| WO | WO-2013/026831 | A1 | 2/2013 |
| WO | WO-2013/026832 | A1 | 2/2013 |
| WO | WO-2013/026833 | A1 | 2/2013 |
| WO | WO-2013/026837 | A1 | 2/2013 |
| WO | WO-2013/026839 | A1 | 2/2013 |
| WO | WO-2013/096291 | A2 | 6/2013 |
| WO | WO-2013/157953 | A1 | 10/2013 |
| WO | WO-2013/157954 | A1 | 10/2013 |
| WO | WO-2014/022540 | A1 | 2/2014 |
| WO | WO-2014/028560 | A2 | 2/2014 |
| WO | WO-2014/047231 | A1 | 3/2014 |
| WO | WO-2014/054804 | A1 | 4/2014 |
| WO | WO-2014/028560 | A3 | 5/2014 |
| WO | WO-2014/081955 | A1 | 5/2014 |
| WO | WO-2014/122143 | A1 | 8/2014 |
| WO | WO-2014/122144 | A1 | 8/2014 |
| WO | WO-2014/122251 | A2 | 8/2014 |
| WO | WO-2014/141152 | A2 | 9/2014 |
| WO | WO-2014/153002 | A1 | 9/2014 |
| WO | WO-2014/122251 | A3 | 10/2014 |
| WO | WO-2014/167022 | A1 | 10/2014 |
| WO | WO-2014/141152 | A3 | 12/2014 |
| WO | WO-2014/191113 | A1 | 12/2014 |
| WO | WO-2014/191113 | A8 | 2/2015 |
| WO | WO-2015/150447 | A1 | 10/2015 |
| WO | WO-2016/020065 | A1 | 2/2016 |
| WO | WO-2016/020332 | A1 | 2/2016 |
| WO | WO-2016/036678 | A1 | 3/2016 |
| WO | WO-2016/055592 | A1 | 4/2016 |
| WO | WO-2016/055593 | A1 | 4/2016 |
| WO | WO-2016/079081 | A1 | 5/2016 |
| WO | WO-2016/079177 | A1 | 5/2016 |

(56) References Cited

FOREIGN PATENT DOCUMENTS

| WO | WO-2016/087531 A1 | 6/2016 |
|---|---|---|
| WO | WO-2016/179003 A1 | 11/2016 |
| WO | WO-2017/021450 A1 | 2/2017 |

OTHER PUBLICATIONS

BBE23702, GenomeQuest Keyword Search Report, dated May 1, 2017 (2 pages).
BBE23705, GenomeQuest Keyword Search Report, dated May 1, 2017 (2 pages).
BBF28771, GenomeQuest Keyword Search Report, dated May 1, 2017 (2 pages).
BBF28775, GenomeQuest Keyword Search Report, dated May 1, 2017 (2 pages).
Bosch et al., "MCSP/CD3-bispecific single-chain antibody construct engages CD4+ and CD8+ T cells for lysis of MCSP-expressing human uveal melanoma cells," AACR 101st Annual Meeting. Apr. 17-21, Washington, DC. 70(8 Suppl) Abstract 5621 (2010).
Carter, "Bispecific human IgG by design," J Immunol Methods. 248(1-2):7-15 (2001).
Conaghan et al., "Targeted killing of colorectal cancer cell lines by a humanised IgG1 monoclonal antibody that binds to membrane-bound carcinoembryonic antigen," Br J Cancer. 98(7):1217-25 (2008).
Edelman et al., "The covalent structure of an entire gammaG immunoglobulin molecule," Proc Natl Acad Sci U S A. 63(1):78-85 (1969).
Holliger et al., "'Diabodies': small bivalent and bispecific antibody fragments," Proc Natl Acad Sci U S A. 90(14):6444-8 (1993).
Holliger et al., "Specific killing of lymphoma cells by cytotoxic T-cells mediated by a bispecific diabody," Protein Eng. 9(3):299-305 (1996).
Honeychurch et al., "Bispecific Ab therapy of B-cell lymphoma: target cell specificity of antibody derivatives appears critical in determining therapeutic outcome," Cancer Immunol Immunother. 45(3-4):171-3 (1997).
Hudson et al., "Engineered antibodies," Nat Med. 9(1):129-34 (2003).
Kipriyanov et al., "Bispecific tandem diabody for tumor therapy with improved antigen binding and pharmacokinetics," J Mol Biol. 293(1):41-56 (1999).
Klein et al., "Progress in overcoming the chain association issue in bispecific heterodimeric IgG antibodies," MAbs. 4(6):653-63 (2012).
Kontermann, "Dual targeting strategies with bispecific antibodies," MAbs. 4(2):182-97 (2012).
MacLean et al., "Anti-CD3:anti-IL-2 receptor-bispecific mAb-mediated immunomodulation. Low systemic toxicity, differential effect on lymphoid tissue, and inhibition of cell-mediated hypersensitivity," J Immunol. 155(7):3674-82 (1995).
Merchant et al., "An efficient route to human bispecific IgG," Nat Biotechnol. 16(7):677-81 (1998).
Moore et al., "A novel bispecific antibody format enables simultaneous bivalent and monovalent co-engagement of distinct target antigens," MAbs. 3(6):546-57 (2011).
Moore et al., "Application of dual affinity retargeting molecules to achieve optimal redirected T-cell killing of B-cell lymphoma," Blood. 117(17):4542-51 (2011) (11 pages).
Nagorsen et al., "Immunomodulatory therapy of cancer with T cell-engaging BiTE antibody blinatumomab," Exp Cell Res. 317(9):1255-60 (2011).
Peng et al., "The CEA/CD3-bispecific antibody MEDI-565 (MT111) binds a nonlinear epitope in the full-length but not a short splice variant of CEA," PLoS One. 7(5):e36412 (2012) (14 pages).
Pessano et al., "The T3/T cell receptor complex: antigenic distinction between the two 20-kd T3 (T3-delta and T3-epsilon) subunits," EMBO J. 4(2):337-44 (1985).
Plückthun, Antibodies from *Escherichia coli*. The Pharmacology of Monoclonal Antibodies. Rosenberg & Moore, 269-315 (1994).
Ridgway et al., "'Knobs-into-holes' engineering of antibody CH3 domains for heavy chain heterodimerization," Protein Eng. 9(7):617-21 (1996).
Riedle et al., "In vivo activation and expansion of T cells by a bi-specific antibody abolishes metastasis formation of human melanoma cells in SCID mice," Int J Cancer. 75(6):908-18 (1998).
Seimetz et al., "Development and approval of the trifunctional antibody catumaxomab (anti-EpCAM x anti-CD3) as a targeted cancer immunotherapy," Cancer Treat Rev. 36(6):458-67 (2010).
Stewart et al., "Humanisation and characterisation of PR1A3, a monoclonal antibody specific for cell-bound carcinoembryonic antigen," Cancer Immunol Immunother. 47(6):299-306 (1999).
Stubenrauch et al., "Impact of molecular processing in the hinge region of therapeutic IgG4 antibodies on disposition profiles in cynomolgus monkeys," Drug Metab Dispos. 38(1):84-91 (2010).
Sun et al., "Anti-CD20/CD3 T cell-dependent bispecific antibody for the treatment of B cell malignancies," Sci Transl Med. 7(287):287ra70 (2015) (11 pages).
Torisu-Itakura et al., "Redirected lysis of human melanoma cells by a MCSP/CD3-bispecific Bite antibody that engages patient-derived T cells," J Immunother. 34(8):597-605 (2011).
Zhu et al., "Identification of heavy chain residues in a humanized anti-CD3 antibody important for efficient antigen binding and T cell activation," J Immunol. 155(4):1903-10 (1995).
International Search Report and Written Opinion for International Patent Application No. PCT/EP2014/053489, dated Jun. 5, 2014 (14 pages).
International Search Report and Written Opinion for International Patent Application No. PCT/EP2014/053490, dated Jun. 10, 2014 (16 pages).
International Search Report for International Patent Application No. PCT/EP2015/067776, dated Nov. 4, 2015 (7 pages).
Booy et al., "Monoclonal and bispecific antibodies as novel therapeutics," Arch Immunol Ther Exp (Warsz). 54(2):85-101 (2006).
Chan et al., "Variable region domain exchange in human IgGs promotes antibody complex formation with accompanying structural changes and altered effector functions," Mol Immunol. 41(5):527-38 (2004).
Miller et al., "Design, construction, and in vitro analyses of multivalent antibodies," J Immunol. 170(9):4854-61 (2003).
Oshimi et al., "Increased lysis of patient CD10-positive leukemic cells by T cells coated with anti-CD3 Fab' antibody cross-linked to anti-CD10 Fab' antibody," Blood. 77(5):1044-9 (1991).
Schaefer et al., "Immunoglobulin domain crossover as a generic approach for the production of bispecific IgG antibodies," Proc Natl Acad Sci USA. 108(27):11187-92 (2011).
Tutt et al., "Trispecific F(ab')3 derivatives that use cooperative signaling via the TCR/CD3 complex and CD2 to activate and redirect resting cytotoxic T cells," J Immunol. 147(1):60-9 (1991).
Wolf et al., "BiTEs: bispecific antibody constructs with unique anti-tumor activity," Drug Discov Today. 10(18):1237-44 (2005).
Lund et al., "Multiple interactions of IgG with its core oligosaccharide can modulate recognition by complement and human Fc gamma receptor I and influence the synthesis of its oligosaccharide chains," J Immunol. 157(11):4963-9 (1996) (8 pages).
Office Action for U.S. Appl. No. 15/879,040, dated Aug. 6, 2019 (16 pages).

\* cited by examiner

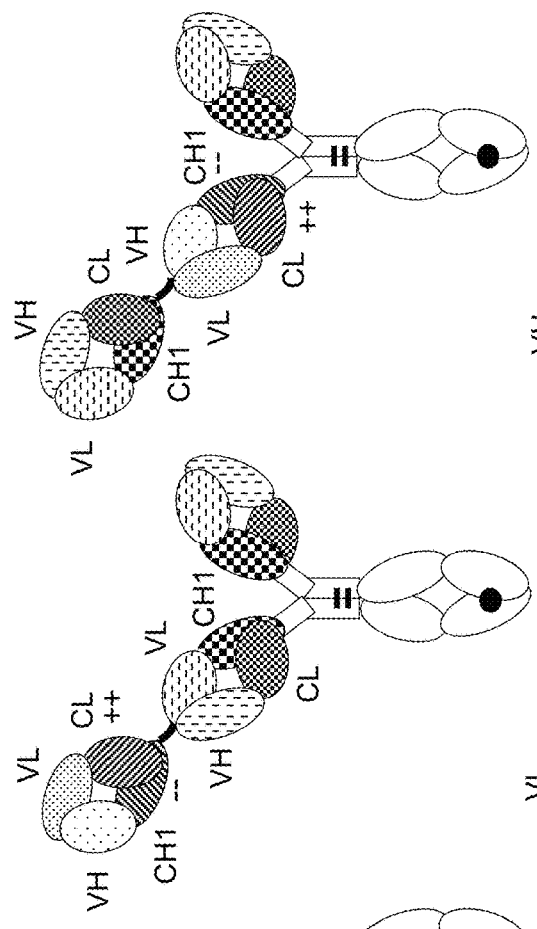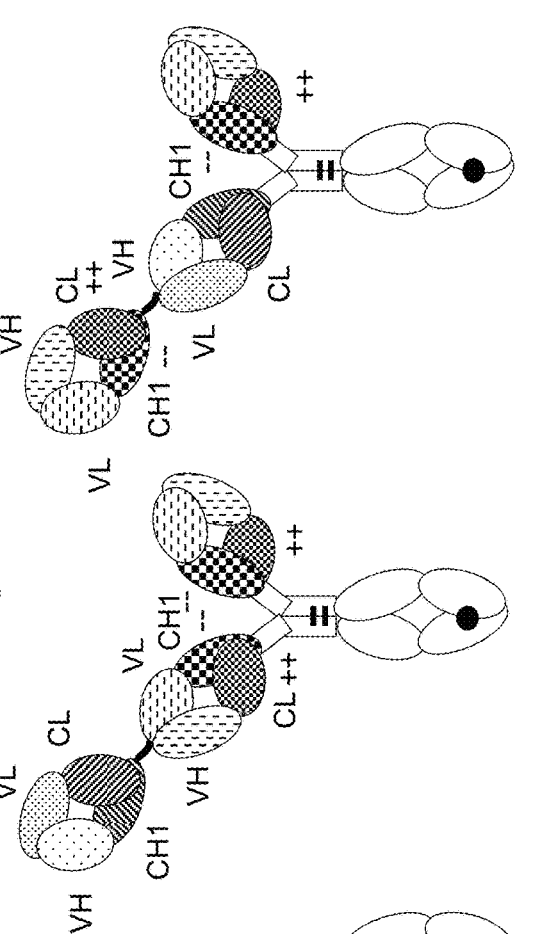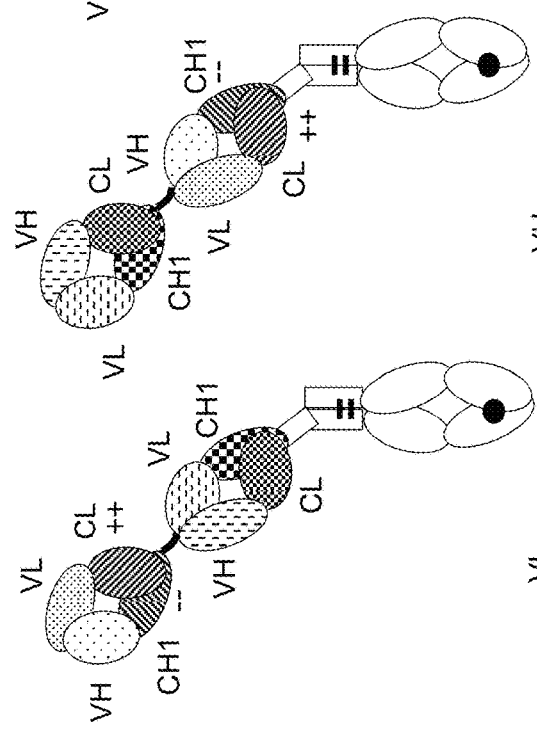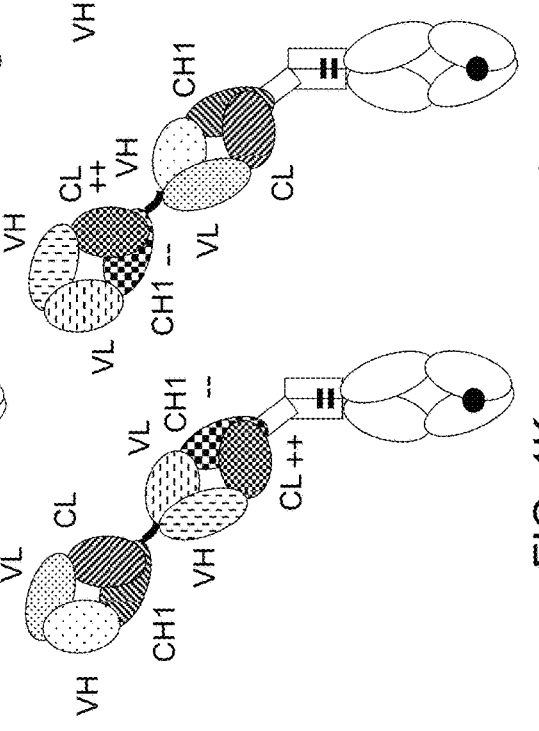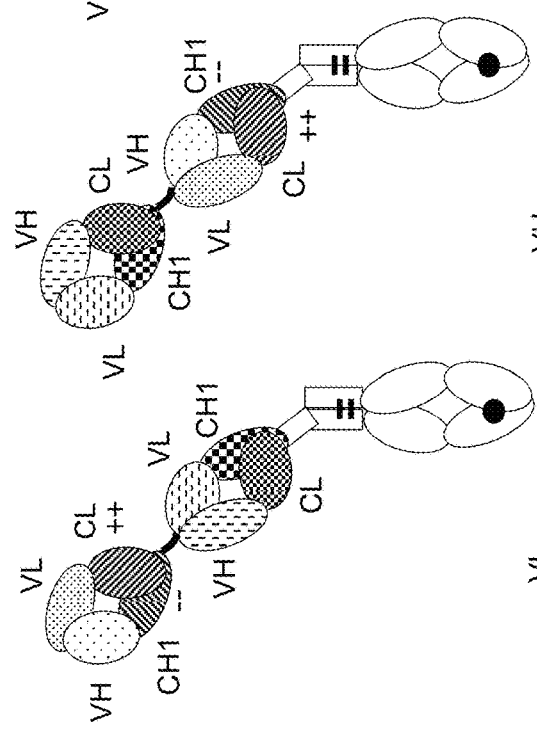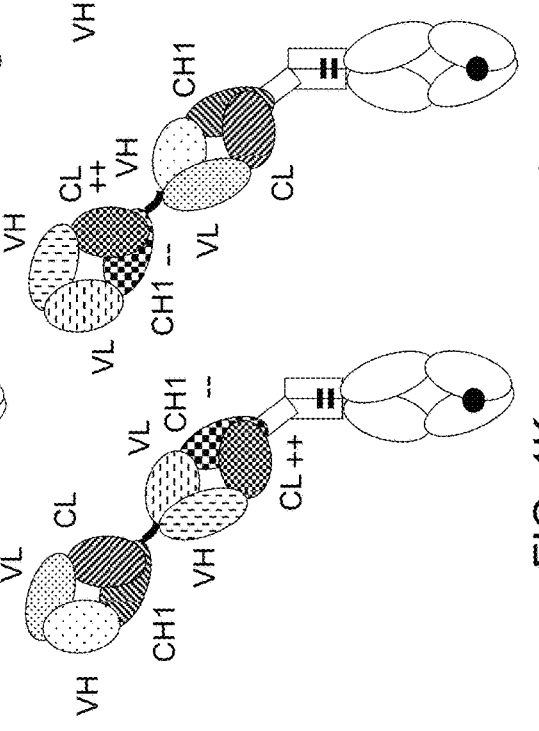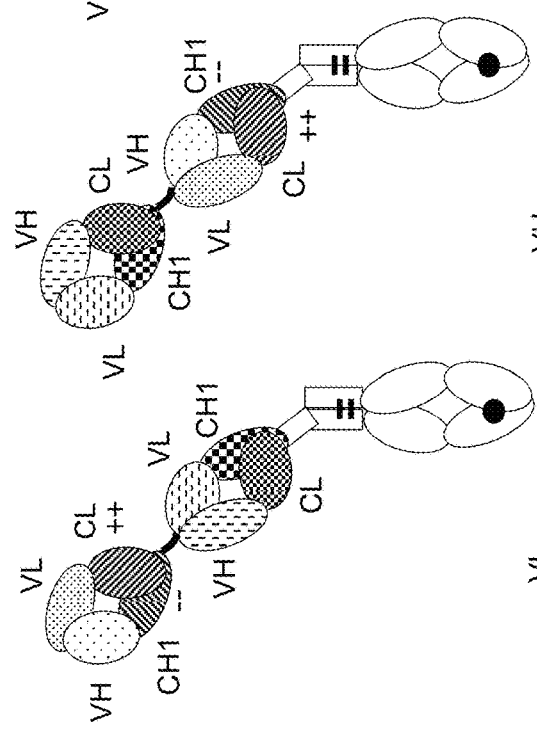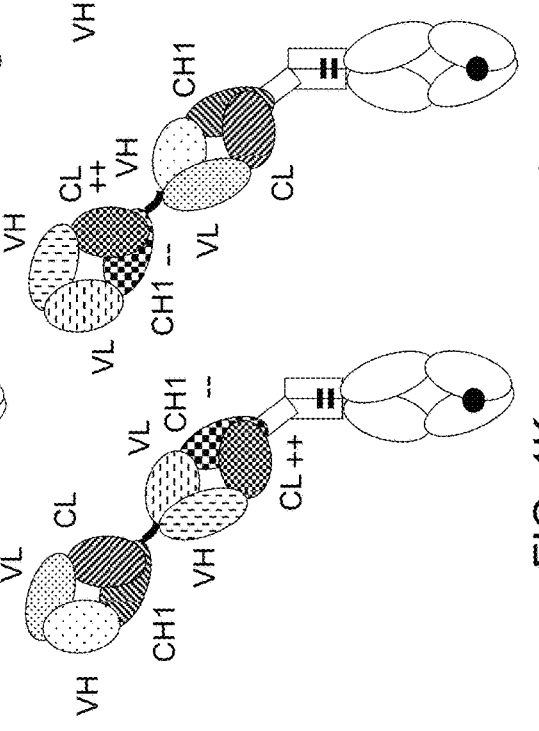

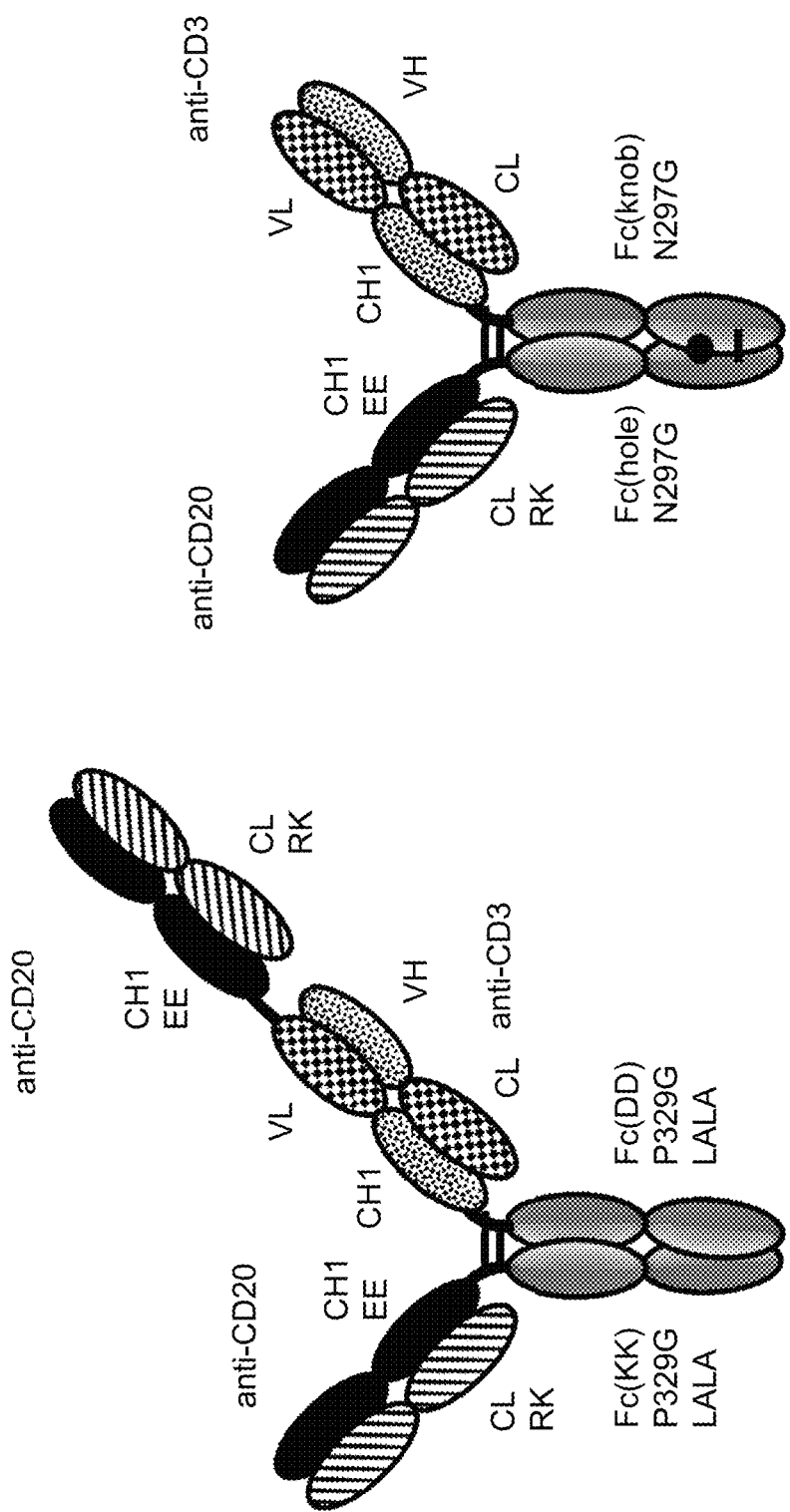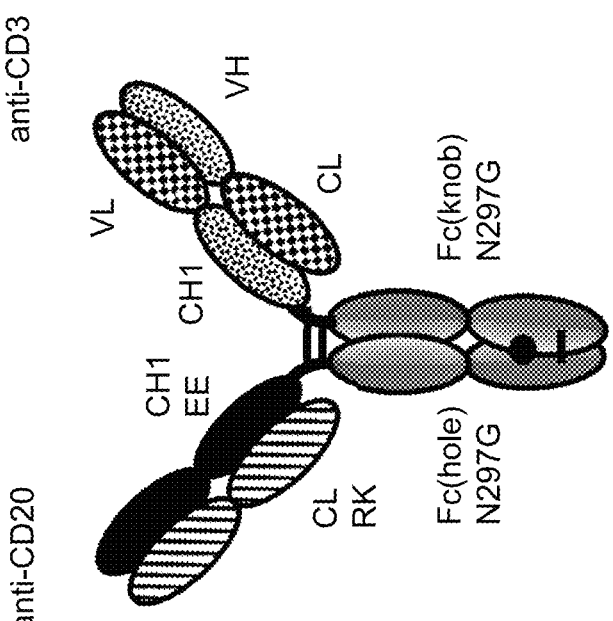
FIG. 2G
FIG. 2H

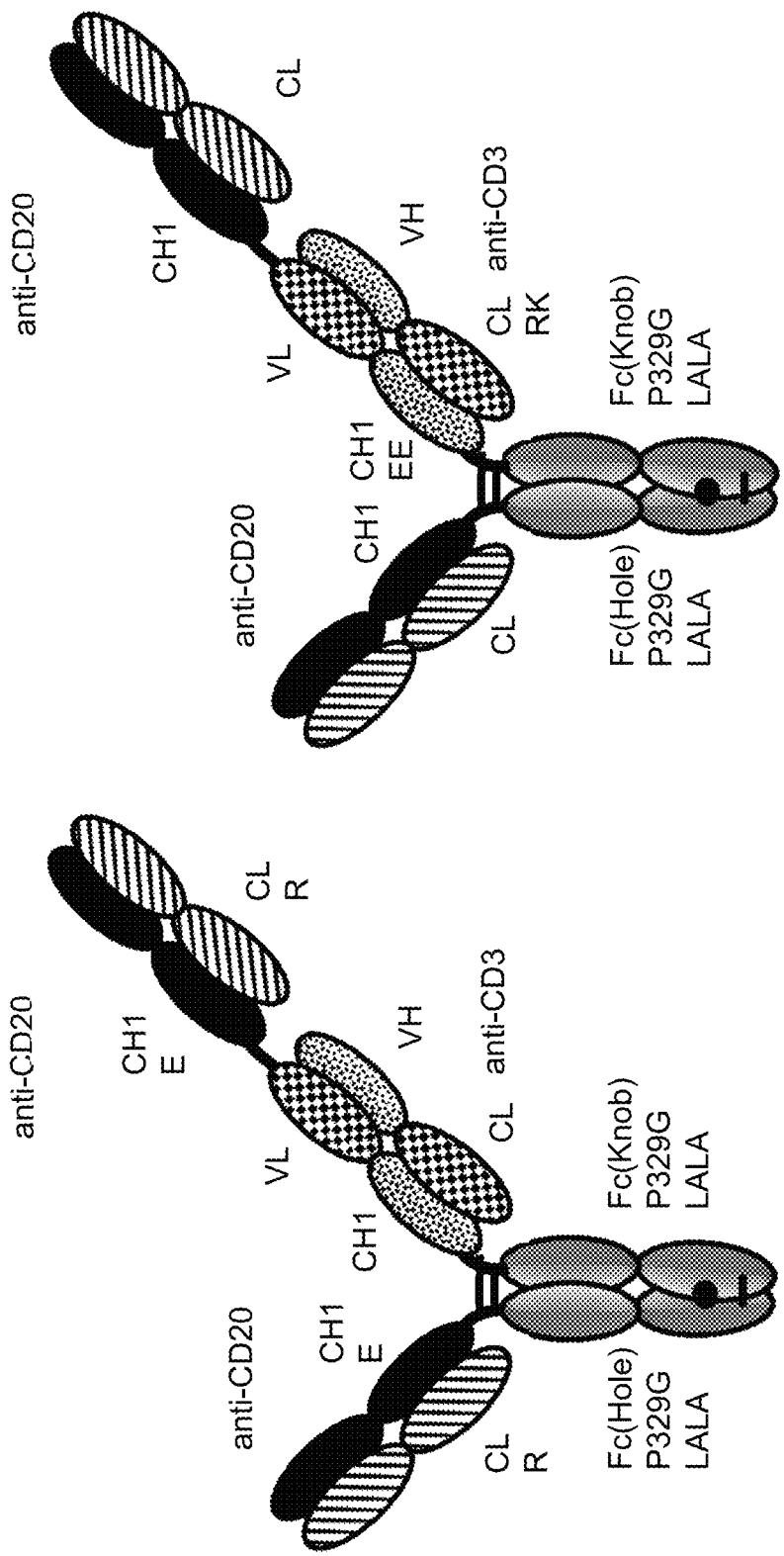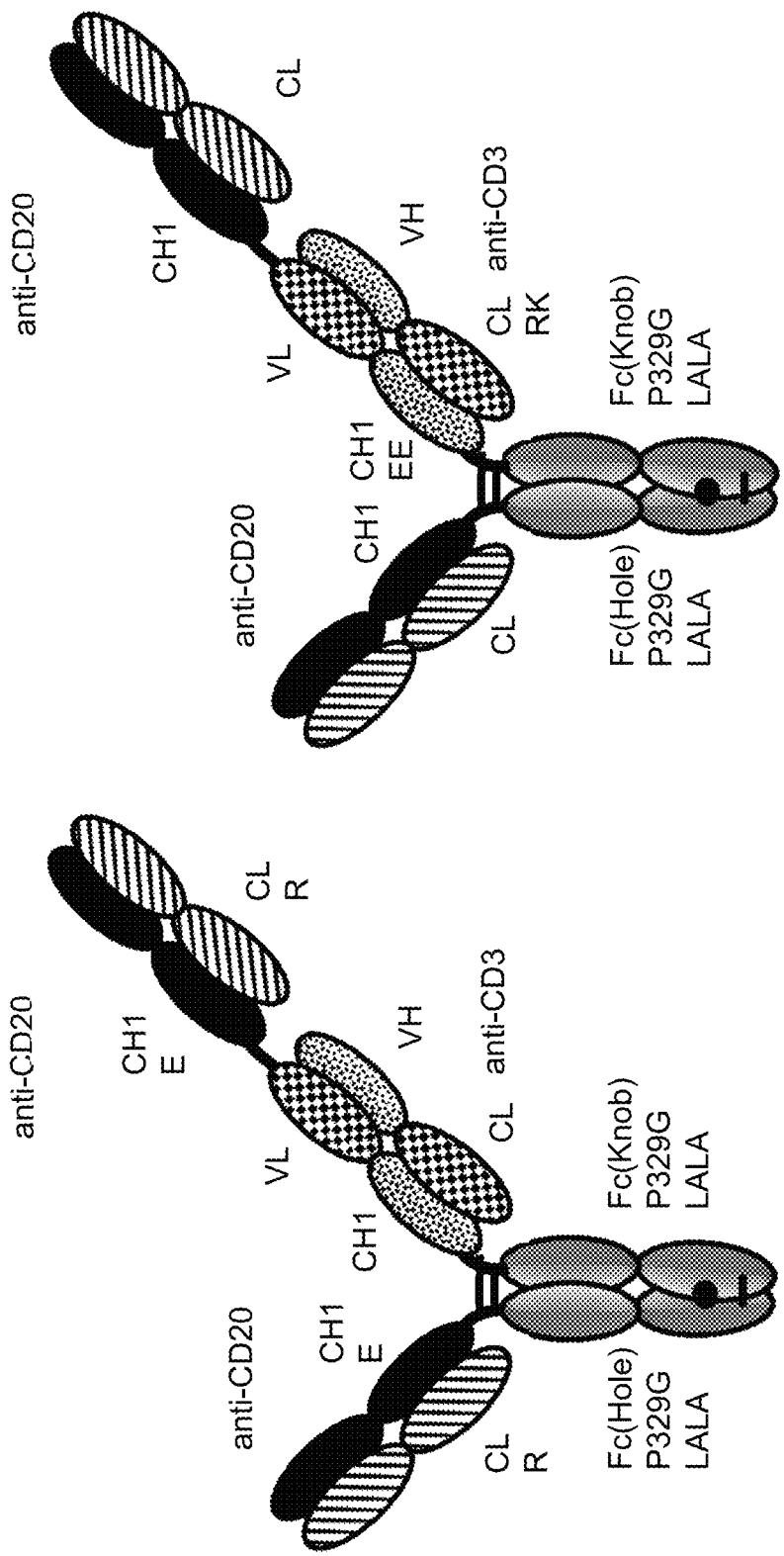
FIG. 2J
FIG. 2K

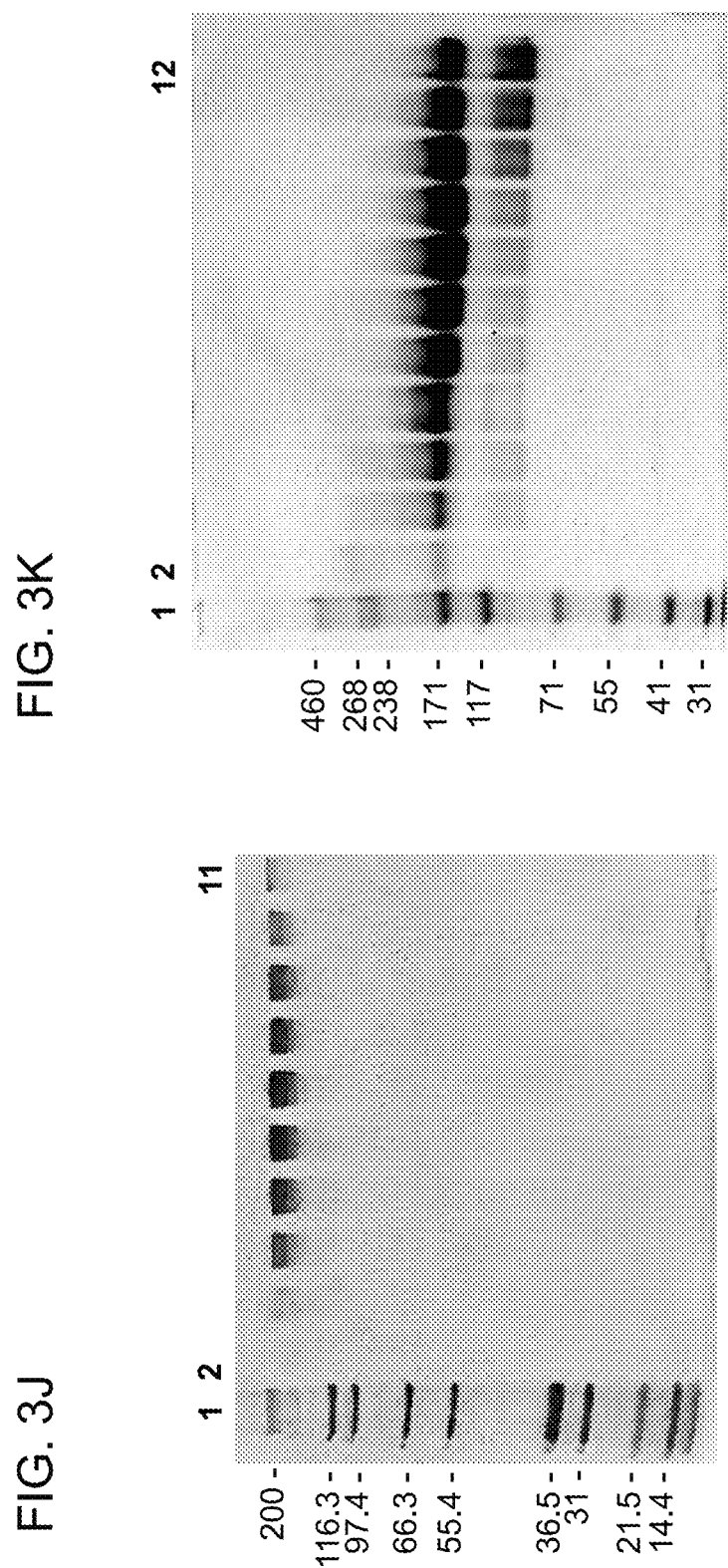

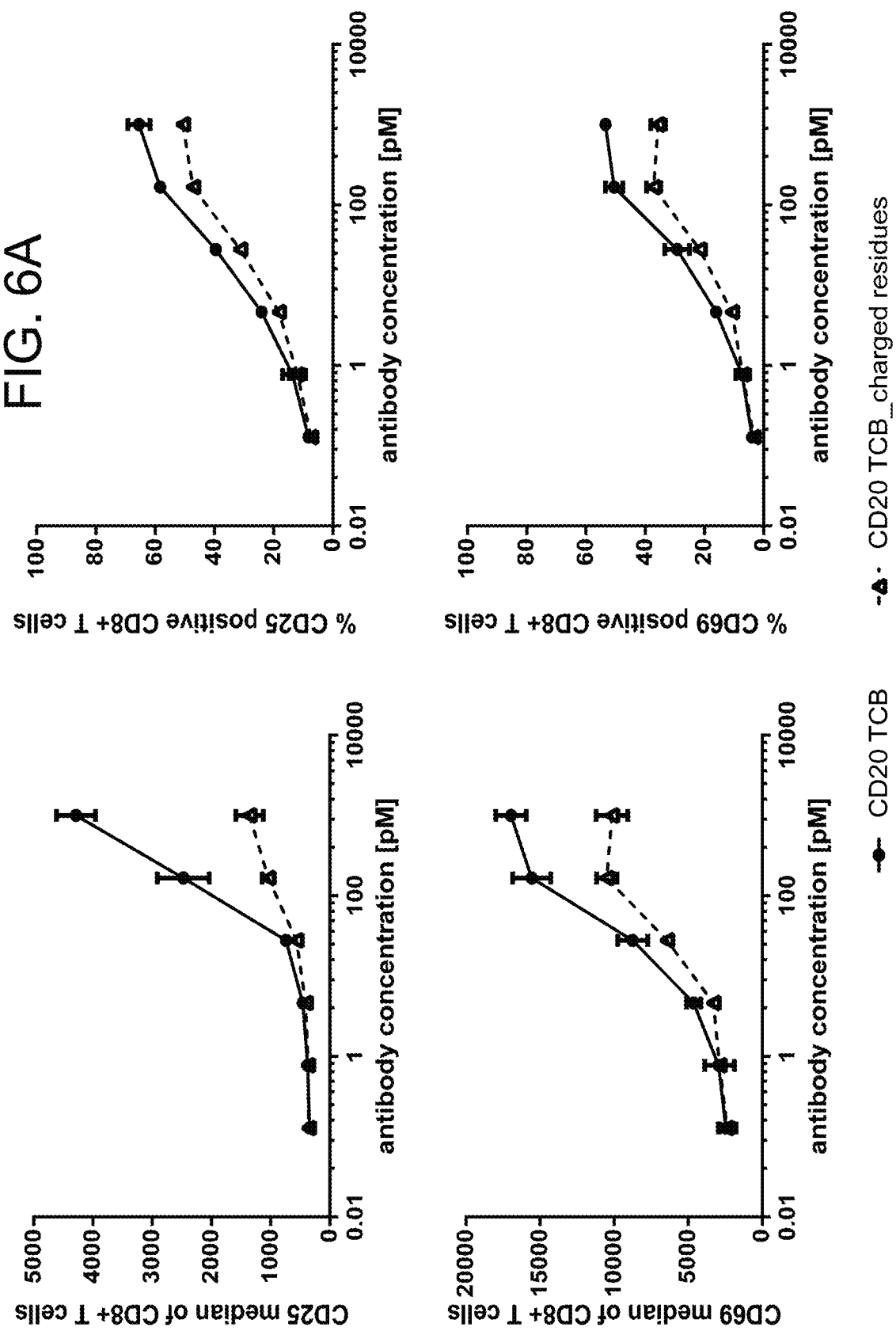

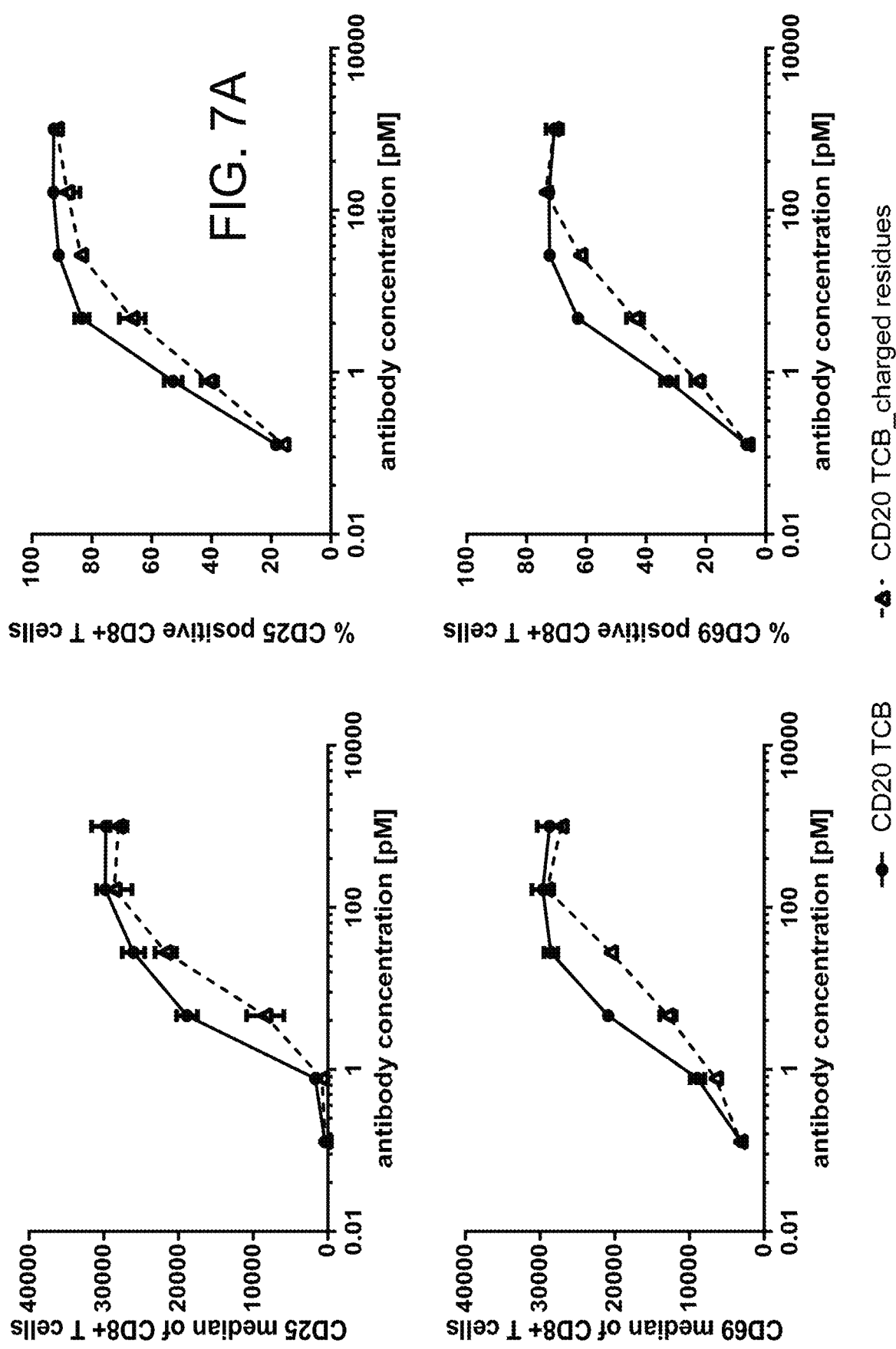

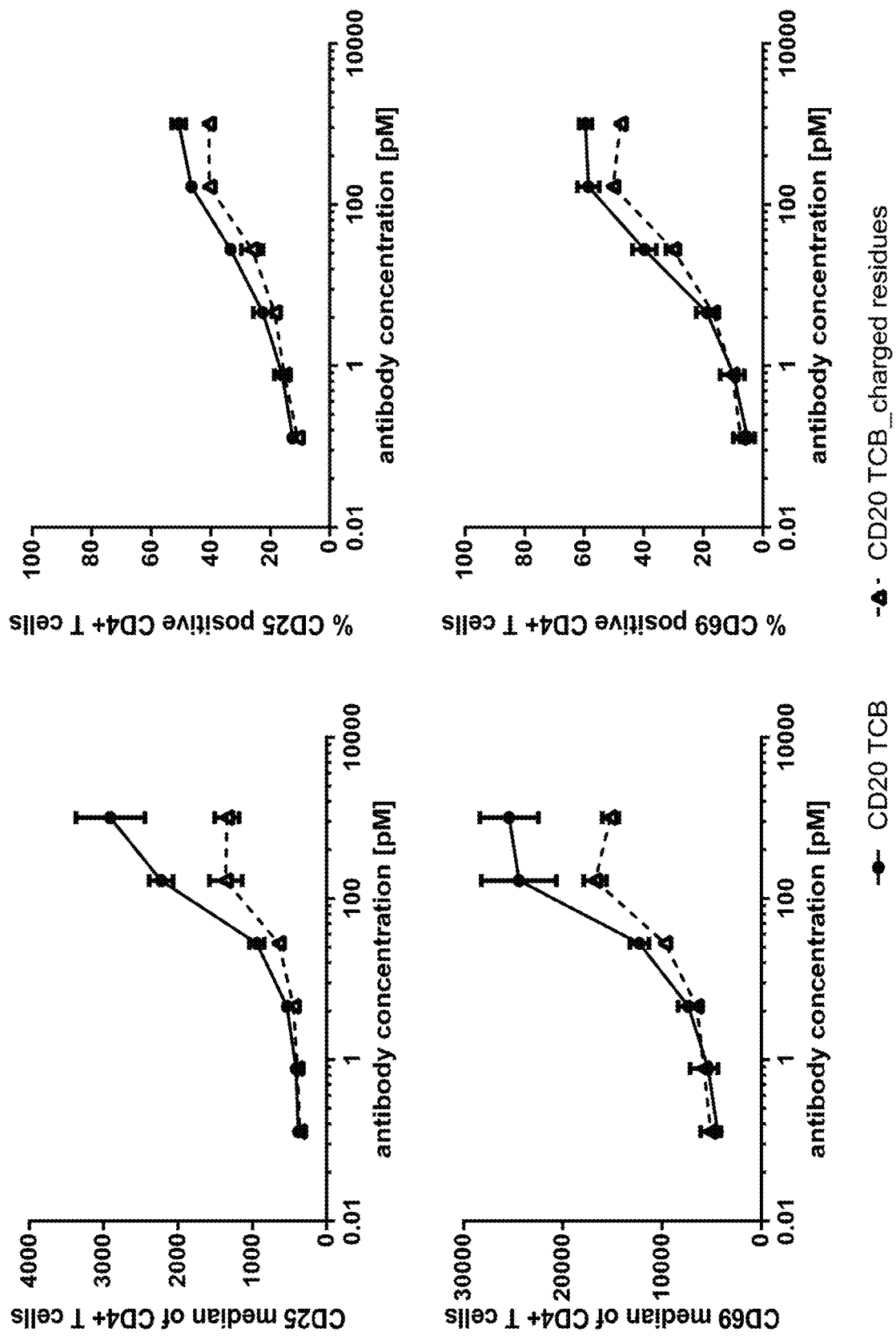

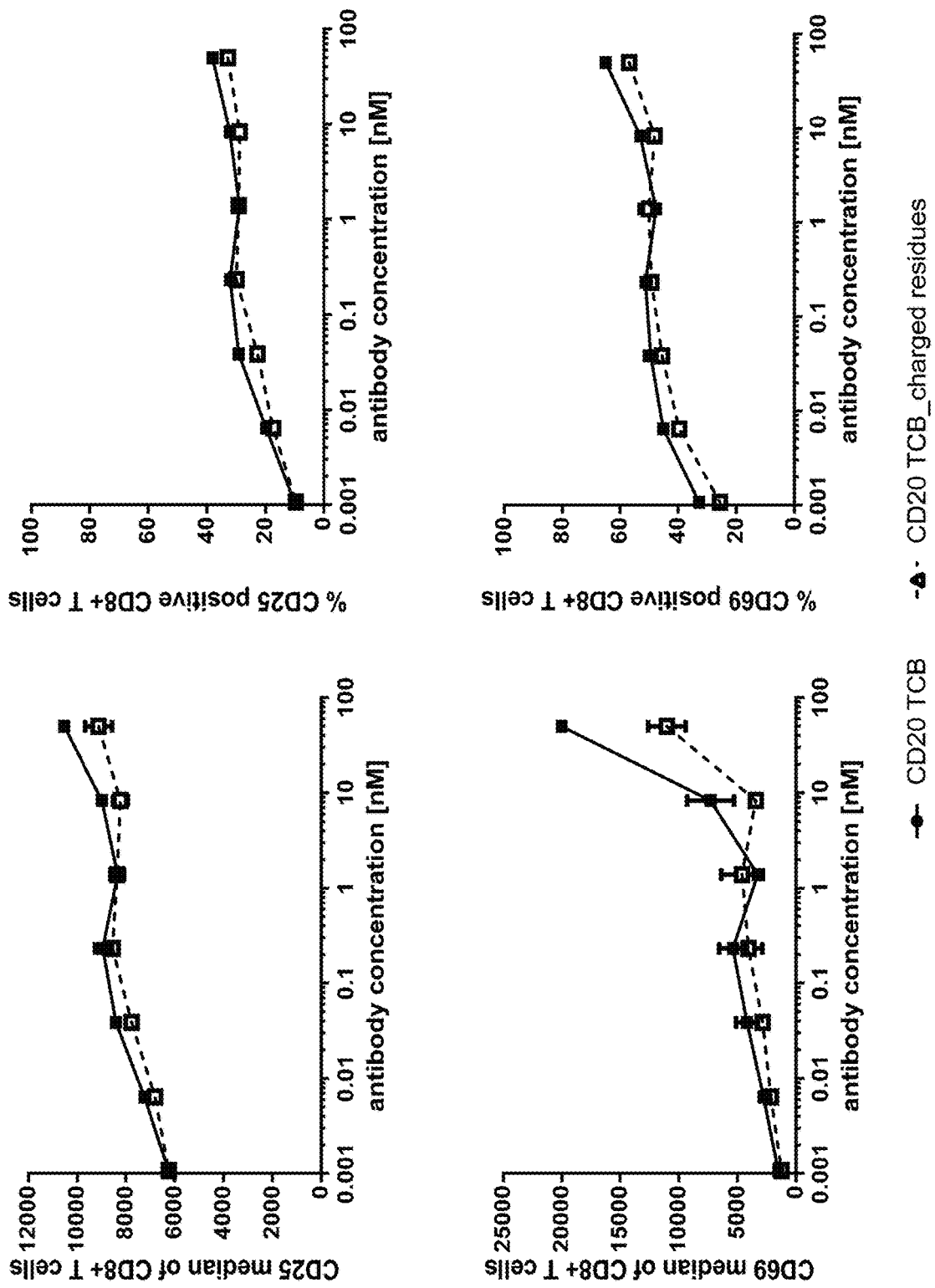

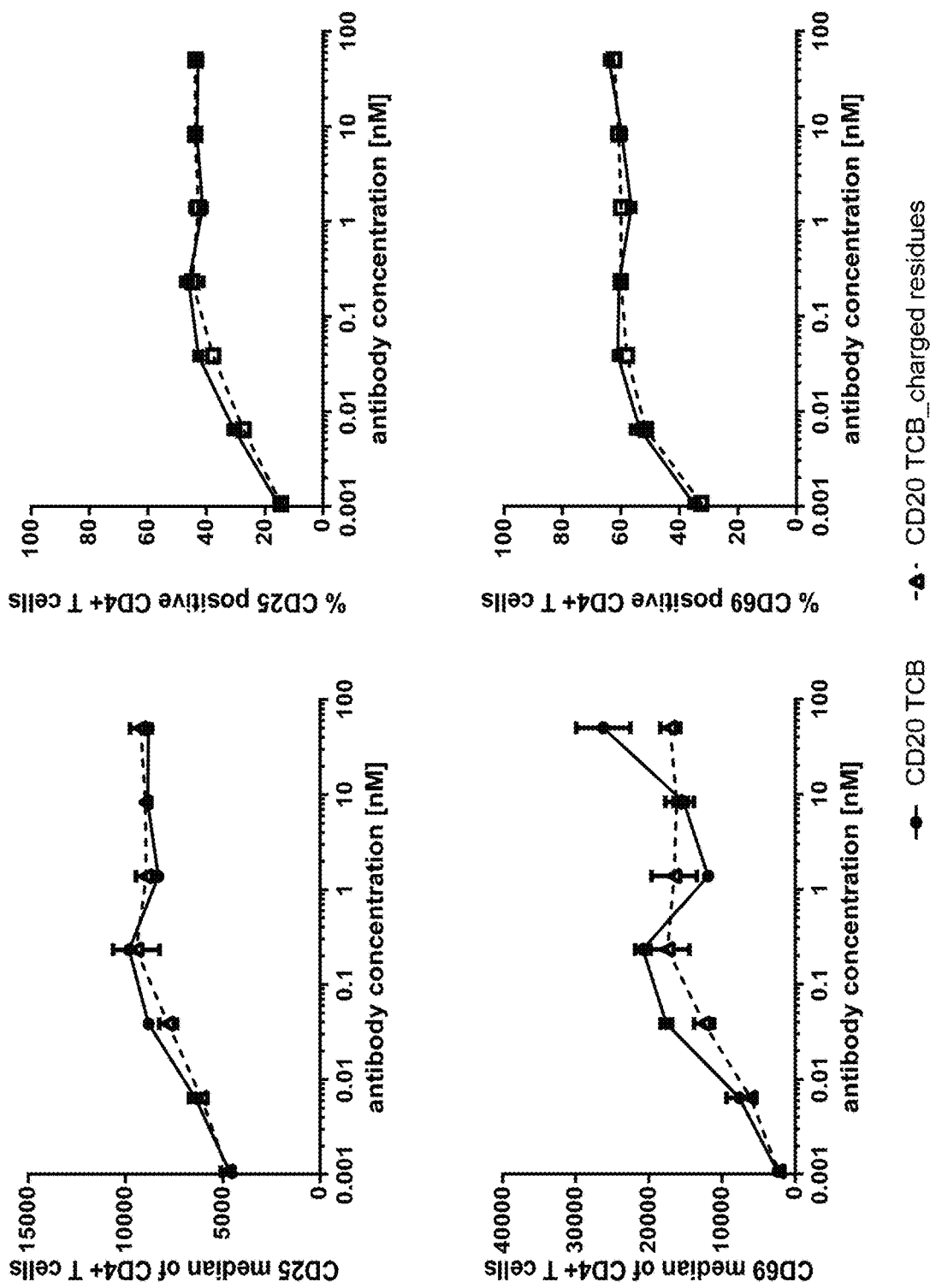

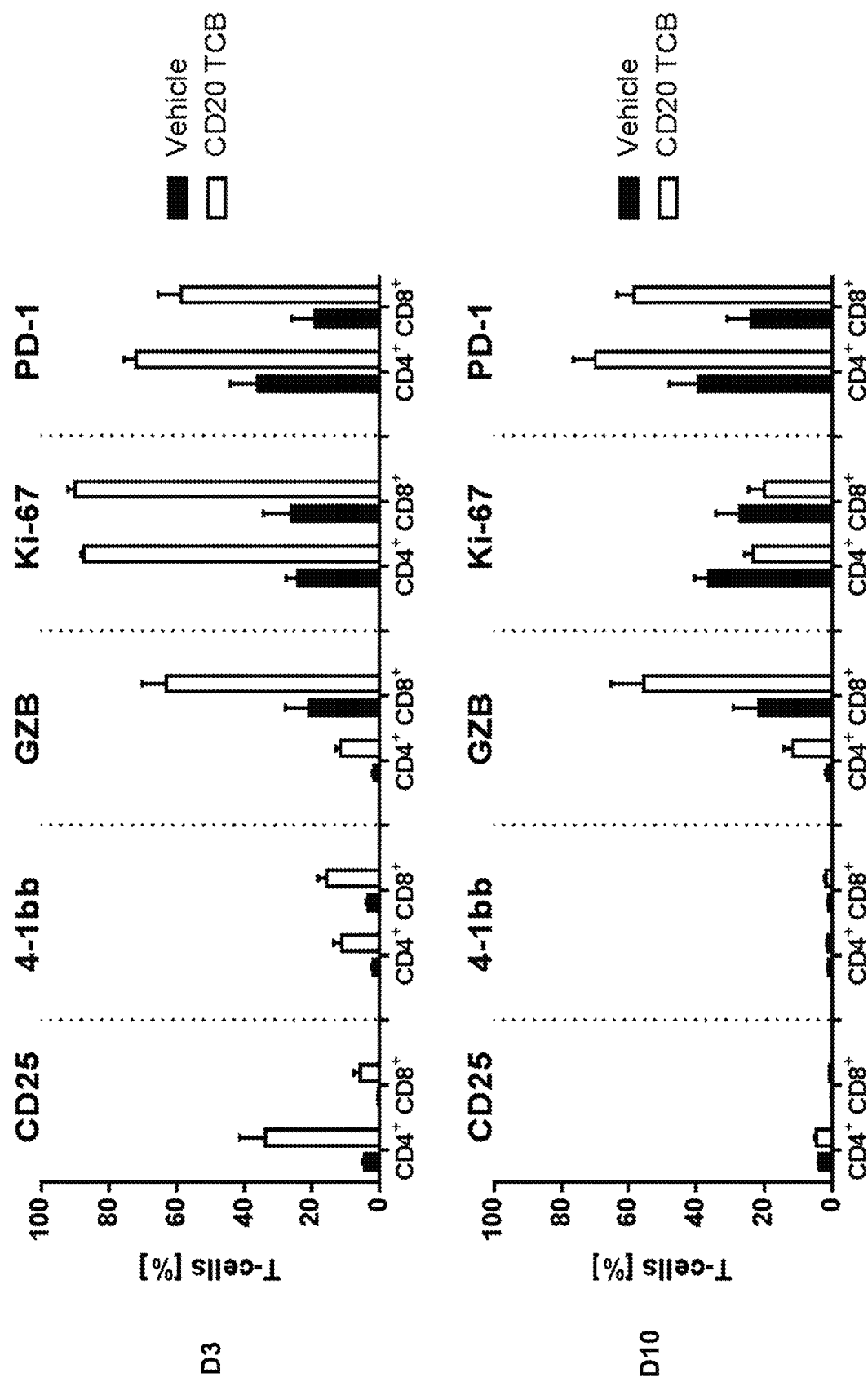

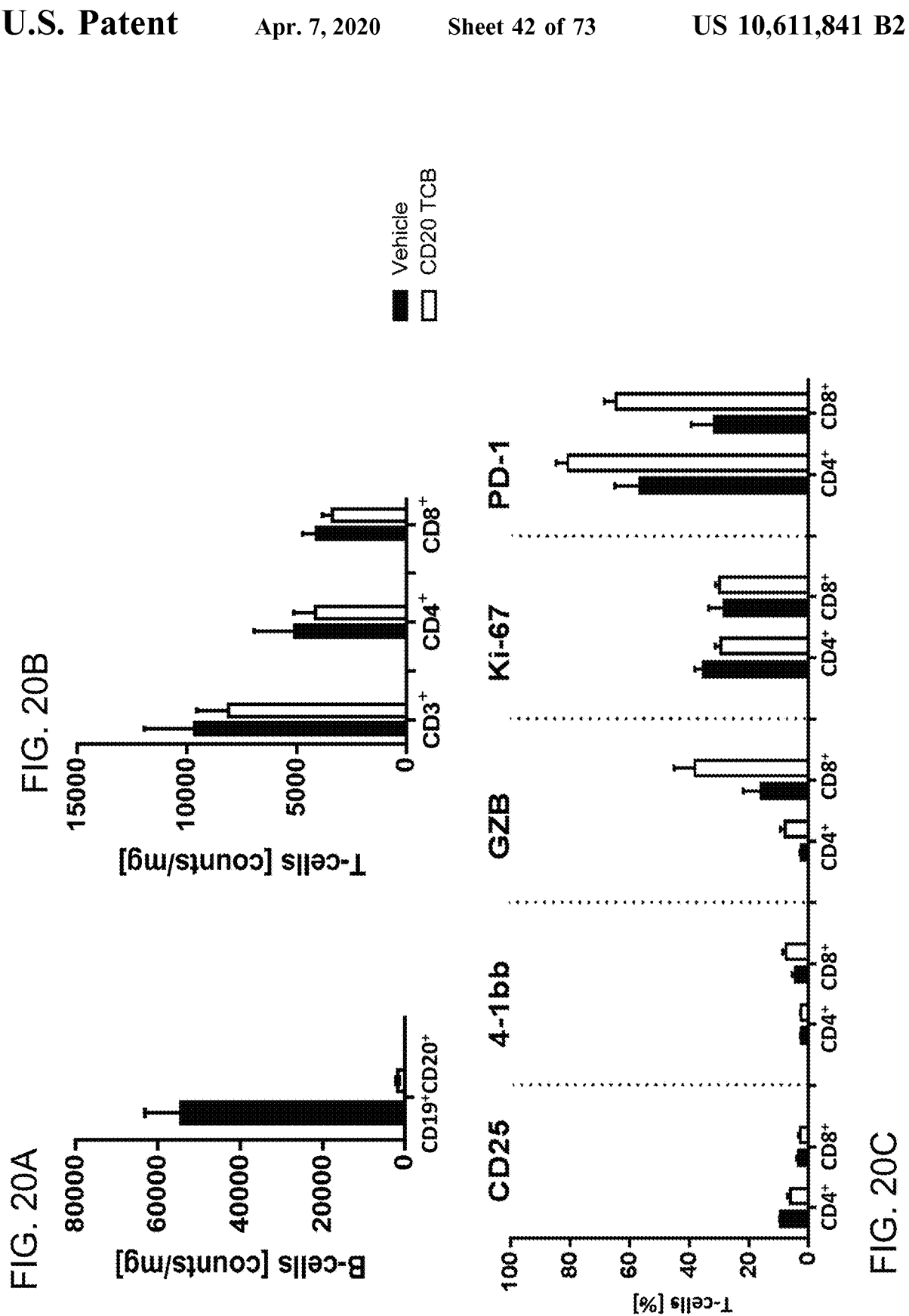

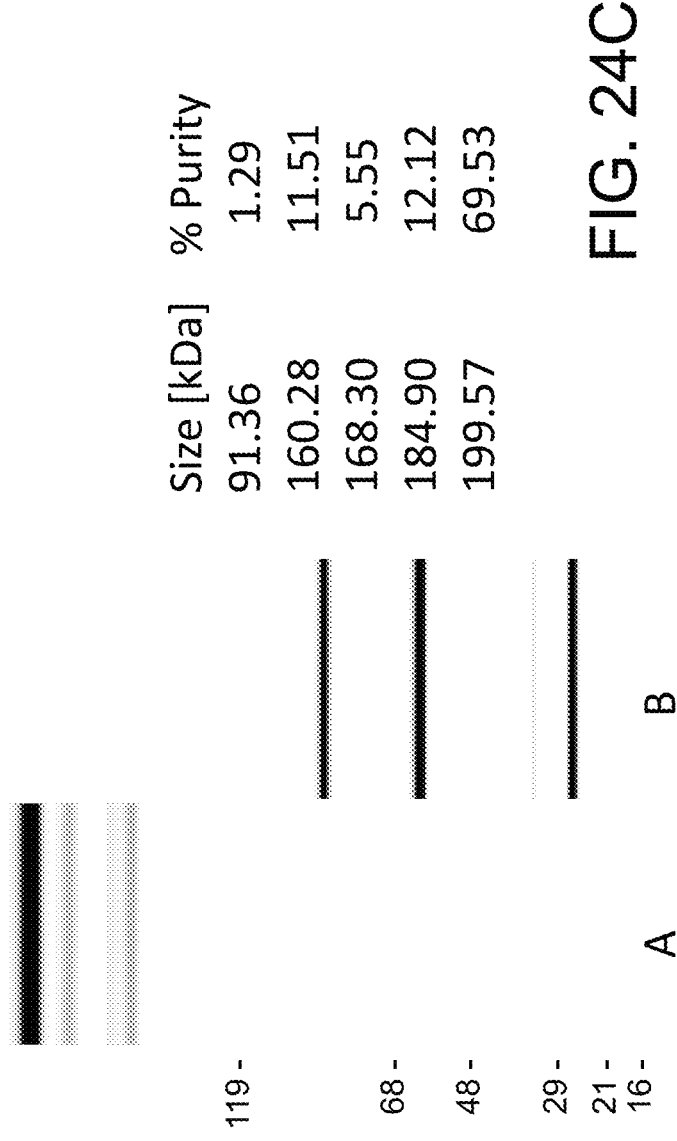

83A10-TCBcv
Pur. methods: PA + SEC
Purity: 91.0%
Yield: 10.3 mg/L
Amount: 10.0 mg
Monomer: 83.9%
LC-MS: 90% correct molecule
 
| | Size [kDa] | % Purity |
|---|---|---|
| | 91.20 | 1.03 |
| | 160.92 | 6.42 |
| | 184.74 | 1.59 |
| | 196.63 | 90.96 |
A  B
FIG. 24D

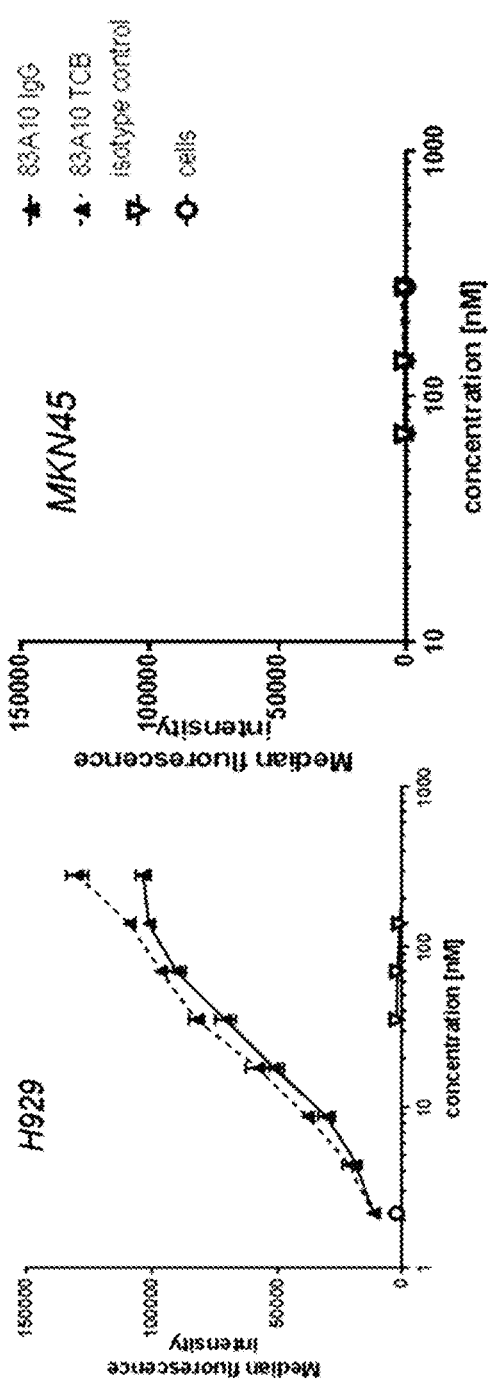
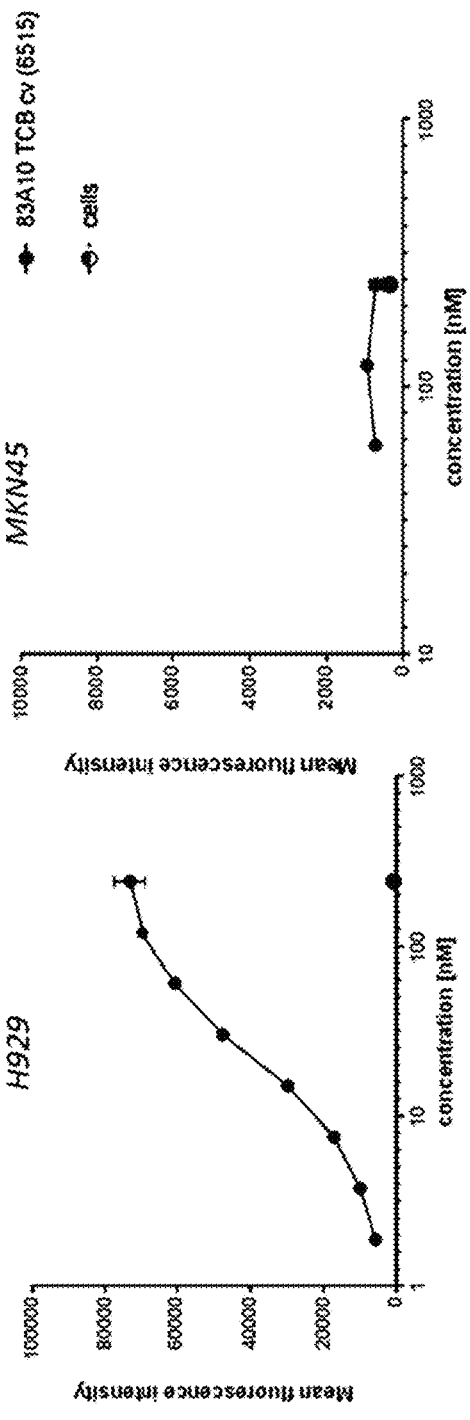
FIG. 25A
FIG. 25B

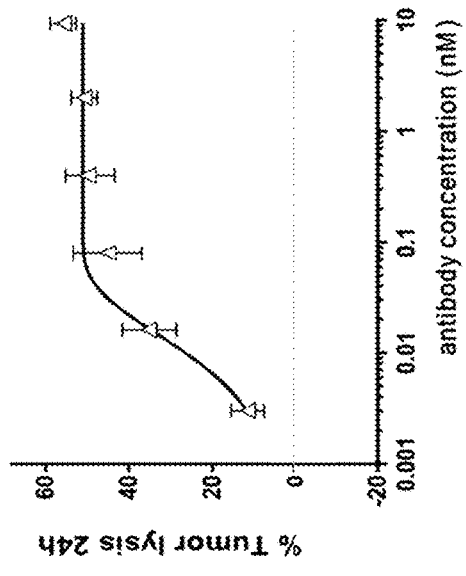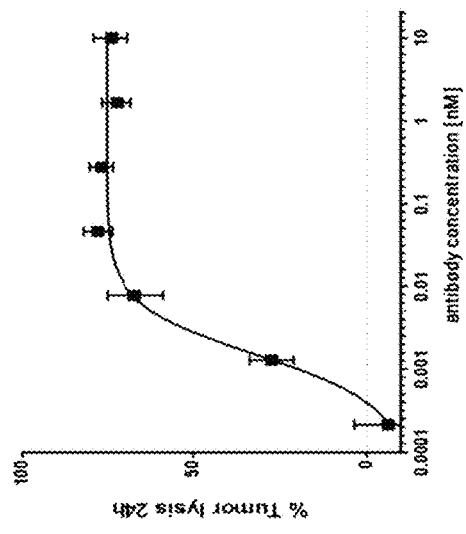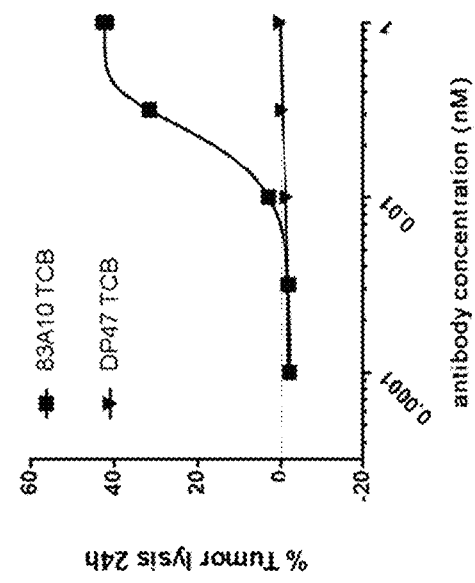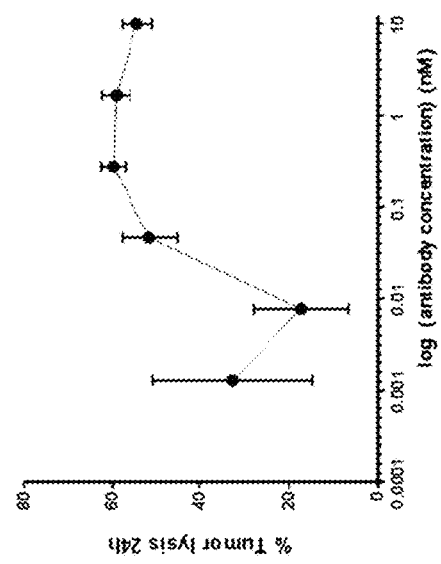
FIG. 26A
FIG. 26B
FIG. 26C
FIG. 26D

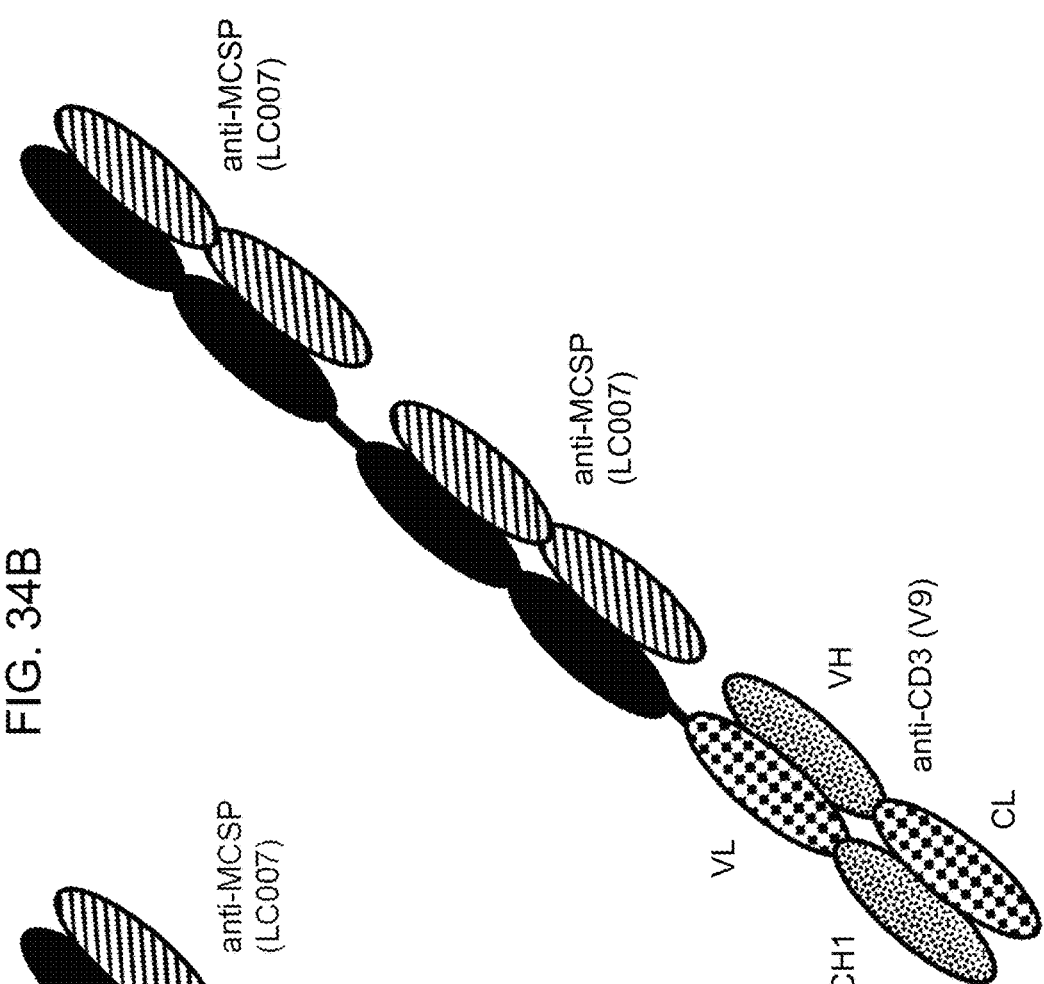
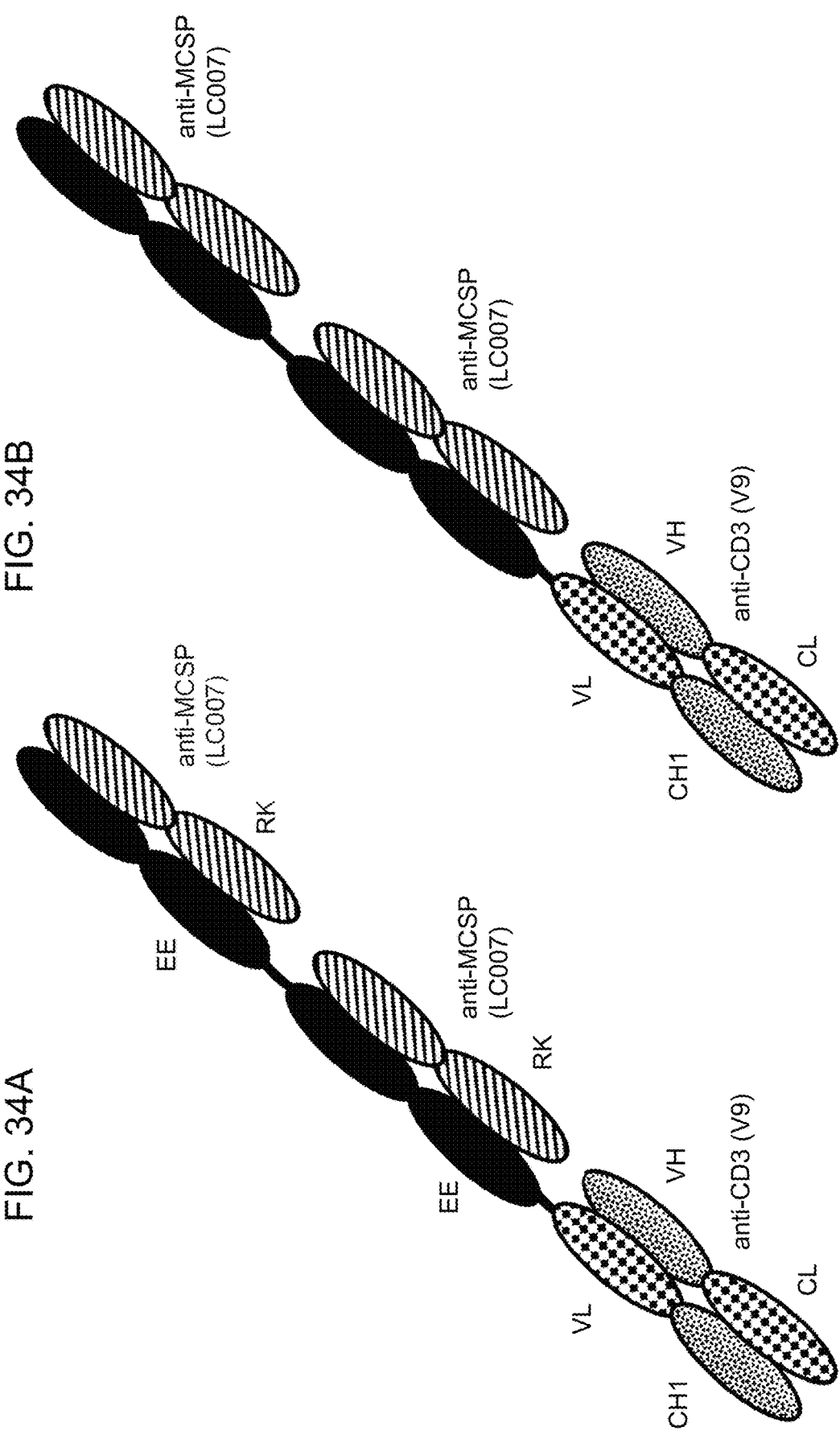
FIG. 34A
FIG. 34B they can be divided to patients by continuous infusion.

SEQUENCE LISTING

<160> NUMBER OF SEQ ID NOS: 73

<210> SEQ ID NO 1
<211> LENGTH: 207
<212> TYPE: PRT
<213> ORGANISM: Homo sapiens

<400> SEQUENCE: 1

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205

<210> SEQ ID NO 2
<211> LENGTH: 198
<212> TYPE: PRT
<213> ORGANISM: Macaca fascicularis

<400> SEQUENCE: 2

Met Gln Ser Gly Thr Arg Trp Arg Val Leu Gly Leu Cys Leu Leu Ser
1               5                   10                  15

Ile Gly Val Trp Gly Gln Asp Gly Asn Glu Glu Met Gly Ser Ile Thr
            20                  25                  30

Gln Thr Pro Tyr Gln Val Ser Ile Ser Gly Thr Thr Val Ile Leu Thr
        35                  40                  45

Cys Ser Gln His Leu Gly Ser Glu Ala Gln Trp Gln His Asn Gly Lys
    50                  55                  60

Asn Lys Glu Asp Ser Gly Asp Arg Leu Phe Leu Pro Glu Phe Ser Glu
65                  70                  75                  80

Met Glu Gln Ser Gly Tyr Tyr Val Cys Tyr Pro Arg Gly Ser Asn Pro
                85                  90                  95

Glu Asp Ala Ser His His Leu Tyr Leu Lys Ala Arg Val Cys Glu Asn
            100                 105                 110

Cys Met Glu Met Asp Val Met Ala Val Ala Thr Ile Val Ile Val Asp

```
              115                 120                 125
Ile Cys Ile Thr Leu Gly Leu Leu Leu Val Tyr Tyr Trp Ser Lys
        130                 135                 140

Asn Arg Lys Ala Lys Ala Lys Pro Val Thr Arg Gly Ala Gly Ala Gly
145                 150                 155                 160

Gly Arg Gln Arg Gly Gln Asn Lys Glu Arg Pro Pro Val Pro Asn
                165                 170                 175

Pro Asp Tyr Glu Pro Ile Arg Lys Gly Gln Gln Asp Leu Tyr Ser Gly
            180                 185                 190

Leu Asn Gln Arg Arg Ile
        195

<210> SEQ ID NO 3
<211> LENGTH: 125
<212> TYPE: PRT
<213> ORGANISM: Artificial Sequence
<220> FEATURE:
<223> OTHER INFORMATION: CD3 VH

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 4
<211> LENGTH: 5
<212> TYPE: PRT
<213> ORGANISM: Artificial Sequence
<220> FEATURE:
<223> OTHER INFORMATION: CD3 HCDR1

<400> SEQUENCE: 4

Thr Tyr Ala Met Asn
1               5

<210> SEQ ID NO 5
<211> LENGTH: 19
<212> TYPE: PRT
<213> ORGANISM: Artificial Sequence
<220> FEATURE:
<223> OTHER INFORMATION: CD3 HCDR2

<400> SEQUENCE: 5

Arg Ile Arg Ser Lys Tyr Asn Asn Tyr Ala Thr Tyr Tyr Ala Asp Ser
1               5                   10                  15

Val Lys Gly
```

<210> SEQ ID NO 6
<211> LENGTH: 14
<212> TYPE: PRT
<213> ORGANISM: Artificial Sequence
<220> FEATURE:
<223> OTHER INFORMATION: CD3 HCDR3

<400> SEQUENCE: 6

His Gly Asn Phe Gly Asn Ser Tyr Val Ser Trp Phe Ala Tyr
1               5                   10

<210> SEQ ID NO 7
<211> LENGTH: 109
<212> TYPE: PRT
<213> ORGANISM: Artificial Sequence
<220> FEATURE:
<223> OTHER INFORMATION: CD3 VL

<400> SEQUENCE: 7

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 8
<211> LENGTH: 14
<212> TYPE: PRT
<213> ORGANISM: Artificial Sequence
<220> FEATURE:
<223> OTHER INFORMATION: CD3 LCDR1

<400> SEQUENCE: 8

Gly Ser Ser Thr Gly Ala Val Thr Thr Ser Asn Tyr Ala Asn
1               5                   10

<210> SEQ ID NO 9
<211> LENGTH: 7
<212> TYPE: PRT
<213> ORGANISM: Artificial Sequence
<220> FEATURE:
<223> OTHER INFORMATION: CD3 LCDR2

<400> SEQUENCE: 9

Gly Thr Asn Lys Arg Ala Pro
1               5

<210> SEQ ID NO 10
<211> LENGTH: 9
<212> TYPE: PRT
<213> ORGANISM: Artificial Sequence
<220> FEATURE:
<223> OTHER INFORMATION: CD3 LCDR3

<400> SEQUENCE: 10

```
Ala Leu Trp Tyr Ser Asn Leu Trp Val
1               5

<210> SEQ ID NO 11
<211> LENGTH: 10
<212> TYPE: PRT
<213> ORGANISM: Artificial Sequence
<220> FEATURE:
<223> OTHER INFORMATION: linker

<400> SEQUENCE: 11

Gly Gly Gly Gly Ser Gly Gly Gly Gly Ser
1               5                   10

<210> SEQ ID NO 12
<211> LENGTH: 11
<212> TYPE: PRT
<213> ORGANISM: Artificial Sequence
<220> FEATURE:
<223> OTHER INFORMATION: linker

<400> SEQUENCE: 12

Asp Gly Gly Gly Gly Ser Gly Gly Gly Gly Ser
1               5                   10

<210> SEQ ID NO 13
<211> LENGTH: 225
<212> TYPE: PRT
<213> ORGANISM: Homo sapiens

<400> SEQUENCE: 13

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220
```

Pro
225

<210> SEQ ID NO 14
<211> LENGTH: 690
<212> TYPE: PRT
<213> ORGANISM: Artificial Sequence
<220> FEATURE:
<223> OTHER INFORMATION: CD20 VH-CH1-CD3 VH-CL-Fc (knob, P329G LALA)

<400> SEQUENCE: 14

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Gly
    210                 215                 220

Gly Gly Gly Ser Gly Gly Gly Ser Glu Val Gln Leu Leu Glu Ser
225                 230                 235                 240

Gly Gly Gly Leu Val Gln Pro Gly Gly Ser Leu Arg Leu Ser Cys Ala
                245                 250                 255

Ala Ser Gly Phe Thr Phe Ser Thr Tyr Ala Met Asn Trp Val Arg Gln
            260                 265                 270

Ala Pro Gly Lys Gly Leu Glu Trp Val Ser Arg Ile Arg Ser Lys Tyr
        275                 280                 285

Asn Asn Tyr Ala Thr Tyr Tyr Ala Asp Ser Val Lys Gly Arg Phe Thr
    290                 295                 300

Ile Ser Arg Asp Asp Ser Lys Asn Thr Leu Tyr Leu Gln Met Asn Ser
305                 310                 315                 320

Leu Arg Ala Glu Asp Thr Ala Val Tyr Tyr Cys Val Arg His Gly Asn
                325                 330                 335

Phe Gly Asn Ser Tyr Val Ser Trp Phe Ala Tyr Trp Gly Gln Gly Thr
            340                 345                 350
```

```
Leu Val Thr Val Ser Ser Ala Ser Val Ala Ala Pro Ser Val Phe Ile
        355                 360                 365

Phe Pro Pro Ser Asp Glu Gln Leu Lys Ser Gly Thr Ala Ser Val Val
370                 375                 380

Cys Leu Leu Asn Asn Phe Tyr Pro Arg Glu Ala Lys Val Gln Trp Lys
385                 390                 395                 400

Val Asp Asn Ala Leu Gln Ser Gly Asn Ser Gln Glu Ser Val Thr Glu
                405                 410                 415

Gln Asp Ser Lys Asp Ser Thr Tyr Ser Leu Ser Ser Thr Leu Thr Leu
                420                 425                 430

Ser Lys Ala Asp Tyr Glu Lys His Lys Val Tyr Ala Cys Glu Val Thr
            435                 440                 445

His Gln Gly Leu Ser Ser Pro Val Thr Lys Ser Phe Asn Arg Gly Glu
        450                 455                 460

Cys Asp Lys Thr His Thr Cys Pro Pro Cys Pro Ala Pro Glu Ala Ala
465                 470                 475                 480

Gly Gly Pro Ser Val Phe Leu Phe Pro Pro Lys Pro Lys Asp Thr Leu
                485                 490                 495

Met Ile Ser Arg Thr Pro Glu Val Thr Cys Val Val Val Asp Val Ser
                500                 505                 510

His Glu Asp Pro Glu Val Lys Phe Asn Trp Tyr Val Asp Gly Val Glu
            515                 520                 525

Val His Asn Ala Lys Thr Lys Pro Arg Glu Glu Gln Tyr Asn Ser Thr
        530                 535                 540

Tyr Arg Val Val Ser Val Leu Thr Val Leu His Gln Asp Trp Leu Asn
545                 550                 555                 560

Gly Lys Glu Tyr Lys Cys Lys Val Ser Asn Lys Ala Leu Gly Ala Pro
                565                 570                 575

Ile Glu Lys Thr Ile Ser Lys Ala Lys Gly Gln Pro Arg Glu Pro Gln
                580                 585                 590

Val Tyr Thr Leu Pro Pro Cys Arg Asp Glu Leu Thr Lys Asn Gln Val
            595                 600                 605

Ser Leu Trp Cys Leu Val Lys Gly Phe Tyr Pro Ser Asp Ile Ala Val
        610                 615                 620

Glu Trp Glu Ser Asn Gly Gln Pro Glu Asn Asn Tyr Lys Thr Thr Pro
625                 630                 635                 640

Pro Val Leu Asp Ser Asp Gly Ser Phe Phe Leu Tyr Ser Lys Leu Thr
                645                 650                 655

Val Asp Lys Ser Arg Trp Gln Gln Gly Asn Val Phe Ser Cys Ser Val
                660                 665                 670

Met His Glu Ala Leu His Asn His Tyr Thr Gln Lys Ser Leu Ser Leu
            675                 680                 685

Ser Pro
    690

<210> SEQ ID NO 15
<211> LENGTH: 447
<212> TYPE: PRT
<213> ORGANISM: Artificial Sequence
<220> FEATURE:
<223> OTHER INFORMATION: CD20 VH-CH1-Fc (hole, P329G LALA)

<400> SEQUENCE: 15

Gln Val Gln Leu Val Gln Ser Gly Ala Glu Val Lys Lys Pro Gly Ser
1               5                   10                  15
```

```
Ser Val Lys Val Ser Cys Lys Ala Ser Gly Tyr Ala Phe Ser Tyr Ser
            20                  25                  30
Trp Ile Asn Trp Val Arg Gln Ala Pro Gly Gln Gly Leu Glu Trp Met
        35                  40                  45
Gly Arg Ile Phe Pro Gly Asp Gly Asp Thr Asp Tyr Asn Gly Lys Phe
50                  55                  60
Lys Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
            85                  90                  95
Ala Arg Asn Val Phe Asp Gly Tyr Trp Leu Val Tyr Trp Gly Gln Gly
            100                 105                 110
Thr Leu Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
            195                 200                 205
Ser Asn Thr Lys Val Asp Lys Lys Val Glu Pro Lys Ser Cys Asp Lys
210                 215                 220
Thr His Thr Cys Pro Pro Cys Pro Ala Pro Glu Ala Ala Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
            275                 280                 285
Ala Lys Thr Lys Pro Arg Glu Glu Gln Tyr Asn Ser Thr Tyr Arg Val
290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Gly Ala Pro Ile Glu Lys
                325                 330                 335
Thr Ile Ser Lys Ala Lys Gly Gln Pro Arg Glu Pro Gln Val Cys Thr
            340                 345                 350
Leu Pro Pro Ser Arg Asp Glu Leu Thr Lys Asn Gln Val Ser Leu Ser
            355                 360                 365
Cys Ala Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Val Ser Lys Leu Thr Val Asp Lys
                405                 410                 415
Ser Arg Trp Gln Gln Gly Asn Val Phe Ser Cys Ser Val Met His Glu
            420                 425                 430
```

Ala Leu His Asn His Tyr Thr Gln Lys Ser Leu Ser Leu Ser Pro
            435                 440                 445

<210> SEQ ID NO 16
<211> LENGTH: 214
<212> TYPE: PRT
<213> ORGANISM: Artificial Sequence
<220> FEATURE:
<223> OTHER INFORMATION: CD3 VL-CH1

<400> SEQUENCE: 16

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Lys
        195                 200                 205

Val Glu Pro Lys Ser Cys
    210

<210> SEQ ID NO 17
<211> LENGTH: 219
<212> TYPE: PRT
<213> ORGANISM: Artificial Sequence
<220> FEATURE:
<223> OTHER INFORMATION: CD20 VL-CL

<400> SEQUENCE: 17

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

```
Ser Arg Val Glu Ala Glu Asp Val Gly Val Tyr Tyr Cys Ala Gln Asn
            85                  90                  95

Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 18
<211> LENGTH: 672
<212> TYPE: PRT
<213> ORGANISM: Artificial Sequence
<220> FEATURE:
<223> OTHER INFORMATION: CD20 VH-CH1(EE)-CD3 VL-CH1-Fc (knob, P329G
      LALA)

<400> SEQUENCE: 18

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
            35                  40                  45

Gly Arg Ile Phe Pro Gly Asp Gly Asp Thr Asp Tyr Asn Gly Lys Phe
50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Glu Lys Val Glu Pro Lys Ser Cys Asp Gly
```

```
                210                 215                 220
Gly Gly Gly Ser Gly Gly Gly Ser Gln Ala Val Thr Gln Glu
225                 230                 235                 240

Pro Ser Leu Thr Val Ser Pro Gly Gly Thr Val Thr Leu Thr Cys Gly
                245                 250                 255

Ser Ser Thr Gly Ala Val Thr Thr Ser Asn Tyr Ala Asn Trp Val Gln
                260                 265                 270

Glu Lys Pro Gly Gln Ala Phe Arg Gly Leu Ile Gly Gly Thr Asn Lys
            275                 280                 285

Arg Ala Pro Gly Thr Pro Ala Arg Phe Ser Gly Ser Leu Leu Gly Gly
            290                 295                 300

Lys Ala Ala Leu Thr Leu Ser Gly Ala Gln Pro Glu Asp Glu Ala Glu
305                 310                 315                 320

Tyr Tyr Cys Ala Leu Trp Tyr Ser Asn Leu Trp Val Phe Gly Gly Gly
                325                 330                 335

Thr Lys Leu Thr Val Leu Ser Ser Ala Ser Thr Lys Gly Pro Ser Val
                340                 345                 350

Phe Pro Leu Ala Pro Ser Ser Lys Ser Thr Ser Gly Gly Thr Ala Ala
            355                 360                 365

Leu Gly Cys Leu Val Lys Asp Tyr Phe Pro Glu Pro Val Thr Val Ser
            370                 375                 380

Trp Asn Ser Gly Ala Leu Thr Ser Gly Val His Thr Phe Pro Ala Val
385                 390                 395                 400

Leu Gln Ser Ser Gly Leu Tyr Ser Leu Ser Ser Val Val Thr Val Pro
                405                 410                 415

Ser Ser Ser Leu Gly Thr Gln Thr Tyr Ile Cys Asn Val Asn His Lys
                420                 425                 430

Pro Ser Asn Thr Lys Val Asp Lys Lys Val Glu Pro Lys Ser Cys Asp
            435                 440                 445

Lys Thr His Thr Cys Pro Pro Cys Pro Ala Pro Glu Ala Ala Gly Gly
            450                 455                 460

Pro Ser Val Phe Leu Phe Pro Pro Lys Pro Lys Asp Thr Leu Met Ile
465                 470                 475                 480

Ser Arg Thr Pro Glu Val Thr Cys Val Val Val Asp Val Ser His Glu
                485                 490                 495

Asp Pro Glu Val Lys Phe Asn Trp Tyr Val Asp Gly Val Glu Val His
            500                 505                 510

Asn Ala Lys Thr Lys Pro Arg Glu Glu Gln Tyr Asn Ser Thr Tyr Arg
            515                 520                 525

Val Val Ser Val Leu Thr Val Leu His Gln Asp Trp Leu Asn Gly Lys
            530                 535                 540

Glu Tyr Lys Cys Lys Val Ser Asn Lys Ala Leu Gly Ala Pro Ile Glu
545                 550                 555                 560

Lys Thr Ile Ser Lys Ala Lys Gly Gln Pro Arg Glu Pro Gln Val Tyr
                565                 570                 575

Thr Leu Pro Pro Cys Arg Asp Glu Leu Thr Lys Asn Gln Val Ser Leu
            580                 585                 590

Trp Cys Leu Val Lys Gly Phe Tyr Pro Ser Asp Ile Ala Val Glu Trp
            595                 600                 605

Glu Ser Asn Gly Gln Pro Glu Asn Asn Tyr Lys Thr Thr Pro Pro Val
            610                 615                 620

Leu Asp Ser Asp Gly Ser Phe Phe Leu Tyr Ser Lys Leu Thr Val Asp
625                 630                 635                 640
```

Lys Ser Arg Trp Gln Gln Gly Asn Val Phe Ser Cys Ser Val Met His
            645                 650                 655

Glu Ala Leu His Asn His Tyr Thr Gln Lys Ser Leu Ser Leu Ser Pro
            660                 665                 670

<210> SEQ ID NO 19
<211> LENGTH: 447
<212> TYPE: PRT
<213> ORGANISM: Artificial Sequence
<220> FEATURE:
<223> OTHER INFORMATION: CD20 VH-CH1(EE)-Fc (hole, P329G LALA)

<400> SEQUENCE: 19

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

```
Thr Ile Ser Lys Ala Lys Gly Gln Pro Arg Glu Pro Gln Val Cys Thr
                340                 345                 350

Leu Pro Pro Ser Arg Asp Glu Leu Thr Lys Asn Gln Val Ser Leu Ser
            355                 360                 365

Cys Ala Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 20
<211> LENGTH: 219
<212> TYPE: PRT
<213> ORGANISM: Artificial Sequence
<220> FEATURE:
<223> OTHER INFORMATION: CD20 VL-CL(RK)

<400> SEQUENCE: 20

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
                20                  25                  30

Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Leu Val Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Arg
        115                 120                 125

Lys Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 21
<211> LENGTH: 232
<212> TYPE: PRT
<213> ORGANISM: Artificial Sequence
```

<220> FEATURE:
<223> OTHER INFORMATION: CD3 VH-CL

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230

<210> SEQ ID NO 22
<211> LENGTH: 687
<212> TYPE: PRT
<213> ORGANISM: Artificial Sequence
<220> FEATURE:
<223> OTHER INFORMATION: BCMA VH-CH1-CD3 VH-CL-Fc (knob, P329G LALA)

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Gly Trp Phe Asp Tyr Trp Gly Gln Gly Thr Leu Val

```
                100                 105                 110
Thr Val Ser Ser Ala Ser Thr Lys Gly Pro Ser Val Phe Pro Leu Ala
            115                 120                 125
Pro Ser Ser Lys Ser Thr Ser Gly Gly Thr Ala Ala Leu Gly Cys Leu
130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
                180                 185                 190
Gly Thr Gln Thr Tyr Ile Cys Asn Val Asn His Lys Pro Ser Asn Thr
            195                 200                 205
Lys Val Asp Lys Lys Val Glu Pro Lys Ser Cys Asp Gly Gly Gly Gly
210                 215                 220
Ser Gly Gly Gly Gly Ser Glu Val Gln Leu Leu Glu Ser Gly Gly Gly
225                 230                 235                 240
Leu Val Gln Pro Gly Gly Ser Leu Arg Leu Ser Cys Ala Ala Ser Gly
                245                 250                 255
Phe Thr Phe Ser Thr Tyr Ala Met Asn Trp Val Arg Gln Ala Pro Gly
            260                 265                 270
Lys Gly Leu Glu Trp Val Ser Arg Ile Arg Ser Lys Tyr Asn Asn Tyr
            275                 280                 285
Ala Thr Tyr Tyr Ala Asp Ser Val Lys Gly Arg Phe Thr Ile Ser Arg
        290                 295                 300
Asp Asp Ser Lys Asn Thr Leu Tyr Leu Gln Met Asn Ser Leu Arg Ala
305                 310                 315                 320
Glu Asp Thr Ala Val Tyr Tyr Cys Val Arg His Gly Asn Phe Gly Asn
                325                 330                 335
Ser Tyr Val Ser Trp Phe Ala Tyr Trp Gly Gln Gly Thr Leu Val Thr
                340                 345                 350
Val Ser Ser Ala Ser Val Ala Ala Pro Ser Val Phe Ile Phe Pro Pro
            355                 360                 365
Ser Asp Glu Gln Leu Lys Ser Gly Thr Ala Ser Val Val Cys Leu Leu
370                 375                 380
Asn Asn Phe Tyr Pro Arg Glu Ala Lys Val Gln Trp Lys Val Asp Asn
385                 390                 395                 400
Ala Leu Gln Ser Gly Asn Ser Gln Glu Ser Val Thr Glu Gln Asp Ser
                405                 410                 415
Lys Asp Ser Thr Tyr Ser Leu Ser Ser Thr Leu Thr Leu Ser Lys Ala
                420                 425                 430
Asp Tyr Glu Lys His Lys Val Tyr Ala Cys Glu Val Thr His Gln Gly
            435                 440                 445
Leu Ser Ser Pro Val Thr Lys Ser Phe Asn Arg Gly Glu Cys Asp Lys
        450                 455                 460
Thr His Thr Cys Pro Pro Cys Pro Ala Pro Glu Ala Ala Gly Gly Pro
465                 470                 475                 480
Ser Val Phe Leu Phe Pro Pro Lys Pro Lys Asp Thr Leu Met Ile Ser
                485                 490                 495
Arg Thr Pro Glu Val Thr Cys Val Val Val Asp Val Ser His Glu Asp
            500                 505                 510
Pro Glu Val Lys Phe Asn Trp Tyr Val Asp Gly Val Glu Val His Asn
        515                 520                 525
```

```
Ala Lys Thr Lys Pro Arg Glu Glu Gln Tyr Asn Ser Thr Tyr Arg Val
    530                 535                 540

Val Ser Val Leu Thr Val Leu His Gln Asp Trp Leu Asn Gly Lys Glu
545                 550                 555                 560

Tyr Lys Cys Lys Val Ser Asn Lys Ala Leu Gly Ala Pro Ile Glu Lys
                565                 570                 575

Thr Ile Ser Lys Ala Lys Gly Gln Pro Arg Glu Pro Gln Val Tyr Thr
            580                 585                 590

Leu Pro Pro Cys Arg Asp Glu Leu Thr Lys Asn Gln Val Ser Leu Trp
        595                 600                 605

Cys Leu Val Lys Gly Phe Tyr Pro Ser Asp Ile Ala Val Glu Trp Glu
    610                 615                 620

Ser Asn Gly Gln Pro Glu Asn Asn Tyr Lys Thr Thr Pro Pro Val Leu
625                 630                 635                 640

Asp Ser Asp Gly Ser Phe Phe Leu Tyr Ser Lys Leu Thr Val Asp Lys
                645                 650                 655

Ser Arg Trp Gln Gln Gly Asn Val Phe Ser Cys Ser Val Met His Glu
            660                 665                 670

Ala Leu His Asn His Tyr Thr Gln Lys Ser Leu Ser Leu Ser Pro
        675                 680                 685

<210> SEQ ID NO 23
<211> LENGTH: 444
<212> TYPE: PRT
<213> ORGANISM: Artificial Sequence
<220> FEATURE:
<223> OTHER INFORMATION: BCMA VH-CH1-Fc (hole, P329G LALA)

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Gly Trp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205
```

```
Lys Val Asp Lys Lys Val Glu Pro Lys Ser Cys Asp Lys Thr His Thr
            210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Cys Thr Leu Pro Pro
            340                 345                 350

Ser Arg Asp Glu Leu Thr Lys Asn Gln Val Ser Leu Ser Cys Ala Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440

<210> SEQ ID NO 24
<211> LENGTH: 214
<212> TYPE: PRT
<213> ORGANISM: Artificial Sequence
<220> FEATURE:
<223> OTHER INFORMATION: CD3 VL-CH1

<400> SEQUENCE: 24

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Ser Ser Ala
            100                 105                 110

Ser Thr Lys Gly Pro Ser Val Phe Pro Leu Ala Pro Ser Ser Lys Ser
        115                 120                 125
```

Thr Ser Gly Gly Thr Ala Ala Leu Gly Cys Leu Val Lys Asp Tyr Phe
            130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Lys
        195                 200                 205

Val Glu Pro Lys Ser Cys
    210

<210> SEQ ID NO 25
<211> LENGTH: 216
<212> TYPE: PRT
<213> ORGANISM: Artificial Sequence
<220> FEATURE:
<223> OTHER INFORMATION: BCMA VL-CL

<400> SEQUENCE: 25

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Tyr Pro Pro
                85                  90                  95

Asp Phe Thr Phe Gly Gln Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 26
<211> LENGTH: 669
<212> TYPE: PRT
<213> ORGANISM: Artificial Sequence
<220> FEATURE:
<223> OTHER INFORMATION: BCMA VH-CH1(EE)-CD3 VL-CH1-Fc (knob, P329G
      LALA)

<400> SEQUENCE: 26

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Leu Gly Trp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Glu Lys Val Glu Pro Lys Ser Cys Asp Gly Gly Gly Gly
    210                 215                 220

Ser Gly Gly Gly Gly Ser Gln Ala Val Val Thr Gln Glu Pro Ser Leu
225                 230                 235                 240

Thr Val Ser Pro Gly Gly Thr Val Thr Leu Thr Cys Gly Ser Ser Thr
                245                 250                 255

Gly Ala Val Thr Thr Ser Asn Tyr Ala Asn Trp Val Gln Glu Lys Pro
            260                 265                 270

Gly Gln Ala Phe Arg Gly Leu Ile Gly Gly Thr Asn Lys Arg Ala Pro
        275                 280                 285

Gly Thr Pro Ala Arg Phe Ser Gly Ser Leu Leu Gly Gly Lys Ala Ala
    290                 295                 300

Leu Thr Leu Ser Gly Ala Gln Pro Glu Asp Glu Ala Glu Tyr Tyr Cys
305                 310                 315                 320

Ala Leu Trp Tyr Ser Asn Leu Trp Val Phe Gly Gly Gly Thr Lys Leu
                325                 330                 335

Thr Val Leu Ser Ser Ala Ser Thr Lys Gly Pro Ser Val Phe Pro Leu
            340                 345                 350

Ala Pro Ser Ser Lys Ser Thr Ser Gly Gly Thr Ala Ala Leu Gly Cys
        355                 360                 365

Leu Val Lys Asp Tyr Phe Pro Glu Pro Val Thr Val Ser Trp Asn Ser
    370                 375                 380

Gly Ala Leu Thr Ser Gly Val His Thr Phe Pro Ala Val Leu Gln Ser
385                 390                 395                 400

Ser Gly Leu Tyr Ser Leu Ser Ser Val Val Thr Val Pro Ser Ser Ser
```

```
                    405                 410                 415
Leu Gly Thr Gln Thr Tyr Ile Cys Asn Val Asn His Lys Pro Ser Asn
            420                 425                 430

Thr Lys Val Asp Lys Lys Val Glu Pro Lys Ser Cys Asp Lys Thr His
        435                 440                 445

Thr Cys Pro Pro Cys Pro Ala Pro Glu Ala Ala Gly Gly Pro Ser Val
    450                 455                 460

Phe Leu Phe Pro Pro Lys Pro Lys Asp Thr Leu Met Ile Ser Arg Thr
465                 470                 475                 480

Pro Glu Val Thr Cys Val Val Val Asp Val Ser His Glu Asp Pro Glu
                485                 490                 495

Val Lys Phe Asn Trp Tyr Val Asp Gly Val Glu Val His Asn Ala Lys
            500                 505                 510

Thr Lys Pro Arg Glu Glu Gln Tyr Asn Ser Thr Tyr Arg Val Val Ser
        515                 520                 525

Val Leu Thr Val Leu His Gln Asp Trp Leu Asn Gly Lys Glu Tyr Lys
    530                 535                 540

Cys Lys Val Ser Asn Lys Ala Leu Gly Ala Pro Ile Glu Lys Thr Ile
545                 550                 555                 560

Ser Lys Ala Lys Gly Gln Pro Arg Glu Pro Gln Val Tyr Thr Leu Pro
                565                 570                 575

Pro Cys Arg Asp Glu Leu Thr Lys Asn Gln Val Ser Leu Trp Cys Leu
            580                 585                 590

Val Lys Gly Phe Tyr Pro Ser Asp Ile Ala Val Glu Trp Glu Ser Asn
        595                 600                 605

Gly Gln Pro Glu Asn Asn Tyr Lys Thr Thr Pro Pro Val Leu Asp Ser
    610                 615                 620

Asp Gly Ser Phe Phe Leu Tyr Ser Lys Leu Thr Val Asp Lys Ser Arg
625                 630                 635                 640

Trp Gln Gln Gly Asn Val Phe Ser Cys Ser Val Met His Glu Ala Leu
                645                 650                 655

His Asn His Tyr Thr Gln Lys Ser Leu Ser Leu Ser Pro
            660                 665

<210> SEQ ID NO 27
<211> LENGTH: 444
<212> TYPE: PRT
<213> ORGANISM: Artificial Sequence
<220> FEATURE:
<223> OTHER INFORMATION: BCMA VH-CH1(EE)-Fc (hole, P329G LALA)

<400> SEQUENCE: 27

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Gly Trp Phe Asp Tyr Trp Gly Gln Gly Thr Leu Val
```

```
            100                 105                 110
Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
            130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Glu Lys Val Glu Pro Lys Ser Cys Asp Lys Thr His Thr
            210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
            325                 330                 335

Lys Ala Lys Gly Gln Pro Arg Glu Pro Gln Val Cys Thr Leu Pro Pro
            340                 345                 350

Ser Arg Asp Glu Leu Thr Lys Asn Gln Val Ser Leu Ser Cys Ala Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
            435                 440

<210> SEQ ID NO 28
<211> LENGTH: 232
<212> TYPE: PRT
<213> ORGANISM: Artificial Sequence
<220> FEATURE:
<223> OTHER INFORMATION: CD3 VH-CL

<400> SEQUENCE: 28

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
```

```
            20                  25                  30
Ala Met Asn Trp Val Arg Gln Ala Pro Gly Lys Gly Leu Glu Trp Val
         35                  40                  45

Ser Arg Ile Arg Ser Lys Tyr Asn Asn Tyr Ala Thr Tyr Tyr Ala Asp
 50                  55                  60

Ser Val Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser Ala Ser Val
            115                 120                 125

Ala Ala Pro Ser Val Phe Ile Phe Pro Pro Ser Asp Glu Gln Leu Lys
        130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230

<210> SEQ ID NO 29
<211> LENGTH: 216
<212> TYPE: PRT
<213> ORGANISM: Artificial Sequence
<220> FEATURE:
<223> OTHER INFORMATION: BCMA VL-CL(RK)

<400> SEQUENCE: 29

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Tyr Pro Pro
                 85                  90                  95

Asp Phe Thr Phe Gly Gln Gly Thr Lys Val Glu Ile Lys Arg Thr Val
                100                 105                 110

Ala Ala Pro Ser Val Phe Ile Phe Pro Pro Ser Asp Arg Lys Leu Lys
            115                 120                 125

Ser Gly Thr Ala Ser Val Val Cys Leu Leu Asn Asn Phe Tyr Pro Arg
        130                 135                 140

Glu Ala Lys Val Gln Trp Lys Val Asp Asn Ala Leu Gln Ser Gly Asn
```

```
                        145                 150                 155                 160
Ser Gln Glu Ser Val Thr Glu Gln Asp Ser Lys Asp Ser Thr Tyr Ser
                    165                 170                 175

Leu Ser Ser Thr Leu Thr Leu Ser Lys Ala Asp Tyr Glu Lys His Lys
                180                 185                 190

Val Tyr Ala Cys Glu Val Thr His Gln Gly Leu Ser Ser Pro Val Thr
            195                 200                 205

Lys Ser Phe Asn Arg Gly Glu Cys
        210                 215

<210> SEQ ID NO 30
<211> LENGTH: 119
<212> TYPE: PRT
<213> ORGANISM: Artificial Sequence
<220> FEATURE:
<223> OTHER INFORMATION: CD20 VH

<400> SEQUENCE: 30

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 31
<211> LENGTH: 115
<212> TYPE: PRT
<213> ORGANISM: Artificial Sequence
<220> FEATURE:
<223> OTHER INFORMATION: CD20 VL

<400> SEQUENCE: 31

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110
```

Arg Thr Val
        115

<210> SEQ ID NO 32
<211> LENGTH: 672
<212> TYPE: PRT
<213> ORGANISM: Artificial Sequence
<220> FEATURE:
<223> OTHER INFORMATION: CD3 VL-CH1-CD20 VH-CH1(EE)-Fc(knob, P329G LALA)

<400> SEQUENCE: 32

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Lys
        195                 200                 205

Val Glu Pro Lys Ser Cys Asp Gly Gly Gly Ser Gly Gly Gly Gly
    210                 215                 220

Ser Gln Val Gln Leu Val Gln Ser Gly Ala Glu Val Lys Lys Pro Gly
225                 230                 235                 240

Ser Ser Val Lys Val Ser Cys Lys Ala Ser Gly Tyr Ala Phe Ser Tyr
                245                 250                 255

Ser Trp Ile Asn Trp Val Arg Gln Ala Pro Gly Gln Gly Leu Glu Trp
            260                 265                 270

Met Gly Arg Ile Phe Pro Gly Asp Gly Asp Thr Asp Tyr Asn Gly Lys
        275                 280                 285

Phe Lys Gly Arg Val Thr Ile Thr Ala Asp Lys Ser Thr Ser Thr Ala
    290                 295                 300

Tyr Met Glu Leu Ser Ser Leu Arg Ser Glu Asp Thr Ala Val Tyr Tyr
305                 310                 315                 320

Cys Ala Arg Asn Val Phe Asp Gly Tyr Trp Leu Val Tyr Trp Gly Gln
                325                 330                 335

Gly Thr Leu Val Thr Val Ser Ser Ala Ser Thr Lys Gly Pro Ser Val
            340                 345                 350

-continued

Phe Pro Leu Ala Pro Ser Ser Lys Ser Thr Ser Gly Thr Ala Ala
            355                 360                 365

Leu Gly Cys Leu Val Glu Asp Tyr Phe Pro Glu Pro Val Thr Val Ser
        370                 375                 380

Trp Asn Ser Gly Ala Leu Thr Ser Gly Val His Thr Phe Pro Ala Val
385                 390                 395                 400

Leu Gln Ser Ser Gly Leu Tyr Ser Leu Ser Ser Val Val Thr Val Pro
                405                 410                 415

Ser Ser Ser Leu Gly Thr Gln Thr Tyr Ile Cys Asn Val Asn His Lys
            420                 425                 430

Pro Ser Asn Thr Lys Val Asp Glu Lys Val Glu Pro Lys Ser Cys Asp
        435                 440                 445

Lys Thr His Thr Cys Pro Pro Cys Pro Ala Pro Glu Ala Ala Gly Gly
    450                 455                 460

Pro Ser Val Phe Leu Phe Pro Pro Lys Pro Lys Asp Thr Leu Met Ile
465                 470                 475                 480

Ser Arg Thr Pro Glu Val Thr Cys Val Val Val Asp Val Ser His Glu
                485                 490                 495

Asp Pro Glu Val Lys Phe Asn Trp Tyr Val Asp Gly Val Glu Val His
            500                 505                 510

Asn Ala Lys Thr Lys Pro Arg Glu Glu Gln Tyr Asn Ser Thr Tyr Arg
        515                 520                 525

Val Val Ser Val Leu Thr Val Leu His Gln Asp Trp Leu Asn Gly Lys
    530                 535                 540

Glu Tyr Lys Cys Lys Val Ser Asn Lys Ala Leu Gly Ala Pro Ile Glu
545                 550                 555                 560

Lys Thr Ile Ser Lys Ala Lys Gly Gln Pro Arg Glu Pro Gln Val Tyr
                565                 570                 575

Thr Leu Pro Pro Cys Arg Asp Glu Leu Thr Lys Asn Gln Val Ser Leu
            580                 585                 590

Trp Cys Leu Val Lys Gly Phe Tyr Pro Ser Asp Ile Ala Val Glu Trp
        595                 600                 605

Glu Ser Asn Gly Gln Pro Glu Asn Asn Tyr Lys Thr Thr Pro Pro Val
    610                 615                 620

Leu Asp Ser Asp Gly Ser Phe Phe Leu Tyr Ser Lys Leu Thr Val Asp
625                 630                 635                 640

Lys Ser Arg Trp Gln Gln Gly Asn Val Phe Ser Cys Ser Val Met His
                645                 650                 655

Glu Ala Leu His Asn His Tyr Thr Gln Lys Ser Leu Ser Leu Ser Pro
            660                 665                 670

<210> SEQ ID NO 33
<211> LENGTH: 672
<212> TYPE: PRT
<213> ORGANISM: Artificial Sequence
<220> FEATURE:
<223> OTHER INFORMATION: CD20 VH-CH1-CD3 VL-CH1-Fc(knob, P329G LALA)

<400> SEQUENCE: 33

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

```
Gly Arg Ile Phe Pro Gly Asp Gly Asp Thr Asp Tyr Asn Gly Lys Phe
 50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asn Val Phe Asp Gly Tyr Trp Leu Val Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Gly
210                 215                 220

Gly Gly Gly Ser Gly Gly Gly Ser Gln Ala Val Val Thr Gln Glu
225                 230                 235                 240

Pro Ser Leu Thr Val Ser Pro Gly Gly Thr Val Thr Leu Thr Cys Gly
                245                 250                 255

Ser Ser Thr Gly Ala Val Thr Thr Ser Asn Tyr Ala Asn Trp Val Gln
            260                 265                 270

Glu Lys Pro Gly Gln Ala Phe Arg Gly Leu Ile Gly Gly Thr Asn Lys
        275                 280                 285

Arg Ala Pro Gly Thr Pro Ala Arg Phe Ser Gly Ser Leu Leu Gly Gly
290                 295                 300

Lys Ala Ala Leu Thr Leu Ser Gly Ala Gln Pro Glu Asp Glu Ala Glu
305                 310                 315                 320

Tyr Tyr Cys Ala Leu Trp Tyr Ser Asn Leu Trp Val Phe Gly Gly Gly
                325                 330                 335

Thr Lys Leu Thr Val Leu Ser Ser Ala Ser Thr Lys Gly Pro Ser Val
            340                 345                 350

Phe Pro Leu Ala Pro Ser Ser Lys Ser Thr Ser Gly Gly Thr Ala Ala
        355                 360                 365

Leu Gly Cys Leu Val Lys Asp Tyr Phe Pro Glu Pro Val Thr Val Ser
370                 375                 380

Trp Asn Ser Gly Ala Leu Thr Ser Gly Val His Thr Phe Pro Ala Val
385                 390                 395                 400

Leu Gln Ser Ser Gly Leu Tyr Ser Leu Ser Ser Val Val Thr Val Pro
                405                 410                 415

Ser Ser Ser Leu Gly Thr Gln Thr Tyr Ile Cys Asn Val Asn His Lys
            420                 425                 430

Pro Ser Asn Thr Lys Val Asp Lys Lys Val Glu Pro Lys Ser Cys Asp
        435                 440                 445

Lys Thr His Thr Cys Pro Pro Cys Pro Ala Pro Glu Ala Ala Gly Gly
450                 455                 460

Pro Ser Val Phe Leu Phe Pro Pro Lys Pro Lys Asp Thr Leu Met Ile
```

```
                  465                 470                 475                 480
        Ser Arg Thr Pro Glu Val Thr Cys Val Val Val Asp Val Ser His Glu
                            485                 490                 495

Asp Pro Glu Val Lys Phe Asn Trp Tyr Val Asp Gly Val Glu Val His
                        500                 505                 510

Asn Ala Lys Thr Lys Pro Arg Glu Glu Gln Tyr Asn Ser Thr Tyr Arg
                    515                 520                 525

Val Val Ser Val Leu Thr Val Leu His Gln Asp Trp Leu Asn Gly Lys
                530                 535                 540

Glu Tyr Lys Cys Lys Val Ser Asn Lys Ala Leu Gly Ala Pro Ile Glu
        545                 550                 555                 560

Lys Thr Ile Ser Lys Ala Lys Gly Gln Pro Arg Glu Pro Gln Val Tyr
                            565                 570                 575

Thr Leu Pro Pro Cys Arg Asp Glu Leu Thr Lys Asn Gln Val Ser Leu
                        580                 585                 590

Trp Cys Leu Val Lys Gly Phe Tyr Pro Ser Asp Ile Ala Val Glu Trp
                    595                 600                 605

Glu Ser Asn Gly Gln Pro Glu Asn Asn Tyr Lys Thr Thr Pro Pro Val
                610                 615                 620

Leu Asp Ser Asp Gly Ser Phe Phe Leu Tyr Ser Lys Leu Thr Val Asp
        625                 630                 635                 640

Lys Ser Arg Trp Gln Gln Gly Asn Val Phe Ser Cys Ser Val Met His
                            645                 650                 655

Glu Ala Leu His Asn His Tyr Thr Gln Lys Ser Leu Ser Leu Ser Pro
                        660                 665                 670

<210> SEQ ID NO 34
<211> LENGTH: 676
<212> TYPE: PRT
<213> ORGANISM: Artificial Sequence
<220> FEATURE:
<223> OTHER INFORMATION: CD20 VH-CH1 CD3 VL-CL-Fc(knob, P329G LALA)

<400> SEQUENCE: 34

Gln Val Gln Leu Val Gln Ser Gly Ala Glu Val Lys Lys Pro Gly Ser
        1               5                   10                  15

Ser Val Lys Val Ser Cys Lys Ala Ser Gly Tyr Ala Phe Ser Tyr Ser
                    20                  25                  30

Trp Ile Asn Trp Val Arg Gln Ala Pro Gly Gln Gly Leu Glu Trp Met
                        35                  40                  45

Gly Arg Ile Phe Pro Gly Asp Gly Asp Thr Asp Tyr Asn Gly Lys Phe
                    50                  55                  60

Lys Gly Arg Val Thr Ile Thr Ala Asp Lys Ser Thr Ser Thr Ala Tyr
        65                  70                  75                  80

Met Glu Leu Ser Ser Leu Arg Ser Glu Asp Thr Ala Val Tyr Tyr Cys
                            85                  90                  95

Ala Arg Asn Val Phe Asp Gly Tyr Trp Leu Val Tyr Trp Gly Gln Gly
                        100                 105                 110

Thr Leu Val Thr Val Ser Ser Ala Ser Thr Lys Gly Pro Ser Val Phe
                    115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
        145                 150                 155                 160

Asn Ser Gly Ala Leu Thr Ser Gly Val His Thr Phe Pro Ala Val Leu
```

```
                    165                 170                 175
Gln Ser Ser Gly Leu Tyr Ser Leu Ser Ser Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Gly
            210                 215                 220

Gly Gly Gly Ser Gly Gly Gly Ser Gln Ala Val Val Thr Gln Glu
225                 230                 235                 240

Pro Ser Leu Thr Val Ser Pro Gly Gly Thr Val Thr Leu Thr Cys Gly
                245                 250                 255

Ser Ser Thr Gly Ala Val Thr Thr Ser Asn Tyr Ala Asn Trp Val Gln
                260                 265                 270

Glu Lys Pro Gly Gln Ala Phe Arg Gly Leu Ile Gly Gly Thr Asn Lys
                275                 280                 285

Arg Ala Pro Gly Thr Pro Ala Arg Phe Ser Gly Ser Leu Leu Gly Gly
            290                 295                 300

Lys Ala Ala Leu Thr Leu Ser Gly Ala Gln Pro Glu Asp Glu Ala Glu
305                 310                 315                 320

Tyr Tyr Cys Ala Leu Trp Tyr Ser Asn Leu Trp Val Phe Gly Gly Gly
                325                 330                 335

Thr Lys Leu Thr Val Leu Ser Ser Ala Ser Val Ala Ala Pro Ser Val
                340                 345                 350

Phe Ile Phe Pro Pro Ser Asp Glu Gln Leu Lys Ser Gly Thr Ala Ser
                355                 360                 365

Val Val Cys Leu Leu Asn Asn Phe Tyr Pro Arg Glu Ala Lys Val Gln
            370                 375                 380

Trp Lys Val Asp Asn Ala Leu Gln Ser Gly Asn Ser Gln Glu Ser Val
385                 390                 395                 400

Thr Glu Gln Asp Ser Lys Asp Ser Thr Tyr Ser Leu Ser Ser Thr Leu
                405                 410                 415

Thr Leu Ser Lys Ala Asp Tyr Glu Lys His Lys Val Tyr Ala Cys Glu
                420                 425                 430

Val Thr His Gln Gly Leu Ser Ser Pro Val Thr Lys Ser Phe Asn Arg
            435                 440                 445

Gly Glu Cys Asp Lys Thr His Thr Cys Pro Pro Cys Pro Ala Pro Glu
            450                 455                 460

Ala Ala Gly Gly Pro Ser Val Phe Leu Phe Pro Pro Lys Pro Lys Asp
465                 470                 475                 480

Thr Leu Met Ile Ser Arg Thr Pro Glu Val Thr Cys Val Val Val Asp
                485                 490                 495

Val Ser His Glu Asp Pro Glu Val Lys Phe Asn Trp Tyr Val Asp Gly
            500                 505                 510

Val Glu Val His Asn Ala Lys Thr Lys Pro Arg Glu Glu Gln Tyr Asn
            515                 520                 525

Ser Thr Tyr Arg Val Val Ser Val Leu Thr Val Leu His Gln Asp Trp
            530                 535                 540

Leu Asn Gly Lys Glu Tyr Lys Cys Lys Val Ser Asn Lys Ala Leu Gly
545                 550                 555                 560

Ala Pro Ile Glu Lys Thr Ile Ser Lys Ala Lys Gly Gln Pro Arg Glu
                565                 570                 575

Pro Gln Val Tyr Thr Leu Pro Pro Cys Arg Asp Glu Leu Thr Lys Asn
                580                 585                 590
```

```
Gln Val Ser Leu Trp Cys Leu Val Lys Gly Phe Tyr Pro Ser Asp Ile
        595                 600                 605

Ala Val Glu Trp Glu Ser Asn Gly Gln Pro Glu Asn Asn Tyr Lys Thr
610                 615                 620

Thr Pro Pro Val Leu Asp Ser Asp Gly Ser Phe Phe Leu Tyr Ser Lys
625                 630                 635                 640

Leu Thr Val Asp Lys Ser Arg Trp Gln Gln Gly Asn Val Phe Ser Cys
                645                 650                 655

Ser Val Met His Glu Ala Leu His Asn His Tyr Thr Gln Lys Ser Leu
            660                 665                 670

Ser Leu Ser Pro
        675

<210> SEQ ID NO 35
<211> LENGTH: 228
<212> TYPE: PRT
<213> ORGANISM: Artificial Sequence
<220> FEATURE:
<223> OTHER INFORMATION: CD3 VH-CH1

<400> SEQUENCE: 35

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
210                 215                 220

Pro Lys Ser Cys
225

<210> SEQ ID NO 36
<211> LENGTH: 681
<212> TYPE: PRT
<213> ORGANISM: Artificial Sequence
```

<220> FEATURE:
<223> OTHER INFORMATION: CD20 VL-CH1-CD3 VH-CH1(EE)-Fc(knob, P329G LALA)

<400> SEQUENCE: 36

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Gly Gly Gly Ser Gly
210                 215                 220

Gly Gly Gly Ser Glu Val Gln Leu Leu Glu Ser Gly Gly Gly Leu Val
225                 230                 235                 240

Gln Pro Gly Gly Ser Leu Arg Leu Ser Cys Ala Ala Ser Gly Phe Thr
                245                 250                 255

Phe Ser Thr Tyr Ala Met Asn Trp Val Arg Gln Ala Pro Gly Lys Gly
            260                 265                 270

Leu Glu Trp Val Ser Arg Ile Arg Ser Lys Tyr Asn Asn Tyr Ala Thr
        275                 280                 285

Tyr Tyr Ala Asp Ser Val Lys Gly Arg Phe Thr Ile Ser Arg Asp Asp
    290                 295                 300

Ser Lys Asn Thr Leu Tyr Leu Gln Met Asn Ser Leu Arg Ala Glu Asp
305                 310                 315                 320

Thr Ala Val Tyr Tyr Cys Val Arg His Gly Asn Phe Gly Asn Ser Tyr
                325                 330                 335

Val Ser Trp Phe Ala Tyr Trp Gly Gln Gly Thr Leu Val Thr Val Ser
            340                 345                 350

Ser Ala Ser Thr Lys Gly Pro Ser Val Phe Pro Leu Ala Pro Ser Ser
        355                 360                 365

Lys Ser Thr Ser Gly Gly Thr Ala Ala Leu Gly Cys Leu Val Glu Asp
    370                 375                 380

Tyr Phe Pro Glu Pro Val Thr Val Ser Trp Asn Ser Gly Ala Leu Thr
385                 390                 395                 400
```

```
Ser Gly Val His Thr Phe Pro Ala Val Leu Gln Ser Ser Gly Leu Tyr
            405                 410                 415

Ser Leu Ser Ser Val Val Thr Val Pro Ser Ser Ser Leu Gly Thr Gln
        420                 425                 430

Thr Tyr Ile Cys Asn Val Asn His Lys Pro Ser Asn Thr Lys Val Asp
    435                 440                 445

Glu Lys Val Glu Pro Lys Ser Cys Asp Lys Thr His Thr Cys Pro Pro
450                 455                 460

Cys Pro Ala Pro Glu Ala Ala Gly Gly Pro Ser Val Phe Leu Phe Pro
465                 470                 475                 480

Pro Lys Pro Lys Asp Thr Leu Met Ile Ser Arg Thr Pro Glu Val Thr
                485                 490                 495

Cys Val Val Val Asp Val Ser His Glu Asp Pro Glu Val Lys Phe Asn
                500                 505                 510

Trp Tyr Val Asp Gly Val Glu Val His Asn Ala Lys Thr Lys Pro Arg
            515                 520                 525

Glu Glu Gln Tyr Asn Ser Thr Tyr Arg Val Val Ser Val Leu Thr Val
        530                 535                 540

Leu His Gln Asp Trp Leu Asn Gly Lys Glu Tyr Lys Cys Lys Val Ser
545                 550                 555                 560

Asn Lys Ala Leu Gly Ala Pro Ile Glu Lys Thr Ile Ser Lys Ala Lys
                565                 570                 575

Gly Gln Pro Arg Glu Pro Gln Val Tyr Thr Leu Pro Pro Cys Arg Asp
            580                 585                 590

Glu Leu Thr Lys Asn Gln Val Ser Leu Trp Cys Leu Val Lys Gly Phe
        595                 600                 605

Tyr Pro Ser Asp Ile Ala Val Glu Trp Glu Ser Asn Gly Gln Pro Glu
    610                 615                 620

Asn Asn Tyr Lys Thr Thr Pro Pro Val Leu Asp Ser Asp Gly Ser Phe
625                 630                 635                 640

Phe Leu Tyr Ser Lys Leu Thr Val Asp Lys Ser Arg Trp Gln Gln Gly
                645                 650                 655

Asn Val Phe Ser Cys Ser Val Met His Glu Ala Leu His Asn His Tyr
            660                 665                 670

Thr Gln Lys Ser Leu Ser Leu Ser Pro
        675                 680

<210> SEQ ID NO 37
<211> LENGTH: 442
<212> TYPE: PRT
<213> ORGANISM: Artificial Sequence
<220> FEATURE:
<223> OTHER INFORMATION: CD20 VL-CH1-Fc(hole, P329G LALA)

<400> SEQUENCE: 37

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80
```

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Ala Ala Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Gly Ala Pro Ile Glu Lys Thr Ile Ser Lys Ala
                325                 330                 335

Lys Gly Gln Pro Arg Glu Pro Gln Val Cys Thr Leu Pro Pro Ser Arg
            340                 345                 350

Asp Glu Leu Thr Lys Asn Gln Val Ser Leu Ser Cys Ala Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Val Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro
        435                 440

<210> SEQ ID NO 38
<211> LENGTH: 215
<212> TYPE: PRT
<213> ORGANISM: Artificial Sequence
<220> FEATURE:
<223> OTHER INFORMATION: CD3 VL-CL(KK)

<400> SEQUENCE: 38

```
Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gln Ala Phe Arg Gly
        35                  40                  45

Leu Ile Gly Gly Thr Asn Lys Arg Ala Pro Gly Thr Pro Ala Arg Phe
50                  55                  60

Ser Gly Ser Leu Leu Gly Gly Lys Ala Ala Leu Thr Leu Ser Gly Ala
65              70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Lys Lys Leu
            115                 120                 125

Gln Ala Asn Lys Ala Thr Leu Val Cys Leu Ile Ser Asp Phe Tyr Pro
130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
            195                 200                 205

Val Ala Pro Thr Glu Cys Ser
            210                 215

<210> SEQ ID NO 39
<211> LENGTH: 226
<212> TYPE: PRT
<213> ORGANISM: Artificial Sequence
<220> FEATURE:
<223> OTHER INFORMATION: CD20 VH-CL

<400> SEQUENCE: 39

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
50                  55                  60

Lys Gly Arg Val Thr Ile Thr Ala Asp Lys Ser Thr Ser Thr Ala Tyr
65              70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Val Ala Ala Pro Ser Val Phe
            115                 120                 125

Ile Phe Pro Pro Ser Asp Glu Gln Leu Lys Ser Gly Thr Ala Ser Val
130                 135                 140
```

```
Val Cys Leu Leu Asn Asn Phe Tyr Pro Arg Glu Ala Lys Val Gln Trp
145                 150                 155                 160

Lys Val Asp Asn Ala Leu Gln Ser Gly Asn Ser Gln Glu Ser Val Thr
                165                 170                 175

Glu Gln Asp Ser Lys Asp Ser Thr Tyr Ser Leu Ser Ser Thr Leu Thr
            180                 185                 190

Leu Ser Lys Ala Asp Tyr Glu Lys His Lys Val Tyr Ala Cys Glu Val
        195                 200                 205

Thr His Gln Gly Leu Ser Ser Pro Val Thr Lys Ser Phe Asn Arg Gly
    210                 215                 220

Glu Cys
225

<210> SEQ ID NO 40
<211> LENGTH: 672
<212> TYPE: PRT
<213> ORGANISM: Artificial Sequence
<220> FEATURE:
<223> OTHER INFORMATION: CD20 VH-CH1(EE)-CD3 VL-CH1-Fc(DD, P329G LALA)

<400> SEQUENCE: 40

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Gly
    210                 215                 220

Gly Gly Gly Ser Gly Gly Gly Ser Gln Ala Val Val Thr Gln Glu
225                 230                 235                 240

Pro Ser Leu Thr Val Ser Pro Gly Gly Thr Val Thr Leu Thr Cys Gly
                245                 250                 255

Ser Ser Thr Gly Ala Val Thr Thr Ser Asn Tyr Ala Asn Trp Val Gln
            260                 265                 270
```

Glu Lys Pro Gly Gln Ala Phe Arg Gly Leu Ile Gly Gly Thr Asn Lys
    275                 280                 285

Arg Ala Pro Gly Thr Pro Ala Arg Phe Ser Gly Ser Leu Leu Gly Gly
    290                 295                 300

Lys Ala Ala Leu Thr Leu Ser Gly Ala Gln Pro Glu Asp Glu Ala Glu
305                 310                 315                 320

Tyr Tyr Cys Ala Leu Trp Tyr Ser Asn Leu Trp Val Phe Gly Gly Gly
                325                 330                 335

Thr Lys Leu Thr Val Leu Ser Ser Ala Ser Thr Lys Gly Pro Ser Val
            340                 345                 350

Phe Pro Leu Ala Pro Ser Ser Lys Ser Thr Ser Gly Gly Thr Ala Ala
        355                 360                 365

Leu Gly Cys Leu Val Lys Asp Tyr Phe Pro Glu Pro Val Thr Val Ser
    370                 375                 380

Trp Asn Ser Gly Ala Leu Thr Ser Gly Val His Thr Phe Pro Ala Val
385                 390                 395                 400

Leu Gln Ser Ser Gly Leu Tyr Ser Leu Ser Ser Val Val Thr Val Pro
                405                 410                 415

Ser Ser Ser Leu Gly Thr Gln Thr Tyr Ile Cys Asn Val Asn His Lys
            420                 425                 430

Pro Ser Asn Thr Lys Val Asp Lys Lys Val Glu Pro Lys Ser Cys Asp
        435                 440                 445

Lys Thr His Thr Cys Pro Pro Cys Pro Ala Pro Glu Ala Ala Gly Gly
    450                 455                 460

Pro Ser Val Phe Leu Phe Pro Pro Lys Pro Lys Asp Thr Leu Met Ile
465                 470                 475                 480

Ser Arg Thr Pro Glu Val Thr Cys Val Val Val Asp Val Ser His Glu
                485                 490                 495

Asp Pro Glu Val Lys Phe Asn Trp Tyr Val Asp Gly Val Glu Val His
            500                 505                 510

Asn Ala Lys Thr Lys Pro Arg Glu Glu Gln Tyr Asn Ser Thr Tyr Arg
        515                 520                 525

Val Val Ser Val Leu Thr Val Leu His Gln Asp Trp Leu Asn Gly Lys
    530                 535                 540

Glu Tyr Lys Cys Lys Val Ser Asn Lys Ala Leu Gly Ala Pro Ile Glu
545                 550                 555                 560

Lys Thr Ile Ser Lys Ala Lys Gly Gln Pro Arg Glu Pro Gln Val Tyr
                565                 570                 575

Thr Leu Pro Pro Ser Arg Asp Glu Leu Thr Lys Asn Gln Val Ser Leu
            580                 585                 590

Thr Cys Leu Val Lys Gly Phe Tyr Pro Ser Asp Ile Ala Val Glu Trp
        595                 600                 605

Glu Ser Asn Gly Gln Pro Glu Asn Asn Tyr Asp Thr Thr Pro Pro Val
    610                 615                 620

Leu Asp Ser Asp Gly Ser Phe Phe Leu Tyr Ser Asp Leu Thr Val Asp
625                 630                 635                 640

Lys Ser Arg Trp Gln Gln Gly Asn Val Phe Ser Cys Ser Val Met His
                645                 650                 655

Glu Ala Leu His Asn His Tyr Thr Gln Lys Ser Leu Ser Leu Ser Pro
            660                 665                 670

<210> SEQ ID NO 41
<211> LENGTH: 447

<212> TYPE: PRT
<213> ORGANISM: Artificial Sequence
<220> FEATURE:
<223> OTHER INFORMATION: CD20 VH-CH1(EE)-Fc(KK, P329G LALA)

<400> SEQUENCE: 41

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Lys Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

```
Ser Asn Gly Gln Pro Glu Asn Asn Tyr Lys Thr Thr Pro Pro Val Leu
385                 390                 395                 400

Lys Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro
        435                 440                 445

<210> SEQ ID NO 42
<211> LENGTH: 447
<212> TYPE: PRT
<213> ORGANISM: Artificial Sequence
<220> FEATURE:
<223> OTHER INFORMATION: CD20 VH-CH1(EE)-Fc(hole, N297G)

<400> SEQUENCE: 42

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gly Ser Thr Tyr Arg Val
    290                 295                 300
```

```
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Ser
                355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro
            435                 440                 445

<210> SEQ ID NO 43
<211> LENGTH: 439
<212> TYPE: PRT
<213> ORGANISM: Artificial Sequence
<220> FEATURE:
<223> OTHER INFORMATION: CD3 VL-CH1-Fc(knob, N297G)

<400> SEQUENCE: 43

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
                20                  25                  30

Asn Tyr Ala Asn Trp Val Gln Glu Lys Pro Gly Gln Ala Phe Arg Gly
            35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Ser Ser Ala
            100                 105                 110

Ser Thr Lys Gly Pro Ser Val Phe Pro Leu Ala Pro Ser Ser Lys Ser
            115                 120                 125

Thr Ser Gly Gly Thr Ala Ala Leu Gly Cys Leu Val Lys Asp Tyr Phe
            130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Lys
            195                 200                 205

Val Glu Pro Lys Ser Cys Asp Lys Thr His Thr Cys Pro Pro Cys Pro
210                 215                 220
```

```
Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
            245                 250                 255

Val Val Asp Val Ser His Glu Asp Pro Glu Val Lys Phe Asn Trp Tyr
        260                 265                 270

Val Asp Gly Val Glu Val His Asn Ala Lys Thr Lys Pro Arg Glu Glu
    275                 280                 285

Gln Tyr Gly Ser Thr Tyr Arg Val Val Ser Val Leu Thr Val Leu His
290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
            325                 330                 335

Pro Arg Glu Pro Gln Val Tyr Thr Leu Pro Pro Cys Arg Asp Glu Leu
        340                 345                 350

Thr Lys Asn Gln Val Ser Leu Trp Cys Leu Val Lys Gly Phe Tyr Pro
    355                 360                 365

Ser Asp Ile Ala Val Glu Trp Glu Ser Asn Gly Gln Pro Glu Asn Asn
370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
            405                 410                 415

Phe Ser Cys Ser Val Met His Glu Ala Leu His Asn His Tyr Thr Gln
        420                 425                 430

Lys Ser Leu Ser Leu Ser Pro
    435

<210> SEQ ID NO 44
<211> LENGTH: 450
<212> TYPE: PRT
<213> ORGANISM: Artificial Sequence
<220> FEATURE:
<223> OTHER INFORMATION: CD20 VH-CH1(EE)-Fc(hole, N297G)

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
        35                  40                  45

Gly Ala Ile Tyr Pro Gly Asn Gly Asp Thr Ser Tyr Asn Gln Lys Phe
    50                  55                  60

Lys Gly Arg Phe Thr Ile Ser Val Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Val Tyr Tyr Ser Asn Ser Tyr Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140
```

Ala Ala Leu Gly Cys Leu Val Glu Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Glu Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Gly Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Cys Thr Leu Pro Pro Ser Arg Asp Glu Leu Thr Lys Asn Gln Val
        355                 360                 365

Ser Leu Ser Cys Ala Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Val Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro
450

<210> SEQ ID NO 45
<211> LENGTH: 213
<212> TYPE: PRT
<213> ORGANISM: Artificial Sequence
<220> FEATURE:
<223> OTHER INFORMATION: CD20 VL-CL(RK)

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

His Trp Tyr Gln Gln Lys Pro Gly Lys Ala Pro Lys Pro Leu Ile Tyr
        35                  40                  45

```
Ala Pro Ser Asn Leu Ala Ser Gly Val Pro Ser Arg Phe Ser Gly Ser
 50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Trp Ser Phe Asn Pro Pro Thr
                 85                  90                  95

Phe Gly Gln Gly Thr Lys Val Glu Ile Lys Arg Thr Val Ala Ala Pro
             100                 105                 110

Ser Val Phe Ile Phe Pro Pro Ser Asp Arg Lys Leu Lys Ser Gly Thr
         115                 120                 125

Ala Ser Val Val Cys Leu Leu Asn Asn Phe Tyr Pro Arg Glu Ala Lys
 130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 46
<211> LENGTH: 5
<212> TYPE: PRT
<213> ORGANISM: Artificial Sequence
<220> FEATURE:
<223> OTHER INFORMATION: CD20 HCDR1

<400> SEQUENCE: 46

Tyr Ser Trp Ile Asn
1               5

<210> SEQ ID NO 47
<211> LENGTH: 17
<212> TYPE: PRT
<213> ORGANISM: Artificial Sequence
<220> FEATURE:
<223> OTHER INFORMATION: CD20 HCDR2

<400> SEQUENCE: 47

Arg Ile Phe Pro Gly Asp Gly Asp Thr Asp Tyr Asn Gly Lys Phe Lys
1               5                   10                  15

Gly

<210> SEQ ID NO 48
<211> LENGTH: 10
<212> TYPE: PRT
<213> ORGANISM: Artificial Sequence
<220> FEATURE:
<223> OTHER INFORMATION: CD20 HCDR3

<400> SEQUENCE: 48

Asn Val Phe Asp Gly Tyr Trp Leu Val Tyr
1               5                   10

<210> SEQ ID NO 49
<211> LENGTH: 16
<212> TYPE: PRT
<213> ORGANISM: Artificial Sequence
```

```
<220> FEATURE:
<223> OTHER INFORMATION: CD20 LCDR1

<400> SEQUENCE: 49

Arg Ser Ser Lys Ser Leu Leu His Ser Asn Gly Ile Thr Tyr Leu Tyr
1               5                   10                  15

<210> SEQ ID NO 50
<211> LENGTH: 7
<212> TYPE: PRT
<213> ORGANISM: Artificial Sequence
<220> FEATURE:
<223> OTHER INFORMATION: CD20 LCDR2

<400> SEQUENCE: 50

Gln Met Ser Asn Leu Val Ser
1               5

<210> SEQ ID NO 51
<211> LENGTH: 9
<212> TYPE: PRT
<213> ORGANISM: Artificial Sequence
<220> FEATURE:
<223> OTHER INFORMATION: CD20 LCDR3

<400> SEQUENCE: 51

Ala Gln Asn Leu Glu Leu Pro Tyr Thr
1               5

<210> SEQ ID NO 52
<211> LENGTH: 673
<212> TYPE: PRT
<213> ORGANISM: Artificial Sequence
<220> FEATURE:
<223> OTHER INFORMATION: Her2 VH-CH1(EE)-CD3 VL-CH1-Fc(knob, P329G LALA)

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Glu Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

-continued

```
Ser Ser Ser Leu Gly Thr Gln Thr Tyr Ile Cys Asn Val Asn His Lys
        195                 200                 205
Pro Ser Asn Thr Lys Val Asp Glu Lys Val Glu Pro Lys Ser Cys Asp
    210                 215                 220
Gly Gly Gly Gly Ser Gly Gly Gly Ser Gln Ala Val Val Thr Gln
225                 230                 235                 240
Glu Pro Ser Leu Thr Val Ser Pro Gly Gly Thr Val Thr Leu Thr Cys
                245                 250                 255
Gly Ser Ser Thr Gly Ala Val Thr Thr Ser Asn Tyr Ala Asn Trp Val
                260                 265                 270
Gln Glu Lys Pro Gly Gln Ala Phe Arg Gly Leu Ile Gly Gly Thr Asn
            275                 280                 285
Lys Arg Ala Pro Gly Thr Pro Ala Arg Phe Ser Gly Ser Leu Leu Gly
            290                 295                 300
Gly Lys Ala Ala Leu Thr Leu Ser Gly Ala Gln Pro Glu Asp Glu Ala
305                 310                 315                 320
Glu Tyr Tyr Cys Ala Leu Trp Tyr Ser Asn Leu Trp Val Phe Gly Gly
                325                 330                 335
Gly Thr Lys Leu Thr Val Leu Ser Ser Ala Ser Thr Lys Gly Pro Ser
                340                 345                 350
Val Phe Pro Leu Ala Pro Ser Ser Lys Ser Thr Ser Gly Gly Thr Ala
            355                 360                 365
Ala Leu Gly Cys Leu Val Lys Asp Tyr Phe Pro Glu Pro Val Thr Val
            370                 375                 380
Ser Trp Asn Ser Gly Ala Leu Thr Ser Gly Val His Thr Phe Pro Ala
385                 390                 395                 400
Val Leu Gln Ser Ser Gly Leu Tyr Ser Leu Ser Ser Val Val Thr Val
                405                 410                 415
Pro Ser Ser Ser Leu Gly Thr Gln Thr Tyr Ile Cys Asn Val Asn His
                420                 425                 430
Lys Pro Ser Asn Thr Lys Val Asp Lys Lys Val Glu Pro Lys Ser Cys
            435                 440                 445
Asp Lys Thr His Thr Cys Pro Pro Cys Pro Ala Pro Glu Ala Ala Gly
            450                 455                 460
Gly Pro Ser Val Phe Leu Phe Pro Pro Lys Pro Lys Asp Thr Leu Met
465                 470                 475                 480
Ile Ser Arg Thr Pro Glu Val Thr Cys Val Val Val Asp Val Ser His
                485                 490                 495
Glu Asp Pro Glu Val Lys Phe Asn Trp Tyr Val Asp Gly Val Glu Val
                500                 505                 510
His Asn Ala Lys Thr Lys Pro Arg Glu Glu Gln Tyr Asn Ser Thr Tyr
            515                 520                 525
Arg Val Val Ser Val Leu Thr Val Leu His Gln Asp Trp Leu Asn Gly
            530                 535                 540
Lys Glu Tyr Lys Cys Lys Val Ser Asn Lys Ala Leu Gly Ala Pro Ile
545                 550                 555                 560
Glu Lys Thr Ile Ser Lys Ala Lys Gly Gln Pro Arg Glu Pro Gln Val
                565                 570                 575
Tyr Thr Leu Pro Pro Cys Arg Asp Glu Leu Thr Lys Asn Gln Val Ser
                580                 585                 590
Leu Trp Cys Leu Val Lys Gly Phe Tyr Pro Ser Asp Ile Ala Val Glu
            595                 600                 605
```

-continued

```
Trp Glu Ser Asn Gly Gln Pro Glu Asn Asn Tyr Lys Thr Thr Pro Pro
            610                 615                 620

Val Leu Asp Ser Asp Gly Ser Phe Phe Leu Tyr Ser Lys Leu Thr Val
625                 630                 635                 640

Asp Lys Ser Arg Trp Gln Gln Gly Asn Val Phe Ser Cys Ser Val Met
                645                 650                 655

His Glu Ala Leu His Asn His Tyr Thr Gln Lys Ser Leu Ser Leu Ser
                660                 665                 670

Pro
```

<210> SEQ ID NO 53
<211> LENGTH: 448
<212> TYPE: PRT
<213> ORGANISM: Artificial Sequence
<220> FEATURE:
<223> OTHER INFORMATION: Her2 VH-CH1(EE)-Fc(hole, P329G LALA)

<400> SEQUENCE: 53

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Glu Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Glu Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
```

```
            290                 295                 300
Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Cys
                340                 345                 350

Thr Leu Pro Pro Ser Arg Asp Glu Leu Thr Lys Asn Gln Val Ser Leu
                355                 360                 365

Ser Cys Ala Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

<210> SEQ ID NO 54
<211> LENGTH: 214
<212> TYPE: PRT
<213> ORGANISM: Artificial Sequence
<220> FEATURE:
<223> OTHER INFORMATION: Her2 VL-CL(RK)

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Arg Lys Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
```

<210> SEQ ID NO 55
<211> LENGTH: 673
<212> TYPE: PRT
<213> ORGANISM: Artificial Sequence
<220> FEATURE:
<223> OTHER INFORMATION: CD3 VL-CH1-Her3 VH-CH1(EE)- Fc(knob, P329G LALA)

<400> SEQUENCE: 55

```
Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Lys
        195                 200                 205

Val Glu Pro Lys Ser Cys Asp Gly Gly Gly Ser Gly Gly Gly Gly
    210                 215                 220

Ser Gln Val Gln Leu Val Gln Ser Gly Ala Glu Val Lys Lys Pro Gly
225                 230                 235                 240

Ala Ser Val Lys Val Ser Cys Lys Ala Ser Gly Tyr Thr Phe Arg Ser
                245                 250                 255

Ser Tyr Ile Ser Trp Val Arg Gln Ala Pro Gly Gln Gly Leu Glu Trp
            260                 265                 270

Met Gly Trp Ile Tyr Ala Gly Thr Gly Ser Pro Ser Tyr Asn Gln Lys
        275                 280                 285

Leu Gln Gly Arg Val Thr Met Thr Thr Asp Thr Ser Thr Ser Thr Ala
    290                 295                 300

Tyr Met Glu Leu Arg Ser Leu Arg Ser Asp Asp Thr Ala Val Tyr Tyr
305                 310                 315                 320

Cys Ala Arg His Arg Asp Tyr Tyr Ser Asn Ser Leu Thr Tyr Trp Gly
                325                 330                 335

Gln Gly Thr Leu Val Thr Val Ser Ser Ala Ser Thr Lys Gly Pro Ser
            340                 345                 350
```

```
Val Phe Pro Leu Ala Pro Ser Ser Lys Ser Thr Ser Gly Gly Thr Ala
            355                 360                 365

Ala Leu Gly Cys Leu Val Glu Asp Tyr Phe Pro Glu Pro Val Thr Val
        370                 375                 380

Ser Trp Asn Ser Gly Ala Leu Thr Ser Gly Val His Thr Phe Pro Ala
385                 390                 395                 400

Val Leu Gln Ser Ser Gly Leu Tyr Ser Leu Ser Ser Val Val Thr Val
                405                 410                 415

Pro Ser Ser Ser Leu Gly Thr Gln Thr Tyr Ile Cys Asn Val Asn His
            420                 425                 430

Lys Pro Ser Asn Thr Lys Val Asp Glu Lys Val Glu Pro Lys Ser Cys
        435                 440                 445

Asp Lys Thr His Thr Cys Pro Pro Cys Pro Ala Pro Glu Ala Ala Gly
450                 455                 460

Gly Pro Ser Val Phe Leu Phe Pro Pro Lys Pro Lys Asp Thr Leu Met
465                 470                 475                 480

Ile Ser Arg Thr Pro Glu Val Thr Cys Val Val Val Asp Val Ser His
                485                 490                 495

Glu Asp Pro Glu Val Lys Phe Asn Trp Tyr Val Asp Gly Val Glu Val
            500                 505                 510

His Asn Ala Lys Thr Lys Pro Arg Glu Glu Gln Tyr Asn Ser Thr Tyr
        515                 520                 525

Arg Val Val Ser Val Leu Thr Val Leu His Gln Asp Trp Leu Asn Gly
    530                 535                 540

Lys Glu Tyr Lys Cys Lys Val Ser Asn Lys Ala Leu Gly Ala Pro Ile
545                 550                 555                 560

Glu Lys Thr Ile Ser Lys Ala Lys Gly Gln Pro Arg Glu Pro Gln Val
                565                 570                 575

Tyr Thr Leu Pro Pro Cys Arg Asp Glu Leu Thr Lys Asn Gln Val Ser
            580                 585                 590

Leu Trp Cys Leu Val Lys Gly Phe Tyr Pro Ser Asp Ile Ala Val Glu
        595                 600                 605

Trp Glu Ser Asn Gly Gln Pro Glu Asn Asn Tyr Lys Thr Thr Pro Pro
    610                 615                 620

Val Leu Asp Ser Asp Gly Ser Phe Phe Leu Tyr Ser Lys Leu Thr Val
625                 630                 635                 640

Asp Lys Ser Arg Trp Gln Gln Gly Asn Val Phe Ser Cys Ser Val Met
                645                 650                 655

His Glu Ala Leu His Asn His Tyr Thr Gln Lys Ser Leu Ser Leu Ser
            660                 665                 670

Pro

<210> SEQ ID NO 56
<211> LENGTH: 448
<212> TYPE: PRT
<213> ORGANISM: Artificial Sequence
<220> FEATURE:
<223> OTHER INFORMATION: Her3 VH-CH1(EE)-Fc(hole, P329G LALA)

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Ser Ser
            20                  25                  30

Tyr Ile Ser Trp Val Arg Gln Ala Pro Gly Gln Gly Leu Glu Trp Met
```

```
                35                  40                  45
Gly Trp Ile Tyr Ala Gly Thr Gly Ser Pro Ser Tyr Asn Gln Lys Leu
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Thr Ala Val Tyr Tyr Cys
                 85                  90                  95

Ala Arg His Arg Asp Tyr Tyr Ser Asn Ser Leu Thr Tyr Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
 130                 135                 140

Leu Gly Cys Leu Val Glu Asp Tyr Phe Pro Glu Pro Val Thr Val Ser
 145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Glu Lys Val Pro Lys Ser Cys Asp
 210                 215                 220

Lys Thr His Thr Cys Pro Pro Cys Pro Ala Pro Glu Ala Ala Gly Gly
 225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
 290                 295                 300

Val Val Ser Val Leu Thr Val Leu His Gln Asp Trp Leu Asn Gly Lys
 305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Cys
                340                 345                 350

Thr Leu Pro Pro Ser Arg Asp Glu Leu Thr Lys Asn Gln Val Ser Leu
                355                 360                 365

Ser Cys Ala Val Lys Gly Phe Tyr Pro Ser Asp Ile Ala Val Glu Trp
 370                 375                 380

Glu Ser Asn Gly Gln Pro Glu Asn Asn Tyr Lys Thr Thr Pro Pro Val
 385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

<210> SEQ ID NO 57
```

<211> LENGTH: 220
<212> TYPE: PRT
<213> ORGANISM: Artificial Sequence
<220> FEATURE:
<223> OTHER INFORMATION: Her3 VL-CL

<400> SEQUENCE: 57

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Ser
                85                  90                  95

Asp Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Arg Lys Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 58
<211> LENGTH: 664
<212> TYPE: PRT
<213> ORGANISM: Artificial Sequence
<220> FEATURE:
<223> OTHER INFORMATION: MCSP VH-CH1(EE)-MCSP VH-CH1(EE)-CD3 VL-CH1

<400> SEQUENCE: 58

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Thr Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Asp Phe Asp Tyr Trp Gly Gln Gly Thr Thr Leu Thr Val Ser Ser

```
            100                 105                 110
Ala Ser Thr Lys Gly Pro Ser Val Phe Pro Leu Ala Pro Ser Ser Lys
            115                 120                 125

Ser Thr Ser Gly Gly Thr Ala Ala Leu Gly Cys Leu Val Glu Asp Tyr
        130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Glu
        195                 200                 205

Lys Val Glu Pro Lys Ser Cys Asp Gly Gly Gly Ser Gly Gly Gly
210                 215                 220

Gly Ser Glu Val Gln Leu Gln Glu Ser Gly Pro Gly Leu Val Lys Pro
225                 230                 235                 240

Ser Gln Ser Leu Ser Leu Thr Cys Ser Val Thr Gly Tyr Ser Ile Thr
                245                 250                 255

Ser Gly Tyr Tyr Trp Asn Trp Ile Arg Gln Phe Pro Gly Asn Lys Leu
            260                 265                 270

Glu Trp Met Gly Tyr Ile Thr Tyr Asp Gly Ser Asn Asn Tyr Asn Pro
        275                 280                 285

Ser Leu Lys Asn Arg Ile Ser Ile Thr Arg Asp Thr Ser Lys Asn Gln
        290                 295                 300

Phe Phe Leu Lys Leu Asn Ser Val Thr Thr Glu Asp Thr Ala Thr Tyr
305                 310                 315                 320

Tyr Cys Ala Asp Phe Asp Tyr Trp Gly Gln Gly Thr Thr Leu Thr Val
                325                 330                 335

Ser Ser Ala Ser Thr Lys Gly Pro Ser Val Phe Pro Leu Ala Pro Ser
            340                 345                 350

Ser Lys Ser Thr Ser Gly Gly Thr Ala Ala Leu Gly Cys Leu Val Glu
        355                 360                 365

Asp Tyr Phe Pro Glu Pro Val Thr Val Ser Trp Asn Ser Gly Ala Leu
        370                 375                 380

Thr Ser Gly Val His Thr Phe Pro Ala Val Leu Gln Ser Ser Gly Leu
385                 390                 395                 400

Tyr Ser Leu Ser Ser Val Val Thr Val Pro Ser Ser Ser Leu Gly Thr
                405                 410                 415

Gln Thr Tyr Ile Cys Asn Val Asn His Lys Pro Ser Asn Thr Lys Val
            420                 425                 430

Asp Glu Lys Val Glu Pro Lys Ser Cys Asp Gly Gly Gly Ser Gly
        435                 440                 445

Gly Gly Gly Ser Asp Ile Gln Met Thr Gln Ser Pro Ser Ser Leu Ser
        450                 455                 460

Ala Ser Val Gly Asp Arg Val Thr Ile Thr Cys Arg Ala Ser Gln Asp
465                 470                 475                 480

Ile Arg Asn Tyr Leu Asn Trp Tyr Gln Gln Lys Pro Gly Lys Ala Pro
                485                 490                 495

Lys Leu Leu Ile Tyr Tyr Thr Ser Arg Leu Glu Ser Gly Val Pro Ser
            500                 505                 510

Arg Phe Ser Gly Ser Gly Ser Gly Thr Asp Tyr Thr Leu Thr Ile Ser
        515                 520                 525
```

```
Ser Leu Gln Pro Glu Asp Phe Ala Thr Tyr Tyr Cys Gln Gln Gly Asn
        530                 535                 540

Thr Leu Pro Trp Thr Phe Gly Gln Gly Thr Lys Val Glu Ile Lys Ser
545                 550                 555                 560

Ser Ala Ser Thr Lys Gly Pro Ser Val Phe Pro Leu Ala Pro Ser Ser
                565                 570                 575

Lys Ser Thr Ser Gly Gly Thr Ala Ala Leu Gly Cys Leu Val Lys Asp
                580                 585                 590

Tyr Phe Pro Glu Pro Val Thr Val Ser Trp Asn Ser Gly Ala Leu Thr
                595                 600                 605

Ser Gly Val His Thr Phe Pro Ala Val Leu Gln Ser Ser Gly Leu Tyr
        610                 615                 620

Ser Leu Ser Ser Val Val Thr Val Pro Ser Ser Ser Leu Gly Thr Gln
625                 630                 635                 640

Thr Tyr Ile Cys Asn Val Asn His Lys Pro Ser Asn Thr Lys Val Asp
                645                 650                 655

Lys Lys Val Glu Pro Lys Ser Cys
            660

<210> SEQ ID NO 59
<211> LENGTH: 229
<212> TYPE: PRT
<213> ORGANISM: Artificial Sequence
<220> FEATURE:
<223> OTHER INFORMATION: CD3 VH-CL

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Gly Leu Glu Trp Val
        35                  40                  45

Ala Leu Ile Asn Pro Tyr Lys Gly Val Ser Thr Tyr Asn Gln Lys Phe
    50                  55                  60

Lys Asp Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser Ala Ser Val Ala Ala Pro
        115                 120                 125

Ser Val Phe Ile Phe Pro Pro Ser Asp Glu Gln Leu Lys Ser Gly Thr
    130                 135                 140

Ala Ser Val Val Cys Leu Leu Asn Asn Phe Tyr Pro Arg Glu Ala Lys
145                 150                 155                 160

Val Gln Trp Lys Val Asp Asn Ala Leu Gln Ser Gly Asn Ser Gln Glu
                165                 170                 175

Ser Val Thr Glu Gln Asp Ser Lys Asp Ser Thr Tyr Ser Leu Ser Ser
            180                 185                 190

Thr Leu Thr Leu Ser Lys Ala Asp Tyr Glu Lys His Lys Val Tyr Ala
        195                 200                 205

Cys Glu Val Thr His Gln Gly Leu Ser Ser Pro Val Thr Lys Ser Phe
    210                 215                 220
```

-continued

```
Asn Arg Gly Glu Cys
225

<210> SEQ ID NO 60
<211> LENGTH: 214
<212> TYPE: PRT
<213> ORGANISM: Artificial Sequence
<220> FEATURE:
<223> OTHER INFORMATION: MCSP VL-CL(RK)

<400> SEQUENCE: 60

Asp Ile Val Leu Thr Gln Ser Pro Ser Ser Leu Ser Ala Ser Leu Gly
1               5                   10                  15

Asp Arg Val Thr Ile Ser Cys Ser Ala Ser Gln Gly Ile Arg Asn Tyr
                20                  25                  30

Leu Asn Trp Tyr Gln Gln Arg Pro Asp Gly Thr Val Lys Leu Leu Ile
            35                  40                  45

Tyr Tyr Thr Ser Ser Leu His Ser Gly Val Pro Ser Arg Phe Ser Gly
50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Arg Lys Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 61
<211> LENGTH: 120
<212> TYPE: PRT
<213> ORGANISM: Artificial Sequence
<220> FEATURE:
<223> OTHER INFORMATION: Her2 VH

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
        50                  55                  60

Lys Gly Arg Phe Thr Ile Ser Ala Asp Thr Ser Lys Asn Thr Ala Tyr
```

```
                65                  70                  75                  80
Leu Gln Met Asn Ser Leu Arg Ala Glu Asp Thr Ala Val Tyr Tyr Cys
                        85                  90                  95

Ser Arg Trp Gly Gly Asp Gly Phe Tyr Ala Met Asp Tyr Trp Gly Gln
                100                 105                 110

Gly Thr Leu Val Thr Val Ser Ser
            115                 120

<210> SEQ ID NO 62
<211> LENGTH: 107
<212> TYPE: PRT
<213> ORGANISM: Artificial Sequence
<220> FEATURE:
<223> OTHER INFORMATION: Her2 VL

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 63
<211> LENGTH: 120
<212> TYPE: PRT
<213> ORGANISM: Artificial Sequence
<220> FEATURE:
<223> OTHER INFORMATION: Her3 VH

<400> SEQUENCE: 63

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Ser Ser
            20                  25                  30

Tyr Ile Ser Trp Val Arg Gln Ala Pro Gly Gln Gly Leu Glu Trp Met
        35                  40                  45

Gly Trp Ile Tyr Ala Gly Thr Gly Ser Pro Ser Tyr Asn Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg His Arg Asp Tyr Tyr Ser Asn Ser Leu Thr Tyr Trp Gly Gln
                100                 105                 110

Gly Thr Leu Val Thr Val Ser Ser
            115                 120

<210> SEQ ID NO 64
<211> LENGTH: 113
```

<212> TYPE: PRT
<213> ORGANISM: Artificial Sequence
<220> FEATURE:
<223> OTHER INFORMATION: Her3 VL

<400> SEQUENCE: 64

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Ser
                85                  90                  95

Asp Tyr Ser Tyr Pro Tyr Thr Phe Gly Gln Gly Thr Lys Leu Glu Ile
            100                 105                 110

Lys

<210> SEQ ID NO 65
<211> LENGTH: 112
<212> TYPE: PRT
<213> ORGANISM: Artificial Sequence
<220> FEATURE:
<223> OTHER INFORMATION: MCSP VH

<400> SEQUENCE: 65

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Thr Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Asp Phe Asp Tyr Trp Gly Gln Gly Thr Thr Leu Thr Val Ser Ser
            100                 105                 110

<210> SEQ ID NO 66
<211> LENGTH: 107
<212> TYPE: PRT
<213> ORGANISM: Artificial Sequence
<220> FEATURE:
<223> OTHER INFORMATION: MCSP VL

<400> SEQUENCE: 66

Asp Ile Val Leu Thr Gln Ser Pro Ser Ser Leu Ser Ala Ser Leu Gly
1               5                   10                  15

Asp Arg Val Thr Ile Ser Cys Ser Ala Ser Gln Gly Ile Arg Asn Tyr
            20                  25                  30

Leu Asn Trp Tyr Gln Gln Arg Pro Asp Gly Thr Val Lys Leu Leu Ile
        35                  40                  45

```
Tyr Tyr Thr Ser Ser Leu His Ser Gly Val Pro Ser Arg Phe Ser Gly
        50                  55                  60

Ser Gly Ser Gly Thr Asp Tyr Ser Leu Thr Ile Ser Asn Leu Glu Pro
 65                  70                  75                  80

Glu Asp Ile Ala Thr Tyr Tyr Cys Gln Gln Tyr Ser Lys Leu Pro Trp
                 85                  90                  95

Thr Phe Gly Gly Gly Thr Lys Leu Glu Ile Lys
            100                 105
```

<210> SEQ ID NO 67
<211> LENGTH: 19
<212> TYPE: PRT
<213> ORGANISM: Artificial Sequence
<220> FEATURE:
<223> OTHER INFORMATION: CD3 HCDR2

<400> SEQUENCE: 67

```
Arg Ile Arg Ser Lys Tyr Asn Asn Tyr Ala Thr Tyr Tyr Ala Asp Ser
 1               5                  10                  15

Val Lys Asp
```

<210> SEQ ID NO 68
<211> LENGTH: 14
<212> TYPE: PRT
<213> ORGANISM: Artificial Sequence
<220> FEATURE:
<223> OTHER INFORMATION: CD3 LCDR1

<400> SEQUENCE: 68

```
Arg Ser Ser Thr Gly Ala Val Thr Thr Ser Asn Tyr Ala Asn
 1               5                  10
```

<210> SEQ ID NO 69
<211> LENGTH: 672
<212> TYPE: PRT
<213> ORGANISM: Artificial Sequence
<220> FEATURE:
<223> OTHER INFORMATION: CD20 VH-CH1(E)-CD3 VL-CH1-Fc(knob, P329G LALA)

<400> SEQUENCE: 69

```
Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Ala Phe Ser Tyr Ser
                20                  25                  30

Trp Ile Asn Trp Val Arg Gln Ala Pro Gly Gln Gly Leu Glu Trp Met
            35                  40                  45

Gly Arg Ile Phe Pro Gly Asp Gly Asp Thr Asp Tyr Asn Gly Lys Phe
        50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asn Val Phe Asp Gly Tyr Trp Leu Val Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
```

```
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Gln Thr Tyr Ile Cys Asn Val Asn His Lys Pro
                195                 200                 205
Ser Asn Thr Lys Val Asp Glu Lys Val Glu Pro Lys Ser Cys Asp Gly
            210                 215                 220
Gly Gly Gly Ser Gly Gly Gly Ser Gln Ala Val Val Thr Gln Glu
225                 230                 235                 240
Pro Ser Leu Thr Val Ser Pro Gly Gly Thr Val Thr Leu Thr Cys Gly
                245                 250                 255
Ser Ser Thr Gly Ala Val Thr Thr Ser Asn Tyr Ala Asn Trp Val Gln
                260                 265                 270
Glu Lys Pro Gly Gln Ala Phe Arg Gly Leu Ile Gly Gly Thr Asn Lys
                275                 280                 285
Arg Ala Pro Gly Thr Pro Ala Arg Phe Ser Gly Ser Leu Leu Gly Gly
            290                 295                 300
Lys Ala Ala Leu Thr Leu Ser Gly Ala Gln Pro Glu Asp Glu Ala Glu
305                 310                 315                 320
Tyr Tyr Cys Ala Leu Trp Tyr Ser Asn Leu Trp Val Phe Gly Gly Gly
                325                 330                 335
Thr Lys Leu Thr Val Leu Ser Ser Ala Ser Thr Lys Gly Pro Ser Val
                340                 345                 350
Phe Pro Leu Ala Pro Ser Ser Lys Ser Thr Ser Gly Gly Thr Ala Ala
                355                 360                 365
Leu Gly Cys Leu Val Lys Asp Tyr Phe Pro Glu Pro Val Thr Val Ser
            370                 375                 380
Trp Asn Ser Gly Ala Leu Thr Ser Gly Val His Thr Phe Pro Ala Val
385                 390                 395                 400
Leu Gln Ser Ser Gly Leu Tyr Ser Leu Ser Ser Val Val Thr Val Pro
                405                 410                 415
Ser Ser Ser Leu Gly Thr Gln Thr Tyr Ile Cys Asn Val Asn His Lys
                420                 425                 430
Pro Ser Asn Thr Lys Val Asp Lys Lys Val Glu Pro Lys Ser Cys Asp
            435                 440                 445
Lys Thr His Thr Cys Pro Pro Cys Pro Ala Pro Glu Ala Ala Gly Gly
450                 455                 460
Pro Ser Val Phe Leu Phe Pro Pro Lys Pro Lys Asp Thr Leu Met Ile
465                 470                 475                 480
Ser Arg Thr Pro Glu Val Thr Cys Val Val Val Asp Val Ser His Glu
                485                 490                 495
Asp Pro Glu Val Lys Phe Asn Trp Tyr Val Asp Gly Val Glu Val His
                500                 505                 510
Asn Ala Lys Thr Lys Pro Arg Glu Glu Gln Tyr Asn Ser Thr Tyr Arg
            515                 520                 525
Val Val Ser Val Leu Thr Val Leu His Gln Asp Trp Leu Asn Gly Lys
                530                 535                 540
Glu Tyr Lys Cys Lys Val Ser Asn Lys Ala Leu Gly Ala Pro Ile Glu
545                 550                 555                 560
Lys Thr Ile Ser Lys Ala Lys Gly Gln Pro Arg Glu Pro Gln Val Tyr
                565                 570                 575
```

```
Thr Leu Pro Pro Cys Arg Asp Glu Leu Thr Lys Asn Gln Val Ser Leu
            580                 585                 590

Trp Cys Leu Val Lys Gly Phe Tyr Pro Ser Asp Ile Ala Val Glu Trp
            595                 600                 605

Glu Ser Asn Gly Gln Pro Glu Asn Asn Tyr Lys Thr Thr Pro Pro Val
            610                 615                 620

Leu Asp Ser Asp Gly Ser Phe Phe Leu Tyr Ser Lys Leu Thr Val Asp
625                 630                 635                 640

Lys Ser Arg Trp Gln Gln Gly Asn Val Phe Ser Cys Ser Val Met His
            645                 650                 655

Glu Ala Leu His Asn His Tyr Thr Gln Lys Ser Leu Ser Leu Ser Pro
            660                 665                 670

<210> SEQ ID NO 70
<211> LENGTH: 447
<212> TYPE: PRT
<213> ORGANISM: Artificial Sequence
<220> FEATURE:
<223> OTHER INFORMATION: CD20 VH-CH1(E)-Fc(hole, P329G LALA)

<400> SEQUENCE: 70

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
            35                  40                  45

Gly Arg Ile Phe Pro Gly Asp Gly Asp Thr Asp Tyr Asn Gly Lys Phe
50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Glu Lys Val Glu Pro Lys Ser Cys Asp Lys
            210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270
```

-continued

```
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Ser
        355                 360                 365

Cys Ala Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 71
<211> LENGTH: 219
<212> TYPE: PRT
<213> ORGANISM: Artificial Sequence
<220> FEATURE:
<223> OTHER INFORMATION: CD20 VL-CL(R)

<400> SEQUENCE: 71

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Arg
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190
```

-continued

Lys His Lys Val Tyr Ala Cys Glu Val Thr His Gln Gly Leu Ser Ser
                195                 200                 205

Pro Val Thr Lys Ser Phe Asn Arg Gly Glu Cys
    210                 215

<210> SEQ ID NO 72
<211> LENGTH: 672
<212> TYPE: PRT
<213> ORGANISM: Artificial Sequence
<220> FEATURE:
<223> OTHER INFORMATION: CD20 VH-CH1-CD3 VL-CH1(EE)-Fc(knob, P329G LALA)

<400> SEQUENCE: 72

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Gly
    210                 215                 220

Gly Gly Gly Ser Gly Gly Gly Ser Gln Ala Val Val Thr Gln Glu
225                 230                 235                 240

Pro Ser Leu Thr Val Ser Pro Gly Gly Thr Val Thr Leu Thr Cys Gly
                245                 250                 255

Ser Ser Thr Gly Ala Val Thr Thr Ser Asn Tyr Ala Asn Trp Val Gln
            260                 265                 270

Glu Lys Pro Gly Gln Ala Phe Arg Gly Leu Ile Gly Gly Thr Asn Lys
        275                 280                 285

Arg Ala Pro Gly Thr Pro Ala Arg Phe Ser Gly Ser Leu Leu Gly Gly
    290                 295                 300

Lys Ala Ala Leu Thr Leu Ser Gly Ala Gln Pro Glu Asp Glu Ala Glu
305                 310                 315                 320

Tyr Tyr Cys Ala Leu Trp Tyr Ser Asn Leu Trp Val Phe Gly Gly Gly
                325                 330                 335

```
Thr Lys Leu Thr Val Leu Ser Ser Ala Ser Thr Lys Gly Pro Ser Val
            340                 345                 350

Phe Pro Leu Ala Pro Ser Ser Lys Ser Thr Ser Gly Gly Thr Ala Ala
            355                 360                 365

Leu Gly Cys Leu Val Glu Asp Tyr Phe Pro Glu Pro Val Thr Val Ser
            370                 375                 380

Trp Asn Ser Gly Ala Leu Thr Ser Gly Val His Thr Phe Pro Ala Val
385                 390                 395                 400

Leu Gln Ser Ser Gly Leu Tyr Ser Leu Ser Ser Val Val Thr Val Pro
                405                 410                 415

Ser Ser Ser Leu Gly Thr Gln Thr Tyr Ile Cys Asn Val Asn His Lys
            420                 425                 430

Pro Ser Asn Thr Lys Val Asp Glu Lys Val Glu Pro Lys Ser Cys Asp
            435                 440                 445

Lys Thr His Thr Cys Pro Pro Cys Pro Ala Pro Glu Ala Ala Gly Gly
            450                 455                 460

Pro Ser Val Phe Leu Phe Pro Pro Lys Pro Lys Asp Thr Leu Met Ile
465                 470                 475                 480

Ser Arg Thr Pro Glu Val Thr Cys Val Val Val Asp Val Ser His Glu
                485                 490                 495

Asp Pro Glu Val Lys Phe Asn Trp Tyr Val Asp Gly Val Glu Val His
                500                 505                 510

Asn Ala Lys Thr Lys Pro Arg Glu Glu Gln Tyr Asn Ser Thr Tyr Arg
            515                 520                 525

Val Val Ser Val Leu Thr Val Leu His Gln Asp Trp Leu Asn Gly Lys
530                 535                 540

Glu Tyr Lys Cys Lys Val Ser Asn Lys Ala Leu Gly Ala Pro Ile Glu
545                 550                 555                 560

Lys Thr Ile Ser Lys Ala Lys Gly Gln Pro Arg Glu Pro Gln Val Tyr
                565                 570                 575

Thr Leu Pro Pro Cys Arg Asp Glu Leu Thr Lys Asn Gln Val Ser Leu
            580                 585                 590

Trp Cys Leu Val Lys Gly Phe Tyr Pro Ser Asp Ile Ala Val Glu Trp
            595                 600                 605

Glu Ser Asn Gly Gln Pro Glu Asn Asn Tyr Lys Thr Thr Pro Pro Val
            610                 615                 620

Leu Asp Ser Asp Gly Ser Phe Phe Leu Tyr Ser Lys Leu Thr Val Asp
625                 630                 635                 640

Lys Ser Arg Trp Gln Gln Gly Asn Val Phe Ser Cys Ser Val Met His
                645                 650                 655

Glu Ala Leu His Asn His Tyr Thr Gln Lys Ser Leu Ser Leu Ser Pro
            660                 665                 670

<210> SEQ ID NO 73
<211> LENGTH: 232
<212> TYPE: PRT
<213> ORGANISM: Artificial Sequence
<220> FEATURE:
<223> OTHER INFORMATION: CD3 VH-CL(RK)

<400> SEQUENCE: 73

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30
```

```
Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser Ala Ser Val
            115                 120                 125

Ala Ala Pro Ser Val Phe Ile Phe Pro Pro Ser Asp Arg Lys Leu Lys
            130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230
```

BISPECIFIC T CELL ACTIVATING ANTIGEN BINDING MOLECULES

CROSS-REFERENCE TO RELATED APPLICATIONS

This application is a divisional of U.S. patent application Ser. No. 14/816,252, filed Aug. 3, 2015, now U.S. Pat. No. 9,914,776, which claims priority to European Patent Application No. EP 14179764.7, filed Aug. 4, 2014, and to European Patent Application No. EP 15170866.6, filed Jun. 5, 2015, the disclosures of which are incorporated herein by reference in their entirety.

SEQUENCE LISTING

The present application contains a Sequence Listing which has been submitted in ASCII format via EFS-Web and is hereby incorporated by reference in its entirety. Said ASCII copy, created on Jan. 22, 2018, is named 51177-009002_Sequence_Listing_1.22.18_ST25.txt and is 185,147 bytes in size.

FIELD OF THE INVENTION

The present invention generally relates to bispecific antigen binding molecules for activating T cells. In addition, the present invention relates to polynucleotides encoding such bispecific antigen binding molecules, and vectors and host cells comprising such polynucleotides. The invention further relates to methods for producing the bispecific antigen binding molecules of the invention, and to methods of using these bispecific antigen binding molecules in the treatment of disease.

BACKGROUND

The selective destruction of an individual cell or a specific cell type is often desirable in a variety of clinical settings. For example, it is a primary goal of cancer therapy to specifically destroy tumor cells, while leaving healthy cells and tissues intact and undamaged.

An attractive way of achieving this is by inducing an immune response against the tumor, to make immune effector cells such as natural killer (NK) cells or cytotoxic T lymphocytes (CTLs) attack and destroy tumor cells. CTLs constitute the most potent effector cells of the immune system, however they cannot be activated by the effector mechanism mediated by the Fc domain of conventional therapeutic antibodies.

In this regard, bispecific antibodies designed to bind with one "arm" to a surface antigen on target cells, and with the second "arm" to an activating, invariant component of the T cell receptor (TCR) complex, have become of interest in recent years. The simultaneous binding of such an antibody to both of its targets will force a temporary interaction between target cell and T cell, causing activation of any cytotoxic T cell and subsequent lysis of the target cell. Hence, the immune response is re-directed to the target cells and is independent of peptide antigen presentation by the target cell or the specificity of the T cell as would be relevant for normal MHC-restricted activation of CTLs. In this context it is crucial that CTLs are only activated when a target cell is presenting the bispecific antibody to them, i.e. the immunological synapse is mimicked. Particularly desirable are bispecific antibodies that do not require lymphocyte preconditioning or co-stimulation in order to elicit efficient lysis of target cells.

Several bispecific antibody formats have been developed and their suitability for T cell mediated immunotherapy investigated. Out of these, the so-called BiTE (bispecific T cell engager) molecules have been very well characterized and already shown some promise in the clinic (reviewed in Nagorsen and Bäuerle, Exp Cell Res 317, 1255-1260 (2011)). BiTEs are tandem scFv molecules wherein two scFv molecules are fused by a flexible linker. Further bispecific formats being evaluated for T cell engagement include diabodies (Holliger et al., Prot Eng 9, 299-305 (1996)) and derivatives thereof, such as tandem diabodies (Kipriyanov et al., J Mol Biol 293, 41-66 (1999)). A more recent development are the so-called DART (dual affinity retargeting) molecules, which are based on the diabody format but feature a C-terminal disulfide bridge for additional stabilization (Moore et al., Blood 117, 4542-51 (2011)). The so-called triomabs, which are whole hybrid mouse/rat IgG molecules and also currently being evaluated in clinical trials, represent a larger sized format (reviewed in Seimetz et al., Cancer Treat Rev 36, 458-467 (2010)).

The variety of formats that are being developed shows the great potential attributed to T cell re-direction and activation in immunotherapy. The task of generating bispecific antibodies suitable therefor is, however, by no means trivial, but involves a number of challenges that have to be met related to efficacy, toxicity, applicability and produceability of the antibodies.

Small constructs such as, for example, BiTE molecules—while being able to efficiently crosslink effector and target cells—have a very short serum half life requiring them to be administered to patients by continuous infusion. IgG-like formats on the other hand—while having the great benefit of a long half life—suffer from toxicity associated with the native effector functions inherent to IgG molecules. Their immunogenic potential constitutes another unfavorable feature of IgG-like bispecific antibodies, especially non-human formats, for successful therapeutic development. Finally, a major challenge in the general development of bispecific antibodies has been the production of bispecific antibody constructs at a clinically sufficient quantity and purity, due to the mispairing of antibody heavy and light chains of different specificities upon co-expression, which decreases the yield of the correctly assembled construct and results in a number of non-functional side products from which the desired bispecific antibody may be difficult to separate.

Different approaches have been taken to overcome the chain association issue in bispecific antibodies (see e.g. Klein et al., mAbs 6, 653-663 (2012)). For example, the 'knobs-into-holes' strategy aims at forcing the pairing of two different antibody heavy chains by introducing mutations into the CH3 domains to modify the contact interface. On one chain bulky amino acids are replaced by amino acids with short side chains to create a 'hole'. Conversely, amino acids with large side chains are introduced into the other CH3 domain, to create a 'knob'. By coexpressing these two heavy chains (and two identical light chains, which have to be appropriate for both heavy chains), high yields of heterodimer ('knob-hole') versus homodimer ('hole-hole' or 'knob-knob') are observed (Ridgway, J. B., et al., Protein Eng. 9 (1996) 617-621; and WO 96/027011). The percentage of heterodimer could be further increased by remodeling the interaction surfaces of the two CH3 domains using a phage display approach and the introduction of a disulfide bridge to stabilize the heterodimers (Merchant, A. M., et al., Nature Biotech. 16 (1998) 677-681; Atwell, S., et al., J. Mol. Biol. 270 (1997) 26-35). New approaches for the knobs-into-holes technology are described in e.g. in EP 1870459 A1.

The 'knobs-into-holes' strategy does, however, not solve the problem of heavy chain-light chain mispairing, which occurs in bispecific antibodies comprising different light chains for binding to the different target antigens.

A strategy to prevent heavy chain-light chain mispairing is to exchange domains between the heavy and light chains of one of the binding arms of a bispecific antibody (see WO 2009/080251, WO 2009/080252, WO 2009/080253, WO 2009/080254 and Schaefer, W. et al, PNAS, 108 (2011) 11187-11191, which relate to bispecific IgG antibodies with a domain crossover).

Exchanging the heavy and light chain variable domains VH and VL in one of the binding arms of the bispecific antibody (WO2009/080252, see also Schaefer, W. et al, PNAS, 108 (2011) 11187-11191) clearly reduces the side products caused by the mispairing of a light chain against a first antigen with the wrong heavy chain against the second antigen (compared to approaches without such domain exchange). Nevertheless, these antibody preparations are not completely free of side products. The main side product is based on a Bence Jones-type interaction (Schaefer, W. et al, PNAS, 108 (2011) 11187-11191; in FIG. S1I of the Supplement). A further reduction of such side products is thus desirable to improve e.g. the yield of such bispecific antibodies.

Given the difficulties and disadvantages associated with currently available bispecific antibodies for T cell mediated immunotherapy, there remains a need for novel, improved formats of such molecules. The present invention provides bispecific antigen binding molecules designed for T cell activation and re-direction that combine good efficacy and produceability with low toxicity and favorable pharmacokinetic properties.

SUMMARY OF THE INVENTION

According to the invention, the ratio of a desired bispecific antibody compared to undesired side products, in particular Bence Jones-type side products occurring in bispecific antibodies with a VH/VL domain exchange in one of their binding arms, can be improved by the introduction of charged amino acids with opposite charges at specific amino acid positions in the CH1 and CL domains.

Thus, in a first aspect the present invention provides a T cell activating bispecific antigen binding molecule comprising
(a) a first Fab molecule which specifically binds to a first antigen;
(b) a second Fab molecule which specifically binds to a second antigen, and wherein the variable domains VL and VH of the Fab light chain and the Fab heavy chain are replaced by each other; wherein the first antigen is an activating T cell antigen and the second antigen is a target cell antigen, or the first antigen is a target cell antigen and the second antigen is an activating T cell antigen; and wherein
i) in the constant domain CL of the first Fab molecule under a) the amino acid at position 124 is substituted independently by lysine (K), arginine (R) or histidine (H) (numbering according to Kabat), and wherein in the constant domain CH1 of the first Fab molecule under a) the amino acid at position 147 or the amino acid at position 213 is substituted independently by glutamic acid (E), or aspartic acid (D) (numbering according to Kabat EU index); or
ii) in the constant domain CL of the second Fab molecule under b) the amino acid at position 124 is substituted independently by lysine (K), arginine (R) or histidine (H) (numbering according to Kabat), and wherein in the constant domain CH1 of the second Fab molecule under b) the amino acid at position 147 or the amino acid at position 213 is substituted independently by glutamic acid (E), or aspartic acid (D) (numbering according to Kabat EU index).

According to the invention, the second Fab molecule is a crossover Fab molecule wherein the variable regions of the Fab light chain and the Fab heavy chain are exchanged. In particular embodiments, the first (and the third, if any) Fab molecule is a conventional Fab molecule. In a further particular embodiment, not more than one Fab molecule capable of specific binding to an activating T cell antigen is present in the T cell activating bispecific antigen binding molecule (i.e. the T cell activating bispecific antigen binding molecule provides monovalent binding to the activating T cell antigen). In a particular embodiment, the first antigen is a target cell antigen and the second antigen is an activating T cell antigen. In a more specific embodiment, the activating T cell antigen is CD3, particularly CD3 epsilon. In one embodiment, the target cell antigen is CD20.

In one embodiment of the T cell activating bispecific antigen binding molecule according to the invention, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 or the amino acid at position 213 is substituted independently by glutamic acid (E), or aspartic acid (D) (numbering according to Kabat EU index).

In a further embodiment, in the constant domain CL of the first Fab molecule under a) the amino acid at position 124 is substituted independently by lysine (K), arginine (R) or histidine (H) (numbering according to Kabat), and in the constant domain CH1 of the first Fab molecule under a) the amino acid at position 147 is substituted independently by glutamic acid (E), or aspartic acid (D) (numbering according to Kabat EU index).

In yet another embodiment, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)) and the amino acid at position 123 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In a particular embodiment, in the constant domain CL of the first Fab molecule under a) the amino acid at position 124 is substituted by lysine (K) (numbering according to Kabat) and the amino acid at position 123 is substituted by lysine (K) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

In another particular embodiment, in the constant domain CL of the first Fab molecule under a) the amino acid at position 124 is substituted by lysine (K) (numbering according to Kabat) and the amino acid at position 123 is substituted by arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

In one embodiment, the T cell activating bispecific antigen binding molecule of the invention comprises
(a) a first Fab molecule which specifically binds to a first antigen;
(b) a second Fab molecule which specifically binds to a second antigen, and wherein the variable domains VL and VH of the Fab light chain and the Fab heavy chain are replaced by each other; wherein the first antigen is a target cell antigen and the second antigen is an activating T cell antigen; and
wherein in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)) and the amino acid at position 123 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index). In an alternative embodiment of the T cell activating bispecific antigen binding molecule according to the invention, in the constant domain CL of the second Fab molecule under b) the amino acid at position 124 is substituted independently by lysine (K), arginine (R) or histidine (H) (numbering according to Kabat) (in one preferred embodiment independently by lysine (K) or arginine (R)), and in the constant domain CH1 of the second Fab molecule under b) the amino acid at position 147 or the amino acid at position 213 is substituted independently by glutamic acid (E), or aspartic acid (D) (numbering according to Kabat EU index).

In a further embodiment, in the constant domain CL of the second Fab molecule under b) the amino acid at position 124 is substituted independently by lysine (K), arginine (R) or histidine (H) (numbering according to Kabat), and in the constant domain CH1 of the second Fab molecule under b) the amino acid at position 147 is substituted independently by glutamic acid (E), or aspartic acid (D) (numbering according to Kabat EU index).

In still another embodiment, in the constant domain CL of the second Fab molecule under b) the amino acid at position 124 is substituted independently by lysine (K), arginine (R) or histidine (H) (numbering according to Kabat) (in one preferred embodiment independently by lysine (K) or arginine (R)) and the amino acid at position 123 is substituted independently by lysine (K), arginine (R) or histidine (H) (numbering according to Kabat) (in one preferred embodiment independently by lysine (K) or arginine (R)), and in the constant domain CH1 of the second Fab molecule under b) the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In one embodiment, in the constant domain CL of the second Fab molecule under b) the amino acid at position 124 is substituted by lysine (K) (numbering according to Kabat) and the amino acid at position 123 is substituted by lysine (K) (numbering according to Kabat), and in the constant domain CH1 of the second Fab molecule under b) the amino acid at position 147 is substituted by glutamic acid (E) (numbering according to Kabat EU index) and the amino acid at position 213 is substituted by glutamic acid (E) (numbering according to Kabat EU index).

In another embodiment, in the constant domain CL of the second Fab molecule under b) the amino acid at position 124 is substituted by lysine (K) (numbering according to Kabat) and the amino acid at position 123 is substituted by arginine (R) (numbering according to Kabat), and in the constant domain CH1 of the second Fab molecule under b) the amino acid at position 147 is substituted by glutamic acid (E) (numbering according to Kabat EU index) and the amino acid at position 213 is substituted by glutamic acid (E) (numbering according to Kabat EU index).

In some embodiments, the T cell activating bispecific antigen binding molecule according to the invention further comprises a third Fab molecule which specifically binds to the first antigen.

In particular embodiments, the third Fab molecule is identical to the first Fab molecule. In these embodiments, the third Fab molecule thus comprises the same amino acid substitutions as the first Fab molecule. Like the first Fab molecule, the third Fab molecule particularly is a conventional Fab molecule.

If a third Fab molecule is present, in a particular embodiment the first and the third Fab molecule specifically bind to a target cell antigen, and the second Fab molecule specifically binds to an activating T cell antigen, particularly CD3, more particularly CD3 epsilon.

In some embodiments of the T cell activating bispecific antigen binding molecule according to the invention the first Fab molecule under a) and the second Fab molecule under b) are fused to each other, optionally via a peptide linker. In a specific embodiment, the second Fab molecule is fused at the C-terminus of the Fab heavy chain to the N-terminus of the Fab heavy chain of the first Fab molecule. In an alternative embodiment, the first Fab molecule is fused at the C-terminus of the Fab heavy chain to the N-terminus of the Fab heavy chain of the second Fab molecule. In embodiments wherein either (i) the second Fab molecule is fused at the C-terminus of the Fab heavy chain to the N-terminus of the Fab heavy chain of the first Fab molecule or (ii) the first Fab molecule is fused at the C-terminus of the Fab heavy chain to the N-terminus of the Fab heavy chain of the second Fab molecule, additionally the Fab light chain of the Fab molecule and the Fab light chain of the second Fab molecule may be fused to each other, optionally via a peptide linker.

In particular embodiments, the T cell activating bispecific antigen binding molecule according to the invention additionally comprises an Fc domain composed of a first and a second subunit capable of stable association.

The T cell activating bispecific antigen binding molecule according to the invention can have different configurations, i.e. the first, second (and optionally third) Fab molecule may be fused to each other and to the Fc domain in different ways. The components may be fused to each other directly or, preferably, via one or more suitable peptide linkers. Where fusion is to the N-terminus of a subunit of the Fc domain, it is typically via an immunoglobulin hinge region.

In one embodiment, the second Fab molecule is fused at the C-terminus of the Fab heavy chain to the N-terminus of the first or the second subunit of the Fc domain. In such embodiment, the first Fab molecule may be fused at the C-terminus of the Fab heavy chain to the N-terminus of the Fab heavy chain of the second Fab molecule or to the N-terminus of the other one of the subunits of the Fc domain.

In one embodiment, the first and the second Fab molecule are each fused at the C-terminus of the Fab heavy chain to the N-terminus of one of the subunits of the Fc domain. In this embodiment, the T cell activating bispecific antigen binding molecule essentially comprises an immunoglobulin molecule, wherein in one of the Fab arms the heavy and light chain variable regions VH and VL are exchanged/replaced by each other (see FIGS. 1A and 1D).

In alternative embodiments, the third Fab molecule is fused at the C-terminus of the Fab heavy chain to the N-terminus of the first or second subunit of the Fc domain. In a particular such embodiment, the second and the third Fab molecule are each fused at the C-terminus of the Fab heavy chain to the N-terminus of one of the subunits of the Fc domain, and the first Fab molecule is fused at the C-terminus of the Fab heavy chain to the N-terminus of the Fab heavy chain of the second Fab molecule. In this embodiment, the T cell activating bispecific antigen binding molecule essentially comprises an immunoglobulin molecule, wherein in one of the Fab arms the heavy and light chain variable regions VH and VL are exchanged/replaced by each other, and wherein an additional (conventional) Fab molecule is N-terminally fused to said Fab arm (see FIGS. 1B and 1E). In another such embodiment, the first and the third Fab molecule are each fused at the C-terminus of the Fab heavy chain to the N-terminus of one of the subunits of the Fc domain, and the second Fab molecule is fused at the C-terminus of the Fab heavy chain to the N-terminus of the Fab heavy chain of the first Fab molecule. In this embodiment, the T cell activating bispecific antigen binding molecule essentially comprises an immunoglobulin molecule with an additional Fab molecule N-terminally fused to one of the immunoglobulin Fab arms, wherein in said additional Fab molecule the heavy and light chain variable regions VH and VL are exchanged/replaced by each other (see FIGS. 1C and 1F).

In all of the different configurations of the T cell activating bispecific antigen binding molecule according to the invention, the amino acid substitutions described herein may either be in the CH1 and CL domains of the first and (if present) the third Fab molecule, or in the CH1 and CL domains of the second Fab molecule. Preferably, they are in the CH1 and CL domains of the first and (if present) the third Fab molecule. In accordance with the concept of the invention, if amino acid substitutions as described herein are made in the first (and, if present, the third) Fab molecule, no such amino acid substitutions are made in the second Fab molecule. Conversely, if amino acid substitutions as described herein are made in the second Fab molecule, no such amino acid substitutions are made in the first (and, if present, the third) Fab molecule.

In particular embodiments of the T cell activating bispecific antigen binding molecule according to the invention, particularly wherein amino acid substitutions as described herein are made in the first (and, if present, the third) Fab molecule, the constant domain CL of the first (and, if present, the third) Fab molecule is of kappa isotype. In other embodiments of the T cell activating bispecific antigen binding molecule according to the invention, particularly wherein amino acid substitutions as described herein are made in the second Fab molecule, the constant domain CL of the second Fab molecule is of kappa isotype. In some embodiments, the constant domain CL of the first (and, if present, the third) Fab molecule and the constant domain CL of the second Fab molecule are of kappa isotype.

In a particular embodiment, the immunoglobulin molecule comprised in the T cell activating bispecific antigen binding molecule according to the invention is an IgG class immunoglobulin. In an even more particular embodiment the immunoglobulin is an IgG$_1$ subclass immunoglobulin. In another embodiment, the immunoglobulin is an IgG$_4$ subclass immunoglobulin.

In a particular embodiment, the invention provides a T cell activating bispecific antigen binding molecule comprising
a) a first Fab molecule which specifically binds to a first antigen;
b) a second Fab molecule which specifically binds to a second antigen, and wherein the variable domains VL and VH of the Fab light chain and the Fab heavy chain are replaced by each other;
c) a third Fab molecule which specifically binds to the first antigen; and
d) an Fc domain composed of a first and a second subunit capable of stable association;
wherein the first antigen is a target cell antigen and the second antigen is an activating T cell antigen, particularly CD3, more particularly CD3 epsilon;
wherein the third Fab molecule under c) is identical to the first Fab molecule under a);
wherein in the constant domain CL of the first Fab molecule under a) and the third Fab molecule under c) the amino acid at position 124 is substituted by lysine (K) (numbering according to Kabat) and the amino acid at position 123 is substituted by lysine (K) or arginine (R) (numbering according to Kabat), and wherein in the constant domain CH1 of the first Fab molecule under a) and the third Fab molecule under c) the amino acid at position 147 is substituted by glutamic acid (E) (numbering according to Kabat EU index) and the amino acid at position 213 is substituted by glutamic acid (E) (numbering according to Kabat EU index); and wherein
(i) the first Fab molecule under a) is fused at the C-terminus of the Fab heavy chain to the N-terminus of the Fab heavy chain of the second Fab molecule under b), and the second Fab molecule under b) and the third Fab molecule under c) are each fused at the C-terminus of the Fab heavy chain to the N-terminus of one of the subunits of the Fc domain under d), or
(ii) the second Fab molecule under b) is fused at the C-terminus of the Fab heavy chain to the N-terminus of the Fab heavy chain of the first Fab molecule under a), and the first Fab molecule under a) and the third Fab molecule under c) are each fused at the C-terminus of the Fab heavy chain to the N-terminus of one of the subunits of the Fc domain under d).

In an even more particular embodiment, the invention provides a T cell activating bispecific antigen binding molecule comprising
a) a first Fab molecule which specifically binds to a first antigen;

b) a second Fab molecule which specifically binds to a second antigen, and wherein the variable domains VL and VH of the Fab light chain and the Fab heavy chain are replaced by each other;
c) a third Fab molecule which specifically binds to the first antigen; and
d) an Fc domain composed of a first and a second subunit capable of stable association;
wherein the first antigen is a target cell antigen and the second antigen is an activating T cell antigen, particularly CD3, more particularly CD3 epsilon;
wherein the third Fab molecule under c) is identical to the first Fab molecule under a);
wherein in the constant domain CL of the first Fab molecule under a) and the third Fab molecule under
c) the amino acid at position 124 is substituted by lysine (K) (numbering according to Kabat) and the amino acid at position 123 is substituted by arginine (R) (numbering according to Kabat), and wherein in the constant domain CH1 of the first Fab molecule under a) and the third Fab molecule under c) the amino acid at position 147 is substituted by glutamic acid (E) (numbering according to Kabat EU index) and the amino acid at position 213 is substituted by glutamic acid (E) (numbering according to Kabat EU index); and
wherein the first Fab molecule under a) is fused at the C-terminus of the Fab heavy chain to the N-terminus of the Fab heavy chain of the second Fab molecule under b), and the second Fab molecule under b) and the third Fab molecule under c) are each fused at the C-terminus of the Fab heavy chain to the N-terminus of one of the subunits of the Fc domain under d).

In a further embodiment, the invention provides a T cell activating bispecific antigen binding molecule comprising
a) a first Fab molecule which specifically binds to a first antigen;
b) a second Fab molecule which specifically binds to a second antigen, and wherein the variable domains VL and VH of the Fab light chain and the Fab heavy chain are replaced by each other; and
c) an Fc domain composed of a first and a second subunit capable of stable association;
wherein
(i) the first antigen is a target cell antigen and the second antigen is an activating T cell antigen, particularly CD3, more particularly CD3 epsilon; or
(ii) the second antigen is a target cell antigen and the first antigen is an activating T cell antigen, particularly CD3, more particularly CD3 epsilon;
wherein in the constant domain CL of the first Fab molecule under a) the amino acid at position 124 is substituted by lysine (K) (numbering according to Kabat) and the amino acid at position 123 is substituted by lysine (K) or arginine (R) (numbering according to Kabat), and wherein in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index); and
wherein the first Fab molecule under a) and the second Fab molecule under b) are each fused at the C-terminus of the Fab heavy chain to the N-terminus of one of the subunits of the Fc domain under c).

In particular embodiments of the T cell activating bispecific antigen binding molecule, the Fc domain is an IgG Fc domain. In a specific embodiment, the Fc domain is an IgG$_1$ Fc domain. In another specific embodiment, the Fc domain is an IgG$_4$ Fc domain. In an even more specific embodiment, the Fc domain is an IgG$_4$ Fc domain comprising the amino acid substitution S228P (Kabat numbering). In particular embodiments the Fc domain is a human Fc domain.

In particular embodiments, the Fc domain comprises a modification promoting the association of the first and the second Fc domain subunit. In a specific such embodiment, an amino acid residue in the CH3 domain of the first subunit of the Fc domain is replaced with an amino acid residue having a larger side chain volume, thereby generating a protuberance within the CH3 domain of the first subunit which is positionable in a cavity within the CH3 domain of the second subunit, and an amino acid residue in the CH3 domain of the second subunit of the Fc domain is replaced with an amino acid residue having a smaller side chain volume, thereby generating a cavity within the CH3 domain of the second subunit within which the protuberance within the CH3 domain of the first subunit is positionable.

In a particular embodiment the Fc domain exhibits reduced binding affinity to an Fc receptor and/or reduced effector function, as compared to a native IgG$_1$ Fc domain. In certain embodiments the Fc domain is engineered to have reduced binding affinity to an Fc receptor and/or reduced effector function, as compared to a non-engineered Fc domain. In one embodiment, the Fc domain comprises one or more amino acid substitution that reduces binding to an Fc receptor and/or effector function. In one embodiment, the one or more amino acid substitution in the Fc domain that reduces binding to an Fc receptor and/or effector function is at one or more position selected from the group of L234, L235, and P329 (Kabat EU index numbering). In particular embodiments, each subunit of the Fc domain comprises three amino acid substitutions that reduce binding to an Fc receptor and/or effector function wherein said amino acid substitutions are L234A, L235A and P329G (Kabat EU index numbering). In one such embodiment, the Fc domain is an IgG$_1$ Fc domain, particularly a human IgG$_1$ Fc domain. In other embodiments, each subunit of the Fc domain comprises two amino acid substitutions that reduce binding to an Fc receptor and/or effector function wherein said amino acid substitutions are L235E and P329G (Kabat EU index numbering). In one such embodiment, the Fc domain is an IgG$_4$ Fc domain, particularly a human IgG$_4$ Fc domain. In one embodiment, the Fc domain of the T cell activating bispecific antigen binding molecule is an IgG$_4$ Fc domain and comprises the amino acid substitutions L235E and S228P (SPLE) (Kabat EU index numbering).

In one embodiment the Fc receptor is an Fcγ receptor. In one embodiment the Fc receptor is a human Fc receptor. In one embodiment, the Fc receptor is an activating Fc receptor. In a specific embodiment, the Fc receptor is human FcγRIIa, FcγRI, and/or FcγRIIIa. In one embodiment, the effector function is antibody-dependent cell-mediated cytotoxicity (ADCC).

In a specific embodiment of the T cell activating bispecific antigen binding molecule according to the invention, the Fab molecule which specifically binds to an activating T cell antigen, particularly CD3, more particularly CD3 epsilon, comprises the heavy chain complementarity determining region (CDR) 1 of SEQ ID NO: 4, the heavy chain CDR 2 of SEQ ID NO: 5, the heavy chain CDR 3 of SEQ ID NO: 6, the light chain CDR 1 of SEQ ID NO: 8, the light chain CDR 2 of SEQ ID NO: 9 and the light chain CDR 3 of SEQ ID NO: 10. In an even more specific embodiment, the Fab molecule which specifically binds to an activating T cell antigen, particularly CD3, more particularly CD3 epsilon, comprises a heavy chain variable region comprising an amino acid sequence that is at least about 95%, 96%, 97%, 98%, 99% or 100% identical to the amino acid sequence of SEQ ID NO: 3 and a light chain variable region comprising an amino acid sequence that is at least about 95%, 96%, 97%, 98%, 99% or 100% identical to the amino acid sequence of SEQ ID NO: 7. In one specific embodiment, the second Fab molecule comprised in the T cell activating bispecific antigen binding molecule according to the invention specifically binds to CD3, more particularly CD3 epsilon, and comprises the heavy chain complementarity determining region (CDR) 1 of SEQ ID NO: 4, the heavy chain CDR 2 of SEQ ID NO: 5, the heavy chain CDR 3 of SEQ ID NO: 6, the light chain CDR 1 of SEQ ID NO: 8, the light chain CDR 2 of SEQ ID NO: 9 and the light chain CDR 3 of SEQ ID NO: 10. In an even more specific embodiment, said second Fab molecule comprises a heavy chain variable region comprising the amino acid sequence of SEQ ID NO: 3 and a light chain variable region comprising the amino acid sequence of SEQ ID NO: 7.

In a further specific embodiment of the T cell activating bispecific antigen binding molecule according to the invention, the Fab molecule which specifically binds to a target cell antigen, particularly CD20, comprises the heavy chain complementarity determining region (CDR) 1 of SEQ ID NO: 46, the heavy chain CDR 2 of SEQ ID NO: 47, the heavy chain CDR 3 of SEQ ID NO: 48, the light chain CDR 1 of SEQ ID NO: 49, the light chain CDR 2 of SEQ ID NO: 50 and the light chain CDR 3 of SEQ ID NO: 51. In an even more specific embodiment, the Fab molecule which specifically binds to a target cell antigen, particularly CD20, comprises a heavy chain variable region comprising an amino acid sequence that is at least about 95%, 96%, 97%, 98%, 99% or 100% identical to the amino acid sequence of SEQ ID NO: 30 and a light chain variable region comprising an amino acid sequence that is at least about 95%, 96%, 97%, 98%, 99% or 100% identical to the amino acid sequence of SEQ ID NO: 31. In one specific embodiment, the first (and, if present, the third) Fab molecule comprised in the T cell activating bispecific antigen binding molecule according to the invention specifically binds to CD20, and comprises the heavy chain complementarity determining region (CDR) 1 of SEQ ID NO: 46, the heavy chain CDR 2 of SEQ ID NO: 47, the heavy chain CDR 3 of SEQ ID NO: 48, the light chain CDR 1 of SEQ ID NO: 49, the light chain CDR 2 of SEQ ID NO: 50 and the light chain CDR 3 of SEQ ID NO: 51. In an even more specific embodiment, said first (and, if present, said third) Fab molecule comprises a heavy chain variable region comprising the amino acid sequence of SEQ ID NO: 30 and a light chain variable region comprising the amino acid sequence of SEQ ID NO: 31.

In a particular aspect, the invention provides a T cell activating bispecific antigen binding molecule comprising
a) a first Fab molecule which specifically binds to a first antigen;
b) a second Fab molecule which specifically binds to a second antigen, and wherein the variable domains VL and VH of the Fab light chain and the Fab heavy chain are replaced by each other;
c) a third Fab molecule which specifically binds to the first antigen; and
d) an Fc domain composed of a first and a second subunit capable of stable association;
wherein
(i) the first antigen is CD20 and the second antigen is CD3, particularly CD3 epsilon;
(ii) the first Fab molecule under a) and the third Fab molecule under c) each comprise the heavy chain complementarity determining region (CDR) 1 of SEQ ID NO: 46, the heavy chain CDR 2 of SEQ ID NO: 47, the heavy chain CDR 3 of SEQ ID NO: 48, the light chain CDR 1 of SEQ ID NO: 49, the light chain CDR 2 of SEQ ID NO: 50 and the light chain CDR 3 of SEQ ID NO: 51, and the second Fab molecule under b) comprises the heavy chain CDR 1 of SEQ ID NO: 4, the heavy chain CDR 2 of SEQ ID NO: 5, the heavy chain CDR 3 of SEQ ID NO: 6, the light chain CDR 1 of SEQ ID NO: 8, the light chain CDR 2 of SEQ ID NO: 9 and the light chain CDR 3 of SEQ ID NO: 10;
(iii) in the constant domain CL of the first Fab molecule under a) and the third Fab molecule under c) the amino acid at position 124 is substituted by lysine (K) (numbering according to Kabat) and the amino acid at position 123 is substituted by lysine (K) or arginine (R), particularly by arginine (R) (numbering according to Kabat), and wherein in the constant domain CH1 of the first Fab molecule under a) and the third Fab molecule under c) the amino acid at position 147 is substituted by glutamic acid (E) (numbering according to Kabat EU index) and the amino acid at position 213 is substituted by glutamic acid (E) (numbering according to Kabat EU index); and
(iv) the first Fab molecule under a) is fused at the C-terminus of the Fab heavy chain to the N-terminus of the Fab heavy chain of the second Fab molecule under b), and the second Fab molecule under b) and the third Fab molecule under c) are each fused at the C-terminus of the Fab heavy chain to the N-terminus of one of the subunits of the Fc domain under d).

In a further aspect, the invention provides a T cell activating bispecific antigen binding molecule comprising
a) a first Fab molecule which specifically binds to a first antigen;
b) a second Fab molecule which specifically binds to a second antigen, and wherein the variable domains VL and VH of the Fab light chain and the Fab heavy chain are replaced by each other;
c) a third Fab molecule which specifically binds to the first antigen; and
d) an Fc domain composed of a first and a second subunit capable of stable association;
wherein
(i) the first antigen is CD20 and the second antigen is CD3, particularly CD3 epsilon;
(ii) the first Fab molecule under a) and the third Fab molecule under c) each comprise the heavy chain complementarity determining region (CDR) 1 of SEQ ID NO: 46, the heavy chain CDR 2 of SEQ ID NO: 47, the heavy chain CDR 3 of SEQ ID NO: 48, the light chain CDR 1 of SEQ ID NO: 49, the light chain CDR 2 of SEQ ID NO: 50 and the light chain CDR 3 of SEQ ID NO: 51, and the second Fab molecule under b) comprises the heavy chain CDR 1 of SEQ ID NO: 4, the heavy chain CDR 2 of SEQ ID NO: 67, the heavy chain CDR 3 of SEQ ID NO: 6, the light chain CDR 1 of SEQ ID NO: 68, the light chain CDR 2 of SEQ ID NO: 9 and the light chain CDR 3 of SEQ ID NO: 10;
(iii) in the constant domain CL of the first Fab molecule under a) and the third Fab molecule under c) the amino acid at position 124 is substituted by lysine (K) (numbering according to Kabat) and the amino acid at position 123 is substituted by lysine (K) or arginine (R), particularly by arginine (R) (numbering according to Kabat), and wherein in the constant domain CH1 of the first Fab molecule under a) and the third Fab molecule under c) the amino acid at position 147 is substituted by glutamic acid (E) (numbering according to Kabat EU index) and the amino acid at position 213 is substituted by glutamic acid (E) (numbering according to Kabat EU index); and (iv) the first Fab molecule under a) is fused at the C-terminus of the Fab heavy chain to the N-terminus of the Fab heavy chain of the second Fab molecule under b), and the second Fab molecule under b) and the third Fab molecule under c) are each fused at the C-terminus of the Fab heavy chain to the N-terminus of one of the subunits of the Fc domain under d).

According to another aspect of the invention there is provided one or more isolated polynucleotide(s) encoding a T cell activating bispecific antigen binding molecule of the invention. The invention further provides one or more expression vector(s) comprising the isolated polynucleotide(s) of the invention, and a host cell comprising the isolated polynucleotide(s) or the expression vector(s) of the invention. In some embodiments the host cell is a eukaryotic cell, particularly a mammalian cell.

In another aspect is provided a method of producing the T cell activating bispecific antigen binding molecule of the invention, comprising the steps of a) culturing the host cell of the invention under conditions suitable for the expression of the T cell activating bispecific antigen binding molecule and b) recovering the T cell activating bispecific antigen binding molecule. The invention also encompasses a T cell activating bispecific antigen binding molecule produced by the method of the invention.

The invention further provides a pharmaceutical composition comprising the T cell activating bispecific antigen binding molecule of the invention and a pharmaceutically acceptable carrier.

Also encompassed by the invention are methods of using the T cell activating bispecific antigen binding molecule and pharmaceutical composition of the invention. In one aspect the invention provides a T cell activating bispecific antigen binding molecule or a pharmaceutical composition of the invention for use as a medicament. In one aspect is provided a T cell activating bispecific antigen binding molecule or a pharmaceutical composition according to the invention for use in the treatment of a disease in an individual in need thereof. In a specific embodiment the disease is cancer.

Also provided is the use of a T cell activating bispecific antigen binding molecule of the invention for the manufacture of a medicament for the treatment of a disease in an individual in need thereof; as well as a method of treating a disease in an individual, comprising administering to said individual a therapeutically effective amount of a composition comprising the T cell activating bispecific antigen binding molecule according to the invention in a pharmaceutically acceptable form. In a specific embodiment the disease is cancer. In any of the above embodiments the individual preferably is a mammal, particularly a human.

The invention also provides a method for inducing lysis of a target cell, particularly a tumor cell, comprising contacting a target cell with a T cell activating bispecific antigen binding molecule of the invention in the presence of a T cell, particularly a cytotoxic T cell.

BRIEF DESCRIPTION OF THE DRAWINGS

FIG. 1. Exemplary configurations of the T cell activating bispecific antigen binding molecules (TCBs) of the invention. (FIG. 1G, FIG. 1K) Illustration of the "1+1 IgG Crossfab" molecule with alternative order of Crossfab and Fab components ("inverted"). (FIG. 1H, FIG. 1L) Illustration of the "1+1 IgG Crossfab" molecule. (FIG. 1I, FIG. 1M) Illustration of the "2+1 IgG Crossfab" molecule with two CrossFabs. (FIG. 1J, FIG. 1N) Illustration of the "2+1 IgG Crossfab" molecule with two CrossFabs and alternative order of Crossfab and Fab components ("inverted").

FIG. 3. (FIG. 3A) Electropherogram of molecule "A", shown in FIG. 2A, (FIG. 3B) electropherogram of molecule "B", shown in FIG. 2B, (FIG. 3C) electropherogram of molecule "C", shown in FIG. 2C, (FIG. 3D) electropherogram of molecule "D", shown in FIG. 2D, (FIG. 3E) electropherogram of molecule "E", shown in FIG. 2E, (FIG. 3F) electropherogram of molecule "F", shown in FIG. 2F, (FIG. 3G) electropherogram of molecule "G", shown in FIG. 2G, (FIG. 3H) electropherogram of molecule "H", shown in FIG. 2H, (FIG. 3I) electropherogram of molecule "I", shown in FIG. 2I, (FIG. 3N) Electropherogram of molecule "J", shown in FIG. 2J, (FIG. 3O) electropherogram of molecule "K", shown in FIG. 2K. Lane A=non-reduced, lane B=reduced. (FIGS. 3J-3L, FIG. 3P, FIG. 3Q) SDS-PAGE analysis of TCBs prepared in Example 1 after the first purification step (Protein A affinity chromatography). (FIG.

3J) 4-12% Bis-Tris SDS-PAGE, non reduced; lane 1=marker (Mark 12, unstained standard, Invitrogen); lane 2-11=fractions from Protein A affinity chromatography of molecule B, (FIG. 3K) 3-8% Tris-Acetate SDS-PAGE, non reduced; lane 1=marker (HiMark, Invitrogen); lane 2-12=fractions from Protein A affinity chromatography of molecule C, (FIG. 3L) 4-12% Bis-Tris SDS-PAGE, non reduced; lane 1=marker (Mark 12, unstained standard, Invitrogen); lane 2-14=fractions from Protein A affinity chromatography of molecule D, (FIG. 3P) 4-12% Bis/Tris SDS PAGE, non reduced; lane 1=marker (Mark 12, Invitrogen); lane 2-10=fractions from Protein A affinity chromatography of molecule J, (FIG. 3Q) 4-12% Bis/Tris SDS PAGE, non reduced; lane 1=marker (Mark 12, Invitrogen); lane 2-12=fractions from Protein A affinity chromatography of molecule K.

FIG. 7. Activation of $CD8^+$ T cells (A) or $CD4^+$ T cells (B) upon T cell-mediated killing of CD20-expressing tumor target cells (Z-138) induced by anti-CD3/anti-CD20 T cell bispecific (TCB) antibodies ("CD20 TCB") with or without charge modifications ("charge residues") (see Example 1).

FIG. 9. Activation of $CD8^+$ T cells (FIG. 9A) or $CD4^+$ T cells (FIG. 9B) upon T cell-mediated killing of CD20-expressing B cells in human healthy whole blood induced by anti-CD3/anti-CD20 T cell bispecific (TCB) antibodies ("CD20 TCB") with or without charge modifications ("charge residues") (see Example 1).

FIG. 13. Tumor cell lysis and subsequent T cell activation mediated by different anti-CD20/anti-CD3 TCB antibody formats.

FIG. 19. Analysis of different surface markers expression on peripheral T-cells three days (D3) and ten days (D10) after vehicle (black bars) or anti-CD20/anti-CD3 TCB antibody (molecule "B" shown in FIG. 2B) (white bars) injection in fully humanized mice.

FIG. 20. Analysis of B-cell frequency (FIG. 20A), T-cell frequency (FIG. 20B) and surface markers expression on T-cells (FIG. 20C) in spleen of vehicle (black bars) or anti-CD20/anti-CD3 TCB antibody (molecule "B" shown in FIG. 2B) (white bars)-treated fully humanized mice at study termination (D10 after first therapeutic injection).

FIGS. 23A and 23B) and the molecule with charge modifications (83A10-TCBcv; FIG. 23C).

FIGS. 24A-24F. CE-SDS analysis (lane A=non-reduced, lane B=reduced, peak table for lane A) of "2+1 IgG Cross-Fab, inverted" molecules used in Example 2, in head-to-head (H2H) comparison after Protein A affinity chromatography (PA) and size exclusion chromatographic (SEC) purification steps.

FIG. 26. Killing of BCMA-positive H929 myeloma cells by anti-BCMA/anti-CD3 TCB antibodies ((FIGS. 26A and 26B) 83A10-TCB, (FIGS. 26C and 26D) 83A10-TCBcv) as measured by LDH release.

FIG. 32.

FIG. 34. Illustration of the TCBs prepared in Example 4. (FIG. 34A) "(Fab)$_2$-CrossFab" with charge modifications (VH/VL exchange in CD3 binder, charge modification in MCSP binders, EE=147E, 213E; RK=123R, 124K), (FIG. 34B) "(Fab)$_2$-CrossFab" without charge modifications (VH/VL exchange in CD3 binder).

DETAILED DESCRIPTION OF THE INVENTION

Definitions

Figure 1C:
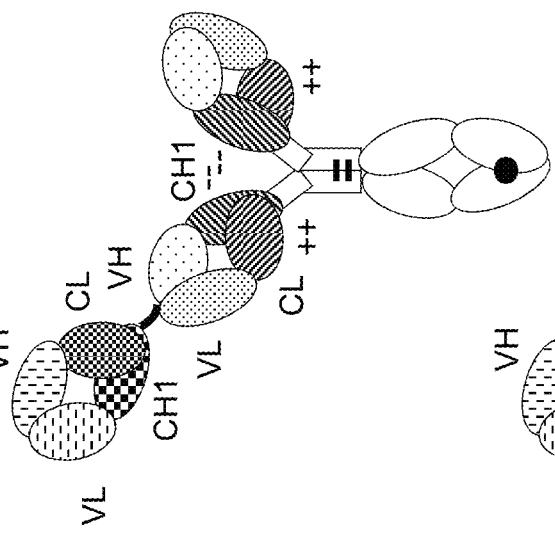
(FIG. 1C, FIG. 1F) Illustration of the "2+1 IgG Crossfab" molecule.

Terms are used herein as generally used in the art, unless otherwise defined in the following.

As used herein, the term "antigen binding molecule" refers in its broadest sense to a molecule that specifically binds an antigenic determinant. Examples of antigen binding molecules are immunoglobulins and derivatives, e.g. fragments, thereof.

The term "bispecific" means that the antigen binding molecule is able to specifically bind to at least two distinct antigenic determinants. Typically, a bispecific antigen binding molecule comprises two antigen binding sites, each of which is specific for a different antigenic determinant. In certain embodiments the bispecific antigen binding molecule is capable of simultaneously binding two antigenic determinants, particularly two antigenic determinants expressed on two distinct cells.

The term "valent" as used herein denotes the presence of a specified number of antigen binding sites in an antigen binding molecule. As such, the term "monovalent binding to an antigen" denotes the presence of one (and not more than one) antigen binding site specific for the antigen in the antigen binding molecule.

An "antigen binding site" refers to the site, i.e. one or more amino acid residues, of an antigen binding molecule which provides interaction with the antigen. For example, the antigen binding site of an antibody comprises amino acid residues from the complementarity determining regions (CDRs). A native immunoglobulin molecule typically has two antigen binding sites, a Fab molecule typically has a single antigen binding site.

As used herein, the term "antigen binding moiety" refers to a polypeptide molecule that specifically binds to an antigenic determinant. In one embodiment, an antigen binding moiety is able to direct the entity to which it is attached (e.g. a second antigen binding moiety) to a target site, for example to a specific type of tumor cell or tumor stroma bearing the antigenic determinant. In another embodiment an antigen binding moiety is able to activate signaling through its target antigen, for example a T cell receptor complex antigen. Antigen binding moieties include antibodies and fragments thereof as further defined herein. Particular antigen binding moieties include an antigen binding domain of an antibody, comprising an antibody heavy chain variable region and an antibody light chain variable region. In certain embodiments, the antigen binding moieties may comprise antibody constant regions as further defined herein and known in the art. Useful heavy chain constant regions include any of the five isotypes: $\alpha$, $\delta$, $\varepsilon$, $\gamma$, or $\mu$. Useful light chain constant regions include any of the two isotypes: $\kappa$ and $\lambda$.

As used herein, the term "antigenic determinant" is synonymous with "antigen" and "epitope," and refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins referred to as antigens herein (e.g. CD3) can be any native form the proteins from any vertebrate source, including mammals such as primates (e.g. humans) and rodents (e.g. mice and rats), unless otherwise indicated. In a particular embodiment the antigen is a human protein. Where reference is made to a specific protein herein, the term encompasses the "full-length", unprocessed protein as well as any form of the protein that results from processing in the cell. The term also encompasses naturally occurring variants of the protein, e.g. splice variants or allelic variants. An exemplary human protein useful as antigen is CD3, particularly the epsilon subunit of CD3 (see UniProt no. P07766 (version 130), NCBI RefSeq no. NP_000724.1, SEQ ID NO: 1 for the human sequence; or UniProt no. Q95LI5 (version 49), NCBI GenBank no. BAB71849.1, SEQ ID NO: 2 for the cynomolgus [*Macaca fascicularis*] sequence). In certain embodiments the T cell activating bispecific antigen binding molecule of the invention binds to an epitope of CD3 or a target cell antigen that is conserved among the CD3 or target cell antigen from different species.

By "specific binding" is meant that the binding is selective for the antigen and can be discriminated from unwanted or non-specific interactions. The ability of an antigen binding moiety to bind to a specific antigenic determinant can be measured either through an enzyme-linked immunosorbent assay (ELISA) or other techniques familiar to one of skill in the art, e.g. surface plasmon resonance (SPR) technique (analyzed on a BIAcore instrument) (Liljeblad et al., Glyco J 17, 323-329 (2000)), and traditional binding assays (Heeley, Endocr Res 28, 217-229 (2002)). In one embodiment, the extent of binding of an antigen binding moiety to an unrelated protein is less than about 10% of the binding of the antigen binding moiety to the antigen as measured, e.g., by SPR. In certain embodiments, an antigen binding moiety that binds to the antigen, or an antigen binding molecule comprising that antigen binding moiety, has a dissociation constant ($K_D$) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

"Affinity" refers to the strength of the sum total of non-covalent interactions between a single binding site of a molecule (e.g., a receptor) and its binding partner (e.g., a ligand). Unless indicated otherwise, as used herein, "binding affinity" refers to intrinsic binding affinity which reflects a 1:1 interaction between members of a binding pair (e.g., an antigen binding moiety and an antigen, or a receptor and its ligand). The affinity of a molecule X for its partner Y can generally be represented by the dissociation constant ($K_D$), which is the ratio of dissociation and association rate constants ($k_{off}$ and $k_{on}$, respectively). Thus, equivalent affinities may comprise different rate constants, as long as the ratio of the rate constants remains the same. Affinity can be measured by well established methods known in the art, including those described herein. A particular method for measuring affinity is Surface Plasmon Resonance (SPR).

"Reduced binding", for example reduced binding to an Fc receptor, refers to a decrease in affinity for the respective interaction, as measured for example by SPR. For clarity the term includes also reduction of the affinity to zero (or below the detection limit of the analytic method), i.e. complete abolishment of the interaction. Conversely, "increased binding" refers to an increase in binding affinity for the respective interaction.

An "activating T cell antigen" as used herein refers to an antigenic determinant expressed on the surface of a T lymphocyte, particularly a cytotoxic T lymphocyte, which is capable of inducing T cell activation upon interaction with an antigen binding molecule. Specifically, interaction of an antigen binding molecule with an activating T cell antigen may induce T cell activation by triggering the signaling cascade of the T cell receptor complex. In a particular embodiment the activating T cell antigen is CD3, particularly the epsilon subunit of CD3 (see UniProt no. P07766 (version 130), NCBI RefSeq no. NP_000724.1, SEQ ID NO: 1 for the human sequence; or UniProt no. Q95LI5 (version 49), NCBI GenBank no. BAB71849.1, SEQ ID NO: 2 for the cynomolgus [*Macaca fascicularis*] sequence).

"T cell activation" as used herein refers to one or more cellular response of a T lymphocyte, particularly a cytotoxic T lymphocyte, selected from: proliferation, differentiation, cytokine secretion, cytotoxic effector molecule release, cytotoxic activity, and expression of activation markers. The T cell activating bispecific antigen binding molecules of the invention are capable of inducing T cell activation. Suitable assays to measure T cell activation are known in the art described herein.

A "target cell antigen" as used herein refers to an antigenic determinant presented on the surface of a target cell, for example a cell in a tumor such as a cancer cell or a cell of the tumor stroma. In a particular embodiment, the target cell antigen is CD20, particularly human CD20 (see UniProt no. P11836).

As used herein, the terms "first", "second" or "third" with respect to Fab molecules etc., are used for convenience of distinguishing when there is more than one of each type of moiety. Use of these terms is not intended to confer a specific order or orientation of the T cell activating bispecific antigen binding molecule unless explicitly so stated.

A "Fab molecule" refers to a protein consisting of the VH and CH1 domain of the heavy chain (the "Fab heavy chain") and the VL and CL domain of the light chain (the "Fab light chain") of an immunoglobulin.

By "fused" is meant that the components (e.g. a Fab molecule and an Fc domain subunit) are linked by peptide bonds, either directly or via one or more peptide linkers.

As used herein, the term "single-chain" refers to a molecule comprising amino acid monomers linearly linked by peptide bonds. In certain embodiments, one of the antigen binding moieties is a single-chain Fab molecule, i.e. a Fab molecule wherein the Fab light chain and the Fab heavy chain are connected by a peptide linker to form a single peptide chain. In a particular such embodiment, the C-terminus of the Fab light chain is connected to the N-terminus of the Fab heavy chain in the single-chain Fab molecule.

By a "crossover" Fab molecule (also termed "Crossfab") is meant a Fab molecule wherein the variable domains of the Fab heavy and light chain are exchanged (i.e. replaced by each other), i.e. the crossover Fab molecule comprises a peptide chain composed of the light chain variable domain VL and the heavy chain constant domain 1 CH1 (VL-CH1, in N- to C-terminal direction), and a peptide chain composed of the heavy chain variable domain VH and the light chain constant domain CL (VH-CL, in N- to C-terminal direction). For clarity, in a crossover Fab molecule wherein the variable domains of the Fab light chain and the Fab heavy chain are exchanged, the peptide chain comprising the heavy chain constant domain 1 CH1 is referred to herein as the "heavy chain" of the crossover Fab molecule. In contrast thereto, by a "conventional" Fab molecule is meant a Fab molecule in its natural format, i.e. comprising a heavy chain composed of the heavy chain variable and constant domains (VH-CH1, in N- to C-terminal direction), and a light chain composed of the light chain variable and constant domains (VL-CL, in N- to C-terminal direction).

The term "immunoglobulin molecule" refers to a protein having the structure of a naturally occurring antibody. For example, immunoglobulins of the IgG class are heterotetrameric glycoproteins of about 150,000 daltons, composed of two light chains and two heavy chains that are disulfide-bonded. From N- to C-terminus, each heavy chain has a variable domain (VH), also called a variable heavy domain or a heavy chain variable region, followed by three constant domains (CH1, CH2, and CH3), also called a heavy chain constant region. Similarly, from N- to C-terminus, each light chain has a variable domain (VL), also called a variable light domain or a light chain variable region, followed by a constant light (CL) domain, also called a light chain constant region. The heavy chain of an immunoglobulin may be assigned to one of five types, called α (IgA), δ (IgD), ε (IgE), γ (IgG), or μ (IgM), some of which may be further divided into subtypes, e.g. $\gamma_1$ ($IgG_1$), $\gamma_2$ ($IgG_2$), $\gamma_3$ ($IgG_3$), $\gamma_4$ ($IgG_4$), $\alpha_1$ ($IgA_1$) and $\alpha_2$ ($IgA_2$). The light chain of an immunoglobulin may be assigned to one of two types, called kappa (κ) and lambda (λ), based on the amino acid sequence of its constant domain. An immunoglobulin essentially consists of two Fab molecules and an Fc domain, linked via the immunoglobulin hinge region.

The term "antibody" herein is used in the broadest sense and encompasses various antibody structures, including but not limited to monoclonal antibodies, polyclonal antibodies, and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$, diabodies, linear antibodies, single-chain antibody molecules (e.g. scFv), and single-domain antibodies. For a review of certain antibody fragments, see Hudson et al., Nat Med 9, 129-134 (2003). For a review of scFv fragments, see e.g. Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046. Diabodies are antibody fragments with two antigen-binding sites that may be bivalent or bispecific. See, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see e.g. U.S. Pat. No. 6,248,516 B1).

Antibody fragments can be made by various techniques, including but not limited to proteolytic digestion of an intact antibody as well as production by recombinant host cells (e.g. E. coli or phage), as described herein.

The term "antigen binding domain" refers to the part of an antibody that comprises the area which specifically binds to and is complementary to part or all of an antigen. An antigen binding domain may be provided by, for example, one or more antibody variable domains (also called antibody variable regions). Particularly, an antigen binding domain comprises an antibody light chain variable domain (VL) and an antibody heavy chain variable domain (VH).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, $6^{th}$ ed., W.H. Freeman and Co., page 91 (2007). A single VH or VL domain may be sufficient to confer antigen-binding specificity.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as "complementarity determining regions" (CDRs), and these terms are used herein interchangeably in reference to portions of the variable region that form the antigen binding regions. This particular region has been described by Kabat et al., Sequences of Proteins of Immunological Interest, 5th Ed. Public Health Service, National Institutes of Health, Bethesda, Md. (1991) and by Chothia et al., J Mol Biol 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table 1 as a comparison. The exact residue numbers which encompass a particular CDR will vary depending on the sequence and size of the CDR. Those skilled in the art can routinely determine which residues comprise a particular CDR given the variable region amino acid sequence of the antibody. The CDR sequences given herein are generally according to the Kabat definition.

TABLE 1

| CDR Definitions[1] | | | |
|---|---|---|---|
| CDR | Kabat | Chothia | AbM[2] |
| $V_H$ CDR1 | 31-35 | 26-32 | 26-35 |
| $V_H$ CDR2 | 50-65 | 52-58 | 50-58 |

TABLE 1-continued

CDR Definitions[1]

| CDR | Kabat | Chothia | AbM[2] |
|---|---|---|---|
| $V_H$ CDR3 | 95-102 | 95-102 | 95-102 |
| $V_L$ CDR1 | 24-34 | 26-32 | 24-34 |
| $V_L$ CDR2 | 50-56 | 50-52 | 50-56 |
| $V_L$ CDR3 | 89-97 | 91-96 | 89-97 |

[1]Numbering of all CDR definitions in Table 1 is according to the numbering conventions set forth by Kabat et al. (see below).
[2]"AbM" with a lowercase "b" as used in Table 1 refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein in connection with variable region sequences, "Kabat numbering" refers to the numbering system set forth by Kabat et al., *Sequences of Proteins of Immunological Interest*, 5th Ed. Public Health Service, National Institutes of Health, Bethesda, Md. (1991). Unless otherwise specified, references to the numbering of specific amino acid residue positions in an antibody variable region are according to the Kabat numbering system.

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, Md. (1991) and is referred to as "numbering according to Kabat" or "Kabat numbering" herein. Specifically the Kabat numbering system (see pages 647-660 of Kabat, et al., Sequences of Proteins of Immunological Interest, 5th ed., Public Health Service, National Institutes of Health, Bethesda, Md. (1991)) is used for the light chain constant domain CL of kappa and lambda isotype and the Kabat EU index numbering system (see pages 661-723) is used for the heavy chain constant domains (CH1, Hinge, CH2 and CH3), which is herein further clarified by referring to "numbering according to Kabat EU index" in this case.

The polypeptide sequences of the sequence listing are not numbered according to the Kabat numbering system. However, it is well within the ordinary skill of one in the art to convert the numbering of the sequences of the Sequence Listing to Kabat numbering.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1 (L1)-FR2-H2(L2)-FR3-H3 (L3)-FR4.

The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The term "Fc domain" or "Fc region" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, antibodies produced by host cells may undergo post-translational cleavage of one or more, particularly one or two, amino acids from the C-terminus of the heavy chain. Therefore an antibody produced by a host cell by expression of a specific nucleic acid molecule encoding a full-length heavy chain may include the full-length heavy chain, or it may include a cleaved variant of the full-length heavy chain (also referred to herein as a "cleaved variant heavy chain"). This may be the case where the final two C-terminal amino acids of the heavy chain are glycine (G446) and lysine (K447, numbering according to Kabat EU index). Therefore, the C-terminal lysine (Lys447), or the C-terminal glycine (Gly446) and lysine (K447), of the Fc region may or may not be present. Amino acid sequences of heavy chains including Fc domains (or a subunit of an Fc domain as defined herein) are denoted herein without C-terminal glycine-lysine dipeptide if not indicated otherwise. In one embodiment of the invention, a heavy chain including a subunit of an Fc domain as specified herein, comprised in a T cell activating bispecific antigen binding molecule according to the invention, comprises an additional C-terminal glycine-lysine dipeptide (G446 and K447, numbering according to EU index of Kabat). In one embodiment of the invention, a heavy chain including a subunit of an Fc domain as specified herein, comprised in a T cell activating bispecific antigen binding molecule according to the invention, comprises an additional C-terminal glycine residue (G446, numbering according to EU index of Kabat). Compositions of the invention, such as the pharmaceutical compositions described herein, comprise a population of T cell activating bispecific antigen binding molecules of the invention. The population of T cell activating bispecific antigen binding molecule may comprise molecules having a full-length heavy chain and molecules having a cleaved variant heavy chain. The population of T cell activating bispecific antigen binding molecules may consist of a mixture of molecules having a full-length heavy chain and molecules having a cleaved variant heavy chain, wherein at least 50%, at least 60%, at least 70%, at least 80% or at least 90% of the T cell activating bispecific antigen binding molecules have a cleaved variant heavy chain. In one embodiment of the invention a composition comprising a population of T cell activating bispecific antigen binding molecules of the invention comprises an T cell activating bispecific antigen binding molecule comprising a heavy chain including a subunit of an Fc domain as specified herein with an additional C-terminal glycine-lysine dipeptide (G446 and K447, numbering according to EU index of Kabat). In one embodiment of the invention a composition comprising a population of T cell activating bispecific antigen binding molecules of the invention comprises an T cell activating bispecific antigen binding molecule comprising a heavy chain including a subunit of an Fc domain as specified herein with an additional C-terminal glycine residue (G446, numbering according to EU index of Kabat). In one embodiment of the invention such a composition comprises a population of T cell activating bispecific antigen binding molecules comprised of molecules comprising a heavy chain including a subunit of an Fc domain as specified herein; molecules comprising a heavy chain including a subunit of a Fc domain as specified herein with an additional C-terminal glycine residue (G446, numbering according to EU index of Kabat); and molecules comprising a heavy chain including a subunit of an Fc domain as specified herein with an additional C-terminal glycine-lysine dipeptide (G446 and K447, numbering according to EU index of Kabat). Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991 (see also above). A "subunit" of an Fc domain as used herein refers to one of the two polypeptides forming the dimeric Fc domain, i.e. a polypeptide comprising C-terminal constant regions of an immunoglobulin heavy chain, capable of stable self-association. For example, a subunit of an IgG Fc domain comprises an IgG CH2 and an IgG CH3 constant domain.

A "modification promoting the association of the first and the second subunit of the Fc domain" is a manipulation of the peptide backbone or the post-translational modifications of an Fc domain subunit that reduces or prevents the association of a polypeptide comprising the Fc domain subunit with an identical polypeptide to form a homodimer. A modification promoting association as used herein particularly includes separate modifications made to each of the two Fc domain subunits desired to associate (i.e. the first and the second subunit of the Fc domain), wherein the modifications are complementary to each other so as to promote association of the two Fc domain subunits. For example, a modification promoting association may alter the structure or charge of one or both of the Fc domain subunits so as to make their association sterically or electrostatically favorable, respectively. Thus, (hetero)dimerization occurs between a polypeptide comprising the first Fc domain subunit and a polypeptide comprising the second Fc domain subunit, which might be non-identical in the sense that further components fused to each of the subunits (e.g. antigen binding moieties) are not the same. In some embodiments the modification promoting association comprises an amino acid mutation in the Fc domain, specifically an amino acid substitution. In a particular embodiment, the modification promoting association comprises a separate amino acid mutation, specifically an amino acid substitution, in each of the two subunits of the Fc domain.

The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

As used herein, the terms "engineer, engineered, engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches.

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics, e.g., reduced binding to an Fc receptor, or increased association with another peptide. Amino acid sequence deletions and insertions include amino- and/or carboxy-terminal deletions and insertions of amino acids. Particular amino acid mutations are amino acid substitutions. For the purpose of altering e.g. the binding characteristics of an Fc region, non-conservative amino acid substitutions, i.e. replacing one amino acid with another amino acid having different structural and/or chemical properties, are particularly preferred. Amino acid substitutions include replacement by non-naturally occurring amino acids or by naturally occurring amino acid derivatives of the twenty standard amino acids (e.g. 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid mutation. For example, a substitution from proline at position 329 of the Fc domain to glycine can be indicated as 329G, G329, $G_{329}$, P329G, or Pro329Gly.

As used herein, term "polypeptide" refers to a molecule composed of monomers (amino acids) linearly linked by amide bonds (also known as peptide bonds). The term "polypeptide" refers to any chain of two or more amino acids, and does not refer to a specific length of the product. Thus, peptides, dipeptides, tripeptides, oligopeptides, "protein," "amino acid chain," or any other term used to refer to a chain of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis. A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded.

By an "isolated" polypeptide or a variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for the purpose of the invention, as are native or recombinant polypeptides which have been separated, fractionated, or partially or substantially purified by any suitable technique.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "polynucleotide" refers to an isolated nucleic acid molecule or construct, e.g. messenger RNA (mRNA), virally-derived RNA, or plasmid DNA (pDNA). A polynucleotide may comprise a conventional phosphodiester bond or a non-conventional bond (e.g. an amide bond, such as found in peptide nucleic acids (PNA). The term "nucleic acid molecule" refers to any one or more nucleic acid segments, e.g. DNA or RNA fragments, present in a polynucleotide.

By "isolated" nucleic acid molecule or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g. ALIGN-2).

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette of the invention comprises polynucleotide sequences that encode bispecific antigen binding molecules of the invention or fragments thereof.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode bispecific antigen binding molecules of the invention or fragments thereof.

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the bispecific antigen binding molecules of the present invention. Host cells include cultured cells, e.g. mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

An "activating Fc receptor" is an Fc receptor that following engagement by an Fc domain of an antibody elicits signaling events that stimulate the receptor-bearing cell to perform effector functions. Human activating Fc receptors include FcγRIIIa (CD16a), FcγRI (CD64), FcγRIIa (CD32), and FcαRI (CD89).

Antibody-dependent cell-mediated cytotoxicity (ADCC) is an immune mechanism leading to the lysis of antibody-coated target cells by immune effector cells. The target cells are cells to which antibodies or derivatives thereof comprising an Fc region specifically bind, generally via the protein part that is N-terminal to the Fc region. As used herein, the term "reduced ADCC" is defined as either a reduction in the number of target cells that are lysed in a given time, at a given concentration of antibody in the medium surrounding the target cells, by the mechanism of ADCC defined above, and/or an increase in the concentration of antibody in the medium surrounding the target cells, required to achieve the lysis of a given number of target cells in a given time, by the mechanism of ADCC. The reduction in ADCC is relative to the ADCC mediated by the same antibody produced by the same type of host cells, using the same standard production, purification, formulation and storage methods (which are known to those skilled in the art), but that has not been engineered. For example the reduction in ADCC mediated by an antibody comprising in its Fc domain an amino acid substitution that reduces ADCC, is relative to the ADCC mediated by the same antibody without this amino acid substitution in the Fc domain. Suitable assays to measure ADCC are well known in the art (see e.g. PCT publication no. WO 2006/082515 or PCT publication no. WO 2012/130831).

An "effective amount" of an agent refers to the amount that is necessary to result in a physiological change in the cell or tissue to which it is administered.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). Particularly, the individual or subject is a human.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical composition, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, T cell activating bispecific antigen binding molecules of the invention are used to delay development of a disease or to slow the progression of a disease.

The term "package insert" is used to refer to instructions customarily included in commercial packages of therapeutic products, that contain information about the indications, usage, dosage, administration, combination therapy, contraindications and/or warnings concerning the use of such therapeutic products.

DETAILED DESCRIPTION OF THE EMBODIMENTS

The invention provides a T cell activating bispecific antigen binding molecule with favorable properties for therapeutic application, in particular with improved produceability (e.g. with respect to purity, yield). The amino acid substitutions in Fab molecules comprised in the T cell activating bispecific antigen binding molecules of the invention are particularly efficient in reducing mispairing of light chains with non-matching heavy chains (Bence-Jones-type side products), which can occur in the production of Fab-based bi-/multispecific antigen binding molecules with a VH/VL exchange in one (or more, in case of molecules comprising more than two antigen-binding Fab molecules) of their binding arms (see also PCT application no. PCT/EP2015/057165, particularly the examples therein, incorporated herein by reference in its entirety).

In a first aspect the invention provides a T cell activating bispecific antigen binding molecule comprising
(a) a first Fab molecule which specifically binds to a first antigen
(b) a second Fab molecule which specifically binds to a second antigen, and wherein the variable domains VL and VH of the Fab light chain and the Fab heavy chain are replaced by each other, wherein the first antigen is an activating T cell antigen and the second antigen is a target cell antigen, or the first antigen is a target cell antigen and the second antigen is an activating T cell antigen; and wherein
i) in the constant domain CL of the first Fab molecule under
  a) the amino acid at position 124 is substituted by a positively charged amino acid (numbering according to Kabat), and wherein in the constant domain CH1 of the first Fab molecule under a) the amino acid at position 147 or the amino acid at position 213 is substituted by a negatively charged amino acid (numbering according to Kabat EU index); or ii) in the constant domain CL of the second Fab molecule under b) the amino acid at position 124 is substituted by a positively charged amino acid (numbering according to Kabat), and wherein in the constant domain CH1 of the second Fab molecule under b) the amino acid at position 147 or the amino acid at position 213 is substituted by a negatively charged amino acid (numbering according to Kabat EU index).

According to the invention, the T cell activating bispecific antigen binding molecule does not comprise both modifications mentioned under i) and ii). The constant domains CL and CH1 of the second Fab molecule are not replaced by each other (i.e. remain unexchanged).

In one embodiment of the T cell activating bispecific antigen binding molecule according to the invention, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 or the amino acid at position 213 is substituted independently by glutamic acid (E), or aspartic acid (D) (numbering according to Kabat EU index).

In a further embodiment, in the constant domain CL of the first Fab molecule under a) the amino acid at position 124 is substituted independently by lysine (K), arginine (R) or histidine (H) (numbering according to Kabat), and in the constant domain CH1 of the first Fab molecule under a) the amino acid at position 147 is substituted independently by glutamic acid (E), or aspartic acid (D) (numbering according to Kabat EU index).

In a particular embodiment, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)) and the amino acid at position 123 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In a more particular embodiment, in the constant domain CL of the first Fab molecule under a) the amino acid at position 124 is substituted by lysine (K) (numbering according to Kabat) and the amino acid at position 123 is substituted by lysine (K) or arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

In an even more particular embodiment, in the constant domain CL of the first Fab molecule under a) the amino acid at position 124 is substituted by lysine (K) (numbering according to Kabat) and the amino acid at position 123 is substituted by arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

In particular embodiments, the constant domain CL of the first Fab molecule under a) is of kappa isotype.

Alternatively, the amino acid substitutions according to the above embodiments may be made in the constant domain CL and the constant domain CH1 of the second Fab molecule under b) instead of in the constant domain CL and the constant domain CH1 of the first Fab molecule under a). In particular such embodiments, the constant domain CL of the second Fab molecule under b) is of kappa isotype.

The T cell activating bispecific antigen binding molecule according to the invention may further comprise a third Fab molecule which specifically binds to the first antigen. In particular embodiments, said third Fab molecule is identical to the first Fab molecule under a). In these embodiments, the amino acid substitutions according to the above embodiments will be made in the constant domain CL and the constant domain CH1 of each of the first Fab molecule and the third Fab molecule. Alternatively, the amino acid substitutions according to the above embodiments may be made in the constant domain CL and the constant domain CH1 of the second Fab molecule under b), but not in the constant domain CL and the constant domain CH1 of the first Fab molecule and the third Fab molecule.

In particular embodiments, the T cell activating bispecific antigen binding molecule according to the invention further comprises an Fc domain composed of a first and a second subunit capable of stable association.

T Cell Activating Bispecific Antigen Binding Molecule Formats

Figure 1F:
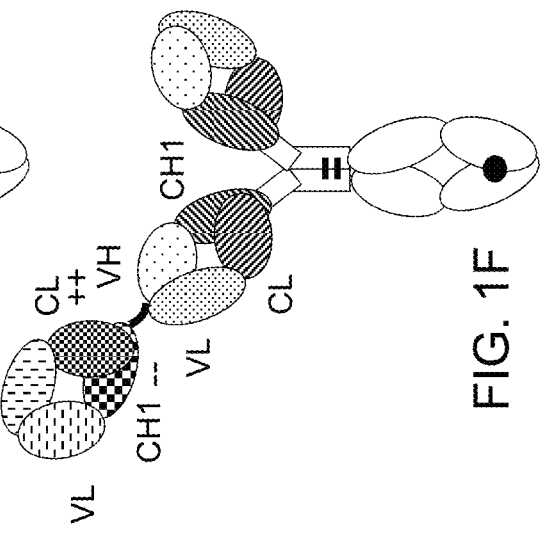
Figure 1B:
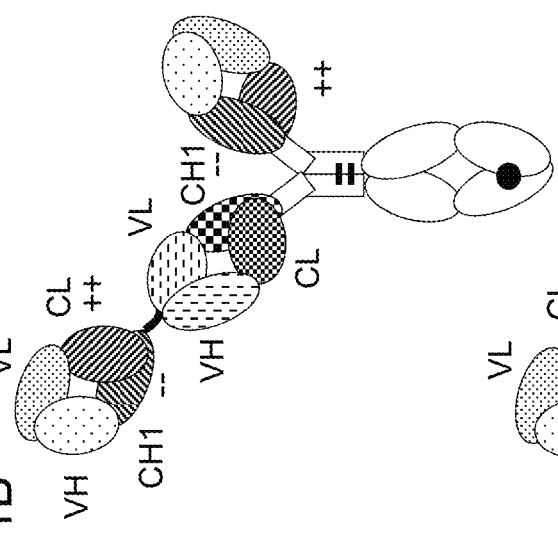
(FIG. 1B, FIG. 1E) Illustration of the "2+1 IgG Crossfab" molecule with alternative order of Crossfab and Fab components ("inverted").
Figure 1E:
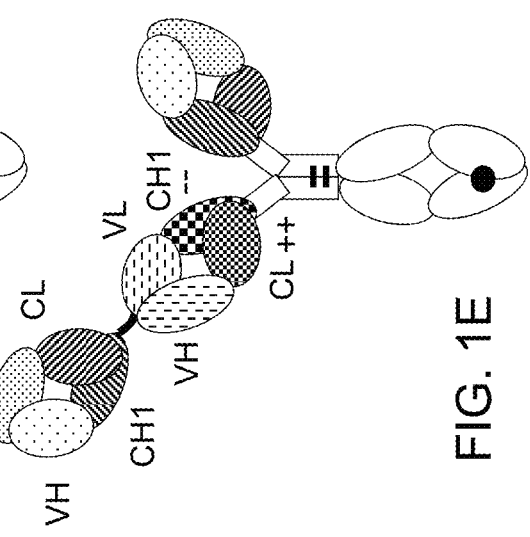
Figure 1A:
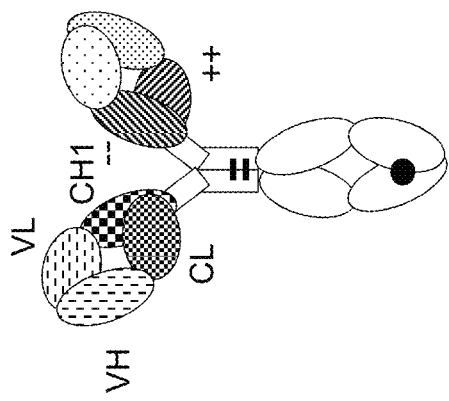
(FIG. 1A, FIG. 1D) Illustration of the "1+1 CrossMab" molecule.
Figure 1D:
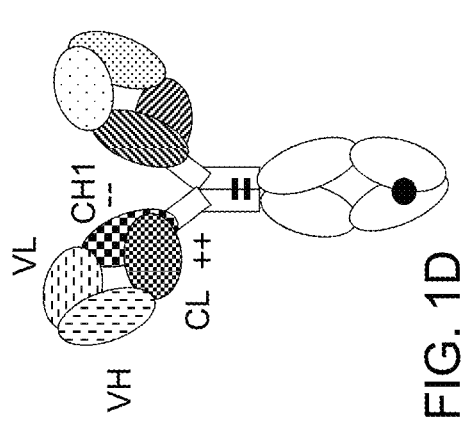
Figures 1O, 1P, 1Q, 1R:
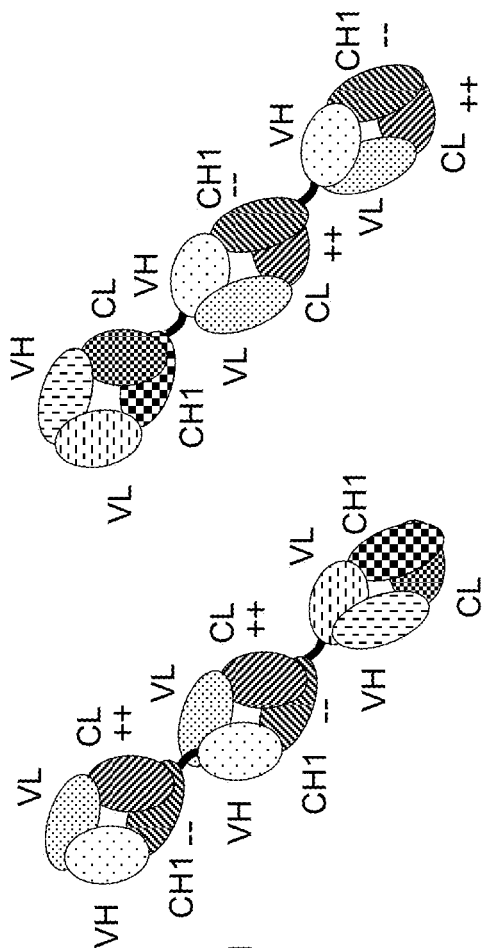
(FIG. 1O, FIG. 1S) Illustration of the "Fab-Crossfab" molecule.
(FIG. 1P, FIG. 1T) Illustration of the "Crossfab-Fab" molecule.
(FIG. 1Q, FIG. 1U) Illustration of the "(Fab)$_2$-Crossfab" molecule.
(FIG. 1R, FIG. 1V) Illustration of the "Crossfab-(Fab)$_2$" molecule.
Figures 1S, 1T, 1U, 1V:
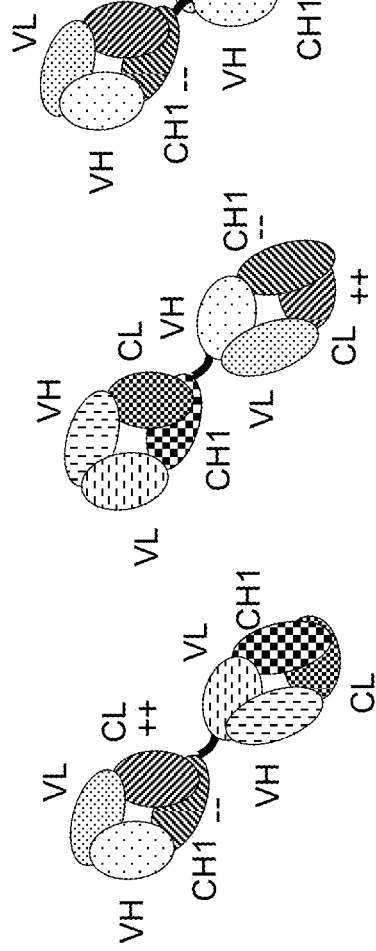
Figure 1X:
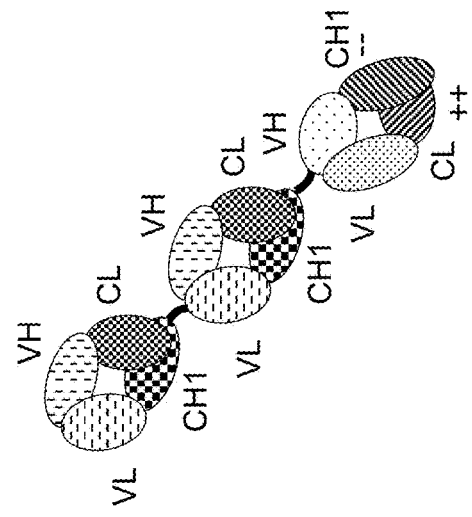
(FIG. 1X, FIG. 1Z) Illustration of the "(Crossfab)$_2$-Fab" molecule. Black dot: optional modification in the Fc domain promoting heterodimerization. ++, −−: amino acids of opposite charges introduced in the CH and CL domains.
Figure 1Z:
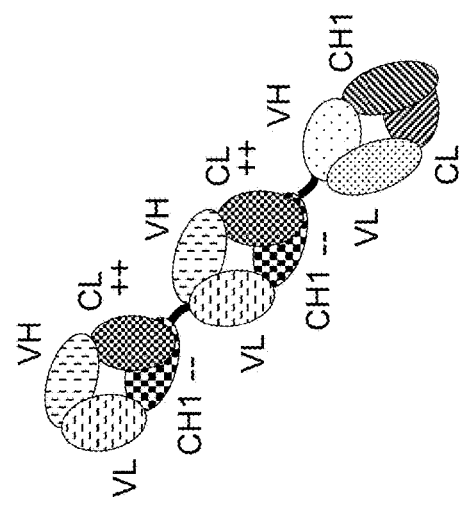

The components of the T cell activating bispecific antigen binding molecule can be fused to each other in a variety of configurations. Exemplary configurations are depicted in FIGS. 1A-1Z.

In particular embodiments, the T cell activating bispecific antigen binding molecule comprises an Fc domain composed of a first and a second subunit capable of stable association.

In some embodiments, the second Fab molecule is fused at the C-terminus of the Fab heavy chain to the N-terminus of the first or the second subunit of the Fc domain.

In one such embodiment, the first Fab molecule is fused at the C-terminus of the Fab heavy chain to the N-terminus of the Fab heavy chain of the second Fab molecule. In a specific such embodiment, the T cell activating bispecific antigen binding molecule essentially consists of the first and the second Fab molecule, the Fc domain composed of a first and a second subunit, and optionally one or more peptide linkers, wherein the first Fab molecule is fused at the C-terminus of the Fab heavy chain to the N-terminus of the Fab heavy chain of the second Fab molecule, and the second Fab molecule is fused at the C-terminus of the Fab heavy chain to the N-terminus of the first or the second subunit of the Fc domain. Such a configuration is schematically depicted in FIGS. 1G and 1K. Optionally, the Fab light chain of the first Fab molecule and the Fab light chain of the second Fab molecule may additionally be fused to each other.

In another such embodiment, the first Fab molecule is fused at the C-terminus of the Fab heavy chain to the N-terminus of the first or second subunit of the Fc domain. In a specific such embodiment, the T cell activating bispecific antigen binding molecule essentially consists of the first and the second Fab molecule, the Fc domain composed of a first and a second subunit, and optionally one or more peptide linkers, wherein the first and the second Fab molecule are each fused at the C-terminus of the Fab heavy chain to the N-terminus of one of the subunits of the Fc domain. Such a configuration is schematically depicted in FIGS. 1A and 1D. The first and the second Fab molecule may be fused to the Fc domain directly or through a peptide linker. In a particular embodiment the first and the second Fab molecule are each fused to the Fc domain through an immunoglobulin hinge region. In a specific embodiment, the immunoglobulin hinge region is a human $IgG_1$ hinge region, particularly where the Fc domain is an $IgG_1$ Fc domain.

In other embodiments, the first Fab molecule is fused at the C-terminus of the Fab heavy chain to the N-terminus of the first or second subunit of the Fc domain.

In one such embodiment, the second Fab molecule is fused at the C-terminus of the Fab heavy chain to the N-terminus of the Fab heavy chain of the first Fab molecule. In a specific such embodiment, the T cell activating bispecific antigen binding molecule essentially consists of the first and the second Fab molecule, the Fc domain composed of a first and a second subunit, and optionally one or more peptide linkers, wherein the second Fab molecule is fused at the C-terminus of the Fab heavy chain to the N-terminus of the Fab heavy chain of the first Fab molecule, and the first Fab molecule is fused at the C-terminus of the Fab heavy chain to the N-terminus of the first or the second subunit of the Fc domain. Such a configuration is schematically depicted in FIGS. 1H and 1L. Optionally, the Fab light chain of the first Fab molecule and the Fab light chain of the second Fab molecule may additionally be fused to each other.

The Fab molecules may be fused to the Fc domain or to each other directly or through a peptide linker, comprising one or more amino acids, typically about 2-20 amino acids. Peptide linkers are known in the art and are described herein. Suitable, non-immunogenic peptide linkers include, for example, $(G_4S)_n$, $(SG_4)_n$, $(G_4S)_n$ or $G_4(SG_4)_n$ peptide linkers. "n" is generally an integer from 1 to 10, typically from 2 to 4. In one embodiment said peptide linker has a length of at least 5 amino acids, in one embodiment a length of 5 to 100, in a further embodiment of 10 to 50 amino acids. In one embodiment said peptide linker is $(GxS)_n$ or $(GxS)_nG_m$ with G=glycine, S=serine, and (x=3, n=3, 4, 5 or 6, and m=0, 1, 2 or 3) or (x=4, n=2, 3, 4 or 5 and m=0, 1, 2 or 3), in one embodiment x=4 and n=2 or 3, in a further embodiment x=4 and n=2. In one embodiment said peptide linker is $(G_4S)_2$. A particularly suitable peptide linker for fusing the Fab light chains of the first and the second Fab molecule to each other is $(G_4S)_2$. An exemplary peptide linker suitable for connecting the Fab heavy chains of the first and the second Fab fragments comprises the sequence (D)-$(G_4S)_2$ (SEQ ID NOs 11 and 12). Additionally, linkers may comprise (a portion of) an immunoglobulin hinge region. Particularly where a Fab molecule is fused to the N-terminus of an Fc domain subunit, it may be fused via an immunoglobulin hinge region or a portion thereof, with or without an additional peptide linker.

A T cell activating bispecific antigen binding molecule with a single antigen binding moiety (such as a Fab molecule) capable of specific binding to a target cell antigen (for example as shown in FIGS. 1A, 1D, 1G, 1H, 1K, and 1L) is useful, particularly in cases where internalization of the target cell antigen is to be expected following binding of a high affinity antigen binding moiety. In such cases, the presence of more than one antigen binding moiety specific for the target cell antigen may enhance internalization of the target cell antigen, thereby reducing its availablity.

In many other cases, however, it will be advantageous to have a T cell activating bispecific antigen binding molecule comprising two or more antigen binding moieties (such as Fab molecules) specific for a target cell antigen (see examples shown in FIG. 1B, 1C, 1E, 1F, 1I, 1J. 1M or 1N), for example to optimize targeting to the target site or to allow crosslinking of target cell antigens.

Accordingly, in particular embodiments, the T cell activating bispecific antigen binding molecule of the invention further comprises a third Fab molecule which specifically binds to the first antigen. The first antigen preferably is the target cell antigen. In one embodiment, the third Fab molecule is a conventional Fab molecule. In one embodiment, the third Fab molecule is identical to the first Fab molecule (i.e. the first and the third Fab molecule comprise the same heavy and light chain amino acid sequences and have the same arrangement of domains (i.e. conventional or crossover)). In a particular embodiment, the second Fab molecule specifically binds to an activating T cell antigen, particularly CD3, and the first and third Fab molecule specifically bind to a target cell antigen.

In alternative embodiments, the T cell activating bispecific antigen binding molecule of the invention further comprises a third Fab molecule which specifically binds to the second antigen. In these embodiments, the second antigen preferably is the target cell antigen. In one such embodiment, the third Fab molecule is a crossover Fab molecule (a Fab molecule wherein the variable domains VH and VL of the Fab heavy and light chains are exchanged/replaced by each other). In one such embodiment, the third Fab molecule is identical to the second Fab molecule (i.e. the second and the third Fab molecule comprise the same heavy and light chain amino acid sequences and have the same arrangement of domains (i.e. conventional or crossover)). In one such embodiment, the first Fab molecule specifically binds to an activating T cell antigen, particularly CD3, and the second and third Fab molecule specifically bind to a target cell antigen.

In one embodiment, the third Fab molecule is fused at the C-terminus of the Fab heavy chain to the N-terminus of the first or second subunit of the Fc domain.

In a particular embodiment, the second and the third Fab molecule are each fused at the C-terminus of the Fab heavy chain to the N-terminus of one of the subunits of the Fc domain, and the first Fab molecule is fused at the C-terminus of the Fab heavy chain to the N-terminus of the Fab heavy chain of the second Fab molecule. In a specific such embodiment, the T cell activating bispecific antigen binding molecule essentially consists of the first, the second and the third Fab molecule, the Fc domain composed of a first and a second subunit, and optionally one or more peptide linkers, wherein the first Fab molecule is fused at the C-terminus of the Fab heavy chain to the N-terminus of the Fab heavy chain of the second Fab molecule, and the second Fab molecule is fused at the C-terminus of the Fab heavy chain to the N-terminus of the first subunit of the Fc domain, and wherein the third Fab molecule is fused at the C-terminus of the Fab heavy chain to the N-terminus of the second subunit of the Fc domain. Such a configuration is schematically depicted in FIGS. 1B and 1E (particular embodiments, wherein the third Fab molecule is a conventional Fab molecule and preferably identical to the first Fab molecule), and FIGS. 1I and 1M (alternative embodiments, wherein the third Fab molecule is a crossover Fab molecule and preferably identical to the second Fab molecule). The second and the third Fab molecule may be fused to the Fc domain directly or through a peptide linker. In a particular embodiment the second and the third Fab molecule are each fused to the Fc domain through an immunoglobulin hinge region. In a specific embodiment, the immunoglobulin hinge region is a human $IgG_1$ hinge region, particularly where the Fc domain is an $IgG_1$ Fc domain. Optionally, the Fab light chain of the first Fab molecule and the Fab light chain of the second Fab molecule may additionally be fused to each other.

In another embodiment, the first and the third Fab molecule are each fused at the C-terminus of the Fab heavy chain to the N-terminus of one of the subunits of the Fc domain, and the second Fab molecule is fused at the C-terminus of the Fab heavy chain to the N-terminus of the Fab heavy chain of the first Fab molecule. In a specific such embodiment, the T cell activating bispecific antigen binding molecule essentially consists of the first, the second and the third Fab molecule, the Fc domain composed of a first and a second subunit, and optionally one or more peptide linkers, wherein the second Fab molecule is fused at the C-terminus of the Fab heavy chain to the N-terminus of the Fab heavy chain of the first Fab molecule, and the first Fab molecule is fused at the C-terminus of the Fab heavy chain to the N-terminus of the first subunit of the Fc domain, and wherein the third Fab molecule is fused at the C-terminus of the Fab heavy chain to the N-terminus of the second subunit of the Fc domain. Such a configuration is schematically depicted in FIGS. 1C and 1F (particular embodiments, wherein the third Fab molecule is a conventional Fab molecule and preferably identical to the first Fab molecule) and in FIGS. 1J and 1N (alternative embodiments, wherein the third Fab molecule is a crossover Fab molecule and preferably identical to the second Fab molecule). The first and the third Fab molecule may be fused to the Fc domain directly or through a peptide linker. In a particular embodiment the first and the third Fab molecule are each fused to the Fc domain through an immunoglobulin hinge region. In a specific embodiment, the immunoglobulin hinge region is a human $IgG_1$ hinge region, particularly where the Fc domain is an $IgG_1$ Fc domain. Optionally, the Fab light chain of the first Fab molecule and the Fab light chain of the second Fab molecule may additionally be fused to each other.

In configurations of the T cell activating bispecific antigen binding molecule wherein a Fab molecule is fused at the C-terminus of the Fab heavy chain to the N-terminus of each of the subunits of the Fc domain through an immunoglobulin hinge regions, the two Fab molecules, the hinge regions and the Fc domain essentially form an immunoglobulin molecule. In a particular embodiment the immunoglobulin molecule is an IgG class immunoglobulin. In an even more particular embodiment the immunoglobulin is an $IgG_1$ subclass immunoglobulin. In another embodiment the immunoglobulin is an $IgG_4$ subclass immunoglobulin. In a further particular embodiment the immunoglobulin is a human immunoglobulin. In other embodiments the immunoglobulin is a chimeric immunoglobulin or a humanized immunoglobulin.

In some of the T cell activating bispecific antigen binding molecule of the invention, the Fab light chain of the first Fab molecule and the Fab light chain of the second Fab molecule are fused to each other, optionally via a peptide linker. Depending on the configuration of the first and the second Fab molecule, the Fab light chain of the first Fab molecule may be fused at its C-terminus to the N-terminus of the Fab light chain of the second Fab molecule, or the Fab light chain of the second Fab molecule may be fused at its C-terminus to the N-terminus of the Fab light chain of the first Fab molecule. Fusion of the Fab light chains of the first and the second Fab molecule further reduces mispairing of unmatched Fab heavy and light chains, and also reduces the number of plasmids needed for expression of some of the T cell activating bispecific antigen binding molecules of the invention. In certain embodiments the T cell activating bispecific antigen binding molecule according to the invention comprises a polypeptide wherein the Fab light chain variable region of the second Fab molecule shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with an Fc domain subunit ($VL_{(2)}$-$CH1_{(2)}$-CH2-CH3(-CH4)), and a polypeptide wherein the Fab heavy chain of the first Fab molecule shares a carboxy-terminal peptide bond with an Fc domain subunit ($VH_{(1)}$-$CH1_{(1)}$-CH2-CH3(-CH4)). In some embodiments the T cell activating bispecific antigen binding molecule further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$). In certain embodiments the polypeptides are covalently linked, e.g., by a disulfide bond.

In some embodiments, the T cell activating bispecific antigen binding molecule comprises a polypeptide wherein the Fab light chain variable region of the second Fab molecule shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab heavy chain of the first Fab molecule, which in turn shares a carboxy-terminal peptide bond with an Fc domain subunit ($VL_{(2)}$-$CH1_{(2)}$-$VH_{(1)}$-$CH1_{(1)}$-CH2-CH3(-CH4)). In other embodiments, the T cell activating bispecific antigen binding molecule comprises a polypeptide wherein the Fab heavy chain of the first Fab molecule shares a carboxy-terminal peptide bond with the Fab light chain variable region of the second Fab molecule which in turn shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with an Fc domain subunit ($VH_{(1)}$-$CH1_{(1)}$-$VL_{(2)}$-$CH1_{(2)}$-CH2-CH3 (-CH4)).

In some of these embodiments the T cell activating bispecific antigen binding molecule further comprises a crossover Fab light chain polypeptide of the second Fab molecule, wherein the Fab heavy chain variable region of the second Fab molecule shares a carboxy-terminal peptide bond with the Fab light chain constant region of the second Fab molecule ($VH_{(2)}$-$CL_{(2)}$), and the Fab light chain polypeptide of the first Fab molecule ($VL_{(1)}$-$CL_{(1)}$). In others of these embodiments the T cell activating bispecific antigen binding molecule further comprises a polypeptide wherein the Fab light chain variable region of the second Fab molecule shares a carboxy-terminal peptide bond with the Fab heavy chain constant region of the second Fab molecule which in turn shares a carboxy-terminal peptide bond with the Fab light chain polypeptide of the first Fab molecule ($VL_{(2)}$-$CH1_{(2)}$-$VL_{(1)}$-$CL_{(1)}$), or a polypeptide wherein the Fab light chain polypeptide of the first Fab molecule shares a carboxy-terminal peptide bond with the Fab heavy chain variable region of the second Fab molecule which in turn shares a carboxy-terminal peptide bond with the Fab light chain constant region of the second Fab molecule ($VL_{(1)}$-$CL_{(1)}$-$VH_{(2)}$-$CL_{(2)}$), as appropriate.

The T cell activating bispecific antigen binding molecule according to these embodiments may further comprise (i) an Fc domain subunit polypeptide (CH2-CH3(-CH4)), or (ii) a polypeptide wherein the Fab heavy chain of a third Fab molecule shares a carboxy-terminal peptide bond with an Fc domain subunit ($VH_{(3)}$-$CH1_{(3)}$-CH2-CH3(-CH4)) and the Fab light chain polypeptide of a third Fab molecule ($VL_{(3)}$-$CL_{(3)}$). In certain embodiments the polypeptides are covalently linked, e.g., by a disulfide bond.

In some embodiments, the first Fab molecule is fused at the C-terminus of the Fab heavy chain to the N-terminus of the Fab heavy chain of the second Fab molecule. In certain such embodiments, the T cell activating bispecific antigen binding molecule does not comprise an Fc domain. In certain embodiments, the T cell activating bispecific antigen binding molecule essentially consists of the first and the second Fab molecule, and optionally one or more peptide linkers, wherein the first Fab molecule is fused at the C-terminus of the Fab heavy chain to the N-terminus of the Fab heavy chain of the second Fab molecule. Such a configuration is schematically depicted in FIGS. 1O and 1S.

In other embodiments, the second Fab molecule is fused at the C-terminus of the Fab heavy chain to the N-terminus of the Fab heavy chain of the first Fab molecule. In certain such embodiments, the T cell activating bispecific antigen binding molecule does not comprise an Fc domain. In certain embodiments, the T cell activating bispecific antigen binding molecule essentially consists of the first and the second Fab molecule, and optionally one or more peptide linkers, wherein the second Fab molecule is fused at the C-terminus of the Fab heavy chain to the N-terminus of the Fab heavy chain of the first Fab molecule. Such a configuration is schematically depicted in FIGS. 1P and 1T.

In some embodiments, the first Fab molecule is fused at the C-terminus of the Fab heavy chain to the N-terminus of the Fab heavy chain of the second Fab molecule, and the T cell activating bispecific antigen binding molecule further comprises a third Fab molecule, wherein said third Fab molecule is fused at the C-terminus of the Fab heavy chain to the N-terminus of the Fab heavy chain of the first Fab molecule. In particular such embodiments, said third Fab molecule is a conventional Fab molecule. In other such embodiments, said third Fab molecule is a crossover Fab molecule as described herein, i.e. a Fab molecule wherein the variable domains VH and VL of the Fab heavy and light chains are exchanged/replaced by each other. In certain such embodiments, the T cell activating bispecific antigen binding molecule essentially consists of the first, the second and the third Fab molecule, and optionally one or more peptide linkers, wherein the first Fab molecule is fused at the C-terminus of the Fab heavy chain to the N-terminus of the Fab heavy chain of the second Fab molecule, and the third Fab molecule is fused at the C-terminus of the Fab heavy chain to the N-terminus of the Fab heavy chain of the first Fab molecule. Such a configuration is schematically depicted in FIGS. 1Q and 1U (particular embodiments, wherein the third Fab molecule is a conventional Fab molecule and preferably identical to the first Fab molecule).

Figure 1W:
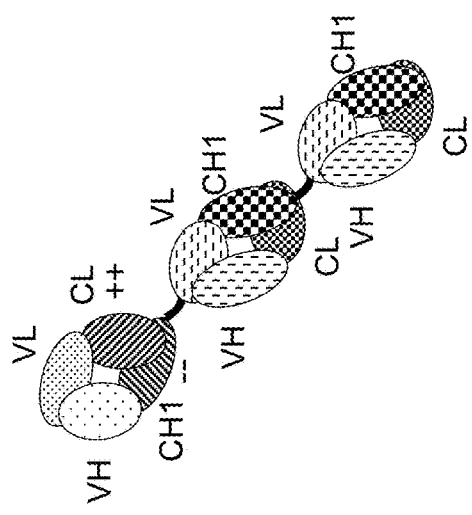
(FIG. 1W, FIG. 1Y) Illustration of the "Fab-(Crossfab)$_2$" molecule.
Figure 1Y:
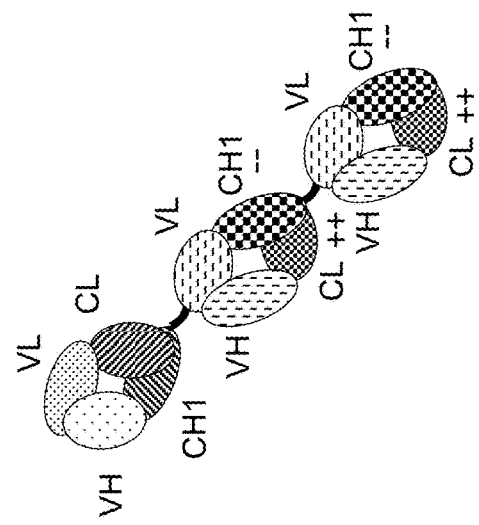

In some embodiments, the first Fab molecule is fused at the C-terminus of the Fab heavy chain to the N-terminus of the Fab heavy chain of the second Fab molecule, and the T cell activating bispecific antigen binding molecule further comprises a third Fab molecule, wherein said third Fab molecule is fused at the N-terminus of the Fab heavy chain to the C-terminus of the Fab heavy chain of the second Fab molecule. In particular such embodiments, said third Fab molecule is a crossover Fab molecule as described herein, i.e. a Fab molecule wherein the variable domains VH and VL of the Fab heavy and light chains are exchanged/replaced by each other. In other such embodiments, said third Fab molecule is a conventional Fab molecule. In certain such embodiments, the T cell activating bispecific antigen binding molecule essentially consists of the first, the second and the third Fab molecule, and optionally one or more peptide linkers, wherein the first Fab molecule is fused at the C-terminus of the Fab heavy chain to the N-terminus of the Fab heavy chain of the second Fab molecule, and the third Fab molecule is fused at the N-terminus of the Fab heavy chain to the C-terminus of the Fab heavy chain of the second Fab molecule. Such a configuration is schematically depicted in FIGS. 1W and 1Y (particular embodiments, wherein the third Fab molecule is a crossover Fab molecule and preferably identical to the second Fab molecule).

In some embodiments, the second Fab molecule is fused at the C-terminus of the Fab heavy chain to the N-terminus of the Fab heavy chain of the first Fab molecule, and the T cell activating bispecific antigen binding molecule further comprises a third Fab molecule, wherein said third Fab molecule is fused at the N-terminus of the Fab heavy chain to the C-terminus of the Fab heavy chain of the first Fab molecule. In particular such embodiments, said third Fab molecule is a conventional Fab molecule. In other such embodiments, said third Fab molecule is a crossover Fab molecule as described herein, i.e. a Fab molecule wherein the variable domains VH and VL of the Fab heavy and light chains are exchanged/replaced by each other. In certain such embodiments, the T cell activating bispecific antigen binding molecule essentially consists of the first, the second and the third Fab molecule, and optionally one or more peptide linkers, wherein the second Fab molecule is fused at the C-terminus of the Fab heavy chain to the N-terminus of the Fab heavy chain of the first Fab molecule, and the third Fab molecule is fused at the N-terminus of the Fab heavy chain to the C-terminus of the Fab heavy chain of the first Fab molecule. Such a configuration is schematically depicted in FIGS. 1R and 1V (particular embodiments, wherein the third Fab molecule is a conventional Fab molecule and preferably identical to the first Fab molecule).

In some embodiments, the second Fab molecule is fused at the C-terminus of the Fab heavy chain to the N-terminus of the Fab heavy chain of the first Fab molecule, and the T cell activating bispecific antigen binding molecule further comprises a third Fab molecule, wherein said third Fab molecule is fused at the C-terminus of the Fab heavy chain to the N-terminus of the Fab heavy chain of the second Fab molecule. In particular such embodiments, said third Fab molecule is a crossover Fab molecule as described herein, i.e. a Fab molecule wherein the variable domains VH and VL of the Fab heavy and light chains are exchanged/replaced by each other. In other such embodiments, said third Fab molecule is a conventional Fab molecule. In certain such embodiments, the T cell activating bispecific antigen binding molecule essentially consists of the first, the second and the third Fab molecule, and optionally one or more peptide linkers, wherein the second Fab molecule is fused at the C-terminus of the Fab heavy chain to the N-terminus of the Fab heavy chain of the first Fab molecule, and the third Fab molecule is fused at the C-terminus of the Fab heavy chain to the N-terminus of the Fab heavy chain of the second Fab molecule. Such a configuration is schematically depicted in FIGS. 1X and 1Z (particular embodiments, wherein the third Fab molecule is a crossover Fab molecule and preferably identical to the first Fab molecule).

In certain embodiments the T cell activating bispecific antigen binding molecule according to the invention comprises a polypeptide wherein the Fab heavy chain of the first Fab molecule shares a carboxy-terminal peptide bond with the Fab light chain variable region of the second Fab molecule, which in turn shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region) ($VH_{(1)}$-$CH1_{(1)}$-$VL_{(2)}$-$CH1_{(2)}$). In some embodiments the T cell activating bispecific antigen binding molecule further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$). In certain embodiments the T cell activating bispecific antigen binding molecule according to the invention comprises a polypeptide wherein the Fab light chain variable region of the second Fab molecule shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab heavy chain of the first Fab molecule ($VL_{(2)}$-$CH1_{(2)}$-$VH_{(1)}$-$CH1_{(1)}$). In some embodiments the T cell activating bispecific antigen binding molecule further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$).

In certain embodiments the T cell activating bispecific antigen binding molecule according to the invention comprises a polypeptide wherein the Fab heavy chain of a third Fab molecule shares a carboxy-terminal peptide bond with the Fab heavy chain of the first Fab molecule, which in turn shares a carboxy-terminal peptide bond with the Fab light chain variable region of the second Fab molecule, which in turn shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region) ($VH_{(3)}$-$CH1_{(3)}$-$VH_{(1)}$-$CH1_{(1)}$-$VL_{(2)}$-$CH1_{(2)}$). In some embodiments the T cell activating bispecific antigen binding molecule further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$). In some embodiments the T cell activating bispecific antigen binding molecule further comprises the Fab light chain polypeptide of a third Fab molecule ($VL_{(3)}$-$CL_{(3)}$).

In certain embodiments the T cell activating bispecific antigen binding molecule according to the invention comprises a polypeptide wherein the Fab light chain variable region of the second Fab molecule shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab heavy chain of the first Fab molecule, which in turn shares a carboxy-terminal peptide bond with the Fab heavy chain of a third Fab molecule ($VL_{(2)}$-$CH1_{(2)}$-$VH_{(1)}$-$CH1_{(1)}$-$VH_{(3)}$-$CH1_{(3)}$). In some embodiments the T cell activating bispecific antigen binding molecule further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$). In some embodiments the T cell activating bispecific antigen binding molecule further comprises the Fab light chain polypeptide of a third Fab molecule ($VL_{(3)}$-$CL_{(3)}$).

In certain embodiments the T cell activating bispecific antigen binding molecule according to the invention comprises a polypeptide wherein the Fab heavy chain of the first Fab molecule shares a carboxy-terminal peptide bond with the Fab light chain variable region of the second Fab molecule, which in turn shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab light chain variable region of a third Fab molecule, which in turn shares a carboxy-terminal peptide bond with the Fab heavy chain constant region of a third Fab molecule (i.e. the third Fab molecule comprises a crossover Fab heavy chain, wherein the heavy chain variable region is replaced by a light chain variable region) ($VH_{(1)}$-$CH1_{(1)}$-$VL_{(2)}$-$CH1_{(2)}$-$VL_{(3)}$-$CH1_{(3)}$). In some embodiments the T cell activating bispecific antigen binding molecule further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$). In some embodiments the T cell activating bispecific antigen binding molecule further comprises a polypeptide wherein the Fab heavy chain variable region of a third Fab molecule shares a carboxy-terminal peptide bond with the Fab light chain constant region of a third Fab molecule ($VH_{(3)}$-$CL_{(3)}$). In certain embodiments the T cell activating bispecific antigen binding molecule according to the invention comprises a polypeptide wherein the Fab light chain variable region of a third Fab molecule shares a carboxy-terminal peptide bond with the Fab heavy chain constant region of a third Fab molecule (i.e. the third Fab molecule comprises a crossover Fab heavy chain, wherein the heavy chain variable region is replaced by a light chain variable region), which in turn shares a carboxy-terminal peptide bond with the Fab light chain variable region of the second Fab molecule, which in turn shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab heavy chain of the first Fab molecule ($VL_{(3)}$-$CH1_{(3)}$-$VL_{(2)}$-$CH1_{(2)}$-$VH_{(1)}$-$CH1_{(1)}$). In some embodiments the T cell activating bispecific antigen binding molecule further comprises a polypeptide wherein the Fab heavy chain variable region of the second Fab molecule shares a carboxy-terminal peptide bond with the Fab light chain constant region of the second Fab molecule (VH$_{(2)}$-CL$_{(2)}$) and the Fab light chain polypeptide of the first Fab molecule (VL$_{(1)}$-CL$_{(1)}$). In some embodiments the T cell activating bispecific antigen binding molecule further comprises a polypeptide wherein the Fab heavy chain variable region of a third Fab molecule shares a carboxy-terminal peptide bond with the Fab light chain constant region of a third Fab molecule (VH$_{(3)}$-CL$_{(3)}$).

According to any of the above embodiments, components of the T cell activating bispecific antigen binding molecule (e.g. Fab molecules, Fc domain) may be fused directly or through various linkers, particularly peptide linkers comprising one or more amino acids, typically about 2-20 amino acids, that are described herein or are known in the art. Suitable, non-immunogenic peptide linkers include, for example, (G$_4$S)$_n$, (SG$_4$)$_n$, (G$_4$S)$_n$ or G$_4$(SG$_4$)$_n$ peptide linkers, wherein n is generally an integer from 1 to 10, typically from 2 to 4.

Fc Domain

The Fc domain of the T cell activating bispecific antigen binding molecule consists of a pair of polypeptide chains comprising heavy chain domains of an immunoglobulin molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other. In one embodiment the T cell activating bispecific antigen binding molecule of the invention comprises not more than one Fc domain.

In one embodiment according the invention the Fc domain of the T cell activating bispecific antigen binding molecule is an IgG Fc domain. In a particular embodiment the Fc domain is an IgG$_1$ Fc domain. In another embodiment the Fc domain is an IgG$_4$ Fc domain. In a more specific embodiment, the Fc domain is an IgG$_4$ Fc domain comprising an amino acid substitution at position S228 (Kabat numbering), particularly the amino acid substitution S228P. This amino acid substitution reduces in vivo Fab arm exchange of IgG$_4$ antibodies (see Stubenrauch et al., Drug Metabolism and Disposition 38, 84-91 (2010)). In a further particular embodiment the Fc domain is human. An exemplary sequence of a human IgG$_1$ Fc region is given in SEQ ID NO: 13.

Fc Domain Modifications Promoting Heterodimerization

T cell activating bispecific antigen binding molecules according to the invention comprise different Fab molecules, fused to one or the other of the two subunits of the Fc domain, thus the two subunits of the Fc domain are typically comprised in two non-identical polypeptide chains. Recombinant co-expression of these polypeptides and subsequent dimerization leads to several possible combinations of the two polypeptides. To improve the yield and purity of T cell activating bispecific antigen binding molecules in recombinant production, it will thus be advantageous to introduce in the Fc domain of the T cell activating bispecific antigen binding molecule a modification promoting the association of the desired polypeptides.

Accordingly, in particular embodiments the Fc domain of the T cell activating bispecific antigen binding molecule according to the invention comprises a modification promoting the association of the first and second subunit of the Fc domain. The site of most extensive protein-protein interaction between the two subunits of a human IgG Fc domain is in the CH3 domain of the Fc domain. Thus, in one embodiment said modification is in the CH3 domain of the Fc domain.

There exist several approaches for modifications in the CH3 domain of the Fc domain in order to enforce heterodimerization, which are well described e.g. in WO 96/27011, WO 98/050431, EP 1870459, WO 2007/110205, WO 2007/147901, WO 2009/089004, WO 2010/129304, WO 2011/90754, WO 2011/143545, WO 2012058768, WO 2013157954, WO 2013096291. Typically, in all such approaches the CH3 domain of the first subunit of the Fc domain and the CH3 domain of the second subunit of the Fc domain are both engineered in a complementary manner so that each CH3 domain (or the heavy chain comprising it) can no longer homodimerize with itself but is forced to heterodimerize with the complementarily engineered other CH3 domain (so that the first and second CH3 domain heterodimerize and no homdimers between the two first or the two second CH3 domains are formed). These different approaches for improved heavy chain heterodimerization are contemplated as different alternatives in combination with the heavy-light chain modifications (VH and VL exchange/replacement in one binding arm and the introduction of substitutions of charged amino acids with opposite charges in the CH1/CL interface) in the T cell activating bispecific antigen binding molecule according to the invention which reduce light chain mispairing and Bence Jones-type side products.

In a specific embodiment said modification promoting the association of the first and the second subunit of the Fc domain is a so-called "knob-into-hole" modification, comprising a "knob" modification in one of the two subunits of the Fc domain and a "hole" modification in the other one of the two subunits of the Fc domain.

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in a particular embodiment, in the CH3 domain of the first subunit of the Fc domain of the T cell activating bispecific antigen binding molecule an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

Preferably said amino acid residue having a larger side chain volume is selected from the group consisting of arginine (R), phenylalanine (F), tyrosine (Y), and tryptophan (W).

Preferably said amino acid residue having a smaller side chain volume is selected from the group consisting of alanine (A), serine (S), threonine (T), and valine (V).

The protuberance and cavity can be made by altering the nucleic acid encoding the polypeptides, e.g. by site-specific mutagenesis, or by peptide synthesis.

In a specific embodiment, in the CH3 domain of the first subunit of the Fc domain (the "knobs" subunit) the threonine residue at position 366 is replaced with a tryptophan residue (T366W), and in the CH3 domain of the second subunit of the Fc domain (the "hole" subunit) the tyrosine residue at position 407 is replaced with a valine residue (Y407V). In one embodiment, in the second subunit of the Fc domain additionally the threonine residue at position 366 is replaced with a serine residue (T366S) and the leucine residue at position 368 is replaced with an alanine residue (L368A) (numberings according to Kabat EU index).

In yet a further embodiment, in the first subunit of the Fc domain additionally the serine residue at position 354 is replaced with a cysteine residue (S354C) or the glutamic acid residue at position 356 is replaced with a cysteine residue (E356C), and in the second subunit of the Fc domain additionally the tyrosine residue at position 349 is replaced by a cysteine residue (Y349C) (numberings according to Kabat EU index). Introduction of these two cysteine residues results in formation of a disulfide bridge between the two subunits of the Fc domain, further stabilizing the dimer (Carter, J Immunol Methods 248, 7-15 (2001)).

In a particular embodiment, the first subunit of the Fc domain comprises amino acid substitutions S354C and T366W, and the second subunit of the Fc domain comprises amino acid substitutions Y349C, T366S, L368A and Y407V (numbering according to Kabat EU index).

In a particular embodiment the Fab molecule which specifically binds an activating T cell antigen is fused (optionally via a Fab molecule which specifically binds to a target cell antigen) to the first subunit of the Fc domain (comprising the "knob" modification). Without wishing to be bound by theory, fusion of the Fab molecule which specifically binds an activating T cell antigen to the knob-containing subunit of the Fc domain will (further) minimize the generation of antigen binding molecules comprising two Fab molecules which bind to an activating T cell antigen (steric clash of two knob-containing polypeptides).

Other techniques of CH3-modification for enforcing the heterodimerization are contemplated as alternatives according to the invention and are described e.g. in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291.

In one embodiment the heterodimerization approach described in EP 1870459 A1, is used alternatively. This approach is based on the introduction of charged amino acids with opposite charges at specific amino acid positions in the CH3/CH3 domain interface between the two subunits of the Fc domain. One preferred embodiment for the T cell activating bispecific antigen binding molecule of the invention are amino acid mutations R409D; K370E in one of the two CH3 domains (of the Fc domain) and amino acid mutations D399K; E357K in the other one of the CH3 domains of the Fc domain (numbering according to Kabat EU index).

In another embodiment the T cell activating bispecific antigen binding molecule of the invention comprises amino acid mutation T366W in the CH3 domain of the first subunit of the Fc domain and amino acid mutations T366S, L368A, Y407V in the CH3 domain of the second subunit of the Fc domain, and additionally amino acid mutations R409D; K370E in the CH3 domain of the first subunit of the Fc domain and amino acid mutations D399K; E357K in the CH3 domain of the second subunit of the Fc domain (numberings according to Kabat EU index).

In another embodiment T cell activating bispecific antigen binding molecule of the invention comprises amino acid mutations S354C, T366W in the CH3 domain of the first subunit of the Fc domain and amino acid mutations Y349C, T366S, L368A, Y407V in the CH3 domain of the second subunit of the Fc domain, or said T cell activating bispecific antigen binding molecule comprises amino acid mutations Y349C, T366W in the CH3 domain of the first subunit of the Fc domain and amino acid mutations S354C, T366S, L368A, Y407V in the CH3 domains of the second subunit of the Fc domain and additionally amino acid mutations R409D; K370E in the CH3 domain of the first subunit of the Fc domain and amino acid mutations D399K; E357K in the CH3 domain of the second subunit of the Fc domain (all numberings according to Kabat EU index).

In one embodiment the heterodimerization approach described in WO 2013/157953 is used alternatively. In one embodiment a first CH3 domain comprises amino acid mutation T366K and a second CH3 domain comprises amino acid mutation L351D (numberings according to Kabat EU index). In a further embodiment the first CH3 domain comprises further amino acid mutation L351K. In a further embodiment the second CH3 domain comprises further an amino acid mutation selected from Y349E, Y349D and L368E (preferably L368E) (numberings according to Kabat EU index).

In one embodiment the heterodimerization approach described in WO 2012/058768 is used alternatively. In one embodiment a first CH3 domain comprises amino acid mutations L351Y, Y407A and a second CH3 domain comprises amino acid mutations T366A, K409F. In a further embodiment the second CH3 domain comprises a further amino acid mutation at position T411, D399, 5400, F405, N390, or K392, e.g. selected from a) T411N, T411R, T411Q, T411K, T411D, T411E or T411W, b) D399R, D399W, D399Y or D399K, c) S400E, S400D, S400R, or S400K, d) F4051, F405M, F405T, F405S, F405V or F405W, e) N390R, N390K or N390D, f) K392V, K392M, K392R, K392L, K392F or K392E (numberings according to Kabat EU index). In a further embodiment a first CH3 domain comprises amino acid mutations L351Y, Y407A and a second CH3 domain comprises amino acid mutations T366V, K409F. In a further embodiment a first CH3 domain comprises amino acid mutation Y407A and a second CH3 domain comprises amino acid mutations T366A, K409F. In a further embodiment the second CH3 domain further comprises amino acid mutations K392E, T411E, D399R and S400R (numberings according to Kabat EU index).

In one embodiment the heterodimerization approach described in WO 2011/143545 is used alternatively, e.g. with the amino acid modification at a position selected from the group consisting of 368 and 409 (numbering according to Kabat EU index).

In one embodiment the heterodimerization approach described in WO 2011/090762, which also uses the knobs-into-holes technology described above, is used alternatively. In one embodiment a first CH3 domain comprises amino acid mutation T366W and a second CH3 domain comprises amino acid mutation Y407A. In one embodiment a first CH3 domain comprises amino acid mutation T366Y and a second CH3 domain comprises amino acid mutation Y407T (numberings according to Kabat EU index).

In one embodiment the T cell activating bispecific antigen binding molecule or its Fc domain is of IgG$_2$ subclass and the heterodimerization approach described in WO 2010/129304 is used alternatively.

In an alternative embodiment a modification promoting association of the first and the second subunit of the Fc domain comprises a modification mediating electrostatic steering effects, e.g. as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable. In one such embodiment a first CH3 domain comprises amino acid substitution of K392 or N392 with a negatively charged amino acid (e.g. glutamic acid (E), or aspartic acid (D), preferably K392D or N392D) and a second CH3 domain comprises amino acid substitution of D399, E356, D356, or E357 with a positively charged amino acid (e.g. lysine (K) or arginine (R), preferably D399K, E356K, D356K, or E357K, and more preferably D399K and E356K). In a further embodiment the first CH3 domain further comprises amino acid substitution of K409 or R409 with a negatively charged amino acid (e.g. glutamic acid (E), or aspartic acid (D), preferably K409D or R409D). In a further embodiment the first CH3 domain further or alternatively comprises amino acid substitution of K439 and/or K370 with a negatively charged amino acid (e.g. glutamic acid (E), or aspartic acid (D)) (all numberings according to Kabat EU index).

In yet a further embodiment the heterodimerization approach described in WO 2007/147901 is used alternatively. In one embodiment a first CH3 domain comprises amino acid mutations K253E, D282K, and K322D and a second CH3 domain comprises amino acid mutations D239K, E240K, and K292D (numberings according to Kabat EU index).

In still another embodiment the heterodimerization approach described in WO 2007/110205 can be used alternatively.

In one embodiment, the first subunit of the Fc domain comprises amino acid substitutions K392D and K409D, and the second subunit of the Fc domain comprises amino acid substitutions D356K and D399K (numbering according to Kabat EU index).

Fc Domain Modifications Reducing Fc Receptor Binding and/or Effector Function

The Fc domain confers to the T cell activating bispecific antigen binding molecule favorable pharmacokinetic properties, including a long serum half-life which contributes to good accumulation in the target tissue and a favorable tissue-blood distribution ratio. At the same time it may, however, lead to undesirable targeting of the T cell activating bispecific antigen binding molecule to cells expressing Fc receptors rather than to the preferred antigen-bearing cells. Moreover, the co-activation of Fc receptor signaling pathways may lead to cytokine release which, in combination with the T cell activating properties and the long half-life of the antigen binding molecule, results in excessive activation of cytokine receptors and severe side effects upon systemic administration. Activation of (Fc receptor-bearing) immune cells other than T cells may even reduce efficacy of the T cell activating bispecific antigen binding molecule due to the potential destruction of T cells e.g. by NK cells.

Accordingly, in particular embodiments, the Fc domain of the T cell activating bispecific antigen binding molecules according to the invention exhibits reduced binding affinity to an Fc receptor and/or reduced effector function, as compared to a native IgG$_1$ Fc domain. In one such embodiment the Fc domain (or the T cell activating bispecific antigen binding molecule comprising said Fc domain) exhibits less than 50%, preferably less than 20%, more preferably less than 10% and most preferably less than 5% of the binding affinity to an Fc receptor, as compared to a native IgG$_1$ Fc domain (or a T cell activating bispecific antigen binding molecule comprising a native IgG$_1$ Fc domain), and/or less than 50%, preferably less than 20%, more preferably less than 10% and most preferably less than 5% of the effector function, as compared to a native IgG$_1$ Fc domain domain (or a T cell activating bispecific antigen binding molecule comprising a native IgG$_1$ Fc domain). In one embodiment, the Fc domain domain (or the T cell activating bispecific antigen binding molecule comprising said Fc domain) does not substantially bind to an Fc receptor and/or induce effector function. In a particular embodiment the Fc receptor is an Fcγ receptor. In one embodiment the Fc receptor is a human Fc receptor. In one embodiment the Fc receptor is an activating Fc receptor. In a specific embodiment the Fc receptor is an activating human Fcγ receptor, more specifically human FcγRIIIa, FcγRI or FcγRIIa, most specifically human FcγRIIIa. In one embodiment the effector function is one or more selected from the group of CDC, ADCC, ADCP, and cytokine secretion. In a particular embodiment the effector function is ADCC. In one embodiment the Fc domain domain exhibits substantially similar binding affinity to neonatal Fc receptor (FcRn), as compared to a native IgG$_1$ Fc domain domain. Substantially similar binding to FcRn is achieved when the Fc domain (or the T cell activating bispecific antigen binding molecule comprising said Fc domain) exhibits greater than about 70%, particularly greater than about 80%, more particularly greater than about 90% of the binding affinity of a native IgG$_1$ Fc domain (or the T cell activating bispecific antigen binding molecule comprising a native IgG$_1$ Fc domain) to FcRn.

In certain embodiments the Fc domain is engineered to have reduced binding affinity to an Fc receptor and/or reduced effector function, as compared to a non-engineered Fc domain. In particular embodiments, the Fc domain of the T cell activating bispecific antigen binding molecule comprises one or more amino acid mutation that reduces the binding affinity of the Fc domain to an Fc receptor and/or effector function. Typically, the same one or more amino acid mutation is present in each of the two subunits of the Fc domain. In one embodiment the amino acid mutation reduces the binding affinity of the Fc domain to an Fc receptor. In one embodiment the amino acid mutation reduces the binding affinity of the Fc domain to an Fc receptor by at least 2-fold, at least 5-fold, or at least 10-fold. In embodiments where there is more than one amino acid mutation that reduces the binding affinity of the Fc domain to the Fc receptor, the combination of these amino acid mutations may reduce the binding affinity of the Fc domain to an Fc receptor by at least 10-fold, at least 20-fold, or even at least 50-fold. In one embodiment the T cell activating bispecific antigen binding molecule comprising an engineered Fc domain exhibits less than 20%, particularly less than 10%, more particularly less than 5% of the binding affinity to an Fc receptor as compared to a T cell activating bispecific antigen binding molecule comprising a non-engineered Fc domain. In a particular embodiment the Fc receptor is an Fcγ receptor. In some embodiments the Fc receptor is a human Fc receptor. In some embodiments the Fc receptor is an activating Fc receptor. In a specific embodiment the Fc receptor is an activating human Fcγ receptor, more specifically human FcγRIIIa, FcγRI or FcγRIIa, most specifically human FcγRIIIa. Preferably, binding to each of these receptors is reduced. In some embodiments binding affinity to a complement component, specifically binding affinity to C1q, is also reduced. In one embodiment binding affinity to neonatal Fc receptor (FcRn) is not reduced. Substantially similar binding to FcRn, i.e. preservation of the binding affinity of the Fc domain to said receptor, is achieved when the Fc domain (or the T cell activating bispecific antigen binding molecule comprising said Fc domain) exhibits greater than about 70% of the binding affinity of a non-engineered form of the Fc domain (or the T cell activating bispecific antigen binding molecule comprising said non-engineered form of the Fc domain) to FcRn. The Fc domain, or T cell activating bispecific antigen binding molecules of the invention comprising said Fc domain, may exhibit greater than about 80% and even greater than about 90% of such affinity. In certain embodiments the Fc domain of the T cell activating bispecific antigen binding molecule is engineered to have reduced effector function, as compared to a non-engineered Fc domain. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced crosslinking of target-bound antibodies, reduced dendritic cell maturation, or reduced T cell priming. In one embodiment the reduced effector function is one or more selected from the group of reduced CDC, reduced ADCC, reduced ADCP, and reduced cytokine secretion. In a particular embodiment the reduced effector function is reduced ADCC. In one embodiment the reduced ADCC is less than 20% of the ADCC induced by a non-engineered Fc domain (or a T cell activating bispecific antigen binding molecule comprising a non-engineered Fc domain).

In one embodiment the amino acid mutation that reduces the binding affinity of the Fc domain to an Fc receptor and/or effector function is an amino acid substitution. In one embodiment the Fc domain comprises an amino acid substitution at a position selected from the group of E233, L234, L235, N297, P331 and P329 (numberings according to Kabat EU index). In a more specific embodiment the Fc domain comprises an amino acid substitution at a position selected from the group of L234, L235 and P329 (numberings according to Kabat EU index). In some embodiments the Fc domain comprises the amino acid substitutions L234A and L235A (numberings according to Kabat EU index). In one such embodiment, the Fc domain is an IgG$_1$ Fc domain, particularly a human IgG$_1$ Fc domain. In one embodiment the Fc domain comprises an amino acid substitution at position P329. In a more specific embodiment the amino acid substitution is P329A or P329G, particularly P329G (numberings according to Kabat EU index). In one embodiment the Fc domain comprises an amino acid substitution at position P329 and a further amino acid substitution at a position selected from E233, L234, L235, N297 and P331 (numberings according to Kabat EU index). In a more specific embodiment the further amino acid substitution is E233P, L234A, L235A, L235E, N297A, N297D or P331S. In particular embodiments the Fc domain comprises amino acid substitutions at positions P329, L234 and L235 (numberings according to Kabat EU index). In more particular embodiments the Fc domain comprises the amino acid mutations L234A, L235A and P329G ("P329G LALA"). In one such embodiment, the Fc domain is an IgG$_1$ Fc domain, particularly a human IgG$_1$ Fc domain. The "P329G LALA" combination of amino acid substitutions almost completely abolishes Fcγ receptor (as well as complement) binding of a human IgG$_1$ Fc domain, as described in PCT publication no. WO 2012/130831, incorporated herein by reference in its entirety. WO 2012/130831 also describes methods of preparing such mutant Fc domains and methods for determining its properties such as Fc receptor binding or effector functions.

IgG$_4$ antibodies exhibit reduced binding affinity to Fc receptors and reduced effector functions as compared to IgG$_1$ antibodies. Hence, in some embodiments the Fc domain of the T cell activating bispecific antigen binding molecules of the invention is an IgG$_4$ Fc domain, particularly a human IgG$_4$ Fc domain. In one embodiment the IgG$_4$ Fc domain comprises amino acid substitutions at position S228, specifically the amino acid substitution S228P (numberings according to Kabat EU index). To further reduce its binding affinity to an Fc receptor and/or its effector function, in one embodiment the IgG$_4$ Fc domain comprises an amino acid substitution at position L235, specifically the amino acid substitution L235E (numberings according to Kabat EU index). In another embodiment, the IgG$_4$ Fc domain comprises an amino acid substitution at position P329, specifically the amino acid substitution P329G (numberings according to Kabat EU index). In a particular embodiment, the IgG$_4$ Fc domain comprises amino acid substitutions at positions S228, L235 and P329, specifically amino acid substitutions S228P, L235E and P329G (numberings according to Kabat EU index). Such IgG$_4$ Fc domain mutants and their Fcγ receptor binding properties are described in PCT publication no. WO 2012/130831, incorporated herein by reference in its entirety.

In a particular embodiment the Fc domain exhibiting reduced binding affinity to an Fc receptor and/or reduced effector function, as compared to a native IgG$_1$ Fc domain, is a human IgG$_1$ Fc domain comprising the amino acid substitutions L234A, L235A and optionally P329G, or a human IgG$_4$ Fc domain comprising the amino acid substitutions S228P, L235E and optionally P329G (numberings according to Kabat EU index).

In certain embodiments N-glycosylation of the Fc domain has been eliminated. In one such embodiment the Fc domain comprises an amino acid mutation at position N297, particularly an amino acid substitution replacing asparagine by alanine (N297A) or aspartic acid (N297D) (numberings according to Kabat EU index).

In addition to the Fc domains described hereinabove and in PCT publication no. WO 2012/130831, Fc domains with reduced Fc receptor binding and/or effector function also include those with substitution of one or more of Fc domain residues 238, 265, 269, 270, 297, 327 and 329 (U.S. Pat. No. 6,737,056) (numberings according to Kabat EU index). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g. by ELISA, or by Surface Plasmon Resonance (SPR) using standard instrumentation such as a BIAcore instrument (GE Healthcare), and Fc receptors such as may be obtained by recombinant expression. A suitable such binding assay is described herein. Alternatively, binding affinity of Fc domains or cell activating bispecific antigen binding molecules comprising an Fc domain for Fc receptors may be evaluated using cell lines known to express particular Fc receptors, such as human NK cells expressing FcγIIIa receptor.

Effector function of an Fc domain, or a T cell activating bispecific antigen binding molecule comprising an Fc domain, can be measured by methods known in the art. A suitable assay for measuring ADCC is described herein. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, Calif.); and CytoTox 96® non-radioactive cytotoxicity assay (Promega, Madison, Wis.)). Useful effector cells for such assays include peripheral blood mononuclear cells (PBMC) and Natural Killer (NK) cells. Alternatively, or additionally, ADCC activity of the molecule of interest may be assessed in vivo, e.g. in a animal model such as that disclosed in Clynes et al., Proc Natl Acad Sci USA 95, 652-656 (1998).

In some embodiments, binding of the Fc domain to a complement component, specifically to C1q, is reduced. Accordingly, in some embodiments wherein the Fc domain is engineered to have reduced effector function, said reduced effector function includes reduced CDC. C1q binding assays may be carried out to determine whether the T cell activating bispecific antigen binding molecule is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

Antigen Binding Moieties

The antigen binding molecule of the invention is bispecific, i.e. it comprises at least two antigen binding moieties capable of specific binding to two distinct antigenic determinants. According to the invention, the antigen binding moieties are Fab molecules (i.e. antigen binding domains composed of a heavy and a light chain, each comprising a variable and a constant domain). In one embodiment said Fab molecules are human. In another embodiment said Fab molecules are humanized. In yet another embodiment said Fab molecules comprise human heavy and light chain constant domains.

At least one of the antigen binding moieties is a crossover Fab molecule. Such modification reduces mispairing of heavy and light chains from different Fab molecules, thereby improving the yield and purity of the T cell activating bispecific antigen binding molecule of the invention in recombinant production. In a particular crossover Fab molecule useful for the T cell activating bispecific antigen binding molecule of the invention, the variable domains of the Fab light chain and the Fab heavy chain (VL and VH, respectively) are exchanged. Even with this domain exchange, however, the preparation of the T cell activating bispecific antigen binding molecule may comprise certain side products due to a so-called Bence Jones-type interaction between mispaired heavy and light chains (see Schaefer et al, PNAS, 108 (2011) 11187-11191). To further reduce mispairing of heavy and light chains from different Fab molecules and thus increase the purity and yield of the desired T cell activating bispecific antigen binding molecule, according to the present invention charged amino acids with opposite charges are introduced at specific amino acid positions in the CH1 and CL domains of either the Fab molecule(s) specifically binding to a target cell antigen, or the Fab molecule specifically binding to an activating T cell antigen. Charge modifications are made either in the conventional Fab molecule(s) comprised in the T cell activating bispecific antigen binding molecule (such as shown e.g. in FIGS. 1A-1C and 1G-1J), or in the crossover Fab molecule(s) comprised in the T cell activating bispecific antigen binding molecule (such as shown e.g. in FIGS. 1D-1F and 1K-1N) (but not in both). In particular embodiments, the charge modifications are made in the conventional Fab molecule(s) comprised in the T cell activating bispecific antigen binding molecule (which in particular embodiments specifically bind(s) to the target cell antigen).

In a particular embodiment according to the invention, the T cell activating bispecific antigen binding molecule is capable of simultaneous binding to a target cell antigen, particularly a tumor cell antigen, and an activating T cell antigen, particularly CD3. In one embodiment, the T cell activating bispecific antigen binding molecule is capable of crosslinking a T cell and a target cell by simultaneous binding to a target cell antigen and an activating T cell antigen. In an even more particular embodiment, such simultaneous binding results in lysis of the target cell, particularly a tumor cell. In one embodiment, such simultaneous binding results in activation of the T cell. In other embodiments, such simultaneous binding results in a cellular response of a T lymphocyte, particularly a cytotoxic T lymphocyte, selected from the group of: proliferation, differentiation, cytokine secretion, cytotoxic effector molecule release, cytotoxic activity, and expression of activation markers. In one embodiment, binding of the T cell activating bispecific antigen binding molecule to the activating T cell antigen, particularly CD3, without simultaneous binding to the target cell antigen does not result in T cell activation.

In one embodiment, the T cell activating bispecific antigen binding molecule is capable of re-directing cytotoxic activity of a T cell to a target cell. In a particular embodiment, said re-direction is independent of MHC-mediated peptide antigen presentation by the target cell and and/or specificity of the T cell.

Particularly, a T cell according to any of the embodiments of the invention is a cytotoxic T cell. In some embodiments the T cell is a CD4$^+$ or a CD8$^+$ T cell, particularly a CD8$^+$ T cell.

Activating T Cell Antigen Binding Fab Molecule

The T cell activating bispecific antigen binding molecule of the invention comprises at least one Fab molecule which specifically binds to an activating T cell antigen (also referred to herein as an "activating T cell antigen binding Fab molecule"). In a particular embodiment, the T cell activating bispecific antigen binding molecule comprises not more than one Fab molecule (or other Fab molecule) capable of specific binding to an activating T cell antigen. In one embodiment the T cell activating bispecific antigen binding molecule provides monovalent binding to the activating T cell antigen.

In particular embodiments, the Fab molecule which specifically binds an activating T cell antigen is a crossover Fab molecule as described herein, i.e. a Fab molecule wherein the variable domains VH and VL of the Fab heavy and light chains are exchanged/replaced by each other. In such embodiments, the Fab molecule(s) which specifically binds a target cell antigen is a conventional Fab molecule. In embodiments where there is more than one Fab molecule which specifically binds to a target cell antigen comprised in the T cell activating bispecific antigen binding molecule, the Fab molecule which specifically binds to an activating T cell antigen preferably is a crossover Fab molecule and the Fab molecules which specifically bind to a target cell antigen are conventional Fab molecules.

In alternative embodiments, the Fab molecule which specifically binds an activating T cell antigen is a conventional Fab molecule. In such embodiments, the Fab molecule(s) which specifically binds a target cell antigen is a crossover Fab molecule as described herein, i.e. a Fab molecule wherein the variable domains VH and VL of the Fab heavy and light chains are exchanged/replaced by each other.

In a particular embodiment the activating T cell antigen is CD3, particularly human CD3 (SEQ ID NO: 1) or cynomolgus CD3 (SEQ ID NO: 2), most particularly human CD3. In a particular embodiment the activating T cell antigen binding Fab molecule is cross-reactive for (i.e. specifically binds to) human and cynomolgus CD3. In some embodiments, the activating T cell antigen is the epsilon subunit of CD3 (CD3 epsilon).

In some embodiments, the activating T cell antigen binding Fab molecule specifically binds to CD3, particularly CD3 epsilon, and comprises at least one heavy chain complementarity determining region (CDR) selected from the group consisting of SEQ ID NO: 4, SEQ ID NO: 5 and SEQ ID NO: 6 and at least one light chain CDR selected from the group of SEQ ID NO: 8, SEQ ID NO: 9, SEQ ID NO: 10.

In one embodiment the CD3 binding Fab molecule comprises a heavy chain variable region comprising the heavy chain CDR1 of SEQ ID NO: 4, the heavy chain CDR2 of SEQ ID NO: 5, the heavy chain CDR3 of SEQ ID NO: 6, and a light chain variable region comprising the light chain CDR1 of SEQ ID NO: 8, the light chain CDR2 of SEQ ID NO: 9, and the light chain CDR3 of SEQ ID NO: 10.

In another embodiment the CD3 binding Fab molecule comprises a heavy chain variable region comprising the heavy chain CDR1 of SEQ ID NO: 4, the heavy chain CDR2 of SEQ ID NO: 67, the heavy chain CDR3 of SEQ ID NO: 6, and a light chain variable region comprising the light chain CDR1 of SEQ ID NO: 68, the light chain CDR2 of SEQ ID NO: 9, and the light chain CDR3 of SEQ ID NO: 10.

In one embodiment the CD3 binding Fab molecule comprises a heavy chain variable region sequence that is at least about 95%, 96%, 97%, 98%, 99% or 100% identical to SEQ ID NO: 3 and a light chain variable region sequence that is at least about 95%, 96%, 97%, 98%, 99% or 100% identical to SEQ ID NO: 7.

In one embodiment the CD3 binding Fab molecule comprises a heavy chain variable region comprising the amino acid sequence of SEQ ID NO: 3 and a light chain variable region comprising the amino acid sequence of SEQ ID NO: 7.

In one embodiment the CD3 binding Fab molecule comprises the heavy chain variable region sequence of SEQ ID NO: 3 and the light chain variable region sequence of SEQ ID NO: 7.

Target Cell Antigen Binding Fab Molecule

The T cell activating bispecific antigen binding molecule of the invention comprises at least one Fab molecule which specifically binds to a target cell antigen (also referred to herein as "target cell antigen binding Fab molecule"). In certain embodiments, the T cell activating bispecific antigen binding molecule comprises two Fab molecules which specifically bind to a target cell antigen. In a particular such embodiment, each of these Fab molecules specifically binds to the same antigenic determinant. In an even more particular embodiment, all of these Fab molecules are identical, i.e. they comprise the same amino acid sequences including the same amino acid substitutions in the CH1 and CL domain as described herein (if any). In one embodiment, the T cell activating bispecific antigen binding molecule comprises an immunoglobulin molecule which specifically binds to a target cell antigen. In one embodiment the T cell activating bispecific antigen binding molecule comprises not more than two Fab molecules which specifically bind to a target cell antigen.

In particular embodiments, the Fab molecule(s) which specifically bind to a target cell antigen is/are a conventional Fab molecule. In such embodiments, the Fab molecule(s) which specifically binds an activating T cell antigen is a crossover Fab molecule as described herein, i.e. a Fab molecule wherein the variable domains VH and VL of the Fab heavy and light chains are exchanged/replaced by each other.

In alternative embodiments, the Fab molecule(s) which specifically bind to a target cell antigen is/are a crossover Fab molecule as described herein, i.e. a Fab molecule wherein the variable domains VH and VL of the Fab heavy and light chains are exchanged/replaced by each other. In such embodiments, the Fab molecule(s) which specifically binds an activating T cell antigen is a conventional Fab molecule.

The target cell antigen binding Fab molecule binds to a specific antigenic determinant and is able to direct the T cell activating bispecific antigen binding molecule to a target site, for example to a specific type of tumor cell that bears the antigenic determinant.

In certain embodiments the target cell antigen binding Fab molecule specifically binds to a cell surface antigen.

In certain embodiments the target cell antigen binding Fab molecule is directed to an antigen associated with a pathological condition, such as an antigen presented on a tumor cell or on a virus-infected cell. Suitable target cell antigens are cell surface antigens, for example, but not limited to, cell surface receptors. In particular embodiments the target cell antigen is a human antigen. Exemplary target cell antigens include CD20, Her2, Her3, MCSP (melanoma-associated chondroitin sulfate proteoglycan, also known as chondroitin sulfate proteoglycan 4), or BCMA (human B cell maturation target, also known as Tumor Necrosis Factor Receptor Superfamily Member 17 (UniProt Q02223)).

In particular embodiments, the target cell antigen is CD20, particularly human CD20. In one embodiment, the target cell antigen is CD20 and the Fab molecule which specifically binds to said target cell antigen comprises a heavy chain variable region comprising the heavy chain complementarity determining region (CDR) 1 of SEQ ID NO: 46, the heavy chain CDR 2 of SEQ ID NO: 47, and the heavy chain CDR 3 of SEQ ID NO: 48, and a light chain variable region comprising the light chain CDR 1 of SEQ ID NO: 49, the light chain CDR 2 of SEQ ID NO: 50 and the light chain CDR 3 of SEQ ID NO: 51. In a further embodiment, the target cell antigen is CD20 and the Fab molecule which specifically binds to said target cell antigen comprises a heavy chain variable region that is at least 95%, 96%, 97%, 98%, or 99% identical to the sequence of SEQ ID NO: 30, and a light chain variable region that is at least 95%, 96%, 97%, 98%, or 99% identical to the sequence of SEQ ID NO: 31, In still a further embodiment, the target cell antigen is CD20 and the Fab molecule which specifically binds to said target cell antigen comprises the heavy chain variable region sequence of SEQ ID NO: 30, and the light chain variable region sequence of SEQ ID NO: 31. In a particular embodiment, the T cell activating bispecific antigen binding molecule comprises a polypeptide that is at least 95%, 96%, 97%, 98%, or 99% identical to the sequence of SEQ ID NO: 18, a polypeptide that is at least 95%, 96%, 97%, 98%, or 99% identical to the sequence of SEQ ID NO: 19, a polypeptide that is at least 95%, 96%, 97%, 98%, or 99% identical to the sequence of SEQ ID NO: 20, and a polypeptide that is at least 95%, 96%, 97%, 98%, or 99% identical to the sequence of SEQ ID NO: 21. In a further particular embodiment, the T cell activating bispecific antigen binding molecule comprises a polypeptide sequence of SEQ ID NO: 18, a polypeptide sequence of SEQ ID NO: 19, a polypeptide sequence of SEQ ID NO: 20 and a polypeptide sequence of SEQ ID NO: 21. In another embodiment, the T cell activating bispecific antigen binding molecule comprises a polypeptide that is at least 95%, 96%, 97%, 98%, or 99% identical to the sequence of SEQ ID NO: 32, a polypeptide that is at least 95%, 96%, 97%, 98%, or 99% identical to the sequence of SEQ ID NO: 19, a polypeptide that is at least 95%, 96%, 97%, 98%, or 99% identical to the sequence of SEQ ID NO: 20, and a polypeptide that is at least 95%, 96%, 97%, 98%, or 99% identical to the sequence of SEQ ID NO: 21. In a further embodiment, the T cell activating bispecific antigen binding molecule comprises a polypeptide sequence of SEQ ID NO: 32, a polypeptide sequence of SEQ ID NO: 19, a polypeptide sequence of SEQ ID NO: 20 and a polypeptide sequence of SEQ ID NO: 21. In still another embodiment, the T cell activating bispecific antigen binding molecule comprises a polypeptide that is at least 95%, 96%, 97%, 98%, or 99% identical to the sequence of SEQ ID NO: 36, a polypeptide that is at least 95%, 96%, 97%, 98%, or 99% identical to the sequence of SEQ ID NO: 37, a polypeptide that is at least 95%, 96%, 97%, 98%, or 99% identical to the sequence of SEQ ID NO: 38, and a polypeptide that is at least 95%, 96%, 97%, 98%, or 99% identical to the sequence of SEQ ID NO: 39. In a further embodiment, the T cell activating bispecific antigen binding molecule comprises a polypeptide sequence of SEQ ID NO: 36, a polypeptide sequence of SEQ ID NO: 37, a polypeptide sequence of SEQ ID NO: 38 and a polypeptide sequence of SEQ ID NO: 39. In a further embodiment, the T cell activating bispecific antigen binding molecule comprises a polypeptide that is at least 95%, 96%, 97%, 98%, or 99% identical to the sequence of SEQ ID NO: 40, a polypeptide that is at least 95%, 96%, 97%, 98%, or 99% identical to the sequence of SEQ ID NO: 41, a polypeptide that is at least 95%, 96%, 97%, 98%, or 99% identical to the sequence of SEQ ID NO: 20, and a polypeptide that is at least 95%, 96%, 97%, 98%, or 99% identical to the sequence of SEQ ID NO: 21. In a further embodiment, the T cell activating bispecific antigen binding molecule comprises a polypeptide sequence of SEQ ID NO: 40, a polypeptide sequence of SEQ ID NO: 41, a polypeptide sequence of SEQ ID NO: 20 and a polypeptide sequence of SEQ ID NO: 21.

In other embodiments, the target antigen is Her2, particularly human Her2. In one embodiment, the target cell antigen is Her2 and the Fab molecule which specifically binds to said target cell antigen comprises a heavy chain variable region that is at least 95%, 96%, 97%, 98%, or 99% identical to the sequence of SEQ ID NO: 61, and a light chain variable region that is at least 95%, 96%, 97%, 98%, or 99% identical to the sequence of SEQ ID NO: 62, In a further embodiment, the target cell antigen is Her2 and the Fab molecule which specifically binds to said target cell antigen comprises the heavy chain variable region sequence of SEQ ID NO: 61, and the light chain variable region sequence of SEQ ID NO: 62. In one embodiment, the T cell activating bispecific antigen binding molecule comprises a polypeptide that is at least 95%, 96%, 97%, 98%, or 99% identical to the sequence of SEQ ID NO: 21, a polypeptide that is at least 95%, 96%, 97%, 98%, or 99% identical to the sequence of SEQ ID NO: 52, a polypeptide that is at least 95%, 96%, 97%, 98%, or 99% identical to the sequence of SEQ ID NO: 53, and a polypeptide that is at least 95%, 96%, 97%, 98%, or 99% identical to the sequence of SEQ ID NO: 54. In a further embodiment, the T cell activating bispecific antigen binding molecule comprises a polypeptide sequence of SEQ ID NO: 21, a polypeptide sequence of SEQ ID NO: 52, a polypeptide sequence of SEQ ID NO: 53 and a polypeptide sequence of SEQ ID NO: 54.

In other embodiments, the target antigen is Her3, particularly human Her3. In one embodiment, the target cell antigen is Her3 and the Fab molecule which specifically binds to said target cell antigen comprises a heavy chain variable region that is at least 95%, 96%, 97%, 98%, or 99% identical to the sequence of SEQ ID NO: 63, and a light chain variable region that is at least 95%, 96%, 97%, 98%, or 99% identical to the sequence of SEQ ID NO: 64, In a further embodiment, the target cell antigen is Her3 and the Fab molecule which specifically binds to said target cell antigen comprises the heavy chain variable region sequence of SEQ ID NO: 63, and the light chain variable region sequence of SEQ ID NO: 64. In one embodiment, the T cell activating bispecific antigen binding molecule comprises a polypeptide that is at least 95%, 96%, 97%, 98%, or 99% identical to the sequence of SEQ ID NO: 21, a polypeptide that is at least 95%, 96%, 97%, 98%, or 99% identical to the sequence of SEQ ID NO: 55, a polypeptide that is at least 95%, 96%, 97%, 98%, or 99% identical to the sequence of SEQ ID NO: 56, and a polypeptide that is at least 95%, 96%, 97%, 98%, or 99% identical to the sequence of SEQ ID NO: 57. In a further embodiment, the T cell activating bispecific antigen binding molecule comprises a polypeptide sequence of SEQ ID NO: 21, a polypeptide sequence of SEQ ID NO: 55, a polypeptide sequence of SEQ ID NO: 56 and a polypeptide sequence of SEQ ID NO: 57.

In other embodiments, the target antigen is melanoma-associated chondroitin sulfate proteoglycan (MCSP), particularly human MCSP. In one embodiment, the target cell antigen is MCSP and the Fab molecule which specifically binds to said target cell antigen comprises a heavy chain variable region that is at least 95%, 96%, 97%, 98%, or 99% identical to the sequence of SEQ ID NO: 65, and a light chain variable region that is at least 95%, 96%, 97%, 98%, or 99% identical to the sequence of SEQ ID NO: 66, In a further embodiment, the target cell antigen is Her2 and the Fab molecule which specifically binds to said target cell antigen comprises the heavy chain variable region sequence of SEQ ID NO: 65, and the light chain variable region sequence of SEQ ID NO: 66.

In some embodiments, the target antigen is BCMA. In other embodiments, the target cell antigen is not BCMA.

Polynucleotides

The invention further provides isolated polynucleotides encoding a T cell activating bispecific antigen binding molecule as described herein or a fragment thereof. In some embodiments, said fragment is an antigen binding fragment.

The polynucleotides encoding T cell activating bispecific antigen binding molecules of the invention may be expressed as a single polynucleotide that encodes the entire T cell activating bispecific antigen binding molecule or as multiple (e.g., two or more) polynucleotides that are co-expressed. Polypeptides encoded by polynucleotides that are co-expressed may associate through, e.g., disulfide bonds or other means to form a functional T cell activating bispecific antigen binding molecule. For example, the light chain portion of a Fab molecule may be encoded by a separate polynucleotide from the portion of the T cell activating bispecific antigen binding molecule comprising the heavy chain portion of the Fab molecule, an Fc domain subunit and optionally (part of) another Fab molecule. When co-expressed, the heavy chain polypeptides will associate with the light chain polypeptides to form the Fab molecule. In another example, the portion of the T cell activating bispecific antigen binding molecule comprising one of the two Fc domain subunits and optionally (part of) one or more Fab molecules could be encoded by a separate polynucleotide from the portion of the T cell activating bispecific antigen binding molecule comprising the other of the two Fc domain subunits and optionally (part of) a Fab molecule. When co-expressed, the Fc domain subunits will associate to form the Fc domain.

In some embodiments, the isolated polynucleotide encodes the entire T cell activating bispecific antigen binding molecule according to the invention as described herein. In other embodiments, the isolated polynucleotide encodes a polypeptides comprised in the T cell activating bispecific antigen binding molecule according to the invention as described herein.

In certain embodiments the polynucleotide or nucleic acid is DNA. In other embodiments, a polynucleotide of the present invention is RNA, for example, in the form of messenger RNA (mRNA). RNA of the present invention may be single stranded or double stranded.

Recombinant Methods

T cell activating bispecific antigen binding molecules of the invention may be obtained, for example, by solid-state peptide synthesis (e.g. Merrifield solid phase synthesis) or recombinant production. For recombinant production one or more polynucleotide encoding the T cell activating bispecific antigen binding molecule (fragment), e.g., as described above, is isolated and inserted into one or more vectors for further cloning and/or expression in a host cell. Such polynucleotide may be readily isolated and sequenced using conventional procedures. In one embodiment a vector, preferably an expression vector, comprising one or more of the polynucleotides of the invention is provided. Methods which are well known to those skilled in the art can be used to construct expression vectors containing the coding sequence of a T cell activating bispecific antigen binding molecule (fragment) along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y (1989). The expression vector can be part of a plasmid, virus, or may be a nucleic acid fragment. The expression vector includes an expression cassette into which the polynucleotide encoding the T cell activating bispecific antigen binding molecule (fragment) (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the T cell activating bispecific antigen binding molecule (fragment) of the invention, or variant or derivative thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit â-globin, as well as other sequences capable of controlling gene expression in eukaryotic cells. Additional suitable transcription control regions include tissue-specific promoters and enhancers as well as inducible promoters (e.g. promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the T cell activating bispecific antigen binding molecule is desired, DNA encoding a signal sequence may be placed upstream of the nucleic acid encoding a T cell activating bispecific antigen binding molecule of the invention or a fragment thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

DNA encoding a short protein sequence that could be used to facilitate later purification (e.g. a histidine tag) or assist in labeling the T cell activating bispecific antigen binding molecule may be included within or at the ends of the T cell activating bispecific antigen binding molecule (fragment) encoding polynucleotide.

In a further embodiment, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one such embodiment a host cell comprises (e.g. has been transformed or transfected with) a vector comprising a polynucleotide that encodes (part of) a T cell activating bispecific antigen binding molecule of the invention. As used herein, the term "host cell" refers to any kind of cellular system which can be engineered to generate the T cell activating bispecific antigen binding molecules of the invention or fragments thereof. Host cells suitable for replicating and for supporting expression of T cell activating bispecific antigen binding molecules are well known in the art. Such cells may be transfected or transduced as appropriate with the particular expression vector and large quantities of vector containing cells can be grown for seeding large scale fermenters to obtain sufficient quantities of the T cell activating bispecific antigen binding molecule for clinical applications. Suitable host cells include prokaryotic microorganisms, such as E. coli, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006). Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells. Plant cell cultures can also be utilized as hosts. See e.g. U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr⁻ CHO cells (Urlaub et al., Proc Natl Acad Sci USA 77, 4216 (1980)); and myeloma cell lines such as Y0, NS0, P3X63 and Sp2/0. For a review of certain mammalian host cell lines suitable for protein production, see, e.g., Yazaki and Wu, Methods in Molecular Biology, Vol. 248 (B.K.C. Lo, ed., Humana Press, Totowa, N.J.), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., Y0, NS0, Sp20 cell).

Standard technologies are known in the art to express foreign genes in these systems. Cells expressing a polypeptide comprising either the heavy or the light chain of an antigen binding domain such as an antibody, may be engineered so as to also express the other of the antibody chains such that the expressed product is an antibody that has both a heavy and a light chain.

In one embodiment, a method of producing a T cell activating bispecific antigen binding molecule according to the invention is provided, wherein the method comprises culturing a host cell comprising a polynucleotide encoding the T cell activating bispecific antigen binding molecule, as provided herein, under conditions suitable for expression of the T cell activating bispecific antigen binding molecule, and recovering the T cell activating bispecific antigen binding molecule from the host cell (or host cell culture medium).

The components of the T cell activating bispecific antigen binding molecule are genetically fused to each other. T cell activating bispecific antigen binding molecule can be designed such that its components are fused directly to each other or indirectly through a linker sequence. The composition and length of the linker may be determined in accordance with methods well known in the art and may be tested for efficacy. Examples of linker sequences between different components of T cell activating bispecific antigen binding molecules are found in the sequences provided herein. Additional sequences may also be included to incorporate a cleavage site to separate the individual components of the fusion if desired, for example an endopeptidase recognition sequence.

In certain embodiments the one or more antigen binding moieties of the T cell activating bispecific antigen binding molecules comprise at least an antibody variable region capable of binding an antigenic determinant. Variable regions can form part of and be derived from naturally or non-naturally occurring antibodies and fragments thereof. Methods to produce polyclonal antibodies and monoclonal antibodies are well known in the art (see e.g. Harlow and Lane, "Antibodies, a laboratory manual", Cold Spring Harbor Laboratory, 1988). Non-naturally occurring antibodies can be constructed using solid phase-peptide synthesis, can be produced recombinantly (e.g. as described in U.S. Pat. No. 4,186,567) or can be obtained, for example, by screening combinatorial libraries comprising variable heavy chains and variable light chains (see e.g. U.S. Pat. No. 5,969,108 to McCafferty).

Any animal species of antibody, antibody fragment, antigen binding domain or variable region can be used in the T cell activating bispecific antigen binding molecules of the invention. Non-limiting antibodies, antibody fragments, antigen binding domains or variable regions useful in the present invention can be of murine, primate, or human origin. If the T cell activating bispecific antigen binding molecule is intended for human use, a chimeric form of antibody may be used wherein the constant regions of the antibody are from a human. A humanized or fully human form of the antibody can also be prepared in accordance with methods well known in the art (see e.g. U.S. Pat. No. 5,565,332 to Winter). Humanization may be achieved by various methods including, but not limited to (a) grafting the non-human (e.g., donor antibody) CDRs onto human (e.g. recipient antibody) framework and constant regions with or without retention of critical framework residues (e.g. those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, Front Biosci 13, 1619-1633 (2008), and are further described, e.g., in Riechmann et al., Nature 332, 323-329 (1988); Queen et al., Proc Natl Acad Sci USA 86, 10029-10033 (1989); U.S. Pat. Nos. 5,821,337, 7,527,791, 6,982,321, and 7,087,409; Jones et al., Nature 321, 522-525 (1986); Morrison et al., Proc Natl Acad Sci 81, 6851-6855 (1984); Morrison and Oi, Adv Immunol 44, 65-92 (1988); Verhoeyen et al., Science 239, 1534-1536 (1988); Padlan, Molec Immun 31(3), 169-217 (1994); Kashmiri et al., Methods 36, 25-34 (2005) (describing SDR (a-CDR) grafting); Padlan, Mol Immunol 28, 489-498 (1991) (describing "resurfacing"); Dall'Acqua et al., Methods 36, 43-60 (2005) (describing "FR shuffling"); and Osbourn et al., Methods 36, 61-68 (2005) and Klimka et al., Br J Cancer 83, 252-260 (2000) (describing the "guided selection" approach to FR shuffling). Human antibodies and human variable regions can be produced using various techniques known in the art. Human antibodies are described generally in van Dijk and van de Winkel, Curr Opin Pharmacol 5, 368-74 (2001) and Lonberg, Curr Opin Immunol 20, 450-459 (2008). Human variable regions can form part of and be derived from human monoclonal antibodies made by the hybridoma method (see e.g. Monoclonal Antibody Production Techniques and Applications, pp. 51-63 (Marcel Dekker, Inc., New York, 1987)). Human antibodies and human variable regions may also be prepared by administering an immunogen to a transgenic animal that has been modified to produce intact human antibodies or intact antibodies with human variable regions in response to antigenic challenge (see e.g. Lonberg, Nat Biotech 23, 1117-1125 (2005). Human antibodies and human variable regions may also be generated by isolating Fv clone variable region sequences selected from human-derived phage display libraries (see e.g., Hoogenboom et al. in Methods in Molecular Biology 178, 1-37 (O'Brien et al., ed., Human Press, Totowa, N.J., 2001); and McCafferty et al., Nature 348, 552-554; Clackson et al., Nature 352, 624-628 (1991)). Phage typically display antibody fragments, either as single-chain Fv (scFv) fragments or as Fab fragments.

In certain embodiments, the antigen binding moieties useful in the present invention are engineered to have enhanced binding affinity according to, for example, the methods disclosed in U.S. Pat. Appl. Publ. No. 2004/0132066, the entire contents of which are hereby incorporated by reference. The ability of the T cell activating bispecific antigen binding molecule of the invention to bind to a specific antigenic determinant can be measured either through an enzyme-linked immunosorbent assay (ELISA) or other techniques familiar to one of skill in the art, e.g. surface plasmon resonance technique (analyzed on a BIACORE T100 system) (Liljeblad, et al., Glyco J 17, 323-329 (2000)), and traditional binding assays (Heeley, Endocr Res 28, 217-229 (2002)). Competition assays may be used to identify an antibody, antibody fragment, antigen binding domain or variable domain that competes with a reference antibody for binding to a particular antigen, e.g. an antibody that competes with the V9 antibody for binding to CD3. In certain embodiments, such a competing antibody binds to the same epitope (e.g. a linear or a conformational epitope) that is bound by the reference antibody. Detailed exemplary methods for mapping an epitope to which an antibody binds are provided in Morris (1996) "Epitope Mapping Protocols," in Methods in Molecular Biology vol. 66 (Humana Press, Totowa, N.J.). In an exemplary competition assay, immobilized antigen (e.g. CD3) is incubated in a solution comprising a first labeled antibody that binds to the antigen (e.g. V9 antibody, described in U.S. Pat. No. 6,054,297) and a second unlabeled antibody that is being tested for its ability to compete with the first antibody for binding to the antigen. The second antibody may be present in a hybridoma supernatant. As a control, immobilized antigen is incubated in a solution comprising the first labeled antibody but not the second unlabeled antibody. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antibody is competing with the first antibody for binding to the antigen. See Harlow and Lane (1988) Antibodies: A Laboratory Manual ch. 14 (Cold Spring Harbor Laboratory, Cold Spring Harbor, N.Y.).

T cell activating bispecific antigen binding molecules prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the T cell activating bispecific antigen binding molecule binds. For example, for affinity chromatography purification of T cell activating bispecific antigen binding molecules of the invention, a matrix with protein A or protein G may be used. Sequential Protein A or G affinity chromatography and size exclusion chromatography can be used to isolate a T cell activating bispecific antigen binding molecule essentially as described in the Examples. The purity of the T cell activating bispecific antigen binding molecule can be determined by any of a variety of well known analytical methods including gel electrophoresis, high pressure liquid chromatography, and the like. For example, the heavy chain fusion proteins expressed as described in the Examples were shown to be intact and properly assembled as demonstrated by reducing SDS-PAGE (see e.g. FIGS. 3A-3Q). Three bands were resolved at approximately Mr 25,000, Mr 50,000 and Mr 75,000, corresponding to the predicted molecular weights of the T cell activating bispecific antigen binding molecule light chain, heavy chain and heavy chain/light chain fusion protein.

Assays

T cell activating bispecific antigen binding molecules provided herein may be identified, screened for, or characterized for their physical/chemical properties and/or biological activities by various assays known in the art.

Affinity Assays

The affinity of the T cell activating bispecific antigen binding molecule for an Fc receptor or a target antigen can be determined in accordance with the methods set forth in the Examples by surface plasmon resonance (SPR), using standard instrumentation such as a BIAcore instrument (GE Healthcare), and receptors or target proteins such as may be obtained by recombinant expression. Alternatively, binding of T cell activating bispecific antigen binding molecules for different receptors or target antigens may be evaluated using cell lines expressing the particular receptor or target antigen, for example by flow cytometry (FACS). A specific illustrative and exemplary embodiment for measuring binding affinity is described in the following and in the Examples below.

According to one embodiment, $K_D$ is measured by surface plasmon resonance using a BIACORE® T100 machine (GE Healthcare) at 25° C.

To analyze the interaction between the Fc-portion and Fc receptors, His-tagged recombinant Fc-receptor is captured by an anti-Penta His antibody (Qiagen) immobilized on CM5 chips and the bispecific constructs are used as analytes. Briefly, carboxymethylated dextran biosensor chips (CM5, GE Healthcare) are activated with N-ethyl-N'-(3-dimethylaminopropyl)-carbodiimide hydrochloride (EDC) and N-hydroxysuccinimide (NHS) according to the supplier's instructions. Anti Penta-His antibody is diluted with 10 mM sodium acetate, pH 5.0, to 40 µg/ml before injection at a flow rate of 5 µl/min to achieve approximately 6500 response units (RU) of coupled protein. Following the injection of the ligand, 1 M ethanolamine is injected to block unreacted groups. Subsequently the Fc-receptor is captured for 60 s at 4 or 10 nM. For kinetic measurements, four-fold serial dilutions of the bispecific construct (range between 500 nM and 4000 nM) are injected in HBS-EP (GE Healthcare, 10 mM HEPES, 150 mM NaCl, 3 mM EDTA, 0.05% Surfactant P20, pH 7.4) at 25° C. at a flow rate of 30 µl/min for 120 s.

To determine the affinity to the target antigen, bispecific constructs are captured by an anti human Fab specific antibody (GE Healthcare) that is immobilized on an activated CM5-sensor chip surface as described for the anti Penta-His antibody. The final amount of coupled protein is approximately 12000 RU. The bispecific constructs are captured for 90 s at 300 nM. The target antigens are passed through the flow cells for 180 s at a concentration range from 250 to 1000 nM with a flowrate of 30 µl/min. The dissociation is monitored for 180 s.

Bulk refractive index differences are corrected for by subtracting the response obtained on reference flow cell. The steady state response was used to derive the dissociation constant $K_D$ by non-linear curve fitting of the Langmuir binding isotherm. Association rates ($k_{on}$) and dissociation rates ($k_{off}$) are calculated using a simple one-to-one Langmuir binding model (BIACORE® T100 Evaluation Software version 1.1.1) by simultaneously fitting the association and dissociation sensorgrams. The equilibrium dissociation constant ($K_D$) is calculated as the ratio $k_{off}/k_{on}$. See, e.g., Chen et al., J Mol Biol 293, 865-881 (1999).

Activity Assays

Biological activity of the T cell activating bispecific antigen binding molecules of the invention can be measured by various assays as described in the Examples. Biological activities may for example include the induction of proliferation of T cells, the induction of signaling in T cells, the induction of expression of activation markers in T cells, the induction of cytokine secretion by T cells, the induction of lysis of target cells such as tumor cells, and the induction of tumor regression and/or the improvement of survival.

Compositions, Formulations, and Routes of Administration

In a further aspect, the invention provides pharmaceutical compositions comprising any of the T cell activating bispecific antigen binding molecules provided herein, e.g., for use in any of the below therapeutic methods. In one embodiment, a pharmaceutical composition comprises any of the T cell activating bispecific antigen binding molecules provided herein and a pharmaceutically acceptable carrier. In another embodiment, a pharmaceutical composition comprises any of the T cell activating bispecific antigen binding molecules provided herein and at least one additional therapeutic agent, e.g., as described below.

Further provided is a method of producing a T cell activating bispecific antigen binding molecule of the invention in a form suitable for administration in vivo, the method comprising (a) obtaining a T cell activating bispecific antigen binding molecule according to the invention, and (b)

formulating the T cell activating bispecific antigen binding molecule with at least one pharmaceutically acceptable carrier, whereby a preparation of T cell activating bispecific antigen binding molecule is formulated for administration in vivo.

Pharmaceutical compositions of the present invention comprise a therapeutically effective amount of one or more T cell activating bispecific antigen binding molecule dissolved or dispersed in a pharmaceutically acceptable carrier. The phrases "pharmaceutical or pharmacologically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains at least one T cell activating bispecific antigen binding molecule and optionally an additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards or corresponding authorities in other countries. Preferred compositions are lyophilized formulations or aqueous solutions. As used herein, "pharmaceutically acceptable carrier" includes any and all solvents, buffers, dispersion media, coatings, surfactants, antioxidants, preservatives (e.g. antibacterial agents, antifungal agents), isotonic agents, absorption delaying agents, salts, preservatives, antioxidants, proteins, drugs, drug stabilizers, polymers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The composition may comprise different types of carriers depending on whether it is to be administered in solid, liquid or aerosol form, and whether it need to be sterile for such routes of administration as injection. T cell activating bispecific antigen binding molecules of the present invention (and any additional therapeutic agent) can be administered intravenously, intradermally, intraarterially, intraperitoneally, intralesionally, intracranially, intraarticularly, intraprostatically, intrasplenically, intrarenally, intrapleurally, intratracheally, intranasally, intravitreally, intravaginally, intrarectally, intratumorally, intramuscularly, intraperitoneally, subcutaneously, subconjunctivally, intravesicularlly, mucosally, intrapericardially, intraumbilically, intraocularally, orally, topically, locally, by inhalation (e.g. aerosol inhalation), injection, infusion, continuous infusion, localized perfusion bathing target cells directly, via a catheter, via a lavage, in cremes, in lipid compositions (e.g. liposomes), or by other method or any combination of the forgoing as would be known to one of ordinary skill in the art (see, for example, Remington's Pharmaceutical Sciences, 18th Ed. Mack Printing Company, 1990, incorporated herein by reference). Parenteral administration, in particular intravenous injection, is most commonly used for administering polypeptide molecules such as the T cell activating bispecific antigen binding molecules of the invention.

Parenteral compositions include those designed for administration by injection, e.g. subcutaneous, intradermal, intralesional, intravenous, intraarterial intramuscular, intrathecal or intraperitoneal injection. For injection, the T cell activating bispecific antigen binding molecules of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the T cell activating bispecific antigen binding molecules may be in powder form for constitution with a suitable vehicle, e.g., sterile pyrogen-free water, before use. Sterile injectable solutions are prepared by incorporating the T cell activating bispecific antigen binding molecules of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein. Suitable pharmaceutically acceptable carriers include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular embodiments, prolonged absorption of an injectable composition can be brought about by the use in the compositions of agents delaying absorption, such as, for example, aluminum monostearate, gelatin or combinations thereof.

In addition to the compositions described previously, the T cell activating bispecific antigen binding molecules may also be formulated as a depot preparation. Such long acting formulations may be administered by implantation (for example subcutaneously or intramuscularly) or by intramuscular injection. Thus, for example, the T cell activating bispecific antigen binding molecules may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions comprising the T cell activating bispecific antigen binding molecules of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

The T cell activating bispecific antigen binding molecules may be formulated into a composition in a free acid or base, neutral or salt form. Pharmaceutically acceptable salts are salts that substantially retain the biological activity of the free acid or base. These include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

Therapeutic Methods and Compositions

Any of the T cell activating bispecific antigen binding molecules provided herein may be used in therapeutic methods. T cell activating bispecific antigen binding molecules of the invention can be used as immunotherapeutic agents, for example in the treatment of cancers.

For use in therapeutic methods, T cell activating bispecific antigen binding molecules of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In one aspect, T cell activating bispecific antigen binding molecules of the invention for use as a medicament are provided. In further aspects, T cell activating bispecific antigen binding molecules of the invention for use in treating a disease are provided. In certain embodiments, T cell activating bispecific antigen binding molecules of the invention for use in a method of treatment are provided. In one embodiment, the invention provides a T cell activating bispecific antigen binding molecule as described herein for use in the treatment of a disease in an individual in need thereof. In certain embodiments, the invention provides a T cell activating bispecific antigen binding molecule for use in a method of treating an individual having a disease comprising administering to the individual a therapeutically effective amount of the T cell activating bispecific antigen binding molecule. In certain embodiments the disease to be treated is a proliferative disorder. In a particular embodiment the disease is cancer. In certain embodiments the method further comprises administering to the individual a therapeutically effective amount of at least one additional therapeutic agent, e.g., an anti-cancer agent if the disease to be treated is cancer. In further embodiments, the invention provides a T cell activating bispecific antigen binding molecule as described herein for use in inducing lysis of a target cell, particularly a tumor cell. In certain embodiments, the invention provides a T cell activating bispecific antigen binding molecule for use in a method of inducing lysis of a target cell, particularly a tumor cell, in an individual comprising administering to the individual an effective amount of the T cell activating bispecific antigen binding molecule to induce lysis of a target cell. An "individual" according to any of the above embodiments is a mammal, preferably a human.

In a further aspect, the invention provides for the use of a T cell activating bispecific antigen binding molecule of the invention in the manufacture or preparation of a medicament. In one embodiment the medicament is for the treatment of a disease in an individual in need thereof. In a further embodiment, the medicament is for use in a method of treating a disease comprising administering to an individual having the disease a therapeutically effective amount of the medicament. In certain embodiments the disease to be treated is a proliferative disorder. In a particular embodiment the disease is cancer. In one embodiment, the method further comprises administering to the individual a therapeutically effective amount of at least one additional therapeutic agent, e.g., an anti-cancer agent if the disease to be treated is cancer. In a further embodiment, the medicament is for inducing lysis of a target cell, particularly a tumor cell. In still a further embodiment, the medicament is for use in a method of inducing lysis of a target cell, particularly a tumor cell, in an individual comprising administering to the individual an effective amount of the medicament to induce lysis of a target cell. An "individual" according to any of the above embodiments may be a mammal, preferably a human.

In a further aspect, the invention provides a method for treating a disease. In one embodiment, the method comprises administering to an individual having such disease a therapeutically effective amount of a T cell activating bispecific antigen binding molecule of the invention. In one embodiment a composition is administered to said individual, comprising the T cell activating bispecific antigen binding molecule of the invention in a pharmaceutically acceptable form. In certain embodiments the disease to be treated is a proliferative disorder. In a particular embodiment the disease is cancer. In certain embodiments the method further comprises administering to the individual a therapeutically effective amount of at least one additional therapeutic agent, e.g., an anti-cancer agent if the disease to be treated is cancer. An "individual" according to any of the above embodiments may be a mammal, preferably a human.

In a further aspect, the invention provides a method for inducing lysis of a target cell, particularly a tumor cell. In one embodiment the method comprises contacting a target cell with a T cell activating bispecific antigen binding molecule of the invention in the presence of a T cell, particularly a cytotoxic T cell. In a further aspect, a method for inducing lysis of a target cell, particularly a tumor cell, in an individual is provided. In one such embodiment, the method comprises administering to the individual an effective amount of a T cell activating bispecific antigen binding molecule to induce lysis of a target cell. In one embodiment, an "individual" is a human.

In certain embodiments the disease to be treated is a proliferative disorder, particularly cancer. Non-limiting examples of cancers include bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer. Other cell proliferation disorders that can be treated using a T cell activating bispecific antigen binding molecule of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases. In certain embodiments the cancer is chosen from the group consisting of renal cell cancer, skin cancer, lung cancer, colorectal cancer, breast cancer, brain cancer, head and neck cancer. A skilled artisan readily recognizes that in many cases the T cell activating bispecific antigen binding molecule may not provide a cure but may only provide partial benefit. In some embodiments, a physiological change having some benefit is also considered therapeutically beneficial. Thus, in some embodiments, an amount of T cell activating bispecific antigen binding molecule that provides a physiological change is considered an "effective amount" or a "therapeutically effective amount". The subject, patient, or individual in need of treatment is typically a mammal, more specifically a human.

In some embodiments, an effective amount of a T cell activating bispecific antigen binding molecule of the invention is administered to a cell. In other embodiments, a therapeutically effective amount of a T cell activating bispecific antigen binding molecule of the invention is administered to an individual for the treatment of disease.

For the prevention or treatment of disease, the appropriate dosage of a T cell activating bispecific antigen binding molecule of the invention (when used alone or in combination with one or more other additional therapeutic agents) will depend on the type of disease to be treated, the route of administration, the body weight of the patient, the type of T cell activating bispecific antigen binding molecule, the severity and course of the disease, whether the T cell activating bispecific antigen binding molecule is administered for preventive or therapeutic purposes, previous or concurrent therapeutic interventions, the patient's clinical history and response to the T cell activating bispecific antigen binding molecule, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

The T cell activating bispecific antigen binding molecule is suitably administered to the patient at one time or over a series of treatments. Depending on the type and severity of the disease, about 1 µg/kg to 15 mg/kg (e.g. 0.1 mg/kg-10 mg/kg) of T cell activating bispecific antigen binding molecule can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the T cell activating bispecific antigen binding molecule would be in the range from about 0.005 mg/kg to about 10 mg/kg. In other non-limiting examples, a dose may also comprise from about 1 microgram/kg body weight, about 5 microgram/kg body weight, about 10 microgram/kg body weight, about 50 microgram/kg body weight, about 100 microgram/kg body weight, about 200 microgram/kg body weight, about 350 microgram/kg body weight, about 500 microgram/kg body weight, about 1 milligram/kg body weight, about 5 milligram/kg body weight, about 10 milligram/kg body weight, about 50 milligram/kg body weight, about 100 milligram/kg body weight, about 200 milligram/kg body weight, about 350 milligram/kg body weight, about 500 milligram/kg body weight, to about 1000 mg/kg body weight or more per administration, and any range derivable therein. In non-limiting examples of a derivable range from the numbers listed herein, a range of about 5 mg/kg body weight to about 100 mg/kg body weight, about 5 microgram/kg body weight to about 500 milligram/kg body weight, etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the T cell activating bispecific antigen binding molecule). An initial higher loading dose, followed by one or more lower doses may be administered. However, other dosage regimens may be useful. The progress of this therapy is easily monitored by conventional techniques and assays.

The T cell activating bispecific antigen binding molecules of the invention will generally be used in an amount effective to achieve the intended purpose. For use to treat or prevent a disease condition, the T cell activating bispecific antigen binding molecules of the invention, or pharmaceutical compositions thereof, are administered or applied in a therapeutically effective amount. Determination of a therapeutically effective amount is well within the capabilities of those skilled in the art, especially in light of the detailed disclosure provided herein.

For systemic administration, a therapeutically effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the T cell activating bispecific antigen binding molecules which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by HPLC.

In cases of local administration or selective uptake, the effective local concentration of the T cell activating bispecific antigen binding molecules may not be related to plasma concentration. One having skill in the art will be able to optimize therapeutically effective local dosages without undue experimentation.

A therapeutically effective dose of the T cell activating bispecific antigen binding molecules described herein will generally provide therapeutic benefit without causing substantial toxicity. Toxicity and therapeutic efficacy of a T cell activating bispecific antigen binding molecule can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. T cell activating bispecific antigen binding molecules that exhibit large therapeutic indices are preferred. In one embodiment, the T cell activating bispecific antigen binding molecule according to the present invention exhibits a high therapeutic index. The data obtained from cell culture assays and animal studies can be used in formulating a range of dosages suitable for use in humans. The dosage lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition (see, e.g., Fingl et al., 1975, in: The Pharmacological Basis of Therapeutics, Ch. 1, p. 1, incorporated herein by reference in its entirety).

The attending physician for patients treated with T cell activating bispecific antigen binding molecules of the invention would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

Other Agents and Treatments

The T cell activating bispecific antigen binding molecules of the invention may be administered in combination with one or more other agents in therapy. For instance, a T cell activating bispecific antigen binding molecule of the invention may be co-administered with at least one additional therapeutic agent. The term "therapeutic agent" encompasses any agent administered to treat a symptom or disease in an individual in need of such treatment. Such additional therapeutic agent may comprise any active ingredients suitable for the particular indication being treated, preferably those with complementary activities that do not adversely affect each other. In certain embodiments, an additional therapeutic agent is an immunomodulatory agent, a cytostatic agent, an inhibitor of cell adhesion, a cytotoxic agent, an activator of cell apoptosis, or an agent that increases the sensitivity of cells to apoptotic inducers. In a particular embodiment, the additional therapeutic agent is an anticancer agent, for example a microtubule disruptor, an antimetabolite, a topoisomerase inhibitor, a DNA intercalator, an alkylating agent, a hormonal therapy, a kinase inhibitor, a receptor antagonist, an activator of tumor cell apoptosis, or an antiangiogenic agent.

Such other agents are suitably present in combination in amounts that are effective for the purpose intended. The effective amount of such other agents depends on the amount of T cell activating bispecific antigen binding molecule used, the type of disorder or treatment, and other factors discussed above. The T cell activating bispecific antigen binding molecules are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the T cell activating bispecific antigen binding molecule of the invention can occur prior to, simultaneously, and/or following, administration of the additional therapeutic agent and/or adjuvant. T cell activating bispecific antigen binding molecules of the invention can also be used in combination with radiation therapy.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is a T cell activating bispecific antigen binding molecule of the invention. The label or package insert indicates that the composition is used for treating the condition of choice. Moreover, the article of manufacture may comprise (a) a first container with a composition contained therein, wherein the composition comprises a T cell activating bispecific antigen binding molecule of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EXAMPLES

The following are examples of methods and compositions of the invention. It is understood that various other embodiments may be practiced, given the general description provided above.
General Methods
Recombinant DNA Techniques Standard methods were used to manipulate DNA as described in Sambrook et al., Molecular cloning: A laboratory manual; Cold Spring Harbor Laboratory Press, Cold Spring Harbor, N.Y., 1989. The molecular biological reagents were used according to the manufacturers' instructions. General information regarding the nucleotide sequences of human immunoglobulins light and heavy chains is given in: Kabat, E. A. et al., (1991) Sequences of Proteins of Immunological Interest, 5$^{th}$ ed., NIH Publication No. 91-3242.
DNA Sequencing DNA sequences were determined by double strand sequencing.
Gene Synthesis Desired gene segments where required were either generated by PCR using appropriate templates or were synthesized by Geneart AG (Regensburg, Germany) from synthetic oligonucleotides and PCR products by automated gene synthesis. In cases where no exact gene sequence was available, oligonucleotide primers were designed based on sequences from closest homologues and the genes were isolated by RT-PCR from RNA originating from the appropriate tissue. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow sub-cloning into the respective expression vectors. All constructs were designed with a 5'-end DNA sequence coding for a leader peptide which targets proteins for secretion in eukaryotic cells.

Example 1

Preparation of T-Cell Bispecific (TCB) Antibodies with and without Charge Modifications (Anti-CD20/Anti-CD3)

Figure 2A:
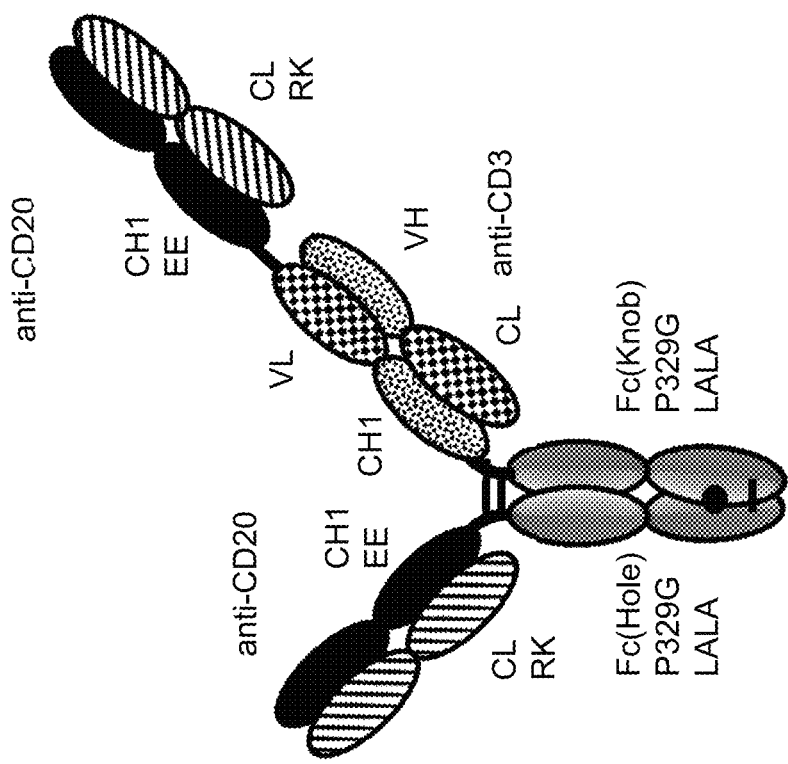
(FIG. 2A) "2+1 IgG CrossFab, inverted" without charge modifications (CH1/CL exchange in CD3 binder), (FIG. 2B) "2+1 IgG CrossFab, inverted" with charge modifications (VH/VL exchange in CD3 binder, charge modification in CD20 binders, EE=147E, 213E; RK=123R, 124K), (FIG. 2C) "2+1 IgG CrossFab" with charge modifications (VH/VL exchange in CD3 binder, charge modification in CD20 binders, EE=147E, 213E; RK=123R, 124K), (FIG. 2D) "2+1 IgG CrossFab, inverted" without charge modifications (VH/VL exchange in CD3 binder), (FIG. 2E) "2+1 IgG CrossFab, inverted" without charge modifications (VH-CH1/VL-CL exchange in CD3 binder), (FIG. 2F) "2+1 IgG CrossFab, inverted" with charge modifications (VH/VL exchange in CD20 binders, charge modification in CD3 binder, EE=147E, 213E; KK=123K, 124K), (FIG. 2G) "2+1 IgG CrossFab, inverted" with charge modifications and DDKK mutation in Fc region (VH/VL exchange in CD3 binder, charge modification in CD20 binders, EE=147E, 213E; RK=123R, 124K), (FIG. 2H) "1+1 CrossMab" with charge modifications (VH/VL exchange in CD3 binder, charge modification in CD20 binder, EE=147E, 213E; RK=123R, 124K), (FIG. 2I) "1+1 CrossMab" with charge modifications (VH/VL exchange in CD3 binder, charge modification in CD20 binder, EE=147E, 213E; RK=123R, 124K, different CD20 binder), (FIG. 2J) "2+1 IgG CrossFab, inverted" with charge modifications 213E, 123R (VH/VL exchange in CD3 binder, charge modification in CD20 binder, E=213E; R=123R), (FIG. 2K) "2+1 IgG CrossFab, inverted" with charge modifications (VH/VL exchange and charge modification in CD3 binder).
Figure 2B:
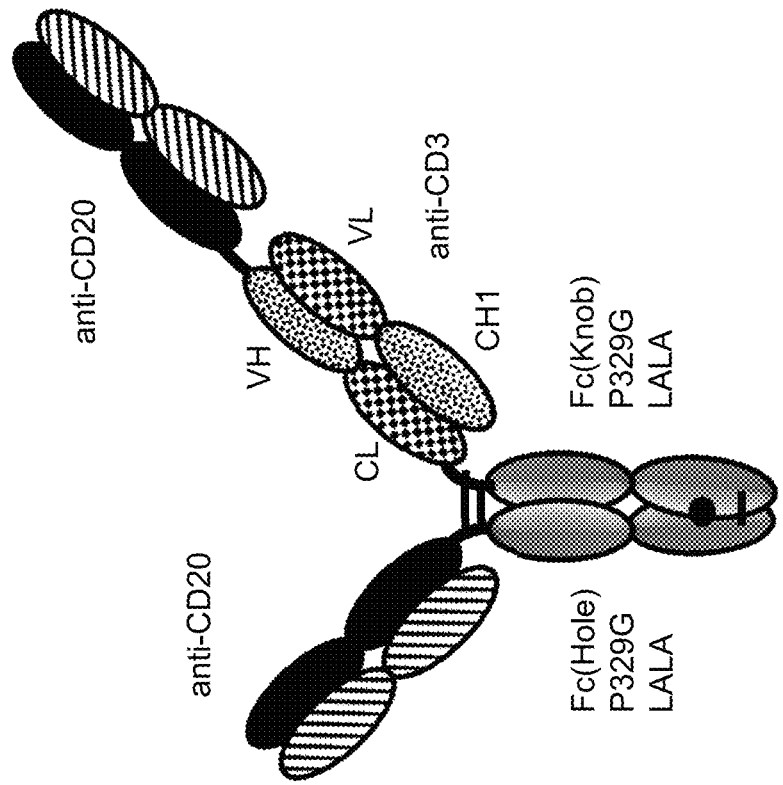
FIG. 2. Illustration of the TCBs prepared in Example 1.
Figure 2C:
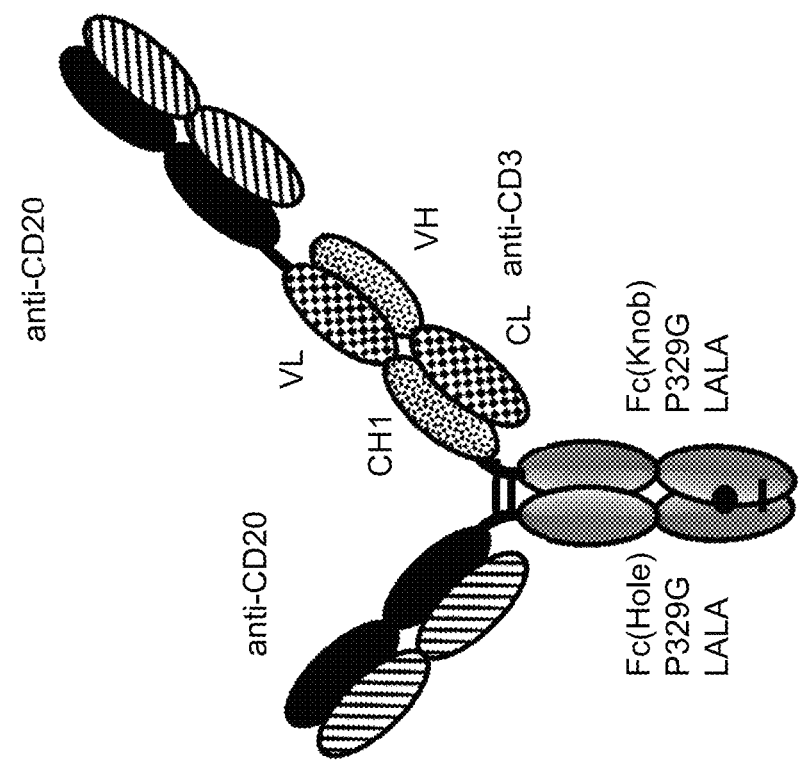
Figure 2D:
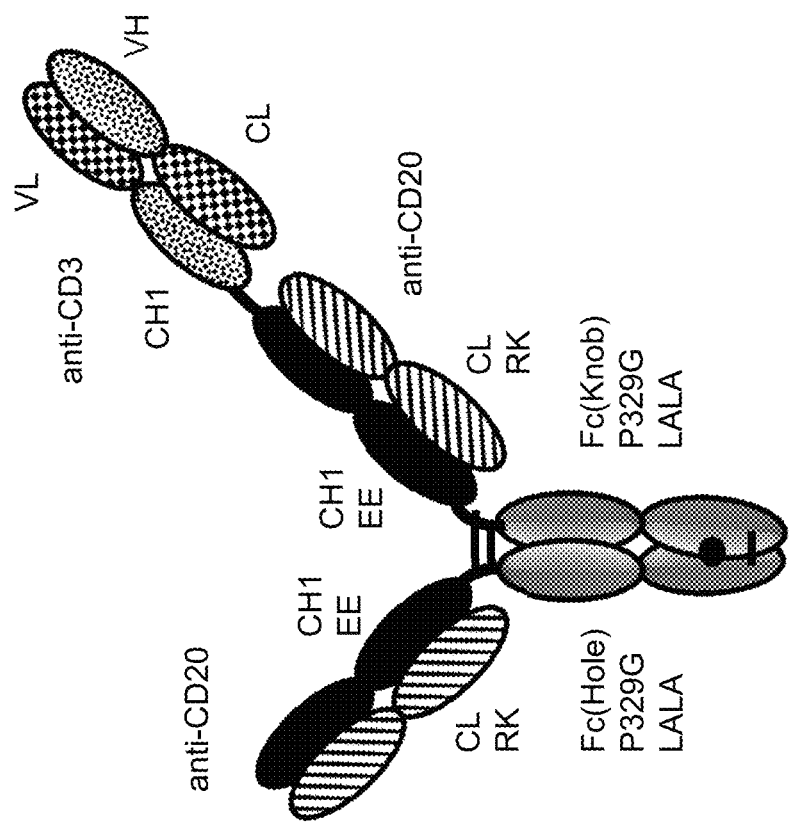
Figure 2E:
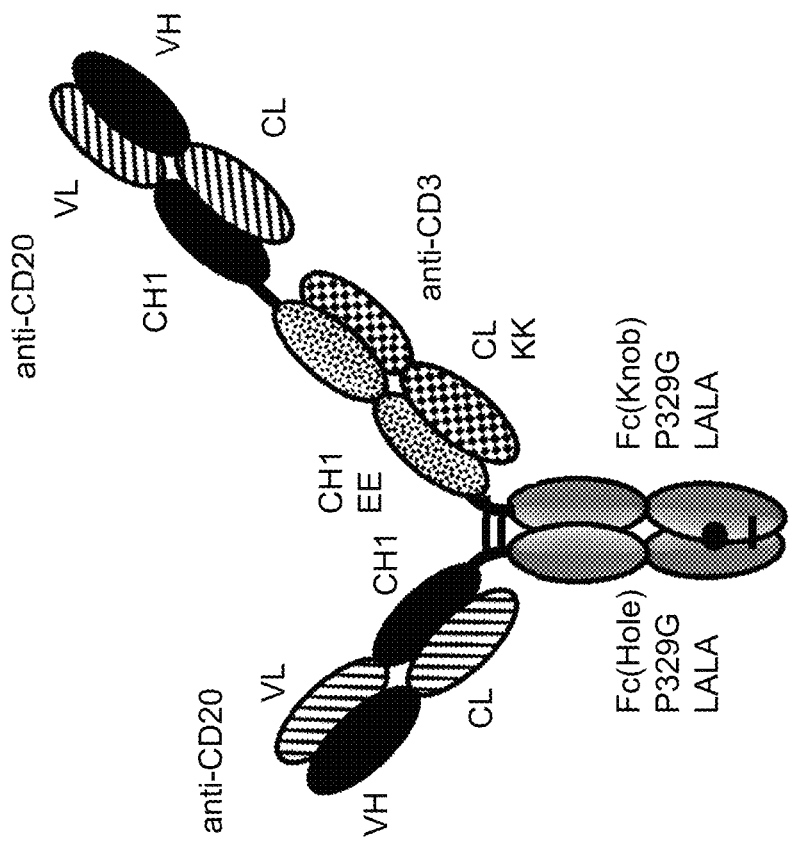
Figure 2F:
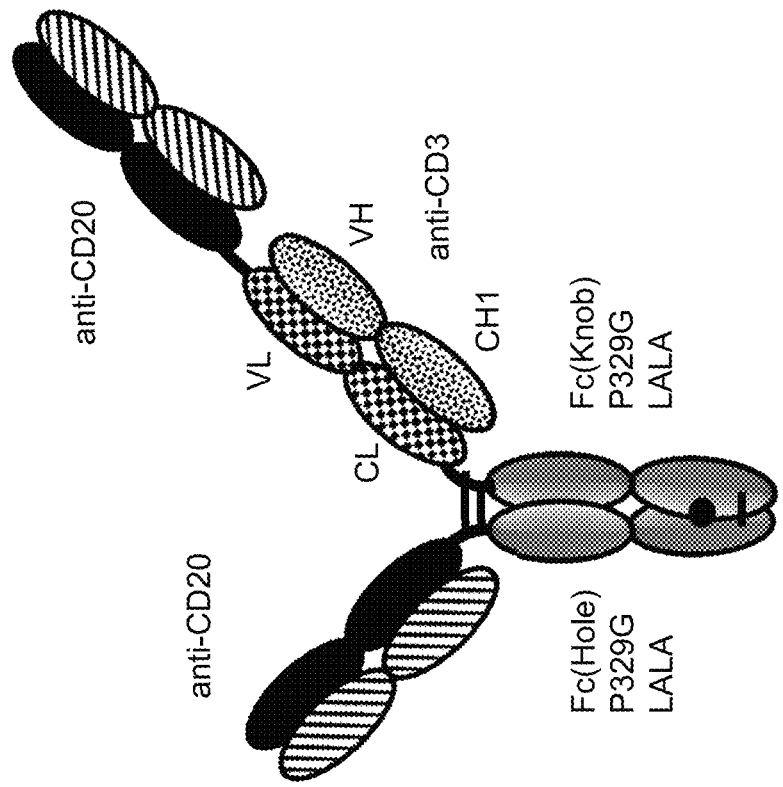
Figure 2I:
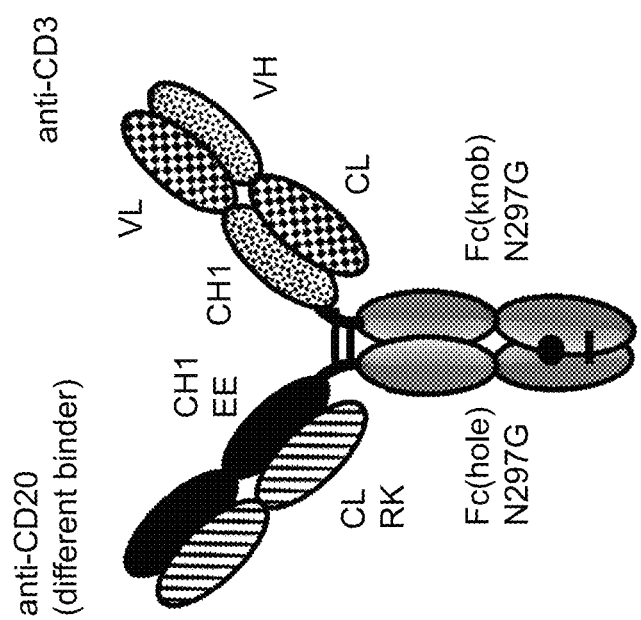

The following molecules were prepared in this example, schematic illustrations thereof are shown in FIGS. 2A-2K:

A. "2+1 IgG CrossFab, inverted" without charge modifications (CH1/CL exchange in CD3 binder) (FIG. 2A, SEQ ID NOs 14-17)
B. "2+1 IgG CrossFab, inverted" with charge modifications (VH/VL exchange in CD3 binder, charge modification in CD20 binders) (FIG. 2B, SEQ ID NOs 18-21)
C. "2+1 IgG CrossFab" with charge modifications (VH/VL exchange in CD3 binder, charge modification in CD20 binders) (FIG. 2C, SEQ ID NOs 32, 19-21)
D. "2+1 IgG CrossFab, inverted" without charge modifications (VH/VL exchange in CD3 binder) (FIG. 2D, SEQ ID NOs 33, 15, 17, 21)
E. "2+1 IgG CrossFab, inverted" without charge modifications (VH-CH1/VL-CL exchange in CD3 binder) (FIG. 2E, SEQ ID NOs 34, 15, 17, 35)
F. "2+1 IgG CrossFab, inverted" with charge modifications (VH/VL exchange in CD20 binders, charge modification in CD3 binder) (FIG. 2F, SEQ ID NOs 36-39)
G. "2+1 IgG CrossFab, inverted" with charge modifications and DDKK mutation in Fc region (VH/VL exchange in CD3 binder, charge modification in CD20 binders) (FIG. 2G, SEQ ID NOs 40, 41, 20, 21)
H. "1+1 CrossMab" with charge modifications (VH/VL exchange in CD3 binder, charge modification in CD20 binder) (FIG. 2H, SEQ ID NOs 42, 43, 20, 21)
I. "1+1 CrossMab" with charge modifications (VH/VL exchange in CD3 binder, charge modification in CD20 binder, different CD20 binder) (FIG. 2I, SEQ ID NOs 43-45, 21)
J. "2+1 IgG CrossFab, inverted" with charge modifications 213E, 123R (VH/VL exchange in CD3 binder, charge modification in CD20 binder) (FIG. 2J, SEQ ID NOs 69-71, 21)
K. "2+1 IgG CrossFab, inverted" with charge modifications (VH/VL exchange and charge modification in CD3 binder) (FIG. 2K, SEQ ID NOs 15, 17, 72, 73).

The variable region of heavy and light chain DNA sequences were subcloned in frame with either the constant heavy chain or the constant light chain pre-inserted into the respective recipient mammalian expression vector. Protein expression is driven by an MPSV promoter and a synthetic polyA signal sequence is present at the 3' end of the CDS. In addition each vector contains an EBV OriP sequence. The molecules were produced by co-transfecting HEK293-EBNA cells growing in suspension with the mammalian expression vectors using polyethylenimine (PEI). The cells were transfected with the corresponding expression vectors in a 1:2:1:1 ratio (A:"vector heavy chain (VH-CH1-VH-CL-CH2-CH3)":"vector light chain (VL-CL)":"vector heavy chain (VH-CH1-CH2-CH3)":"vector light chain (VL-CH1)"; B, D, G, J, K:"vector heavy chain (VH-CH1-VL-CH1-CH2-CH3)":"vector light chain (VL-CL)":"vector heavy chain (VH-CH1-CH2-CH3)":"vector light chain (VH-CL)"; C:"vector heavy chain (VL-CH1-VH-CH1-CH2-CH3)":"vector light chain (VL-CL)":"vector heavy chain (VH-CH1-CH2-CH3)":"vector light chain (VH-CL)"; E:"vector heavy chain (VH-CH1-VL-CL-CH2-CH3)":"vector light chain (VL-CL)":"vector heavy chain (VH-CH1-CH2-CH3)":"vector light chain (VH-CH1)"; F:"vector heavy chain (VL-CH1-VH-CH1-CH2-CH3)":"vector light chain (VH-CL)":"vector heavy chain (VL-CH1-CH2-CH3)":"vector light chain (VH-CH1)") or a 1:1:1:1 ratio (H, I:"vector heavy chain (VL-CH1-CH2-CH3)":"vector light chain (VL-CL)":"vector heavy chain (VH-CH1-CH2-CH3)":"vector light chain (VH-CL)").

For transfection, HEK293 EBNA cells were cultivated in suspension serum free in Excell culture medium containing 6 mM L-glutamine and 250 mg/l G418. For the production in 600 ml tubespin flasks (max. working volume 400 ml) 600 million HEK293 EBNA cells were seeded 24 hours before transfection. For transfection, cells were centrifuged for 5 min at 210×g, and supernatant was replaced by 20 ml pre-warmed CD CHO medium. Expression vectors are mixed in 20 ml CD CHO medium to a final amount of 400 μg DNA. After addition of 1080 μl PEI solution (2.7 μg/ml) the mixture was vortexed for 15 s and subsequently incubated for 10 min at room temperature. Afterwards cells were mixed with the DNA/PEI solution, transferred to a 600 ml tubespin flask and incubated for 3 hours at 37° C. in an incubator with a 5% $CO_2$ atmosphere. After incubation, 360 ml Excell+6 mM L-glutamine+5 g/L Pepsoy+1.0 mM VPA medium was added and cells were cultivated for 24 hours. One day after transfection 7% Feed 1 (Lonza) was added. After 7 days cultivation supernatant was collected for purification by centrifugation for 20-30 min at 3600×g (Sigma 8K centrifuge), the solution was sterile filtered (0.22 mm filter) and sodium azide in a final concentration of 0.01% w/v was added. The solution was kept at 4° C.

The concentration of the constructs in the culture medium was determined by ProteinA-HPLC. The basis of separation was binding of Fc-containing molecules on ProteinA at pH 8.0 and step elution from pH 2.5. There were two mobile phases. These were Tris (10 mM)-glycine (50 mM)-NaCl (100 mM) buffers, identical except that they were adjusted to different pHs (8 and 2.5). The column body was an Upchurch 2×20 mm pre-column with an internal volume of ~63 μl packed with POROS 20A. 100 μl of each sample was injected on equilibrated material with a flow rate of 0.5 ml/min. After 0.67 minutes the sample was eluted with a pH step to pH 2.5. Quantitation was done by determination of 280 nm absorbance and calculation using a standard curve with a concentration range of human $IgG_1$ from 16 to 166 mg/l.

The secreted protein was purified from cell culture supernatants by affinity chromatography using Protein A affinity chromatography, followed by a size exclusion chromatographic step.

For affinity chromatography supernatant was loaded on a HiTrap ProteinA HP column (CV=5 mL, GE Healthcare) equilibrated with 25 ml 20 mM sodium phosphate, 20 mM sodium citrate, pH 7.5. Unbound protein was removed by washing with at least 10 column volumes 20 mM sodium phosphate, 20 mM sodium citrate, 0.5 M sodium chloride, pH 7.5, followed by an additional wash step using 6 column volumes 10 mM sodium phosphate, 20 mM sodium citrate, 0.5 M sodium chloride, pH 5.45. The column was washed subsequently with 20 ml 10 mM MES, 100 mM sodium chloride, pH 5.0, and target protein was eluted in 6 column volumes 20 mM sodium citrate, 100 mM sodium chloride, 100 mM glycine, pH 3.0. Protein solution was neutralized by adding 1/10 of 0.5 M sodium phosphate, pH 8.0. Target protein was concentrated and filtrated prior to loading on a HiLoad Superdex 200 column (GE Healthcare) equilibrated with 20 mM histidine, 140 mM sodium chloride, 0.01% Tween-20, pH 6.0. Molecule A had to be purified by an additional preparative size exclusion chromatography (SEC) step to achieve a final monomer content of 100%. Therefore, fractions with high monomer content from the first size exclusion step were pooled, concentrated and again loaded on a HiLoad Superdex 200 column (GE Healthcare). This additional purification step was not necessary for the other molecules (depending on the side product profile, however, pooling of fractions and therefore recovery after the first size exclusion chromatography was different for these molecules).

Purity and molecular weight of the molecules was analyzed after the first purification step (Protein A affinity chromatography) by SDS-PAGE in the absence of a reducing agent and staining with Coomassie (SimpleBlue™ SafeStain, Invitrogen). The NuPAGE® Pre-Cast gel system (Invitrogen, USA) was used according to the manufacturer's instruction (4-12% Tris-Acetate gels or 4-12% Bis-Tris).

The protein concentration of purified protein samples was determined by measuring the optical density (OD) at 280 nm, using the molar extinction coefficient calculated on the basis of the amino acid sequence.

Purity and molecular weight of molecules after the final purification step were analyzed by CE-SDS analyses in the presence and absence of a reducing agent. The Caliper LabChip GXII system (Caliper lifescience) was used according to the manufacturer's instruction. 2 μg sample was used for analyses. The aggregate content of antibody samples was analyzed using a TSKgel G3000 SW XL analytical size-exclusion column (Tosoh) in 25 mM $K_2HPO_4$, 125 mM NaCl, 200 mM L-arginine monohydrochloride, 0.02% (w/v) $NaN_3$, pH 6.7 running buffer at 25° C.

All molecules were produced and purified following the same method (except for molecule A having been subjected to an additional SEC step, as indicated above).

Molecule A showed a high aggregate content after the first preparative size exclusion chromatography. The content of aggregates after this purification step could not be determined since there was no baseline separation of high molecular weight impurities and the monomeric fraction. To obtain 100% monomeric material an additional preparative size exclusion chromatography step was necessary. Molecule B was 100% monomeric after one preparative size exclusion chromatography.

The concentration in the supernatant was higher for molecule A, but the final yield was (due to the high aggregate content) 2.3 fold lower than for molecule B (Table 2).

Figure 3B:
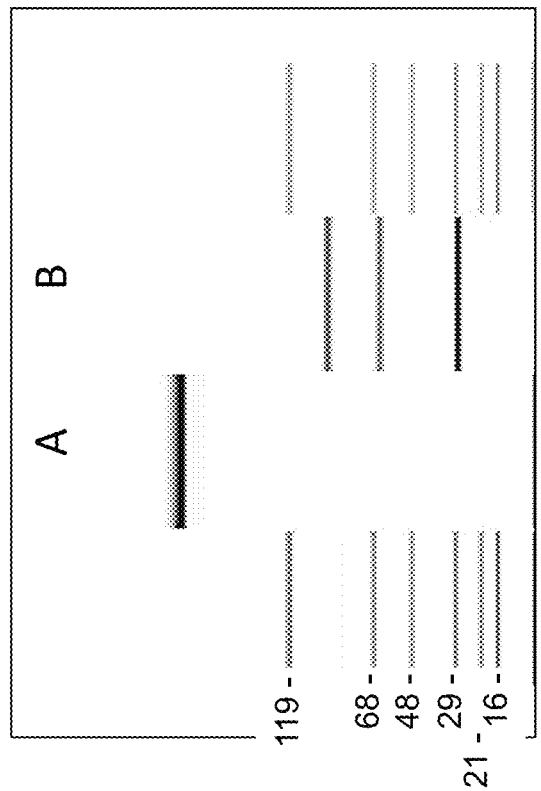
(FIGS. 3A-3I, FIG. 3N, FIG. 3O) CE-SDS analysis of the TCBs prepared in Example 1 (final purified preparations).
Figure 3A:
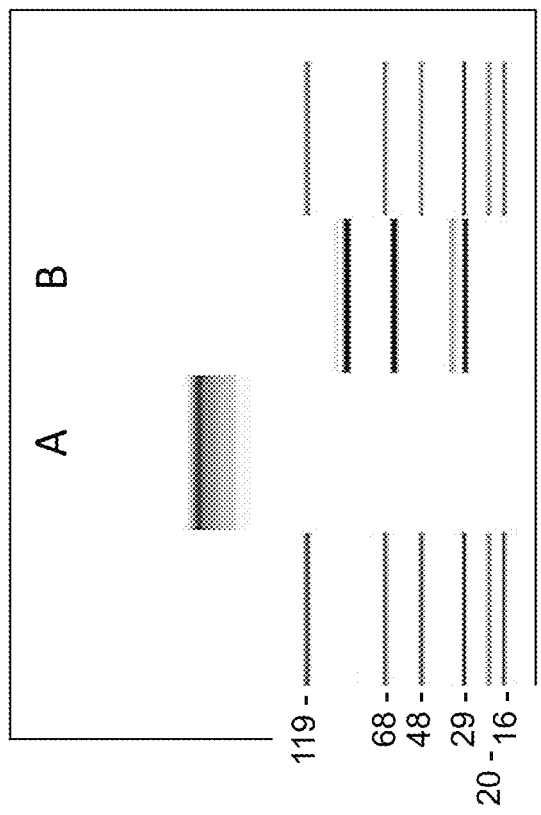
Figure 3C:
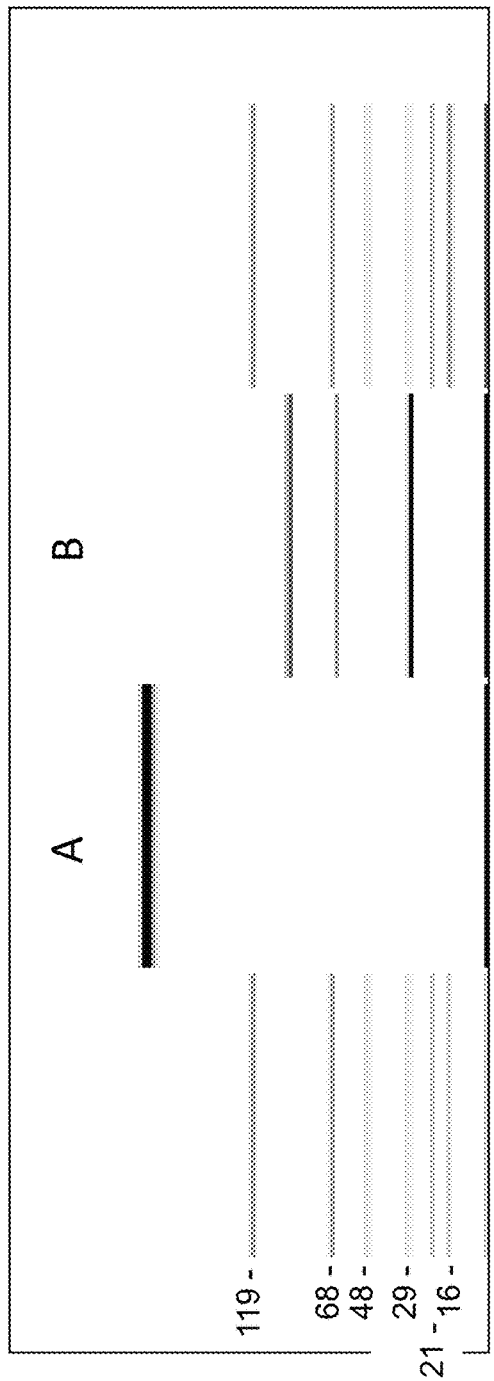
Figure 3D:
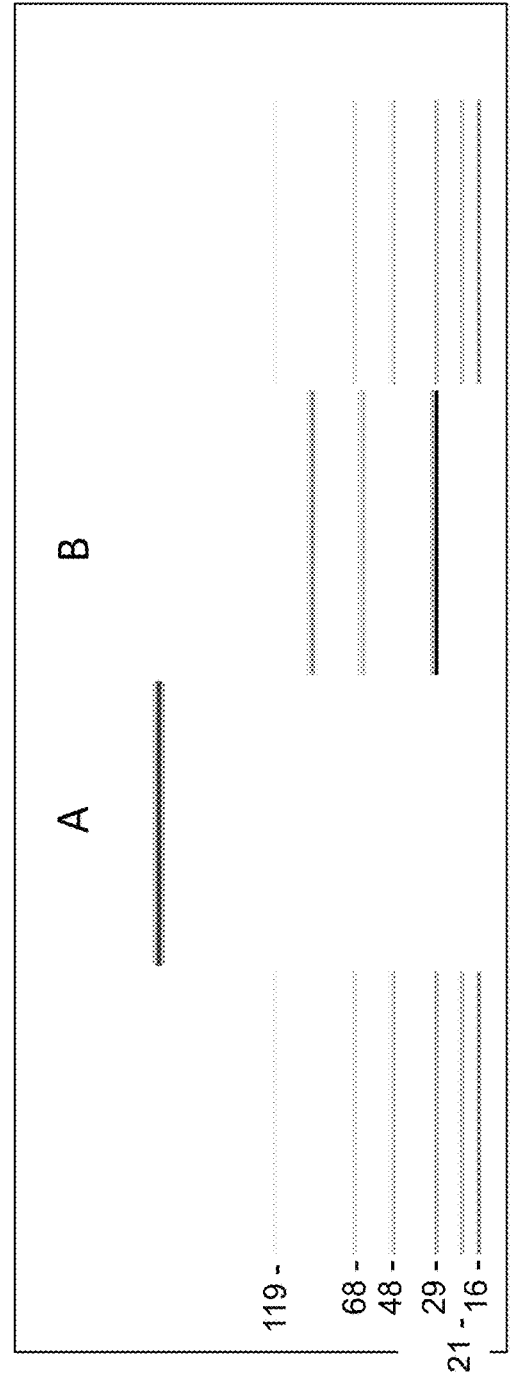
Figure 3E:
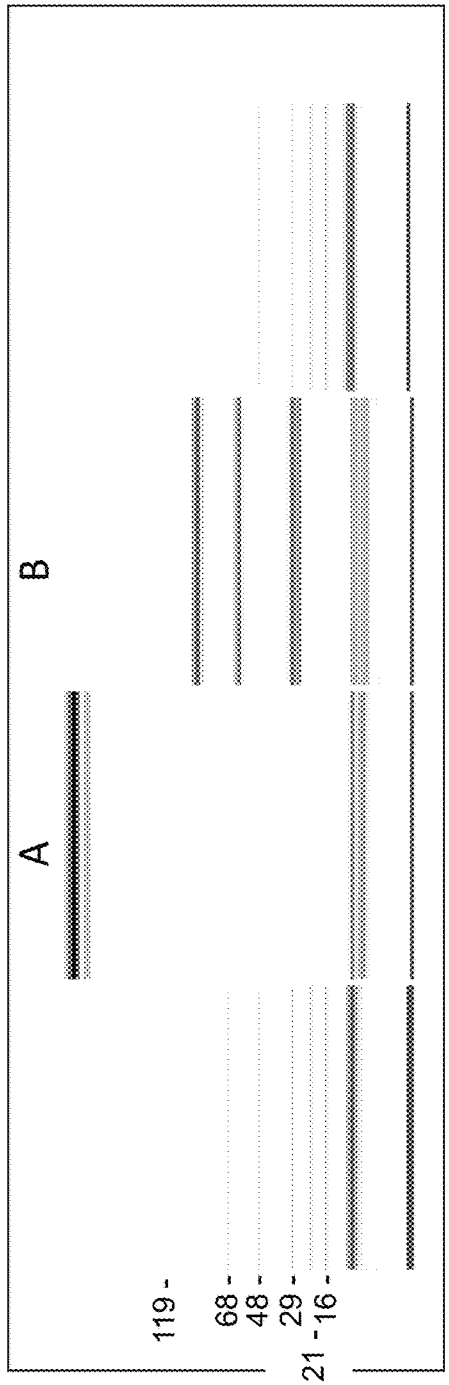
Figure 3F:
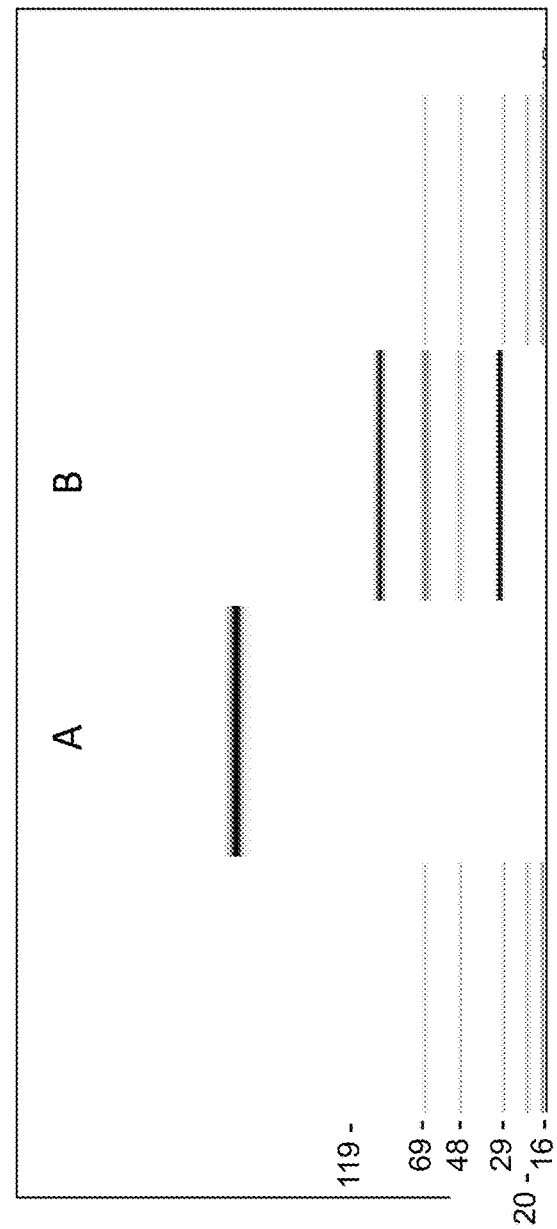
Figure 3G:
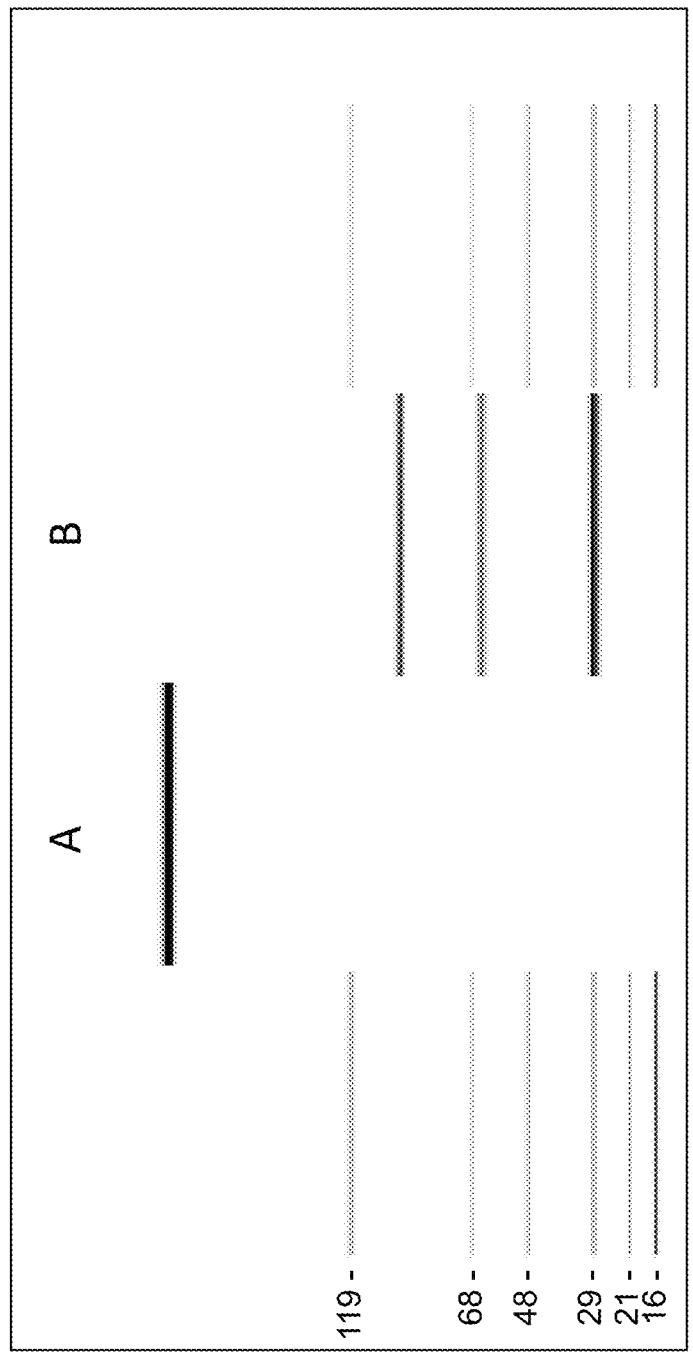
Figure 3H:
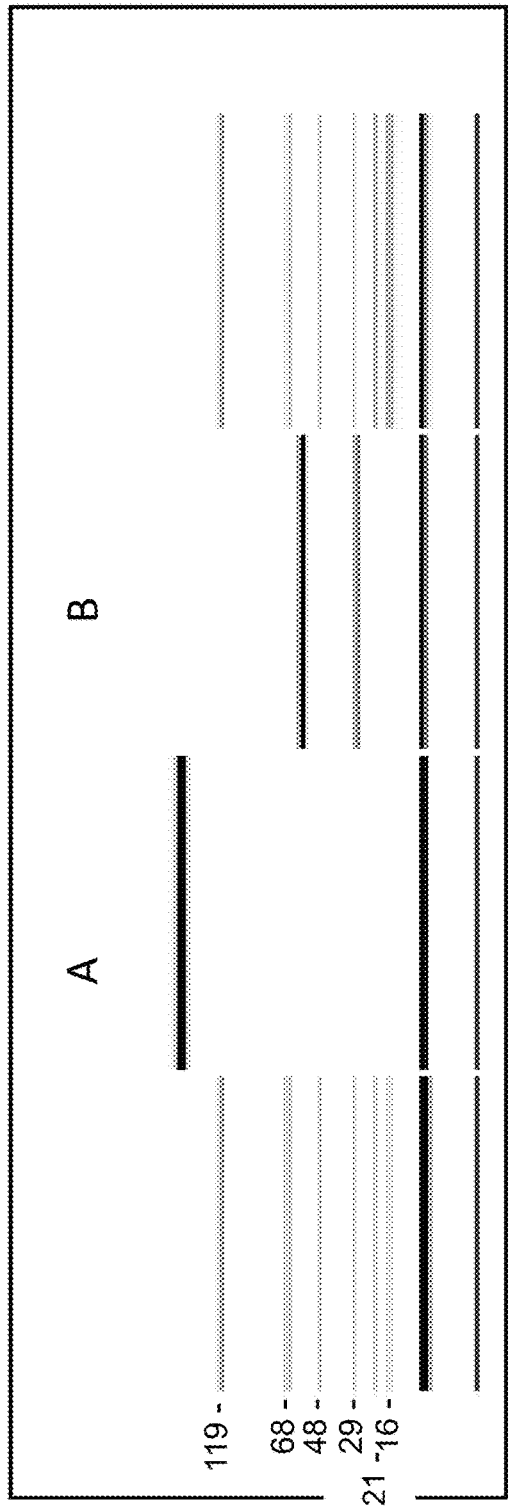
Figure 3I:
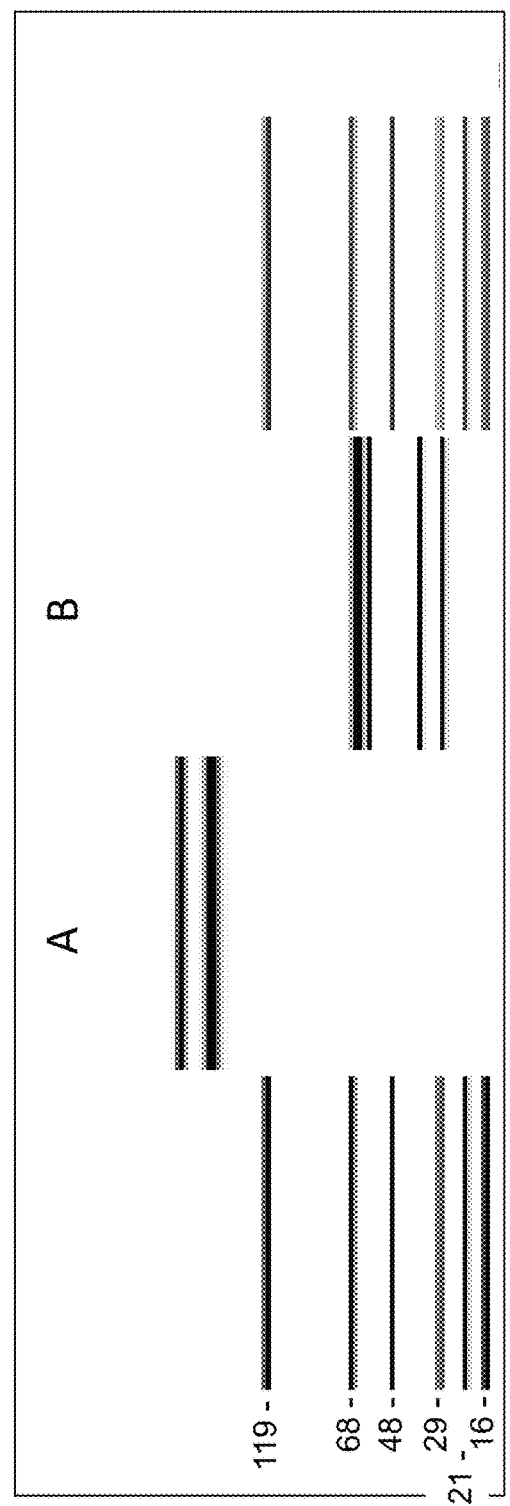
Figure 3L:
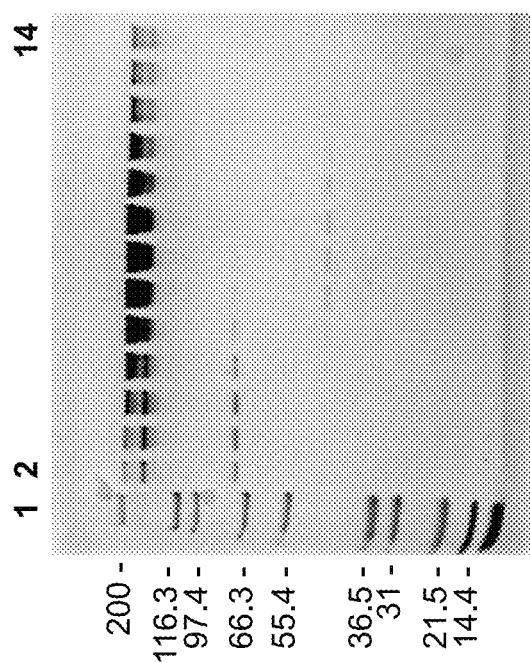
Figure 3M:
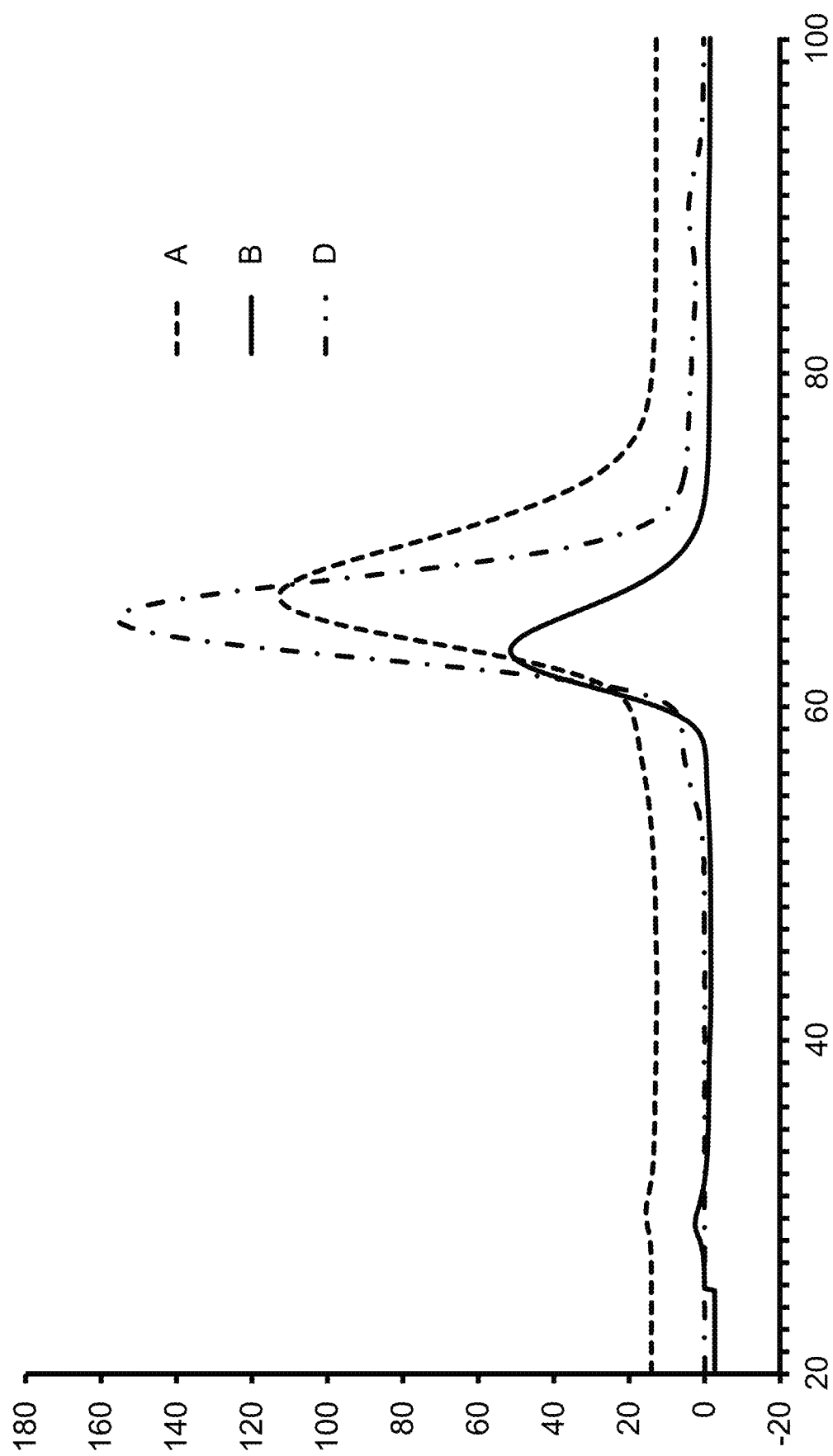
(FIG. 3M) Preparative size exclusion chromatography (SEC; first purification step) of TCBs prepared in Example 1 (molecule A (first SEC step), B and D, as indicated).
Figure 3N:
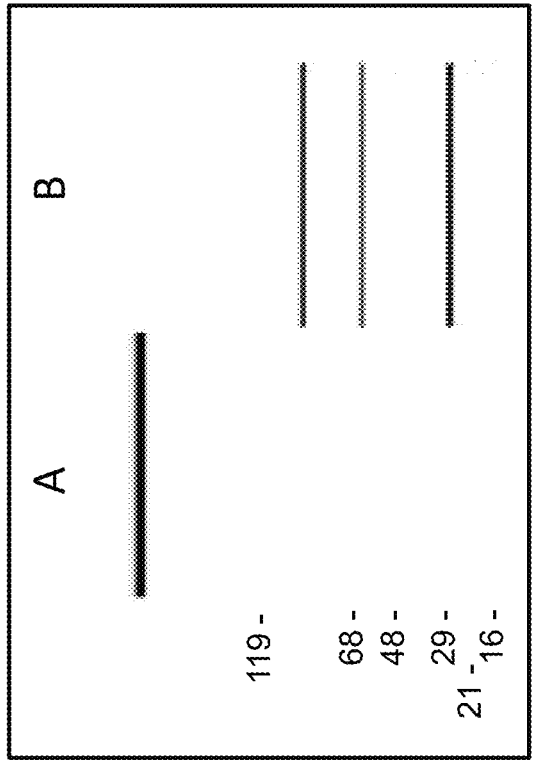

The final purity shown by CE-SDS analyses was higher for molecule B than for molecule A (Table 3, FIGS. 3A and 3B). FIGS. 3M and 3N show chromatograms of the SEC purification step (preparative SEC) wherein molecule A has a broad peak as compared to molecule B, indicating that the preparation of molecule A loaded on the SEC is not homogenous while the preparation of molecule B is largely monomeric.

Molecule C could be produced with high titer but compared to molecule B the final recovery was lower due to a high content of side products that could not be completely removed by the applied chromatography methods (Table 2; Table 3; FIGS. 3B and 3J, and FIGS. 3C and 3K). As shown in FIGS. 3B and 3K, the SDS-PAGE analysis after the Protein A purification step showed no side product for molecule B, while the preparation of molecule C contains some side products appearing at an apparent molecular weight of 100 kDa.

Figure 3O:
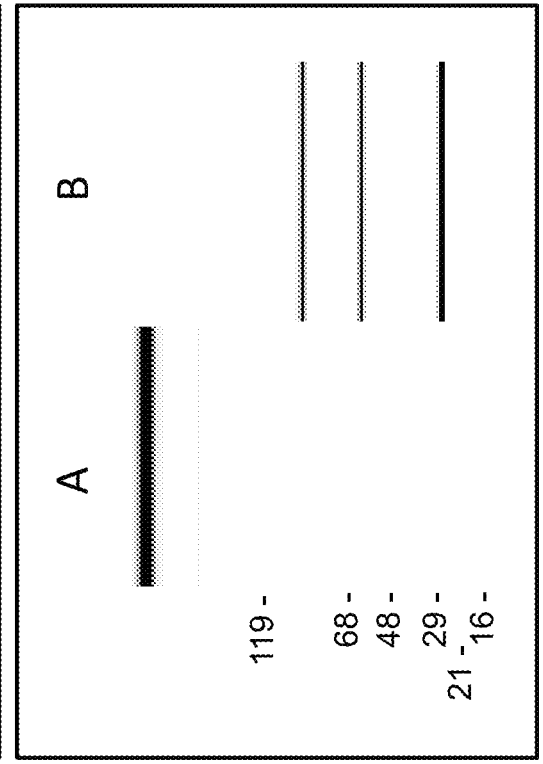

Molecule D differs from molecule B only in the absence of the charged residues in the anti-CD20 Fabs. This molecule could also be produced transiently with high titer but as already described for molecule C the final quality shown on analytical SEC (98% monomer for molecule D, vs. 100% monomer for molecule B) and the recovery was lower than for molecule B due to a high content of side products (Table 2; Table 3; FIGS. 3B and 3J and FIGS. 3D and 3L). As shown in FIGS. 3J and 3L, the SDS-PAGE analysis after the Protein A purification step showed no side product for molecule B, while the preparation of molecule D contains some side products appearing at an apparent molecular weight of 66 kDa and 40 kDa. FIGS. 3N and 3O show chromatograms of the SEC purification step (preparative SEC) wherein molecule D has a broad peak as compared to molecule B, indicating that the preparation of molecule D loaded on the SEC is not homogenous while the preparation of molecule B is largely monomeric.

Also the titer of the production of molecule E was high but the final product contained still low molecular weight impurities as shown by analytical SEC and capillary electrophoresis (Table 2; Table 3; FIG. 3E).

In contrast to molecule B, molecule F has the VH-VL exchange on the Fab of the tumor target binding moiety whereas the charge modifications have been introduced in the anti-CD3 Fab. This molecule could be produced with high titers too, but the final recovery was low due to side products. For the anti-CD20/anti-CD3 TCB the format with charge modifications in the anti-CD20 Fab is preferable with regard to production and purification.

Molecule G is a molecule with charge modifications in the Fc region ("DD"=K392D; K409D in one of the subunits of the Fc domain, "KK"=D356K; D399K in the other of the subunits of the Fc domain (EU numbering), replacing the "knob into hole" mutation. The generation of bispecific molecules is fostered by the introduction of two aspartic acid residues on one heavy chain and two lysine residues in the second heavy chain (FIG. 2G). This molecule could be produced with high titer but the final product has still some high molecular and low molecular weight impurities shown by analytical SEC and capillary electrophoresis (Table 2; Table 3) whereas the side products could be completely removed for the same molecule carrying the "knob into hole" mutation (molecule B). Molecule I, which differs from molecule H in its CD20 binder, showed a higher aggregate content after the final preparative size exclusion chromatography compared to molecule H. The final purity shown by CE-SDS analyses was higher for molecule H than for the molecule I (Table 3; FIGS. 3H and 3I). Also the recovery for molecule H was 40% higher than for molecule I (Table 2). This result shows that the quality of the molecule is also dependent on the antibody used in the T cell bispecific format.

Figure 3Q:
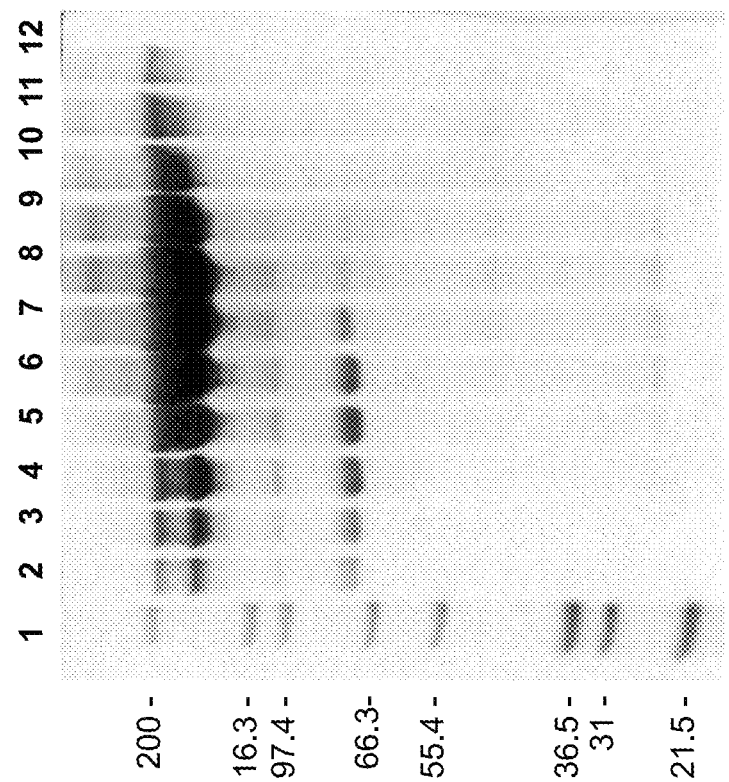
Figure 3P:
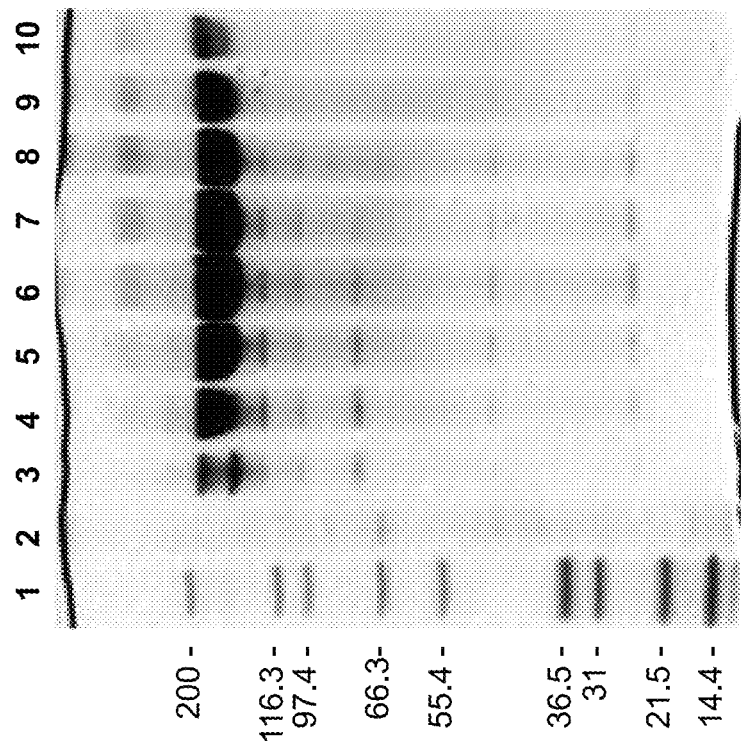

The productions of molecule J and molecule K had a good starting titer which led to a good yield. However, the final recovery of around 20% for both molecules was well below the 48% achieved with molecule B (Table 2). Both molecules are similar in final quality with >99% monomer content (Table 2). The purity in non-reduced CE-SDS is better for molecule J (which lacks the charge modifications at position 124 of the CL domain and position 147 of the CH1 domain) with nearly 99% compared to molecule K (having charge modifications and a VL-VH exchange in the CD3 binder) with 90% (Table 3, FIGS. 3N and 3O). Molecule J showed some precipitation during the concentration step after affinity chromatography. Molecule K has charge modifications in the CD3 binding CrossFab rather than the CD20 binding Fabs. This has an impact on the final quality as shown by CE-SDS (Table 3, FIG. 3O). The difference in quality is mostly visible after the first purification step on SDS-Page (FIGS. 3P and 3Q). Molecule K contains more side products at 150 kDa and 70 kDa (half molecules and constructs probably missing light chains) than molecule J. Both molecules have the same thermal stability which is similar to molecule B (Table 4).

For the anti-CD20/anti-CD3 TCB the "inverted" version with charge modifications on the anti CD20 Fab (molecule B) is the format that could be produced with the highest recovery and final quality.

TABLE 2

Summary of production and purification of anti-CD20/anti-CD3 TCB molecules with and without charge modifications.

| Molecule | Titer (mg/l) | Recovery [%] | Yield (mg/l) | Analytical SEC (HMW/Monomer/LMW) [%] | App. purity determined by LC-MS [%] |
| --- | --- | --- | --- | --- | --- |
| A | 16.7 | 7.2 | 1.2 | 0/100/0 * | 85-90 * |
| B | 5.5 | 48.2 | 2.8 | 0/100/0 | 93 |
| C | 25 | 12.9 | 3.24 | 4/93/3 | nd |
| D | 55 | 9.8 | 5.42 | 2/98/0 | nd |
| E | 30.5 | 3.3 | 0.99 | 0/96.3/3.7 | nd |
| F | 57 | 11.8 | 6.43 | 3.4/96.6/0 | nd |
| G | 56 | 21 | 11.8 | 3.75/92.3/3.43 | nd |
| H | 29 | 9.2 | 2.66 | 2/98/0 | nd |
| I | 52.5 | 5.8 | 3.05 | 2.7/95.3/2 | nd |
| J | 77 | 18 | 17.4 | 0.7/99.3/0 | nd |
| K | 71.5 | 21.8 | 15.5 | 0/99.7/0.3 | nd |

* final product, after two SEC steps

TABLE 3

CE-SDS analyses (non-reduced) of anti-CD20/anti-CD3 TCB molecules with and without charge modifications.

| Molecule | Peak # | Size [kDa] | Purity [%] |
| --- | --- | --- | --- |
| A | 1 | 34.13 | 0.49 |
|   | 2 | 55.10 | 0.58 |
|   | 3 | 58.89 | 0.97 |
|   | 4 | 152.30 | 1.76 |
|   | 5 | 165.95 | 2.25 |
|   | 6 | 177.64 | 7.75 |
|   | 7 | 186.15 | 14.06 |
|   | 8 | 194.17 | 18.37 |
|   | 9 | 201.68 | 53.77 |
| B | 1 | 160.09 | 0.57 |
|   | 2 | 180.70 | 1.62 |
|   | 3 | 194.42 | 97.81 |
| C | 1 | 131.12 | 0.82 |
|   | 2 | 141.45 | 3.45 |
|   | 3 | 182.86 | 2.39 |
|   | 4 | 192.1 | 13.5 |
|   | 5 | 198.13 | 79.84 |
| D | 1 | 207.04 | 100 |
| E | 1 | 176.36 | 0.67 |
|   | 2 | 196.54 | 14.36 |
|   | 3 | 209.22 | 84.97 |
| F | 1 | 30.41 | 0.55 |
|   | 2 | 65.04 | 1.33 |
|   | 3 | 198.80 | 2.05 |
|   | 4 | 203.10 | 7.94 |
|   | 5 | 213.93 | 88.12 |
| G | 1 | 96.50 | 1.67 |
|   | 2 | 208.46 | 96.77 |
|   | 3 | 216.11 | 1.55 |
| H | 1 | 131.98 | 1.13 |
|   | 2 | 140.64 | 1.96 |
|   | 3 | 153.02 | 92.24 |
|   | 4 | 161.24 | 4.67 |
| I | 1 | 55.75 | 1.88 |
|   | 2 | 158.62 | 50.78 |
|   | 3 | 178.6 | 46.14 |
|   | 4 | 218.64 | 1.2 |
| J | 1 | 186.5 | 1.4 |
|   | 2 | 198.2 | 98.6 |
| K | 1 | 164.7 | 4 |
|   | 2 | 182.4 | 6 |
|   | 3 | 200.1 | 90 |

Molecular Weight Confirmation by LC-MS Analyses
Deglycosylation

To confirm homogeneous preparation of the molecules, the final protein solution was analyzed by LC-MS analyses. To remove heterogeneity introduced by carbohydrates, the constructs were treated with PNGaseF. For this purpose, the pH of the protein solution was adjusted to pH 7.0 by adding 2 µl 2 M Tris to 20 µg protein with a concentration of 0.5 mg/ml. 0.8 µg PNGaseF was added and incubated for 12 h at 37° C.

LC-MS Analysis—On Line Detection

The LC-MS method was performed on an Agilent HPLC 1200 coupled to a TOF 6441 mass spectrometer (Agilent). The chromatographic separation was performed on a Macherey Nagel Polysterene column; RP1000-8 (8 µm particle size, 4.6×250 mm; cat. No. 719510). Eluent A was 5% acetonitrile and 0.05% (v/v) formic acid in water, eluent B was 95% acetonitrile, 5% water and 0.05% formic acid. The flow rate was 1 ml/min, the separation was performed at 40° C. and with 6 µg (15 µl) protein sample obtained with the treatment described before.

| Time (min.) | % B |
| --- | --- |
| 0.5 | 15 |
| 10 | 60 |
| 12.5 | 100 |
| 14.5 | 100 |
| 14.6 | 15 |
| 16 | 15 |
| 16.1 | 100 |

During the first four minutes the eluate was directed into the waste to prevent salt contamination of the mass spectrometer. The ESI-source was running with a drying gas flow of 12 l/min, a temperature of 350° C. and a nebulizer pressure of 60 psi. The MS spectra were acquired using a fragmentor voltage of 380 V and a mass range 700 to 3200 m/z in positive ion mode. MS data are acquired by the instrument software from 4 to 17 minutes.

The preparation of molecule A had about 10-15% molecules with mispaired light chains and traces of free or linked light chains. The preparation of molecule B had traces of molecules comprising two CD3 light chains. Impurities such as free light chain or linked light chain could not be detected (Table 2).

Thermal Stability by Static Light Scattering

Thermal stability was monitored by Static Light Scattering (SLS) and by measuring the intrinsic protein fluorescence in response to applied temperature stress.

30 µg of filtered protein sample with a protein concentration of 1 mg/ml was applied in duplicate to Optim 2 (Avacta Analytical Ltd; GB). The temperature was ramped from 25 to 85° C. at 0.1° C./min, with the radius and total scattering intensity being collected. For determination of intrinsic protein fluorescence the sample was excited at 295 nm and emission was collected between 266 and 473 nm. Thermal stability was determined for all molecules, results are shown in Table 4. The aggregation temperature ($T_{Agg}$) determined by dynamic light scattering and the melting temperature ($T_M$) measured by protein fluorescence after applying a temperature gradient was comparable for all molecules with $T_{Agg}$ ranging from 54-58° C. and $T_M$ ranging from 56-60° C. (Table 4).

TABLE 4

Thermal stability of anti-CD20/anti-CD3 TCB molecules with and without charge modifications.

| Molecule | $T_{Aggregation}$ [° C.] | $T_M$ [° C.] |
| --- | --- | --- |
| A | 54.4 | 55.9 |
| B | 54.3 | 56.4 |
| C | 56 | 59 |
| D | 56 | 59 |
| E | 56 | 60 |
| F | 58 | 60 |
| G | 57 | 59 |
| H | 55 | 56 |
| I | 53 | 57 |
| J | 54 | 55 |
| K | 54 | 55 |

Binding to CD3 and CD20 of Anti-CD3/Anti-CD20 TCB Antibodies

The binding to CD3 of anti-CD3/anti-CD20 T cell bispecific (TCB) antibodies with or without charge modifications (molecules "A" and "B" above) was measured using human CD3-expressing Jurkat cells. The binding to CD20 was determined using human CD20-expressing Z-138 cells. Suspension cells were harvested, washed once with PBS, and viability and cell density determined using Vicell. The suspension cells were resuspended at 2×10$^6$ cells/ml in FACS buffer. 100 µl of the cell suspension were seeded into a 96 well round bottom plate. Each step was performed at 4° C. The plates were centrifuged at 360×g for 5 min and the supernatant was removed. Antibody dilutions were prepared in PBS/0.1% BSA. 30 µl of the diluted anti-CD3/anti-CD20 TCB antibodies or FACS buffer were added to the wells and the cells were incubated for 30 min at 4° C. After the incubation, 120 µl FACS buffer were added per well, the plate was centrifuged for 5 min at 350×g, and the supernatant was removed. The washing step was repeated once. 30 µl pre-diluted secondary antibody was added per well, as indicated in the plate layout. The plates were incubated for further 30 min at 4° C. After the incubation, 120 µl FACS buffer were added per well, the plates were centrifuged for 5 min at 350×g, and the supernatant was removed. The washing step was repeated once for all plates but the plate with Jurkat cells, which were fixed directly after this one washing step. The cells were fixed using 100 µl BD Fixation buffer per well (# BD Biosciences, 554655) at 4° C. for 20-30 min. Cells were re-suspended in 80 µl/well FACS buffer for the FACS measurement using a BD FACS CantoII.

Figure 4:
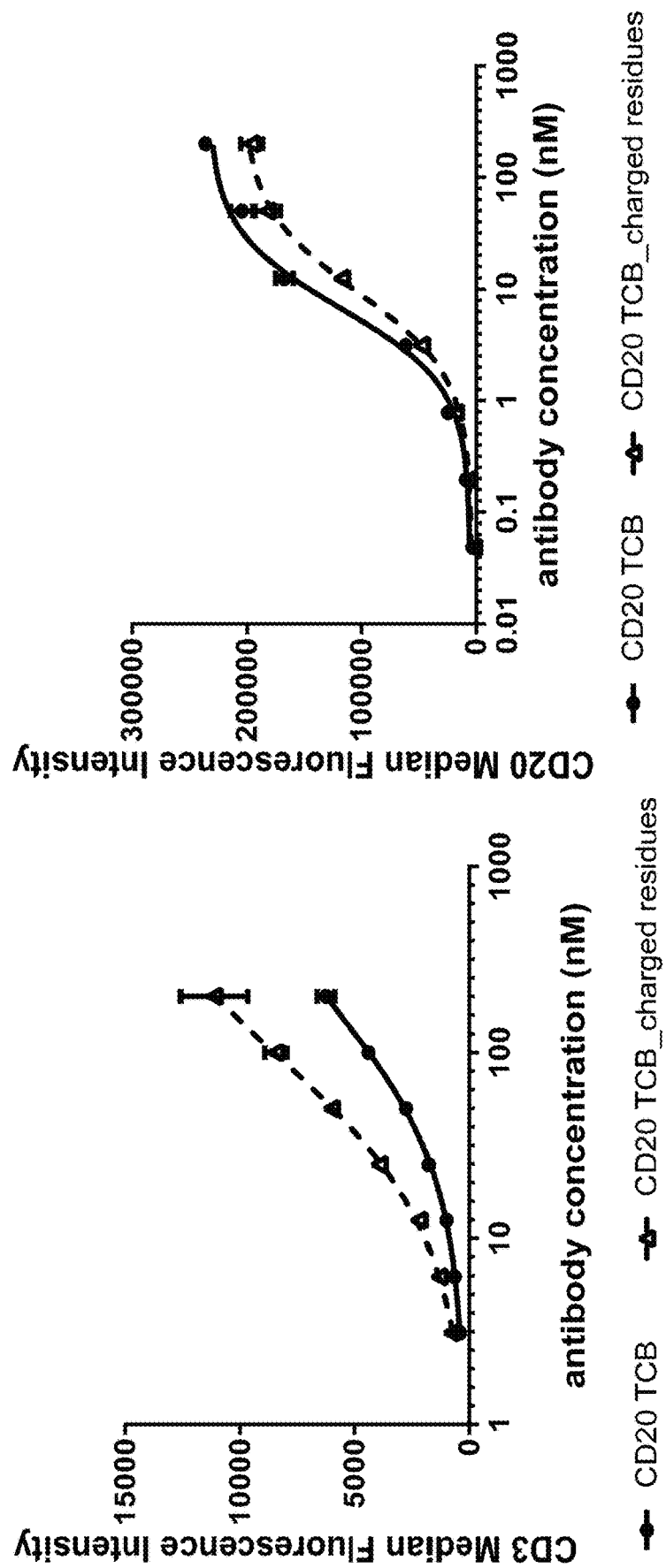
FIG. 4. CD3 and CD20 binding of anti-CD3/anti-CD20 T cell bispecific (TCB) antibodies ("CD20 TCB") with or without charge modifications ("charge residues") (see Example 1).
Figure 5:
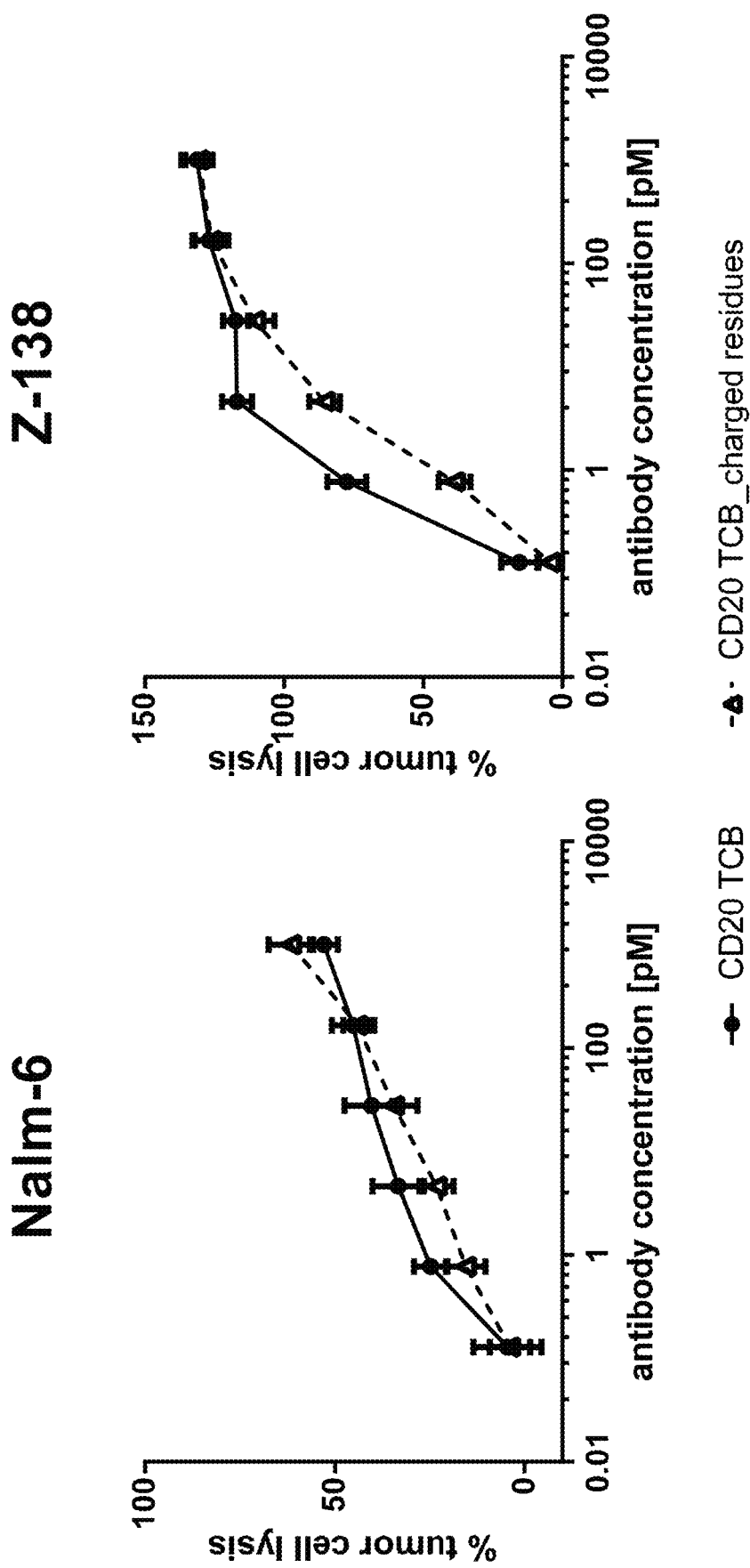
FIG. 5. Tumor cell lysis induced by anti-CD3/anti-CD20 T cell bispecific (TCB) antibodies ("CD20 TCB") with or without charge modifications ("charge residues") upon 22 h incubation with human PBMCs (see Example 1).
Figure 6B:
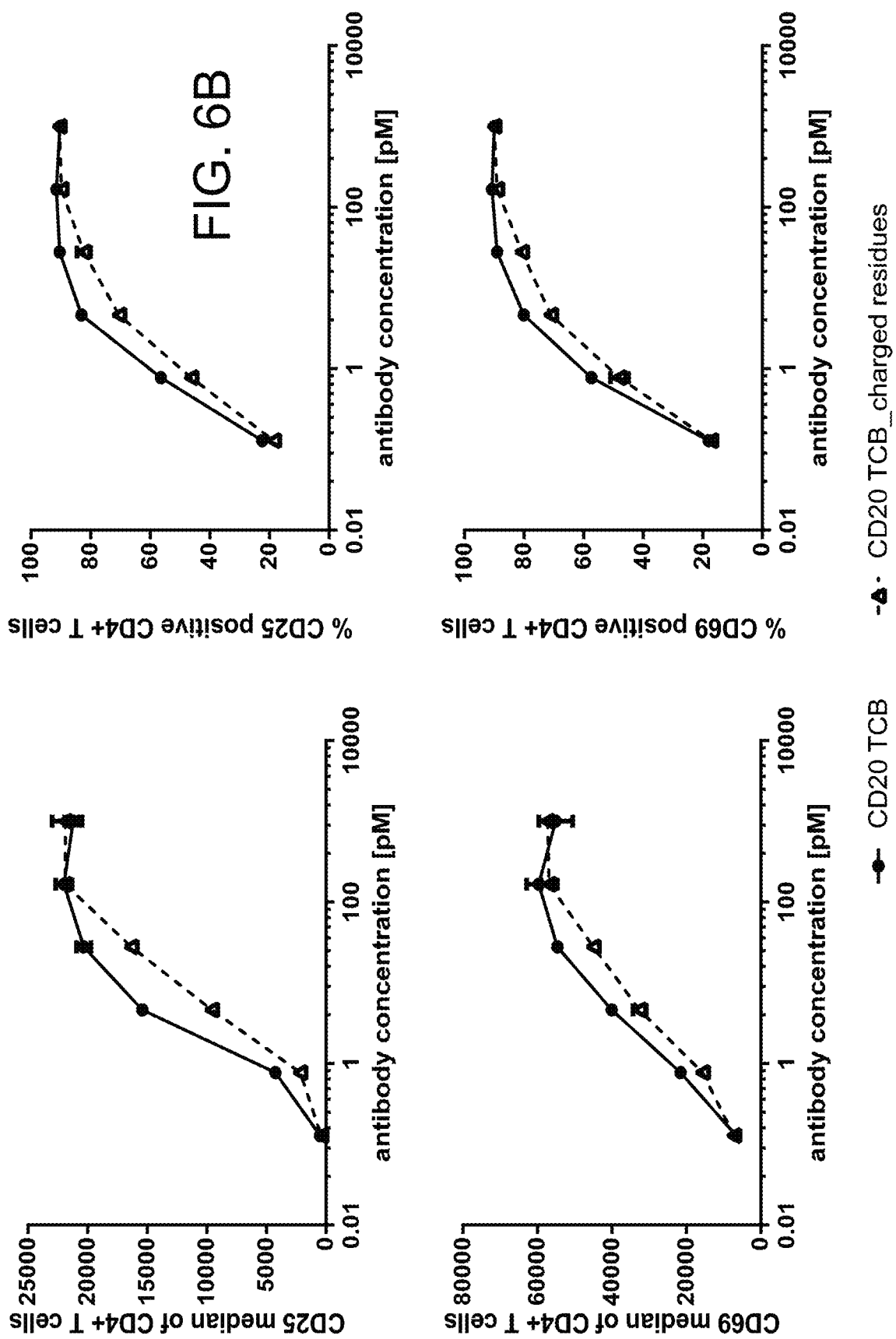
FIG. 6. Activation of $CD8^+$ T cells (A) or $CD4^+$ T cells (B) upon T cell-mediated killing of CD20-expressing tumor target cells (Nalm-6) induced by anti-CD3/anti-CD20 T cell bispecific (TCB) antibodies ("CD20 TCB") with or without charge modifications ("charge residues") (see Example 1).

The result of this experiment is shown in FIG. 4.

Tumor Cell Lysis and CD4$^+$ and CD8+ T Cell Activation Upon T Cell-Mediated Killing of CD20-Expressing Tumor Target Cells Induced by Anti-CD3/Anti-CD20 TCB Antibodies T cell-mediated killing of target cells and activation of T cells induced by anti-CD3/anti-CD20 TCB antibodies with or without charge modifications (molecules "A" and "B" above) was assessed on Z-138 and Nalm-6 tumor cells. Human PBMCs were used as effectors and killing as well as T cell activation detected 22 h after incubation with the bispecific antibody. Briefly, target cells were harvested, washed, and plated at density of 30 000 cells/well using round-bottom 96-well plates. Peripheral blood mononuclear cells (PBMCs) were prepared by Histopaque density centrifugation of fresh blood from healthy human donors. Fresh blood was diluted with sterile PBS and layered over Histopaque gradient (Sigma, # H8889). After centrifugation (450×g, 30 minutes, room temperature), the plasma above the PBMC-containing interphase was discarded and PBMCs transferred in a new falcon tube subsequently filled with 50 ml PBS. The mixture was centrifuged (400×g, 10 minutes, room temperature), the supernatant discarded and the PBMC pellet washed twice with sterile PBS (centrifugation steps 350×g, 10 minutes). The resulting PBMC population was counted automatically (ViCell) and kept in RPMI1640 medium containing 10% FCS and 1% L-alanyl-L-glutamine (Biochrom, K0302) in cell incubator (37° C., 5% $CO_2$) until further use (no longer than 24 h). For the killing assay, the antibodies were added at indicated concentrations (range of 1000 pM-0.1 pM in triplicates). PBMCs were added to target cells at the final E:T ratio of 6:1. After the incubation, plates were centrifuged at 420×g for 4 min and 50 µl/well was transferred into fresh 96-flat bottom plates for LDH detection. LDH detection was performed using a Cytotoxicity Detection Kit (Roche #11644793001) according to the instructions of the manufacturer. The remaining cells were washed with PBS containing 0.1% BSA. Surface staining for CD8 (APCCy7 anti-human CD8, Biolegend #301016), CD4 (FITC anti-human CD4, Biolegend #300506), CD69 (BV421 anti-human CD69 Biolegend #310930) and CD25 (PECy7 anti-human CD25 Biolegend #302612) was performed according to the suppliers' indications. After 30 min at 4° C. cells were washed twice with 150 µl/well PBS containing 0.1% BSA and fixed using 100 µl/well 2% PFA. The measurement was performed using a BD FACS CantoII.

The result of this experiment is shown in FIGS. 5, 6A-6B, and 7A-7B. Both molecules display comparable activity in terms of tumor cell lysis and T cell activation.

Figure 8:
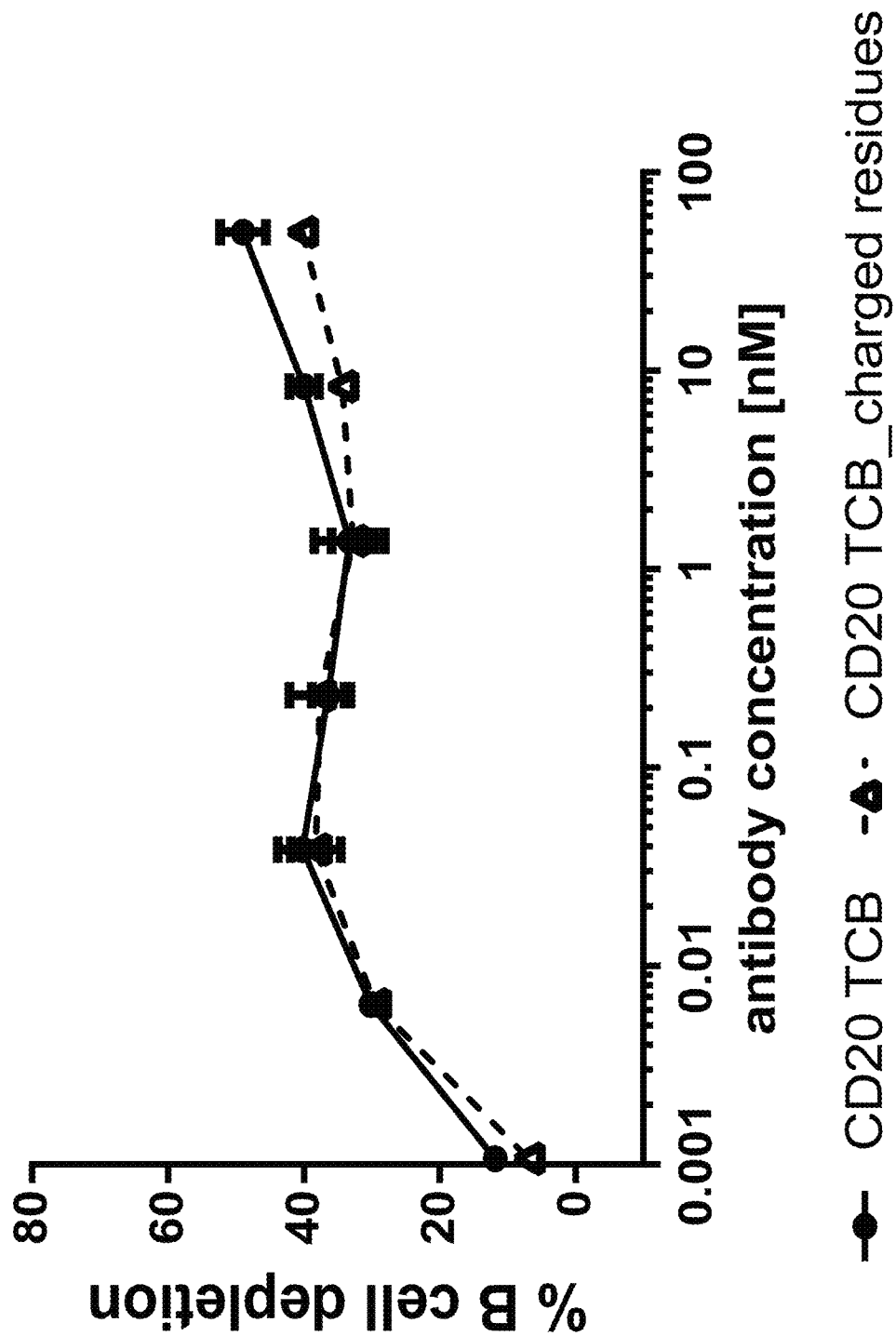
FIG. 8. B cell depletion in healthy human whole blood upon incubation with anti-CD3/anti-CD20 T cell bispecific (TCB) antibodies ("CD20 TCB") with or without charge modifications ("charge residues"); 22 h assay (see Example 1).

B Cell Depletion and $CD4^+$ and CD8+ T Cell Activation Upon T Cell-Mediated Killing of Healthy Human B Cells Induced by Anti-CD3/Anti-CD20 TCB Antibodies in Human Whole Blood Human whole blood from a healthy donor was incubated with anti-CD3/anti-CD20 TCB antibodies with or without charge modifications (molecules "A" and "B" above) at indicated concentrations (range of 50000 pM-1 pM in triplicates). After 22 h, the blood was mixed and 35 µl were collected for staining with 20 µl FACS antibody mix containing CD8 (APCCy7 anti-human CD8, Biolegend #301016), CD4 (FITC anti-human CD4, Biolegend #300506), CD69 (BV421 anti-human CD69 Biolegend #310930) and CD25 (PECy7 anti-human CD25, Biolegend #302612), CD22 (APC anti-human CD22, Biolegend #302510) and CD45 (PerCPCy5.5 anti-human CD45, Biolegend #304028). After 15 minutes incubation at room temperature, the blood was fixed with FACS Lysing solution (BD, #349202) and analyzed by flow cytometry. B cell depletion was calculated based on the ratio of B cell numbers and $CD4^+$ T cell numbers setting the untreated samples to 0% B cell depletion. The result of this experiment is shown in FIGS. 8 and 9A-9B. Both molecules display comparable activity in terms of B cell depletion in the whole blood and T cell activation.

Binding of Anti-CD3/Anti-CD20 TCB Antibody to Human CD20- and CD3-Expressing Target Cells The binding of the anti-CD3/anti-CD20 TCB antibody shown as molecule "B" above was tested on human CD20-expressing Diffuse Large-Cell B Cell Lymphoma (DLBCL) cell line (WSU DLCL2, $0.5-1×10^6$ CD20 binding sites) and CD3-expressing immortalized T lymphocyte line (Jurkat). Briefly, cells were harvested, counted, checked for viability and resuspended at $1.5×10^6$ cells/ml in FACS buffer (PBS 0.1% BSA). 100 µl of cell suspension (containing $0.15×10^6$ cells) were incubated in round-bottom 96-well plate for 30 min at 4° C. with increasing concentrations of the CD20 TCB (50 pM-200 nM), washed twice with cold PBS 0.1% BSA, re-incubated for further 30 min at 4° C. with diluted PE-conjugated AffiniPure F(ab') 2 Fragment goat anti-human IgG Fcg Fragment Specific secondary antibody (Jackson Immuno Research Lab PE #109-116-170), washed twice with cold PBS 0.1% BSA, fixed by addition of 2% PFA and analyzed by FACS using a FACS Cantoll (Software FACS Diva) excluding dead cells from analysis by FSC/SSC gating.

Figure 10B:
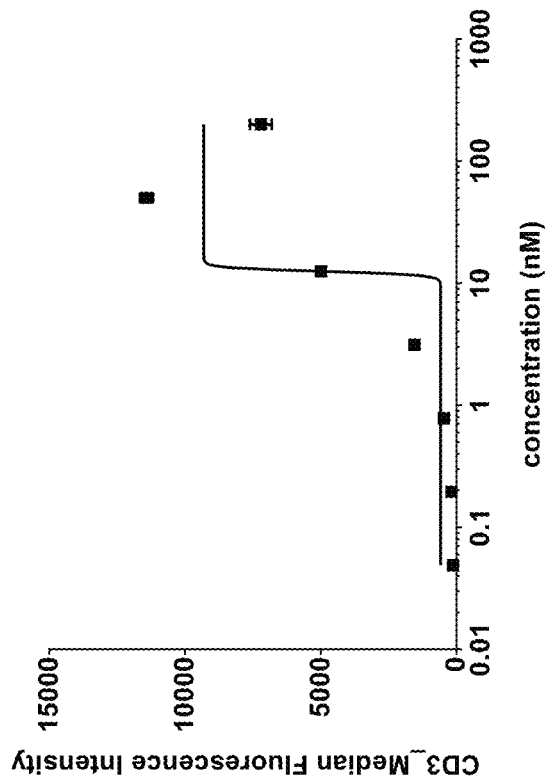
FIG. 10. Binding of anti-CD20/anti-CD3 TCB (molecule "B" shown in FIG. 2B) to human CD20-(FIG. 10A) and CD3-expressing (FIG. 10B) target cells.
Figure 10A:
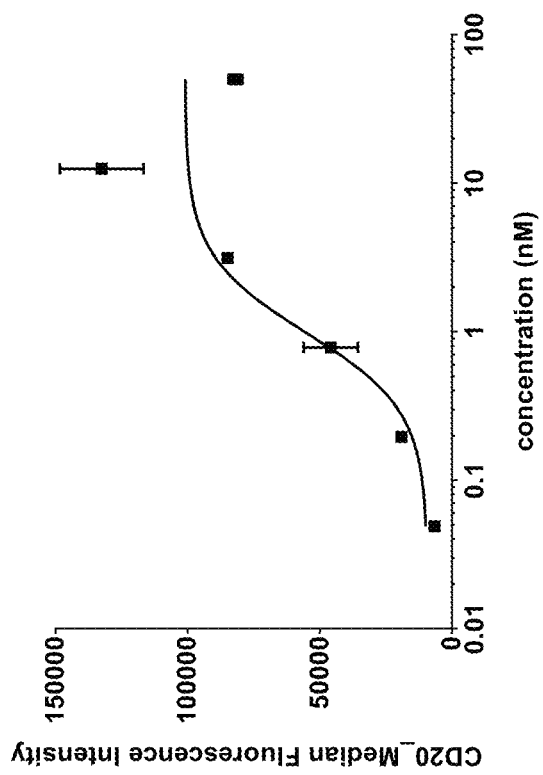

Results are shown in FIG. 10A (binding to WSU DLCL2 cells) and FIG. 10B (binding to Jurkat cells). Binding curves and the EC50 values related to binding were calculated using GraphPadPrism5. EC50 values were 0.98 nM (bivalent binding to CD20-expressing WSU DLCL2 cells) and approximately 12.5 nM (monovalent binding to CD3-expressing Jurkat cells).

Binding of Anti-CD3/Anti-CD20 TCB Antibody to Human and Cynomolgus Monkey CD20- and CD3-Expressing Target Cells The crossreactivity of the anti-CD3/anti-CD20 TCB antibody shown as molecule "B" above was evaluated by assessing binding to human and cynomolgus monkey CD20-expressing B cells and CD3-expressing CD4 and CD8 T cells. Briefly, heparinized human and cynomolgus monkey blood from healthy donors was used to isolate PBMCs by density centrifugation. Isolated PBMCs were counted, checked for viability and resuspended at $4×10^6$ cells/ml in FACS buffer (100 µl PBS 0.1% BSA). 100 µl of cell suspension (containing $0.4×10^6$ cells) were plated into 96-well_U-bottom plate and centrifuged (420×g, 4 min). After removal of the supernatants, PBMCs were incubated for 30 min at 4° C. with increasing concentrations of the CD20 TCB-AlexaFlour488 (200 pM-200 nM), washed twice with cold PBS 0.1% BSA, re-incubated for further 30 min at 4° C. with human/cynomolgus cross-reactive antibodies: anti-CD19 (in house, clone 8B8)-AlexaFluor647, anti-CD4 (BD, #552838, clone L200)-PerCPCy5.5 and anti-CD8 (BD, #555367, clone RPA-T8)-PE. After 30 min, PBMCs were washed twice with cold PBS 0.1% BSA and treated with FACS Lysing solution (BD, #349202) followed by FACS analysis using a FACS Cantoll (Software FACS Diva). Binding curves were obtained using GraphPad-Prism5.

Figure 11B:
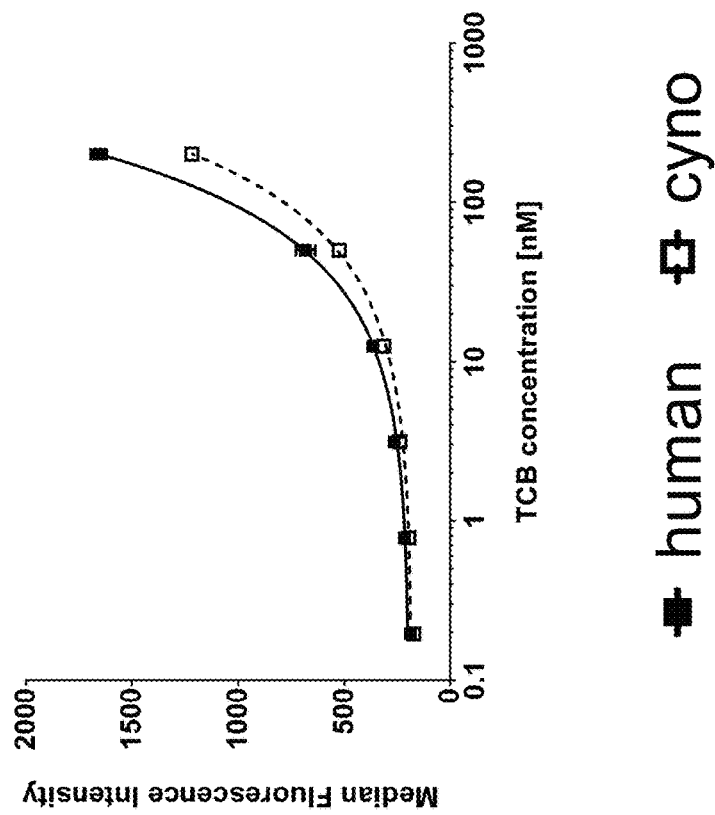
FIG. 11. Binding of anti-CD20/anti-CD3 TCB (molecule "B" shown in FIG. 2B) to human and cynomolgus monkey CD20- and CD3-expressing target cells.
(FIG. 11A) B-cells, (FIG. 11B) CD4 T cells, (FIG. 11C) CD8 T cells.
Figure 11A:
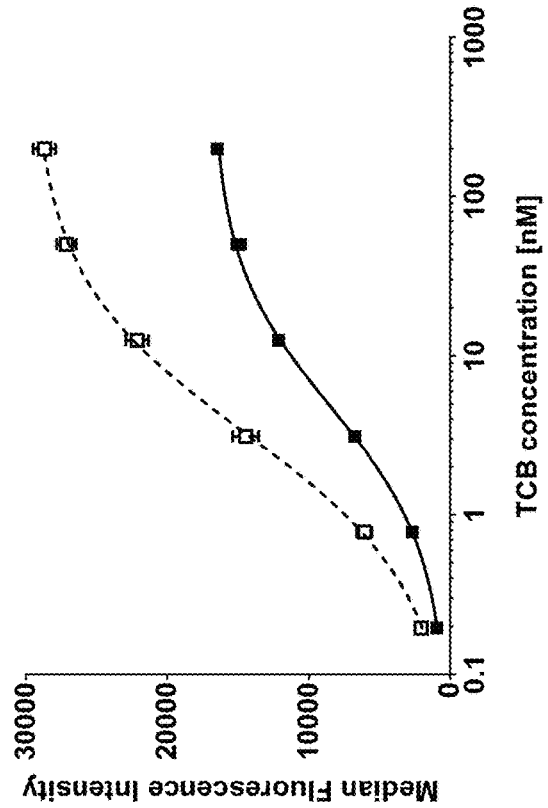
Figure 11C:
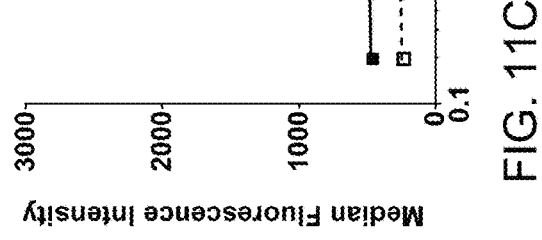

Results are shown in FIG. 11A (binding to human and cynomolgus monkey B cells), FIG. 11B (binding to human and cynomolgus monkey CD4 T cells) and FIG. 11C (binding to human and cynomolgus monkey CD8 T cells). The EC50 values related to binding to CD20-expressing B cells, calculated using GraphPadPrism5, were 4.8 nM (human B cells) and 3.3 nM (cynomolgus B cells).

Tumor Cell Lysis Mediated by Different Anti-CD20/Anti-CD3 TCB Antibody Formats

Tumor cell lysis mediated by different anti-CD20/anti-CD3 TCB antibody formats (molecules "B", "A" "C" and "H" shown above) was assessed on Z138 cells (mantle cell lymphoma, $0.06-0.23×10^6$ CD20 binding sites). Human PBMCs were used as effectors and tumor lysis was detected at 21-24 h of incubation with the different bispecific antibody formats. Briefly, target cells were harvested, washed, and plated at density of 50 000 cells/well using U-bottom 96-well plates. Peripheral blood mononuclear cells (PBMCs) were prepared by Histopaque density centrifugation of healthy human blood. Fresh blood was diluted with sterile PBS and layered over Histopaque gradient (Sigma, # H8889). After centrifugation (450×g, 30 minutes, room temperature, w/o brake), the plasma above the PBMC-containing interphase was discarded and PBMCs transferred in a new falcon tube subsequently filled with 50 ml of PBS. The mixture was centrifuged (350×g, 10 minutes, room temperature), the supernatant discarded and the PBMC pellet washed with sterile PBS (300×g, 10 minutes). The resulting PBMC population was counted automatically (Vi-Cell) and stored in RPMI1640 medium containing 10% FCS and 1% L-alanyl-L-glutamine (Biochrom, K0302) at 37° C., 5% $CO_2$ in cell incubator until further use (no longer than 24 h). For the tumor lysis assay, the antibodies were added at the indicated concentrations (range of 0.1 pM-1 nM in triplicates). PBMCs were added to target cells at final E:T ratio of 6:1. Tumor cell lysis was assessed after 21-24 h of incubation at 37° C., 5% $CO_2$ by quantification of LDH released into cell supernatants by apoptotic/necrotic cells (LDH detection kit, Roche Applied Science, #11 644 793 001). Maximal lysis of the target cells (=100%) was achieved by incubation of target cells with 1% Triton X-100. Minimal lysis (=0%) refers to target cells co-incubated with effector cells without bispecific construct.

Figure 12A:
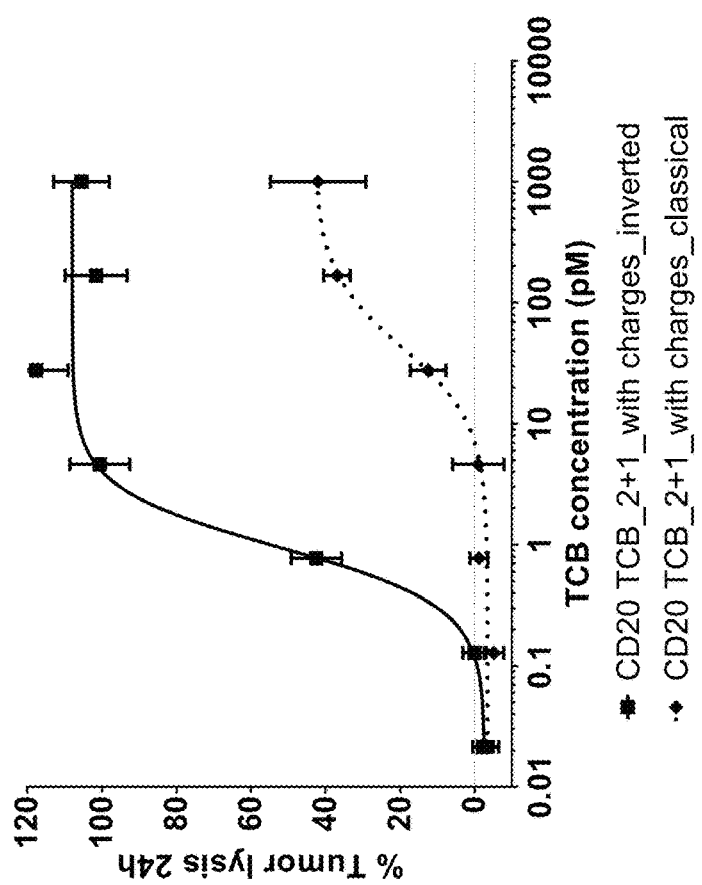
FIGS. 12A-12B. Tumor cell lysis mediated by different anti-CD20/anti-CD3 TCB antibody formats.
Figure 12B:
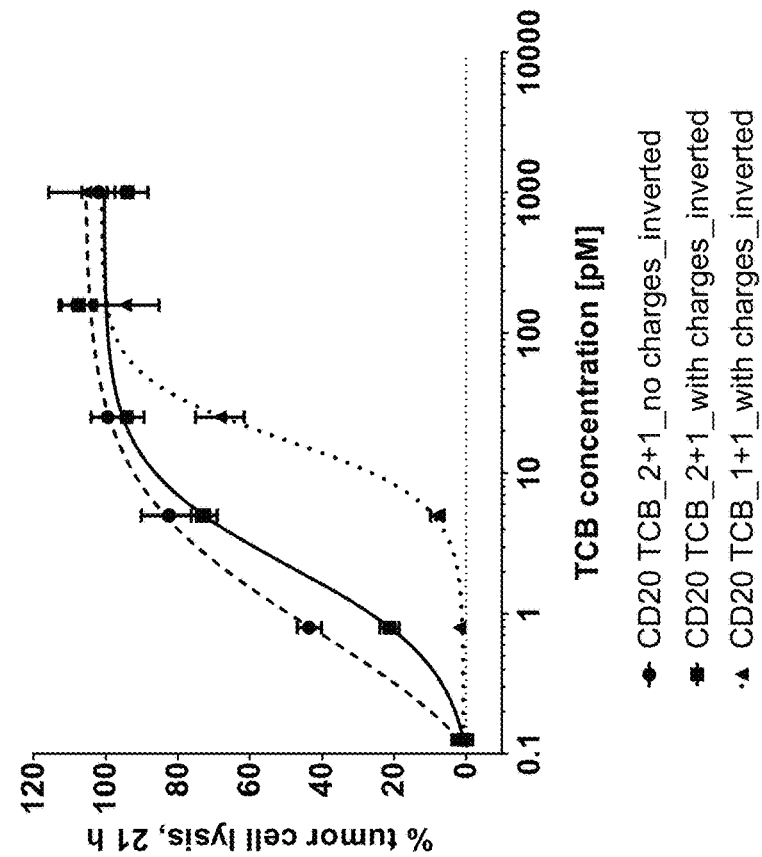
Figure 13A:
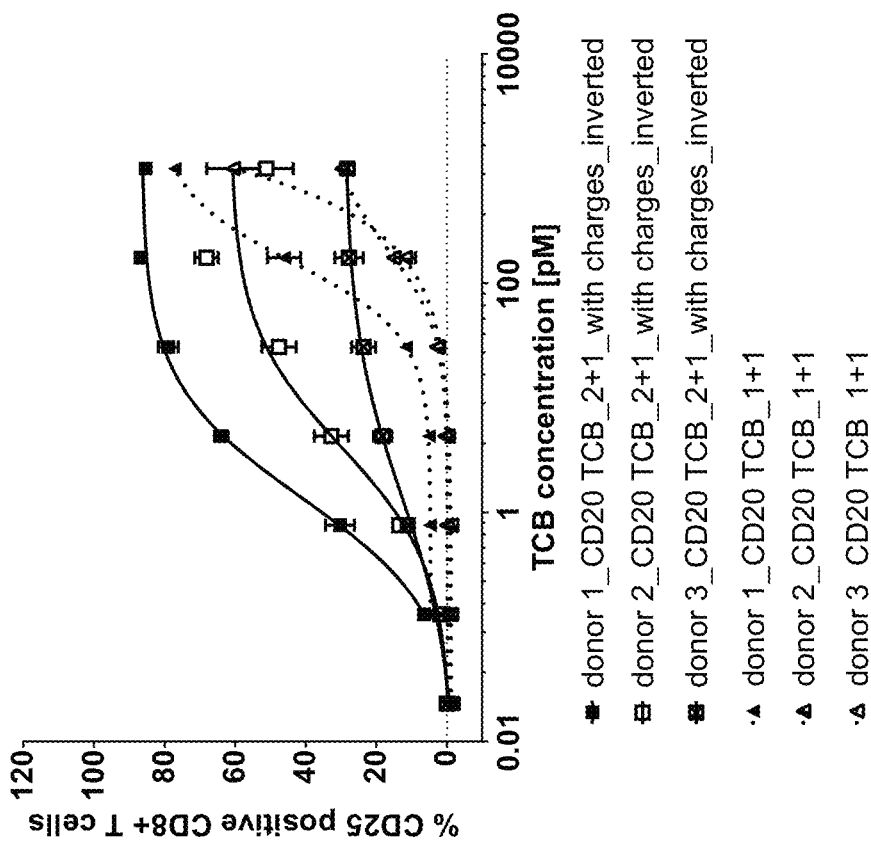
(FIGS. 13A-13C) Lysis of Z138 tumor target cells by PBMC effector cells from three different human donors.
Figure 13B:
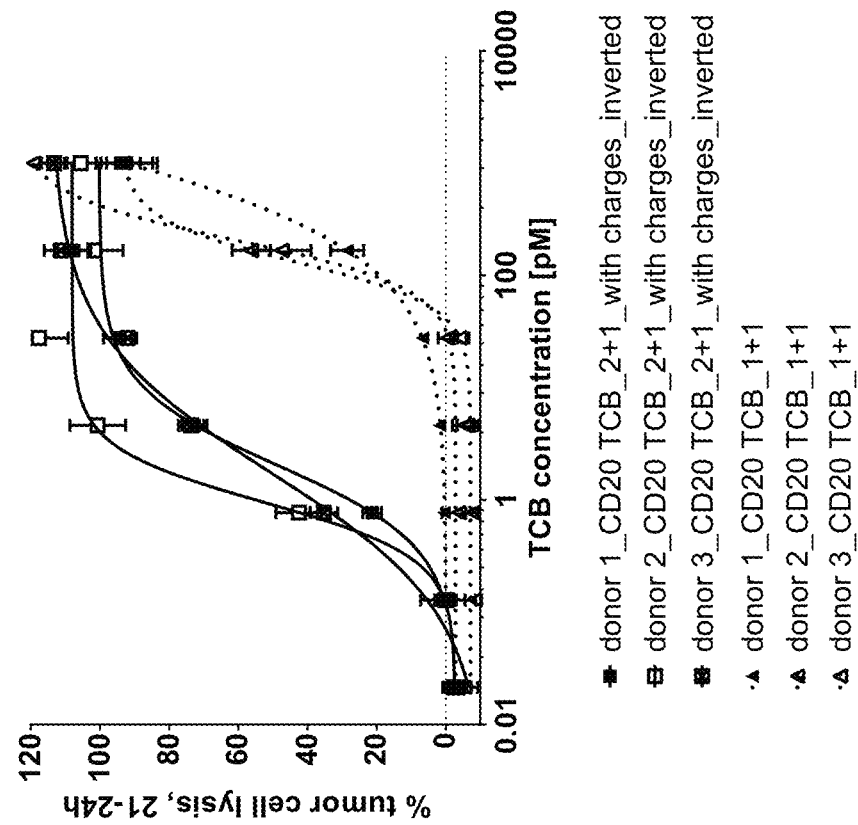
Figure 13C:
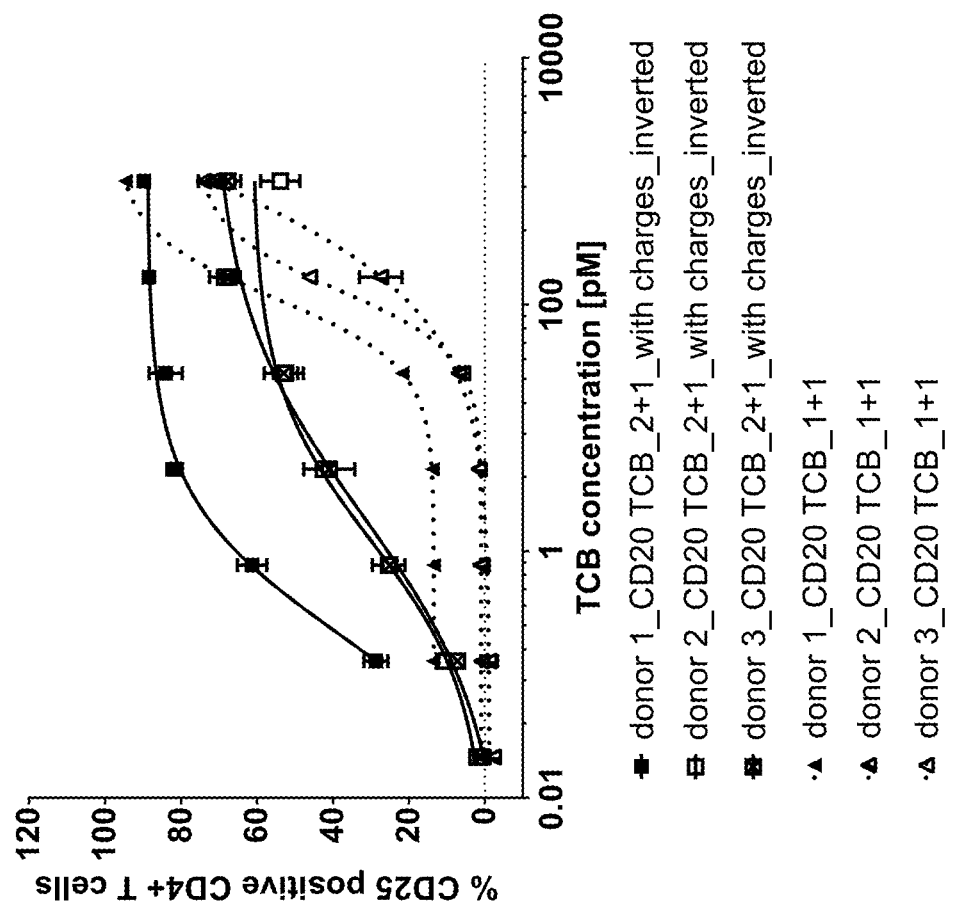
Figure 13D:
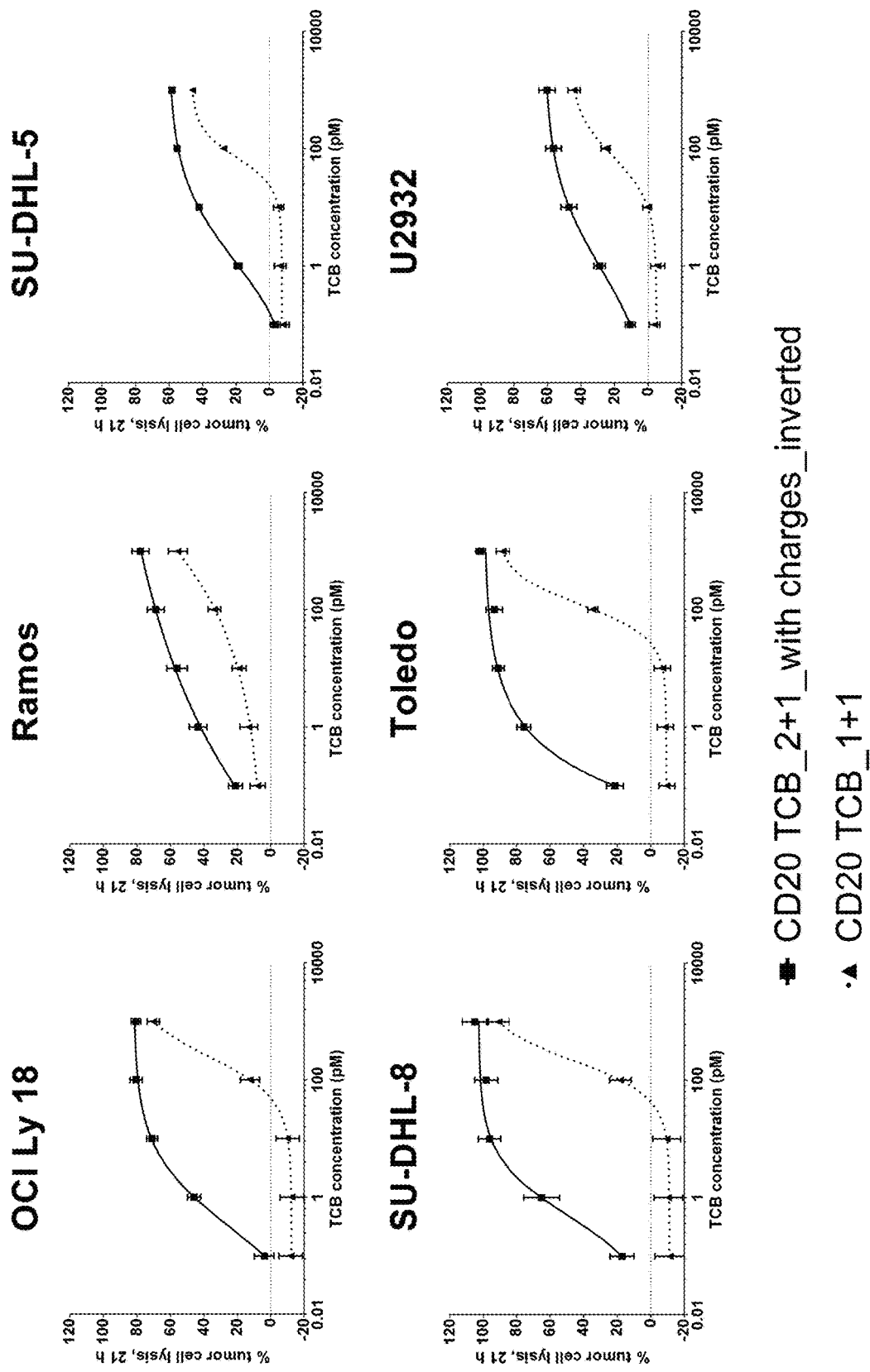
(FIG. 13D) Lysis of a panel of DLBCL tumor cell lines as indicated.

FIGS. 12A and 12B shows that different CD20 TCB antibody formats induced a strong and target-specific lysis of CD20+ target cells. Panel A shows that the "CD20 TCB_2+1_with charges, inverted" (molecule "B" shown above) displays comparable activity to the "CD20 TCB_2+1_no charges, inverted" (molecule "A" shown above) and that both are more potent than the "CD20 TCB_1+1_with charges" format (molecule "H" shown above). Panel B shows that "CD20 TCB_2+1_with charges, inverted" (molecule "B" shown above) is more potent than "CD20 TCB_2+1_with charges, classical" format (molecule "C" shown above). The EC50 values related to killing assays, calculated using GraphPadPrism5 are given in Table 5.

TABLE 5

EC50 values (pM) of tumor cell lysis mediated by different anti-CD20/anti-CD3 TCB antibody formats evaluated using CD20-expressing Z138 tumor target cells.

| Panel | CD20 antibody format | EC50 [pM] |
| --- | --- | --- |
| A | CD20 TCB_2+1_with charges, inverted (molecule B) | 2.18 |
| A | CD20 TCB_2+1_no charges, inverted (molecule A) | 0.76 |
| A | CD20 TCB_1+1_with charges (molecule H) | 17.54 |
| B | CD20 TCB_2+1_with charges, inverted (molecule B) | 0.96 |
| B | CD20 TCB_2+1_with charges, classical (molecule C) | 43.34 |

Tumor Cell Lysis and Subsequent T Cell Activation Mediated by Different Anti-CD20/Anti-CD3 TCB Antibody Formats Tumor cell lysis mediated by different anti-CD20/anti-CD3 TCB antibody formats (molecules "B" and "H" shown above) was further assessed on Z138 cells (mantle cell lymphoma) using human PBMCs derived from three different healthy donors as well as on a broader panel of DLBCL lines including OCI Ly-18 (0.06-0.2×10⁶ CD20 binding sites), Ramos (0.1-0.4×10⁶ CD20 binding sites), SU-DHL-5 (0.13-0.21×10⁶ CD20 binding sites), SU-DHL-8 (CD20 binding sites below detection limit of the assay), Toledo (0.02×10⁶ CD20 binding sites) and U2932 (0.09-0.4×10⁶ CD20 binding sites) cell lines. Tumor cell harvest, PBMC isolation, and assay conditions were identical to the ones described in the previous example. E:T ratio for the assays shown in FIGS. 13A-13C was 6:1, for the assay shown in FIG. 13D it was 3:1. Tumor cell lysis was assessed after 21 h of incubation at 37° C., 5% $CO_2$ by quantification of LDH released into cell supernatants by apoptotic/necrotic cells (LDH detection kit, Roche Applied Science, #11 644 793 001). For the assessment of T cell activation occurring upon tumor cell lysis, PBMCs were transferred to a round-bottom 96-well plate, centrifuged at 400×g for 5 min and washed twice with PBS containing 0.1% BSA. Surface staining for CD8 (APCCy7 anti-human CD8 Biolegend, #301016), CD4 (FITC anti-human CD4, Biolegend #300506) and CD25 (PECy7 anti-human CD25 Biolegend #302612) was performed according to the suppliers' indications. Cells were washed twice with 150 µl/well PBS containing 0.1% BSA and fixed using 2% PFA or FACS Lysing solution (BD, #349202). Samples were analyzed at BD FACS CantoII. FIGS. 13A-13D shows that the "CD20 TCB_2+1_with charges, inverted" antibody format (molecule "B" shown above) is more potent than "CD20 TCB_1+1" antibody format (molecule "H" shown above) as assessed by detection of both tumor cell lysis (Panels A, D) and T cell activation (Panel B, C) using PBMCs from different donors. The EC50 values related to tumor lysis and T cell activation of Z138 cells are given in Table 6a. The EC50 values related to tumor lysis assays of a panel of DLBCL cell lines are given in Table 6b. The EC50 values were calculated using GraphPadPrism5.

TABLE 6a

EC50 values (pM) of tumor cell lysis and T cell activation mediated by anti-CD20/anti-CD3 TCB antibodies using CD20-expressing Z138 tumor cells.

| CD20 antibody format | EC50 [pM] 24 h (average of 3 donors) |
| --- | --- |
| CD20 TCB_2+1_with charges, inverted (tumor lysis) (molecule B) | 1.6 |
| CD20 TCB_1+1 (tumor lysis) (molecule H) | 751 |
| CD20 TCB_2+1_with charges, inverted (CD8 T cell activation) (molecule B) | 2.2 |
| CD20 TCB_1+1 (CD8 T cell activation) (molecule H) | 174.8 |
| CD20 TCB_2+1_with charges, inverted (CD4 T cell activation) (molecule B) | 1.2 |
| CD20 TCB_1+1 (CD4 T cell activation) (molecule H) | 122 |

TABLE 6b

EC50 values (pM) of tumor lysis of a panel of DLBCL tumor cell lines mediated by anti-CD20/anti-CD3 TCB antibodies.

| EC50 [pM] 24 h of tumor lysis | CD20 TCB_2+1_with charges, inverted (molecule B) | CD20 TCB_1+1 (molecule H) |
| --- | --- | --- |
| Ocly-18 | 0.3 | 250.4 |
| Ramos | n.d. | n.d. |
| SU-DHL-5 | 1.2 | 69.7 |
| SU-DHL-8 | 0.5 | 218.9 |
| Toledo | n.d. | 120.2 |
| U2932 | 0.9 | 72.7 |

B Cell Depletion in Human Whole Blood Mediated by Different Anti-CD20/Anti-CD3 TCB Antibody Formats Normal B cell depletion mediated by different anti-CD20/anti-CD3 TCB antibody formats (molecules "B" and "H" shown above) and by obinutuzumab was further assessed using fresh human blood from healthy volunteers. Briefly, fresh blood was collected in heparin-containing syringes.

Blood aliquots (180 μL/well) were placed in 96-deep well plates, supplemented with TCB or antibody dilutions (10 μL/well+10 μL/well PBS) and incubated for 24 h at 37° C. in 5% $CO_2$ in a humidified cell incubator. After incubation, blood was mixed by pipetting up and down before 35 μL blood aliquots were transferred in 96-well U-bottom plates and incubated with fluorescent anti-CD45 (APC, Biolegend, #304037), anti-CD4 (PerCPCy5.5, BD, #552838), anti-CD8 (APCCy7, Biolegend, #301016), anti-CD19 (PE, Biolegend, #302208), anti-CD25 (PECy7, Biolegend, #302612) and anti-CD69 (BV421, Biolegend, #310930) in total 55 μL volume for flow cytometry. After 15 min incubation at room temperature (in the dark) 180 μL/well of FACS lysis solution (BD Biosciences) was added to deplete erythrocytes and to fix cells prior to flow cytometry.

Figure 14:
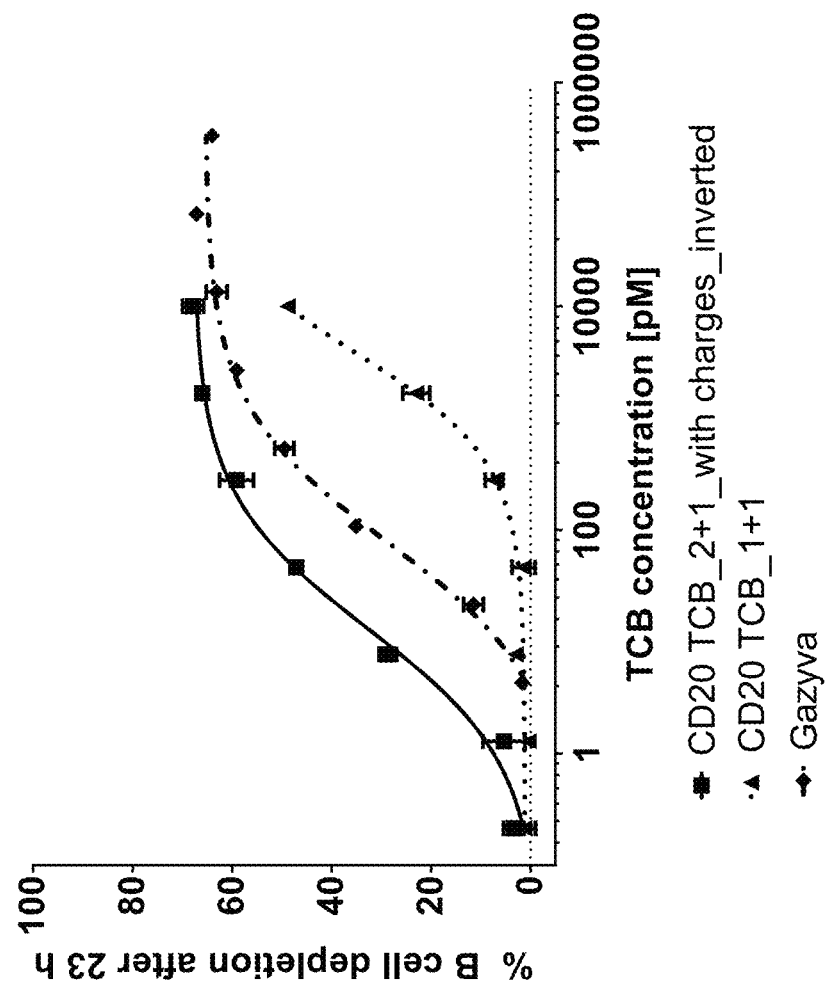
FIG. 14. B cell depletion in human whole blood mediated by different anti-CD20/anti-CD3 TCB antibody formats.

FIG. 14 shows that the "CD20 TCB_2+1_with charges, inverted" (molecule "B" above) is more potent in depleting normal B cells than both obinutuzumab (Gazyva) and "CD20 TCB_1+1" with charges (molecule "H" above).

TABLE 7

EC50 values (pM) of B cell depletion in normal human whole blood mediated by different CD20-targeting antibodies.

| CD20-targeting antibodies | EC50 [pM] 24 h |
|---|---|
| CD20 TCB_2+1_with charges, inverted (molecule B) | 13.2 |
| Obinutuzumab (Gazyva ®) | 79.2 |
| CD20 TCB_1+1 (molecule H) | 3753 |

Figure 15:
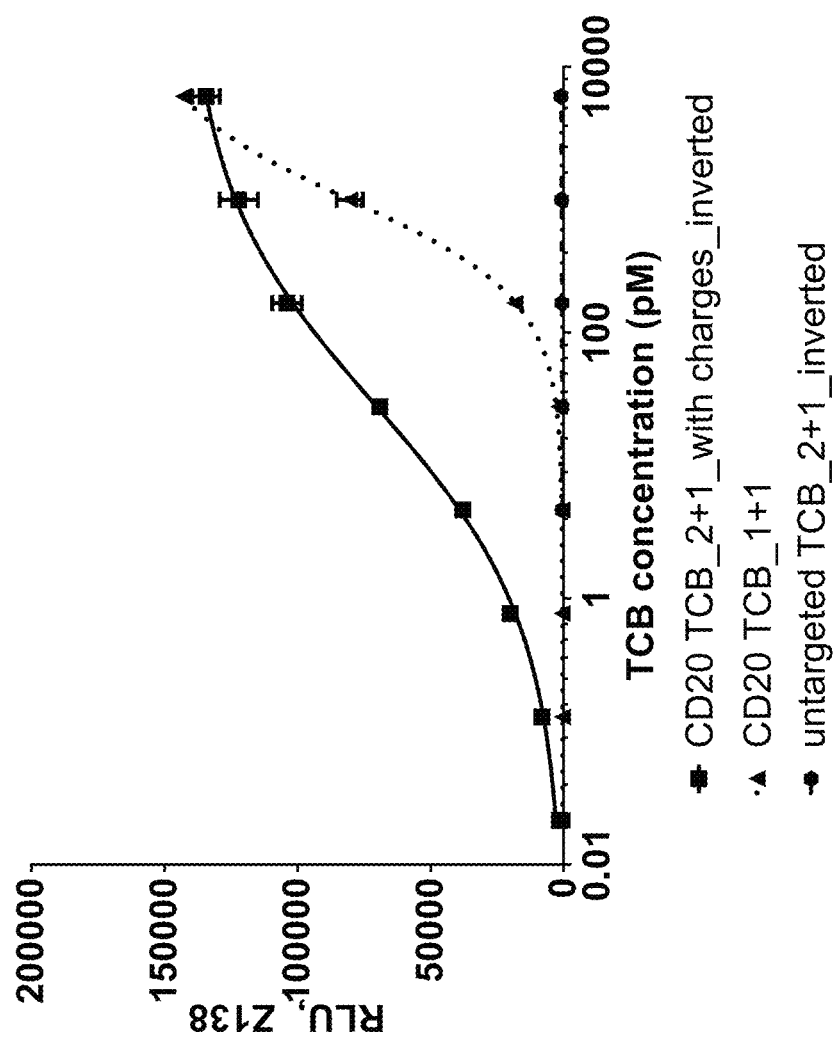
FIG. 15. Activation of T cells by different anti-CD20/anti-CD3 TCB antibody formats, assessed by quantification of the intensity of CD3 downstream signaling using Jurkat-NFAT reporter assay.

Activation of T Cells Assessed by Quantification of the Intensity of CD3 Downstream Signaling Using Jurkat-NFAT Reporter Assay The capacity of different anti-CD20/anti-CD3 TCB antibody formats to induce T cell cross-linking and subsequently T cell activation was assessed using co-cultures of CD20-expressing tumor target cells and Jurkat-NFAT reporter cells (a CD3-expressing human acute lymphatic leukemia reporter cell line with a NFAT promoter, GloResponse Jurkat NFAT-RE-luc2P, Promega # CS176501). Upon simultaneous binding of anti-CD20/anti-CD3 TCB to CD20 antigen (expressed on tumor cells) and CD3 antigen (expressed on Jurkat-NFAT reporter cells), the NFAT promoter is activated and leads to expression of active firefly luciferase. The intensity of luminescence signal (obtained upon addition of luciferase substrate) is proportional to the intensity of CD3 activation and signaling. Jurkat-NFAT reporter cells grow in suspension and were cultured in RPMI1640, 2 g/l glucose, 2 g/l $NaHCO_3$, 10% FCS, 25 mM HEPES, 2 mM L-glutamin, 1×NEAA, 1× sodium-pyruvate at 0.1-0.5 mio cells per ml, 200 μg per ml hygromycin. For the assay, tumor target cells (Z138) were harvested and viability determined using ViCell. 50 μl/well of diluted antibodies or medium (for controls) was added to target cells. 20 000 cells/well were plated in a flat-bottom, white-walled 96-well-plate (#655098, Greiner bio-one). Subsequently, Jurkat-NFAT reporter cells were harvested and viability assessed using ViCell. Cells were resuspended at 2 mio cells/ml in cell culture medium without hygromycin B and added to tumor cells at $0.1 \times 10^6$ cells/well (50 μl/well) to obtain a final E:T of 5:1 and a final volume of 100 μl per well. Cells were incubated for 6 h at 37° C. in a humidified incubator. At the end of incubation time, 100 μl/well of ONE-Glo solution (1:1 ONE-Glo and assay medium volume per well) were added to wells and incubated for 10 min at room temperature in the dark. Luminescence was detected using WALLAC Victor3 ELISA reader (PerkinElmer2030), 5 sec/well as detection time. FIG. 15 shows that "CD20 TCB_2+1_with charges, inverted" (molecule "B" above) leads to stronger T cell activation and signaling downstream of CD3 than "CD20 TCB_1+1" (molecule "H" above).

TABLE 8

EC50 values (pM) of CD3 activation detected using Jurkat-NFAT reporter cells.

| CD20 antibody format | EC50 [pM] |
|---|---|
| CD20 TCB_2+1_with charges, inverted (molecule B) | 28.98 |
| CD20 TCB_1+1 (molecule H) | 1001 |

Single Dose PK of Anti-CD20/Anti-CD3 TCB in Healthy NOG Mice

Figure 16:
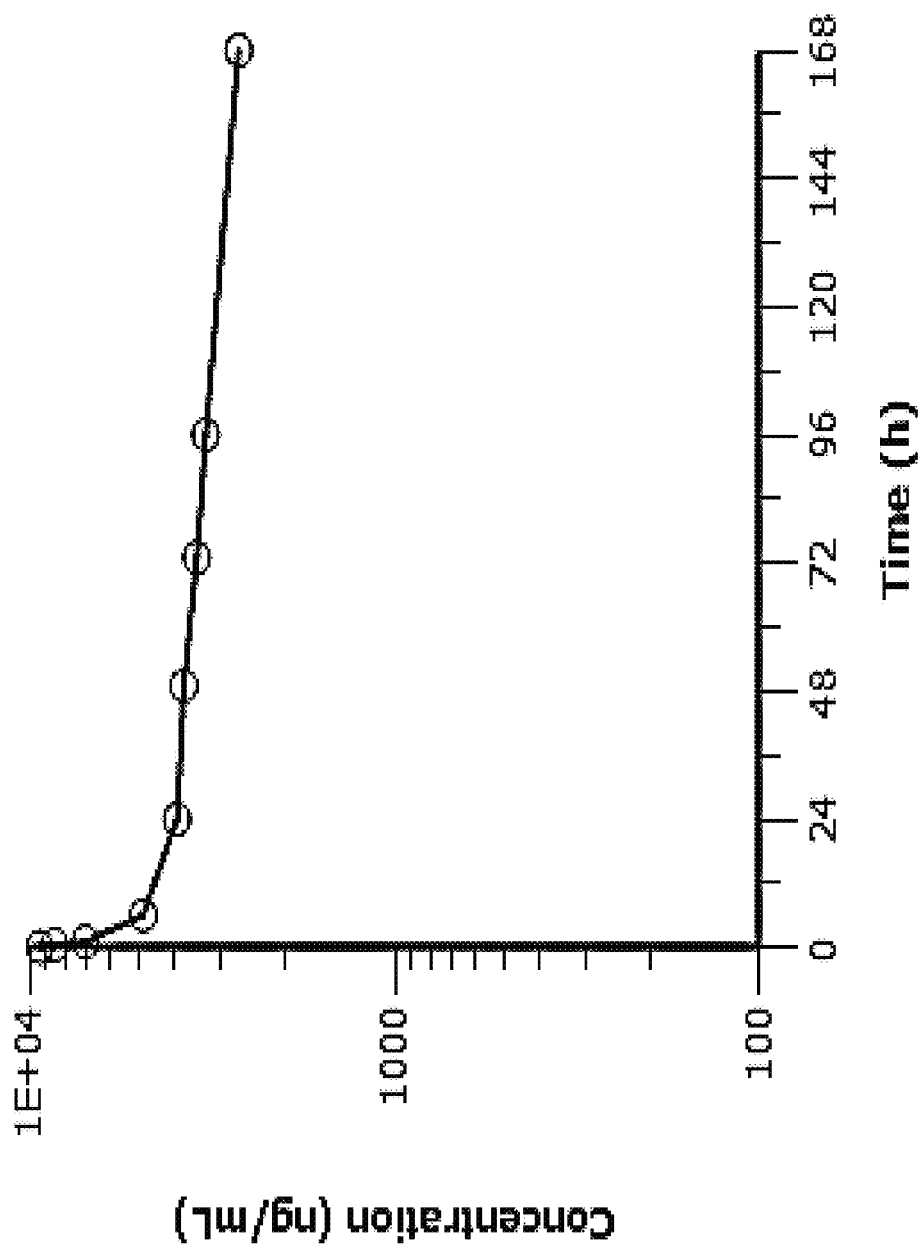
FIG. 16. Pharmacokinetic parameters of a 0.5 mg/kg i.v. bolus administration of anti-CD20/anti-CD3 TCB antibody (molecule "B" shown in FIG. 2B) from sparse sampling data in NOG mice.

A single dose pharmacokinetic study (SDPK) was performed to evaluate exposure of anti-CD20/anti-CD3 TCB molecule "B" (hereinafter called "CD20 TCB") during efficacy studies (FIG. 16). An i.v. bolus administration of 0.5 mg/kg was administered to NOG mice and blood samples were taken at selected time points for pharmacokinetic evaluation. A generic immunoassay was used for measuring total concentrations of the CD20 TCB. The calibration range of the standard curve for the CD20 TCB was 0.78 to 50 ng/ml, where 15 ng/ml is the lower limit of quantification (LLOQ).

A biphasic decline was observed with a beta half-life of 10 days (non-compartmental analysis) and clearance of 8 mL/d/kg (2-compartmental model). The half-life and clearance was as expected as compared to a normal untargeted IgG (Table 9).

Phoenix v6.2 from Pharsight Ltd was used for PK analysis, modelling and simulation.

TABLE 9

Pharmacokinetic parameters of a 0.5 mg/kg i.v. bolus administration of CD20 TCB in NOG mice.

| Half-life | 10 days |
|---|---|
| Clearance | 7.9 mL/d/kg |
| Cmax | 9.4 ug/mL |
| AUC | 1554 h*ug/mL |

In Vivo B-Cell Depletion Activity of Anti-CD20/Anti-CD3 TCB

Peripheral B-cell depletion activity of CD20 TCB was tested in fully humanized NOD/Shi-scid/IL-2Rγ$^{null}$ (NOG) mice.

Figure 17:
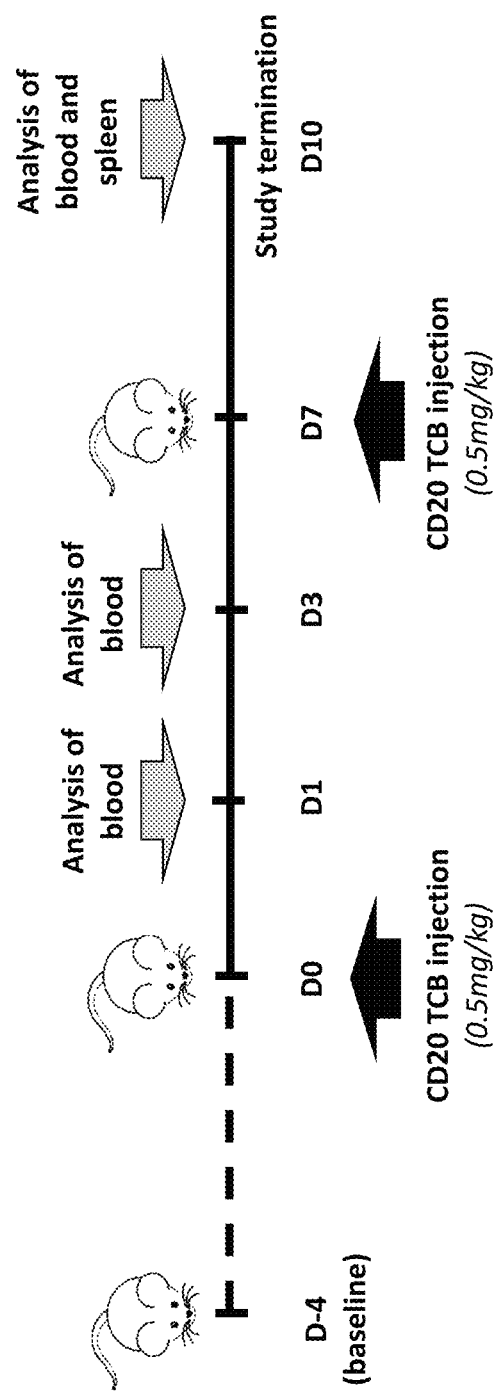
FIG. 17. Schematic representation of the study design to assess B cell depletion activity of anti-CD20/anti-CD3 TCB antibody (molecule "B" shown in FIG. 2B) in fully humanized NOG mice.
Figure 18B:
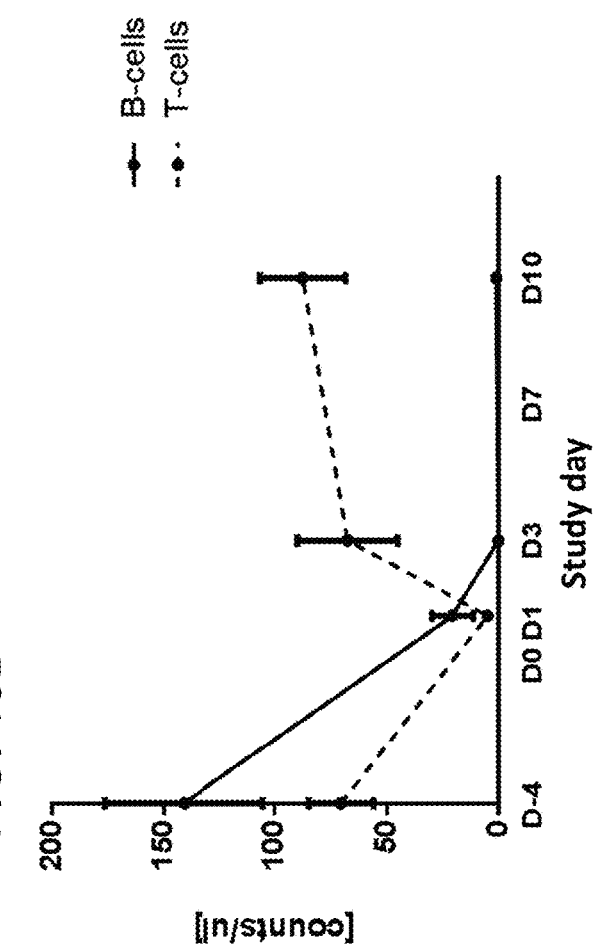
FIG. 18. Kinetics of B-cell and T-cell frequency in blood of fully humanized NOG mice treated with (FIG. 18B) anti-CD20/anti-CD3 TCB antibody (molecule "B" shown in FIG. 2B) or (FIG. 18A) vehicle control. D0, D7: days of therapy injection.
Figure 18A:
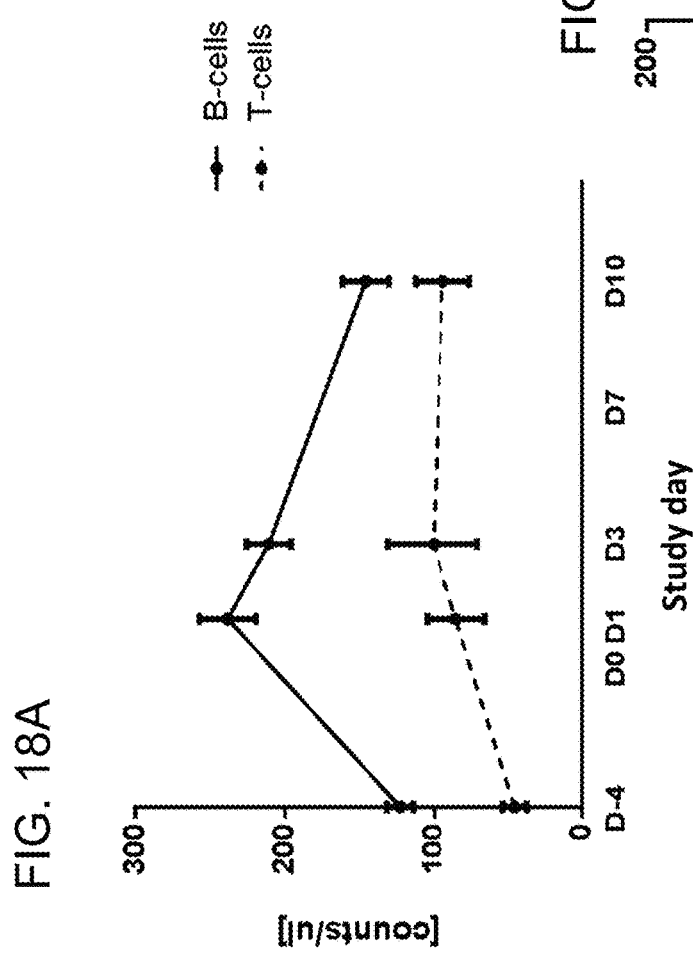

Fully humanized NOG mice at 14 weeks of age, bearing physiological levels of circulating human B- and T-cells (Hayakawa J. et al. (2009), Stem Cells 27(1), 175-182), were treated either with vehicle (n=7) or with CD20 TCB (n=6) at the dose of 0.5 mg/kg administered intravenously (i.v.) once per week. As shown on the study design in FIG. 17, mice were bled for B cell and T-cell analysis one and three days after the first therapeutic injection (D1, D3), and three days after the second (D10), at which time point the study was terminated. At the latter time point, spleens were also harvested for B-cell and T-cell analysis Mice were screened 4 days before therapeutic injection (D-4) as baseline reference for circulating B- and T-cell counts. FIGS. 18A and 18B shows B- and T-cell counts analysed by ex vivo flow cytometry in blood of vehicle (left panel) and CD20 TCB (right panel)-treated mice at the different time points. Results demonstrate that circulating B-cells were very efficiently depleted already one day after CD20 TCB injection, and their number remained undetectable for the whole study duration. On the contrary, circulating T-cell count only transiently dropped at D1 after therapeutic injection, returned to baseline levels at D3, and remained stable for the whole study duration. T-cell activation status was also analysed in blood of treated mice at D3 and D10 after first therapeutic injection, by means of ex vivo flow cytometry using different T-cell surface markers and the proliferation marker Ki67 (FIG. 19). T-cells from CD20 TCB-treated mice showed an activated phenotype at D3 after therapeutic injection (upper panel), with up-regulation of the activation markers CD25, 4-1BB, PD-1 and granzyme-B (GZB) in both CD4 and CD8 T-cell compartments, compared to T-cells from vehicle control. T-cells from treated mice also expressed higher levels of the proliferation marker Ki67. At D10 after first therapeutic injection, most of the T-cell activation markers had returned to baseline levels with the exception of GZB and PD-1, which were still expressed at higher levels compared to vehicle control.

FIGS. 20A-20C shows the results of B-cell and T-cell analyses done on spleens of vehicle and CD20 TCB-treated mice at study termination (D10). CD20 TCB treatment mediated a very efficient B cell depletion also in this secondary lymphoid organ (FIG. 20A), while T-cell counts showed levels comparable to vehicle control (FIG. 20B). The T cell activation status (FIG. 20C) was similar to that observed in blood, with higher expression of GZB and PD-1 in splenic T cells of treated mice compared to vehicle control.

Altogether these results demonstrate that CD20 TCB treatment can mediate a very efficient depletion of peripheral B-cells already one day after therapy injection, with B-cells remaining undetectable until study termination (three days after second therapeutic injection). B-cells are also efficiently depleted in spleen of treated mice. B-cell depletion activity is paralleled by a transient T-cell activation in blood of treated animals, which returns to baseline levels three days after therapeutic injection, with the exception of GZB and PD-1 activation markers, which remain expressed at a higher level compared to untreated controls.

Anti-Tumor Activity of Anti-CD20/Anti-CD3 TCB in WSU-DLCL2 Model

Figure 21:
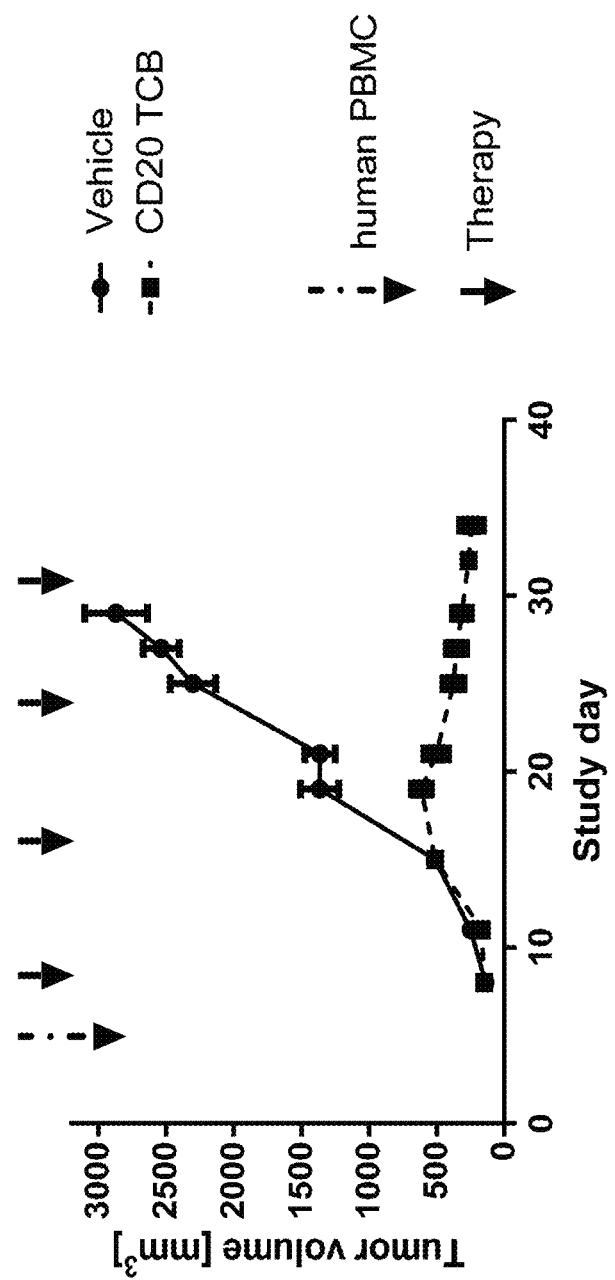
FIG. 21. Anti-tumor activity of anti-CD20/anti-CD3 TCB antibody (molecule "B" shown in FIG. 2B) (0.5 mg/kg, once a week) in the WSU-DLCL2 model in NOG mice with huPBMC transfer.

Anti-tumor activity of CD20 TCB was tested in NOG mice bearing the human diffuse large B cell lymphoma cell line WSU-DLCL2 and transferred with human peripheral mononuclear cells (PBMC). Briefly, female NOG mice were injected sub-cutaneously (s.c.) with $1.5 \times 10^6$ WSU-DLCL2 cells (originally obtained from the European Collection of Cell Culture). When average tumor volume reached 200 mm$^3$, mice received intra-peritoneal injection of human PBMC ($10 \times 10^6$ cells per mouse) as source human T-cells. Two days later, mice received CD20 TCB therapy i.v. at a dose of 0.5 mg/kg administered once a week. As depicted in FIG. 21, CD20 TCB shows a potent anti-tumor activity, with almost complete tumor regression observed at study termination (day 34).

Example 2

Preparation of "2+1 IgG CrossFab, Inverted" T-Cell Bispecific Antibody with and without Charge Modifications (Anti-BCMA/Anti-CD3)

Figure 22:
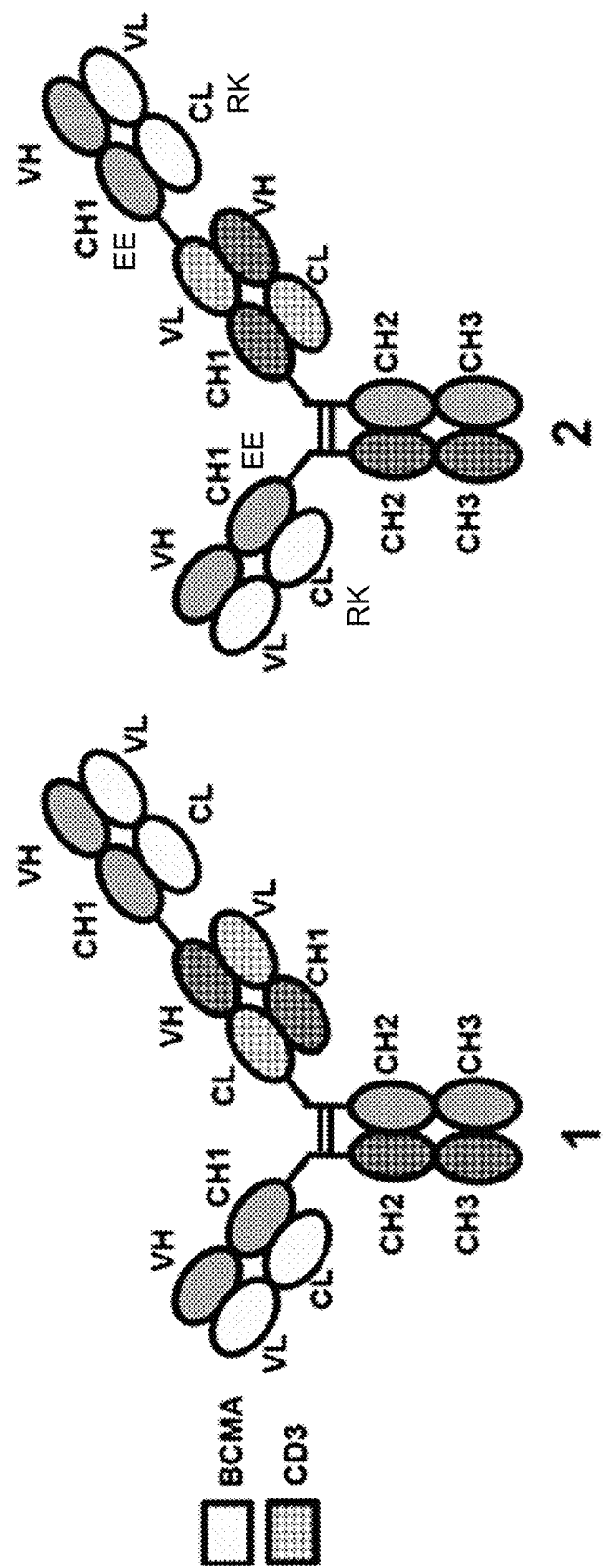
FIG. 22. Illustration of the "2+1 IgG CrossFab, inverted" molecules prepared in Example 2. (1) Molecule without charge modifications, (2) molecule with charge modifications in the CH1 and CL domains of the Fab molecules which specifically bind to BCMA (EE=147E, 213E; KK=123K, 124K).

Schematic illustrations of the molecules prepared in this example are shown in FIG. 22. The anti-BCMA/anti-CD3 "2+1 IgG CrossFab, inverted" molecule without charge modifications (referred to in this example as "83A10-TCB") comprises the amino acid sequences of SEQ ID NOs 22-25, the anti-BCMA/anti-CD3 "2+1 IgG CrossFab, inverted" molecule with charge modifications (referred to in this example as "83A10-TCBcv") comprises the amino acid sequences of SEQ ID NOs 26-29. For the generation of BCMAxCD3 bispecific antibody vectors, the IgG1 derived bispecific molecules consist at least of two antigen binding moieties capable of binding specifically to two distinct antigenic determinants CD3 and BCMA. The antigen binding moieties are Fab fragments composed of a heavy and a light chain, each comprising a variable and a constant region. At least one of the Fab fragments was a "Crossfab" fragment, wherein VH and VL were exchanged. The exchange of VH and VL within the Fab fragment assures that Fab fragments of different specificity do not have identical domain arrangements. The bispecific molecule design was monovalent for CD3 and bivalent for BCMA where one Fab fragment was fused to the N-terminus of the inner CrossFab (2+1). The bispecific molecule contained an Fc part in order for the molecule to have a longer half-life. The molecules were produced by co-transfecting HEK293 EBNA cells growing in suspension with the mammalian expression vectors using polyethylenimine (PEI). For preparation of 2+1 CrossFab-IgG constructs, cells were transfected with the corresponding expression vectors in a 1:2:1:1 ratio ("vector Fc(knob)":"vector light chain":"vector light chain CrossFab":"vector heavy chain-CrossFab").

For bispecific antibodies, introduction of a replacement/exchange in one binding arm "Crossfab" clearly reduces the side-products but the preparation is not completely free of side-products (described in detail in WO2009/080252 and Schaefer, W. et al, PNAS, 108 (2011) 11187-1191). Thus, to further reduce side-products caused by the mismatch of a light chain against a first antigen with the wrong heavy chain against the second antigen and to improve the yield of the bispecific antibody, an additional approach is applied to the molecule by introducing substitutions of charged amino acids with the opposite charge at specific amino acid positions in the CH1 and CL domains in the constant domain CL of the first light chain under a) the amino acid at position 124 is substituted independently by lysine (K), arginine (R) or histidine (H) (numbering according to Kabat) (in one preferred embodiment independently by lysine (K), arginine (R)), and wherein in the constant domain CH1 of the first heavy chain under a) the amino acid at position 147 or the amino acid at position 213 is substituted independently by glutamic acid (E), or aspartic acid (D) (numbering according to Kabat); or ii) in the constant domain CL of the second light chain under b) the amino acid at position 124 is substituted independently by lysine (K), arginine (R) or Histidine (H) (numbering according to Kabat) (in one preferred embodiment independently by lysine (K), arginine (R)), and wherein in the constant domain CH1 of the second heavy chain under b) the amino acid at positions 147 or the amino acid at position 213 is substituted independently by glutamic acid (E), or aspartic acid (D) (numbering according to Kabat).

For the production of the bispecific antibodies, bispecific antibodies were expressed by transient co-transfection of the respective mammalian expression vectors in HEK293-EBNA cells, which were cultivated in suspension, using polyethylenimine (PEI). One day prior to transfection, the HEK293-EBNA cells were seeded at 1.5 Mio viable cells/mL in Ex-Cell medium supplemented with 6 mM of L-Glutamine. For every mL of final production volume, 2.0 Mio viable cells were centrifuged (5 minutes at 210×g). The supernatant was aspirated and the cells resuspended in 100 µL of CD CHO medium. The DNA for every mL of final production volume was prepared by mixing 1 µg of DNA (Ratio heavy chain:modified heavy chain:light chain:modified light chain=1:1:2:1) in 100 µL of CD CHO medium. After addition of 0.27 µL of PEI solution (1 mg/mL) the mixture was vortexed for 15 seconds and left at room temperature for 10 minutes. After 10 minutes, the resuspended cells and DNA/PEI mixture were put together and then transferred into an appropriate container which was placed in a shaking device (37° C., 5% $CO_2$). After a 3 hours incubation time 800 µL of Ex-Cell Medium, supplemented with 6 mM L-Glutamine, 1.25 mM valproic acid and 12.5% Pepsoy (50 g/L), was added for every mL of final Production volume. After 24 hours, 70 µL of Feed (SF40, Lonza) was added for every mL of final production volume. After 7 days or when the cell viability was equal or lower than 70%, the cells were separated from the supernatant by centrifugation and sterile filtration. The antibodies were purified by an affinity step and one or two polishing steps, being cation exchange chromatography and size exclusion chromatography. When required, an additional polishing step was used.

For the affinity step the supernatant was loaded on a protein A column (HiTrap Protein A FF, 5 mL, GE Healthcare) equilibrated with 6 CV 20 mM sodium phosphate, 20 mM sodium citrate, pH 7.5. After a washing step with the same buffer the antibody was eluted from the column by step elution with 20 mM sodium phosphate, 100 mM sodium chloride, 100 mM Glycine, pH 3.0. The fractions with the desired antibody were immediately neutralized by 0.5 M Sodium Phosphate, pH 8.0 (1:10), pooled and concentrated by centrifugation. The concentrate was sterile filtered and processed further by cation exchange chromatography and/or size exclusion chromatography.

For the cation exchange chromatography step the concentrated protein was diluted 1:10 with the elution buffer used for the affinity step and loaded onto a cation exchange colume (Poros 50 HS, Applied Biosystems). After two washing steps with the equilibration buffer and a washing buffer resp. 20 mM sodium phosphate, 20 mM sodium citrate, 20 mM TRIS, pH 5.0 and 20 mM sodium phosphate, 20 mM sodium citrate, 20 mM TRIS, 100 mM sodium chloride pH 5.0 the protein was eluted with a gradient using 20 mM sodium phosphate, 20 mM sodium citrate, 20 mM TRIS, 100 mM sodium chloride pH 8.5. The fractions containing the desired antibody were pooled, concentrated by centrifugation, sterile filtered and processed further a size exclusion step.

For the size exclusion step the concentrated protein was injected in a XK16/60 HiLoad Superdex 200 column (GE Healthcare), and 20 mM Histidine, 140 mM Sodium Chloride, pH 6.0 with or without Tween20 as formulation buffer. The fractions containing the monomers were pooled, concentrated by centrifugation and sterile filtered into a sterile vial.

Determination of the antibody concentration was done by measurement of the absorbance at 280 nm, using the theoretical value of the absorbance of a 0.1% solution of the antibody. This value was based on the amino acid sequence and calculated by GPMAW software (Lighthouse data).

Purity and monomer content of the final protein preparation was determined by CE-SDS (Caliper LabChip GXII system (Caliper Life Sciences)) resp. HPLC (TSKgel G3000 SW XL analytical size exclusion column (Tosoh)) in a 25 mM potassium phosphate, 125 mM Sodium chloride, 200 mM L-arginine monohydrochloride, 0.02% (w/v) Sodium azide, pH 6.7 buffer.

To verify the molecular weight of the final protein preparations and confirm the homogeneous preparation of the molecules final protein solution, liquid chromatography-mass spectometry (LC-MS) was used. A deglycosylation step was first performed. To remove heterogeneity introduced by carbohydrates, the constructs were treated with PNGaseF (ProZyme). Therefore, the pH of the protein solution was adjusted to pH7.0 by adding 2 µl 2 M Tris to 20 µg protein with a concentration of 0.5 mg/ml. 0.8 µg PNGaseF was added and incubated for 12 h at 37° C. The LC-MS online detection was then performed. LC-MS method was performed on an Agilent HPLC 1200 coupled to a TOF 6441 mass spectrometer (Agilent). The chromatographic separation was performed on a Macherey Nagel Polysterene column; RP1000-8 (8 µm particle size, 4.6×250 mm; cat. No. 719510). Eluent A was 5% acetonitrile and 0.05% (v/v) formic acid in water, eluent B was 95% acetonitrile, 5% water and 0.05% formic acid. The flow rate was 1 ml/min, the separation was performed at 40° C. and 6 µg (15 µl) of a protein sample obtained with a treatment as described before.

| Time (min.) | % B |
|---|---|
| 0.5 | 15 |
| 10 | 60 |
| 12.5 | 100 |
| 14.5 | 100 |
| 14.6 | 15 |
| 16 | 15 |
| 16.1 | 100 |

During the first 4 minutes, the eluate was directed into the waste to protect the mass spectrometer from salt contamination. The ESI-source was running with a drying gas flow of 12 l/min, a temperature of 350° C. and a nebulizer pressure of 60 psi. The MS spectra were acquired using a fragmentor voltage of 380 V and a mass range 700 to 3200 m/z in positive ion mode using. MS data were acquired by the instrument software from 4 to 17 minutes.

Figure 23A:
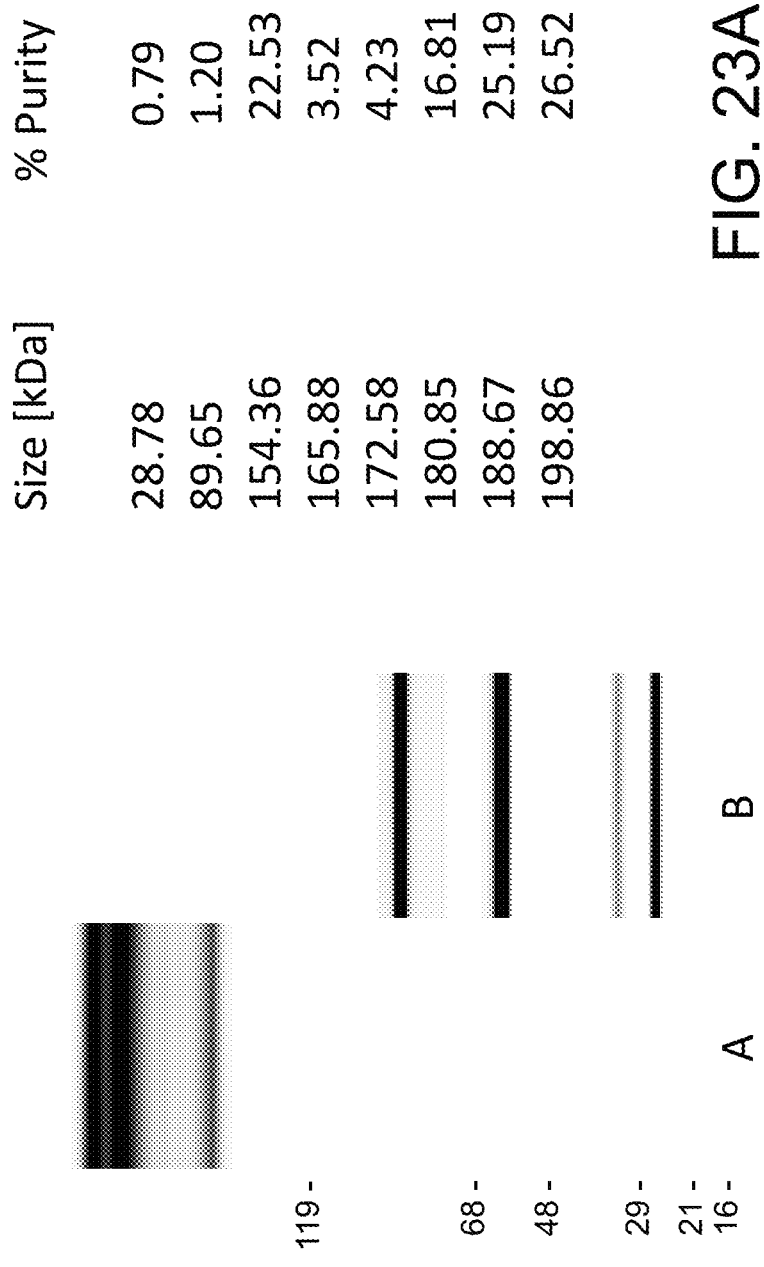
FIGS. 23A-23C. CE-SDS analysis (lane A=non-reduced, lane B=reduced, peak table for lane A) of "2+1 IgG CrossFab, inverted" molecules used in Example 2. Different methods of purification (Protein A affinity chromatography (PA), size exclusion chromatography (SEC), cation exchange chromatography (cIEX), and a final size exclusion chromatographic step (re-SEC)) were applied for the molecule without charge modifications (83A10-TCB.
Figure 23B:
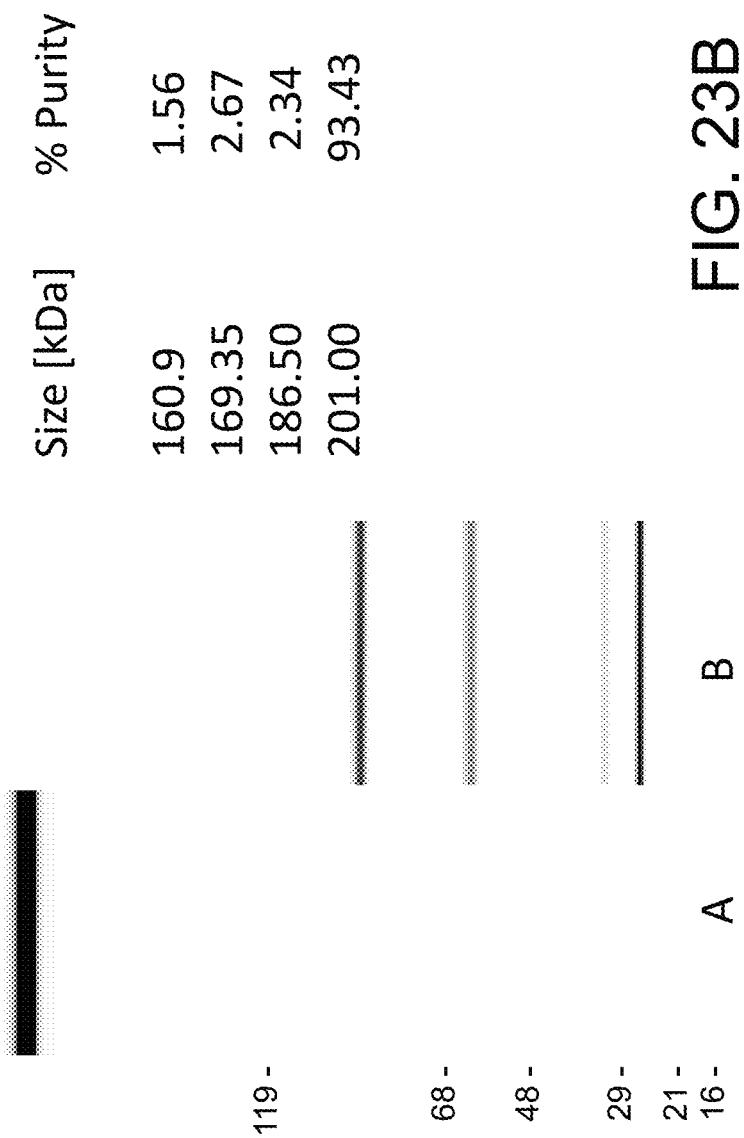
Figure 23C:
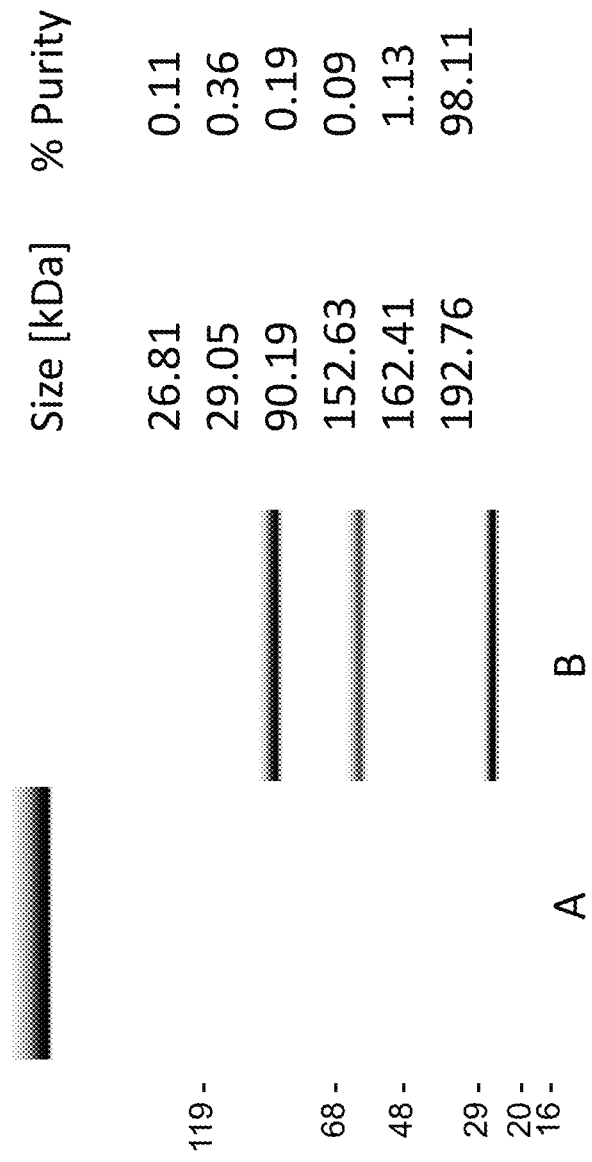

FIGS. 23A-23C depicts the CE-SDS (non-reduced) graphs of the final protein preparations after different methods of purification for 83A10-TCB and 83A10-TCBcv antibodies. Protein A (PA) affinity chromatography and size exclusion chromatographic (SEC) purification steps applied to 83A10-TCB antibody resulted in a purity of <30% and 82.8% of monomer content (A). When additional purifications steps including cation exchange chromatography (cIEX) and a final size exclusion chromatographic (re-SEC) steps were applied to the final protein preparations in (A), the purity was increased to 93.4% but the monomer content remained the same and the yield was significantly reduced to 0.42 mg/L. However, when specific charge modifications were applied to 83A10 anti-BCMA Fab CL-CH1, namely 83A10-TCBcv antibody, a superior production/purification profile of the TCB molecule, as demonstrated by a purity of 95.3%, monomer content of 100% and yield of up to 3.3 mg/L, could already be observed even when PA+cIEX+SEC purification steps were applied (C) in comparison to (B) with a production/purification profile showing a 7.9-fold lower yield and 17.2% lower monomer content despite including an additional re-SEC purification step.

A head-to-head production run to compare the production/purification profile of 83A10-TCB vs. 83A10-TCBcv antibodies was then conducted to further evaluate the advantages of the CL-CH1 charge modifications applied to the antibodies. As depicted in FIGS. 24A-24F, properties of 83A10-TCB and 83A10-TCBcv antibodies were measured side-by-side and compared after each purification steps 1)

Figure 24A:
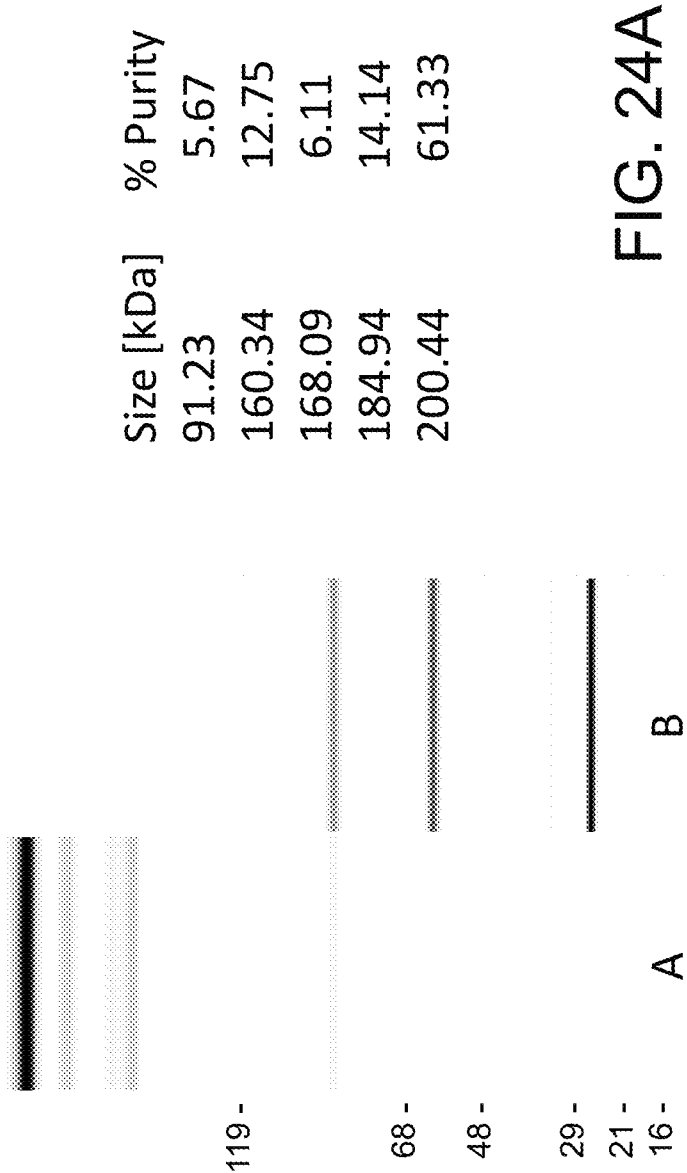
Figure 24B:
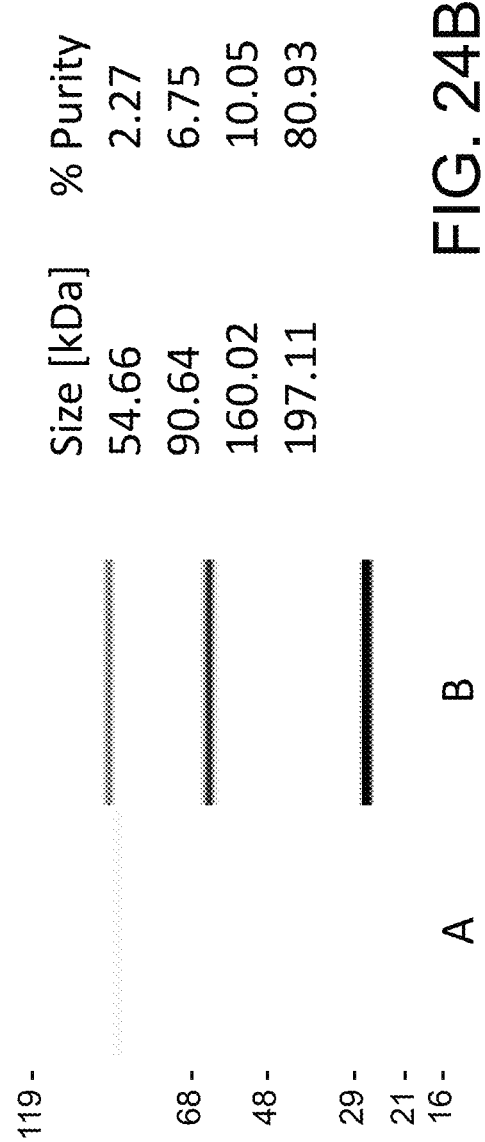
Figure 24E:
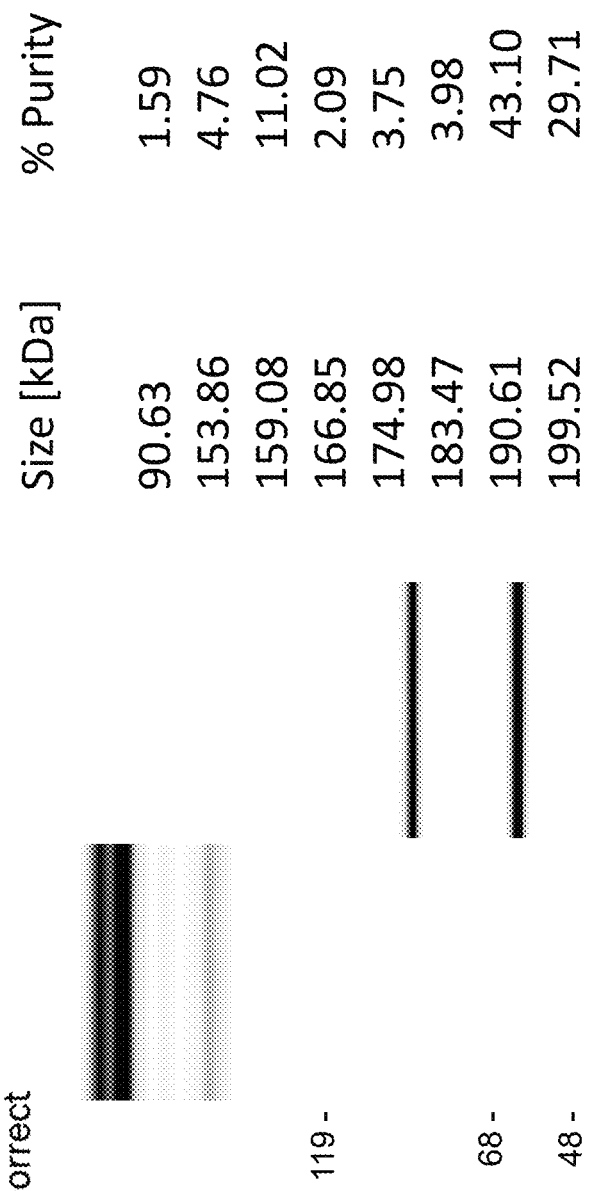
Figure 24F:
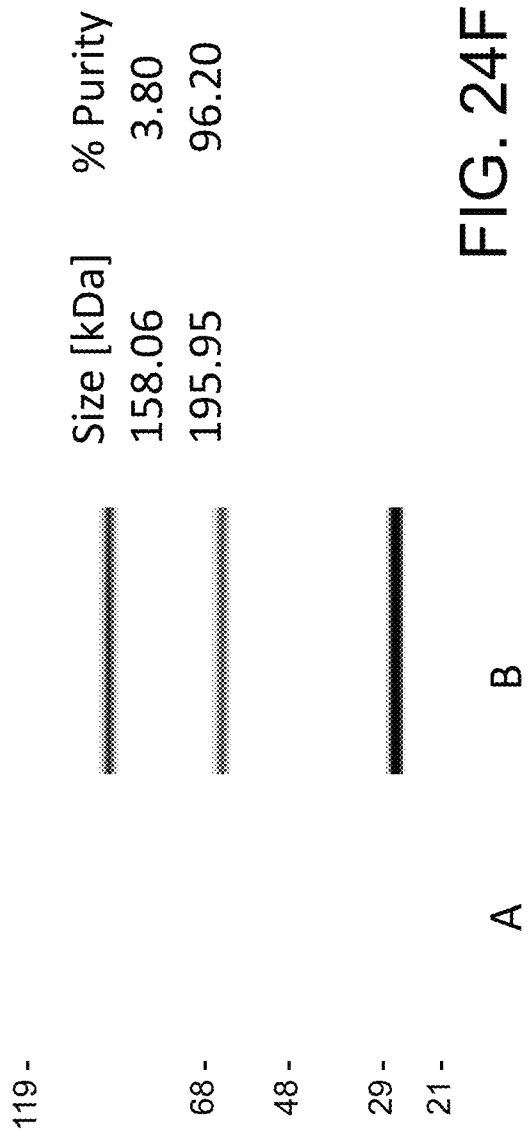

PA affinity chromatography only (A, B), 2) PA affinity chromatography then SEC (C, D) and 3) PA affinity chromatography then SEC then cIEX and re-SEC (E, F). The CE-SDS (non-reduced) graphs of the final protein solutions after the respective methods of purification for 83A10-TCB and 83A10-TCBcv antibodies are demonstrated in FIGS. 24A-24F. As shown in FIGS. 24A and 24B, improvements with applying the charge variants to the TCB antibody were already observed after purification by PA affinity chromatography only. In this head-to-head study, PA affinity chromatography purification step applied to 83A10-TCB antibody resulted in a purity of 61.3%, a yield of 26.2 mg/L and 63.7% of monomer content (24A). In comparison, when 83A10-TCBcv antibody was purified by PA affinity chromatography all the properties were improved with a better purity of 81.0%, a better yield of 51.5 mg/L and 68.2% of monomer content (24B). When an additional SEC purifications step was applied to the final protein preparations as seen in FIGS. 24A and 24B, 83A10-TCB gained a purity of 69.5%, a yield of 14.1 mg/L and 74.7% of monomer content as compared to 83A10-TCBcv with improved purity and monomer content of up to 91.0% and 83.9% respectively, and a yield of 10.3 mg/L. Even though the yield was slightly less (i.e. 27% less) for 83A10-TCBcv than for 83A10-TCB in this particular experiment, the percentage of correct molecule was much better for 83A10-TCBcv than for 83A10-TCB, respectively 90% vs. 40-60%, as measured by LC-MS. In the third head-to-head comparison, 83A10-TCB and 83A10-TCBcv final protein preparations from FIGS. 24C and 24D were pooled with approximately 1 L (equivolume) of respective final protein preparations from another purification batch (same production) following PA affinity chromatography purification step only. The pooled protein preparations were then being further purified by cIEX and SEC purification methods. As depicted in FIGS. 24E and 24F, improvement of the production/purification profile of the TCB antibody with the charge variants was consistently observed when compared to TCB antibody without charge variant. After several steps of purification methods (i.e. PA+/−SEC+cIEX+SEC) were used to purify 83A10-TCB antibody, only 43.1% purity was reached and 98.3% of monomer content could be achieved but to the detriment of the yield which was reduced to 0.43 mg/L. The percentage of correct molecule as measured by LC-MS was still poor with 60-70%. At the end, the quality of the final protein preparation was not acceptable for in vitro use. In stark contrast, when the same multiple purification steps with the same chronology were applied to 83A10-TCBcv antibody, 96.2% purity and 98.9% of monomer content were reached as well as 95% of correct molecule as measured by LC-MS. The yield however was also greatly reduced to 0.64 mg/L after cIEX purification step. The results show that better purity, higher monomer content, higher percentage of correct molecule and better yield can be achieved with 83A10-TCBcv antibody only after two standard purification steps i.e. PA affinity chromatography and SEC (FIG. 24D) while such properties could not be achieved with 83A10-TCB even when additional purification steps were applied (FIG. 24E).

Table 10 summarizes the properties of 83A10-TCB as compared to 83A10-TCVcv following PA purification step. Table 11 summarizes the properties of 83A10-TCB as compared to 83A10-TCVcv following PA and SEC purification steps. Table 12 summarizes the properties of 83A10-TCB as compared to 83A10-TCVcv following PA and SEC plus PA alone then cIEX and re-SEC purification steps. For Tables 10 to 12, the values in bold highlight the superior property as compared between 83A10-TCB vs. 83A10-TCVcv. With one exception which may not be representative, all the production/purification parameters and values resulting from the 3 head-to-head comparison experiments were superior for 83A10-TCBcv as compared to 83A10-TCB. The overall results clearly demonstrate that advantages in production/purification features could be achieved with applying CL-CH1 charge modifications to TCB antibodies and that only two purification steps (i.e PA affinity chromatography and SEC) were required to achieve already high quality protein preparations with very good developability properties.

TABLE 10

Production/purification profile of anti-BCMA/anti-CD3 T cell bispecific antibodies following protein A affinity chromatography purification step.

| | 83A10-TCB | 83A10-TCBcv |
|---|---|---|
| Purity (%) | 61.3 | 81.0 |
| Yield (mg/L) | 26.2 | 51.5 |
| Amount (mg) | 24.3 | 50.2 |
| Monomer (%) | 63.7 | 68.2 |
| Correct molecule by LC-MS (%) | n.d. | n.d |

TABLE 11

Production/purification profile of anti-BCMA/anti-CD3 T cell bispecific antibodies following protein A affinity chromatography and size exclusion chromatography purification steps.

| | 83A10-TCB | 83A10-TCBcv |
|---|---|---|
| Purity (%) | 69.5 | 91.0 |
| Yield (mg/L) | 14.1 | 10.3 |
| Amount (mg) | 13.1 | 10.0 |
| Monomer (%) | 74.7 | 83.9 |
| Correct molecule by LC-MS (%) | 40-60 | 90 |

TABLE 12

Production/purification profile of anti-BCMA/anti-CD3 T cell bispecific antibodies following 1.a) protein A affinity chromatography and size exclusion chromatography and 1.b) protein A affinity chromatography only pooled together then 2) cation exchange chromatography and 3) final size exclusion chromatography purification steps.

| | 83A10-TCB | 83A10-TCBcv |
|---|---|---|
| Purity (%) | 43.1 | 96.2 |
| Yield (mg/L) | 0.43 | 0.64 |
| Amount (mg) | 0.73 | 1.27 |
| Monomer (%) | 98.3 | 98.9 |
| Correct molecule by LC-MS (%) | 60-70% | >95% |

Binding of Anti-BCMA/Anti-CD3 T-Cell Bispecific Antibodies to BCMA-Positive Multiple Myeloma Cell Lines (Flow Cytometry)

Figure 25C:
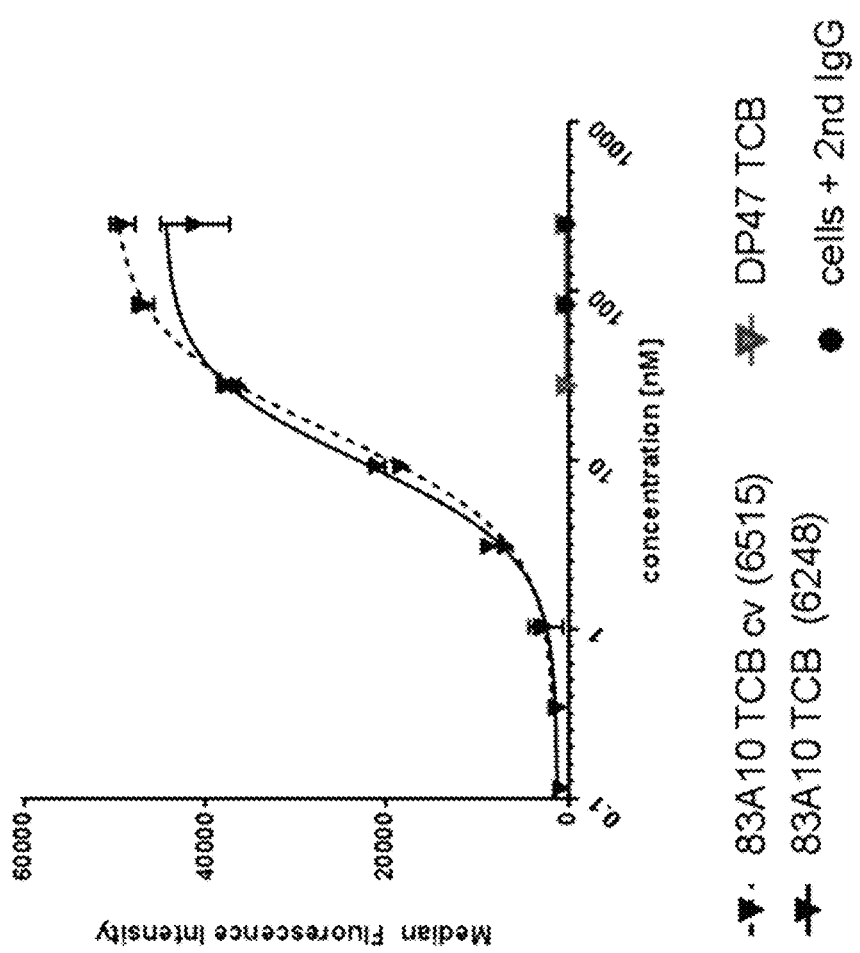
FIG. 25. Flow cytometry analysis of binding of anti-BCMA/anti-CD3 T-cell bispecific antibodies to BCMA-positive multiple myeloma cell lines.
(FIG. 25A) 83A10-TCB on H929 cells and MKN45 cells, (FIG. 25B) 83A10-TCBcv on H929 cells and MKN45 cells, (FIGS. 25C and 25D) comparison of 83A10-TCB and 83A10-TCBcv on H929 cells.
Figure 25D:
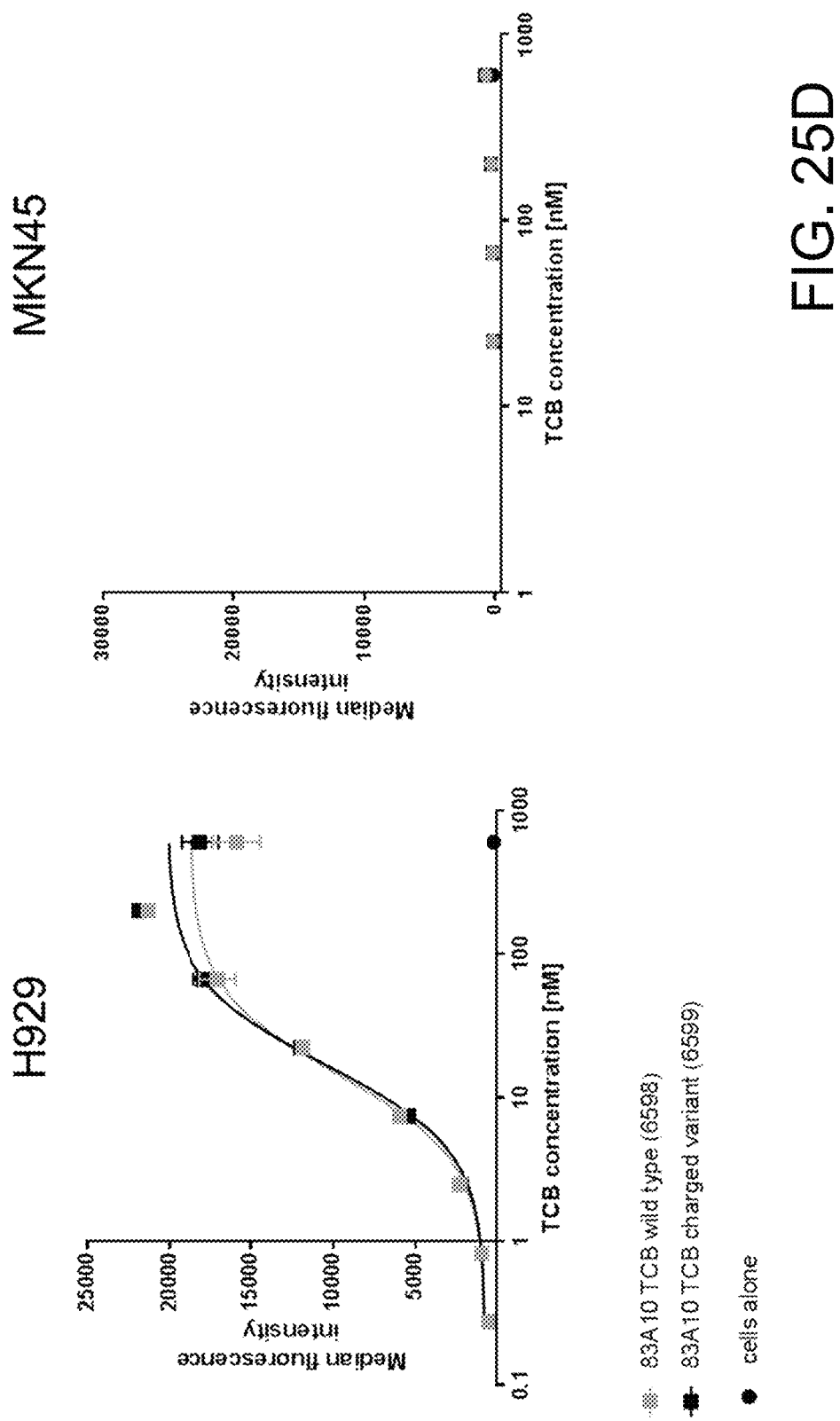

Anti-BCMA/anti-CD3 TCB antibodies (83A10-TCB, 13A4-TCBcv) were analyzed by flow cytometry for binding to human BCMA on BCMA-expressing NCI-H929 cells (ATCC® CRL-9068TM). MKN45 (human gastric adenocarcinoma cell line that does not express BCMA) was used as negative control. Briefly, cultured cells were harvested, counted and cell viability was evaluated using ViCell. Viable cells were then adjusted to $2 \times 10^6$ cells per ml in BSA-containing FACS Stain Buffer (BD Biosciences). 100 μl of this cell suspension were further aliquoted per well into a round-bottom 96-well plate and incubated with 30 µl of the anti-BCMA antibodies or corresponding IgG control for 30 min at 4° c. All Anti-BCMA/anti-CD3 TCB antibodies (and TCB controls) were titrated and analyzed in final concentration range between 1-300 nM. Cells were then centrifuged (5 min, 350×g), washed with 120 µl/well FACS Stain Buffer (BD Biosciences), resuspended and incubated for an additional 30 min at 4° C. with fluorochrome-conjugated PE-conjugated AffiniPure F(ab')2 Fragment goat anti-human IgG Fc Fragment Specific (Jackson Immuno Research Lab; 109-116-170). Cells were then washed twice with Stain Buffer (BD Biosciences), fixed using 100 ul BD Fixation buffer per well (# BD Biosciences, 554655) at 4° C. for 20 min, resuspended in 120 µl FACS buffer and analyzed using BD FACS CantoII. As depicted in FIGS. 25A-25D, the mean fluorescence intensity of anti-BCMA/anti-CD3 TCB antibodies were plotted in function of antibody concentrations; (A) 83A10-TCB on H929 cells and MKN45 cells, (B) 83A10-TCBcv on H929 cells and MKN45 cells. When applicable, EC50 were calculated using Prism GraphPad (LaJolla, Calif., USA) and EC50 values denoting the antibody concentration required to reach 50% of the maximal binding for the binding of 83A10-TCB and 83A10-TCBcv to H929 cells are summarized in Table 13. FIG. 25C shows that 83A10-TCB and 83A10-TCBcv bind to H929 cells in a concentration-dependent manner and with similar potency. Such results are expected since 83A10-TCB and 83A10-TCBcv molecules share identical CDR sequences on the respective VL and VH variable domains. DP47-TCB control antibody did not bind to BCMA-positive H929 myeloma cells as measured by a lack of increase in median fluorescence intensity. In a second head-to-head comparison experiment, 83A10-TCB and 83A10-TCBcv were evaluated for binding to BCMA-positive H929 cells and lack of binding to BCMA/CD3-negative MKN45 cells. As depicted in FIG. 25D, 83A10-TCB and 83A10-TCBcv bind to BCMA-positive H929 cells in a concentration-dependent manner and with similar potency. EC50 values for the binding of 83A10-TCB and 83A10-TCBcv to H929 cells for this second experiment are summarized in Table 14.

TABLE 13

EC50 values for binding of anti-BCMA/anti-CD3 TCB antibodies to H929 cells (Experiment 1).

| Anti-BCMA/anti-CD3 TCB molecules | EC50 (nM) | EC50 (µg/ml) |
|---|---|---|
| 83A10-TCB | 9.8 | 1.9 |
| 83A10-TCBcv | 14.5 | 2.8 |

TABLE 14

EC50 values for binding of anti-BCMA/anti-CD3 TCB antibodies to H929 cells (Experiment 2).

| Anti-BCMA/anti-CD3 TCB molecules | EC50 (nM) | EC50 (µg/ml) |
|---|---|---|
| 83A10-TCB | 16.9 | 3.25 |
| 83A10-TCBcv | 14.5 | 2.8 |

Redirected T-Cell Cytotoxicity of BCMA-High Expressing H929 Myeloma Cells Induced by Anti-BCMA/Anti-CD3 T Cell Bispecific Antibodies (LDH Release Assay)

Anti-BCMA/anti-CD3 TCB antibodies were also analyzed for their potential to induce T cell-mediated apoptosis in BCMA-high expressing myeloma cells upon crosslinking of the construct via binding of the antigen binding moieties to BCMA on cells. Briefly, human BCMA-expressing H929 multiple myeloma target cells were harvested with Cell Dissociation Buffer, washed and resuspended in RPMI supplemented with 10% fetal bovine serum (Invitrogen). Approximately 30,000 cells per well were plated in a round-bottom 96-well plate and the respective dilution of the antibody construct was added for a desired final concentration (in triplicates); final concentrations ranging from 0.1 pM to 10 nM. For an appropriate comparison, all TCB constructs and controls were adjusted to the same molarity. Human total T cells (effector) were added into the wells to obtain a final effector: target (E:T) ratio of 5:1. When human PBMC were used as effector cells, a final E:T ratio of 10:1 was used. Negative control groups were represented by effector or target cells only. As a positive control for the activation of human pan T cells, 1 µg/ml PHA-M (Sigma # L8902) was used. For normalization, maximal lysis of the H929 MM target cells (=100%) was determined by incubation of the target cells with a final concentration of 1% Triton X-100, inducing cell death. Minimal lysis (=0%) was represented by target cells co-incubated with effector cells only, i.e. without any T cell bispecific antibody. After 20-24 h incubation at 37° C., 5% $CO_2$, LDH release from the apoptotic/necrotic myeloma target cells into the supernatant was then measured with the LDH detection kit (Roche Applied Science), following the manufacturer's instructions. The percentage of LDH release was plotted against the concentrations of anti-BCMA/anti-CD3 T cell bispecific antibodies in concentration-response curves. When applicable, the EC50 values were measured using Prism software (GraphPad) and determined as the TCB antibody concentration that results in 50% of maximum LDH release. As shown in FIGS. 26A-26D, anti-BCMA/anti-CD3 TCB antibodies ((FIGS. 26A and 26B) 83A10-TCB, (FIGS. 26C and 26D) 83A10-TCBcv) induced a concentration-dependent killing of BCMA-positive H929 myeloma cells as measured by LDH release. The killing of H929 cells was specific since DP47-TCB control antibody which does not bind to BCMA-positive target cells did not induce LDH release, even at the highest concentration of 1 nM (A). Even though EC50 values were not measurable with the use of Prism (GraphPad) statistical software for 83A10-TCB (A, B) and 83A10-TCBcv (C, Experiment 1), the magnitude of EC50 values could be approximately estimated to low picomolar range potency for both non-charged and charged TCB molecules. In a second experiment, the effect of 83A10-TCBcv was evaluated in the redirected T-cell killing assay and an EC50 value could be measured to 1.5 pM. The authors could not exclude that the slightly lower EC50 value (slightly better potency) could be due to blood donor variability. However, the magnitude of potency to kill H929 cells was definitely in the low picomolar range. The overall results suggest that 83A10-TCB (without charge variant) vs. 83A10-TCBcv (with charge variant) shows similar biological properties in cell-based assays.

TABLE 15

EC50 values and estimations for redirected T-cell killing of H929 cells induced by anti-BCMA/anti-CD3 TCB antibodies.

| Anti-BCMA/anti-CD3 TCB molecules | EC50 (pM) | EC50 (µg/ml) |
|---|---|---|
| 83A10-TCB (Experiment 1) | Low pM range (approx. <20) | Single digit |
| 83A10-TCB (Experiment 2) | Low pM range (approx. <20) | Single digit |

TABLE 15-continued

EC50 values and estimations for redirected T-cell killing
of H929 cells induced by anti-BCMA/anti-CD3 TCB antibodies.

| Anti-BCMA/anti-CD3 TCB molecules | EC50 (pM) | EC50 (μg/ml) |
|---|---|---|
| 83A10-TCBcv (Experiment 1) | Low pM range (approx. <20) | Single digit |
| 83A10-TCBcv (Experiment 2) | 1.5 | 0.3 |

Example 3

Preparation of "2+1 IgG CrossFab, Inverted" T-Cell Bispecific Antibody with Charge Modifications (Anti-Her2/Anti-CD3) and "2+1 IgG CrossFab" T-Cell Bispecific Antibody with Charge Modifications (Anti-Her3/Anti-CD3)

Figure 27A:
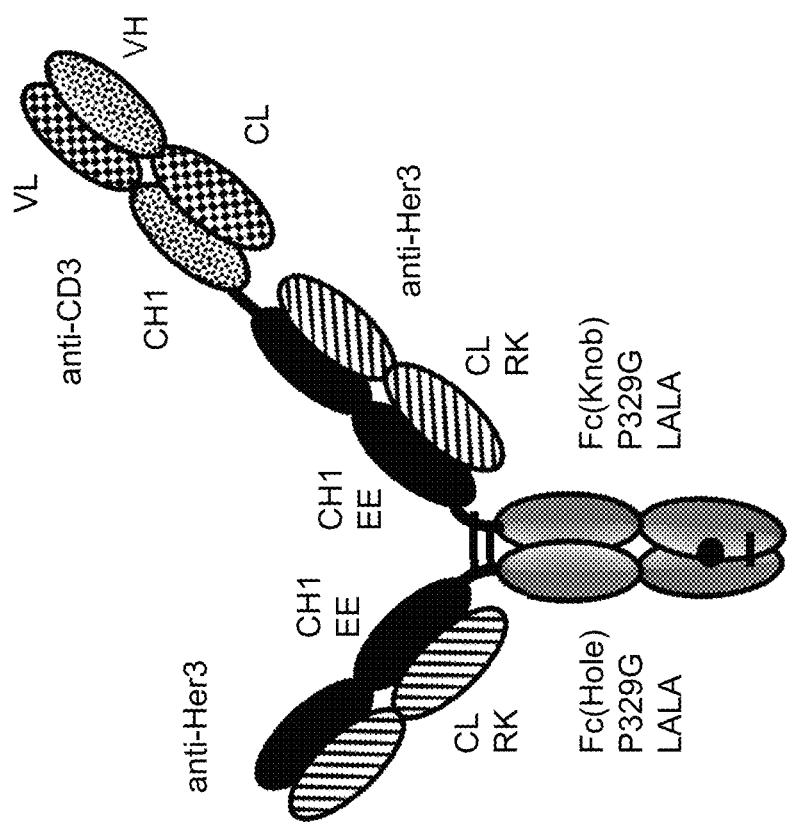
(FIG. 27A) "2+1 IgG CrossFab, inverted" with charge modifications (VH/VL exchange in CD3 binder, charge modification in Her2 binders, EE=147E, 213E; RK=123R, 124K), (FIG. 27B) "2+1 IgG CrossFab" with charge modifications (VH/VL exchange in CD3 binder, charge modification in Her3 binders, EE=147E, 213E; RK=123R, 124K).
Figure 27B:
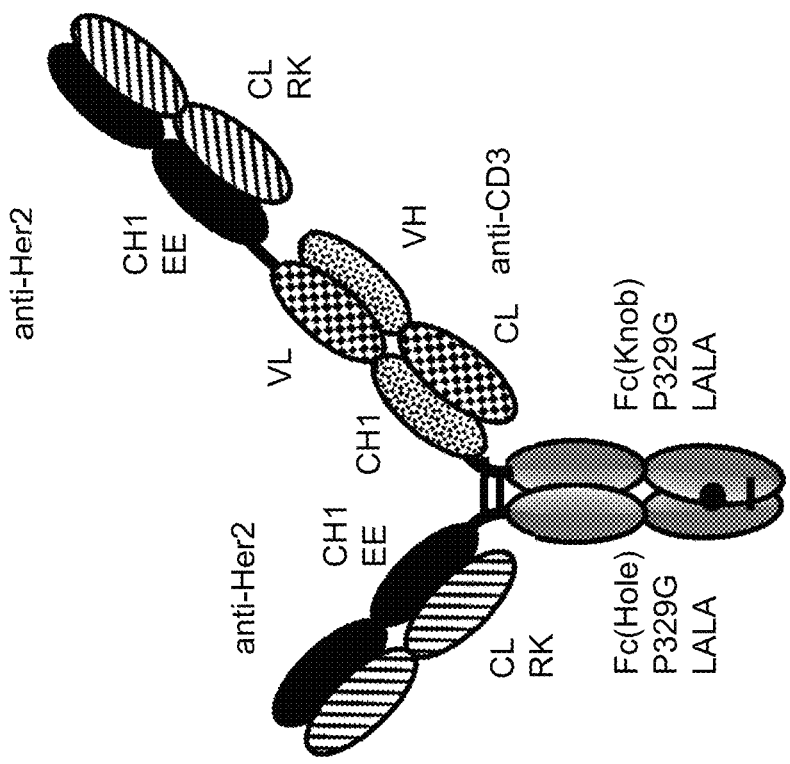
FIG. 27. Illustration of the TCBs prepared in Example 3.
Figure 28A:
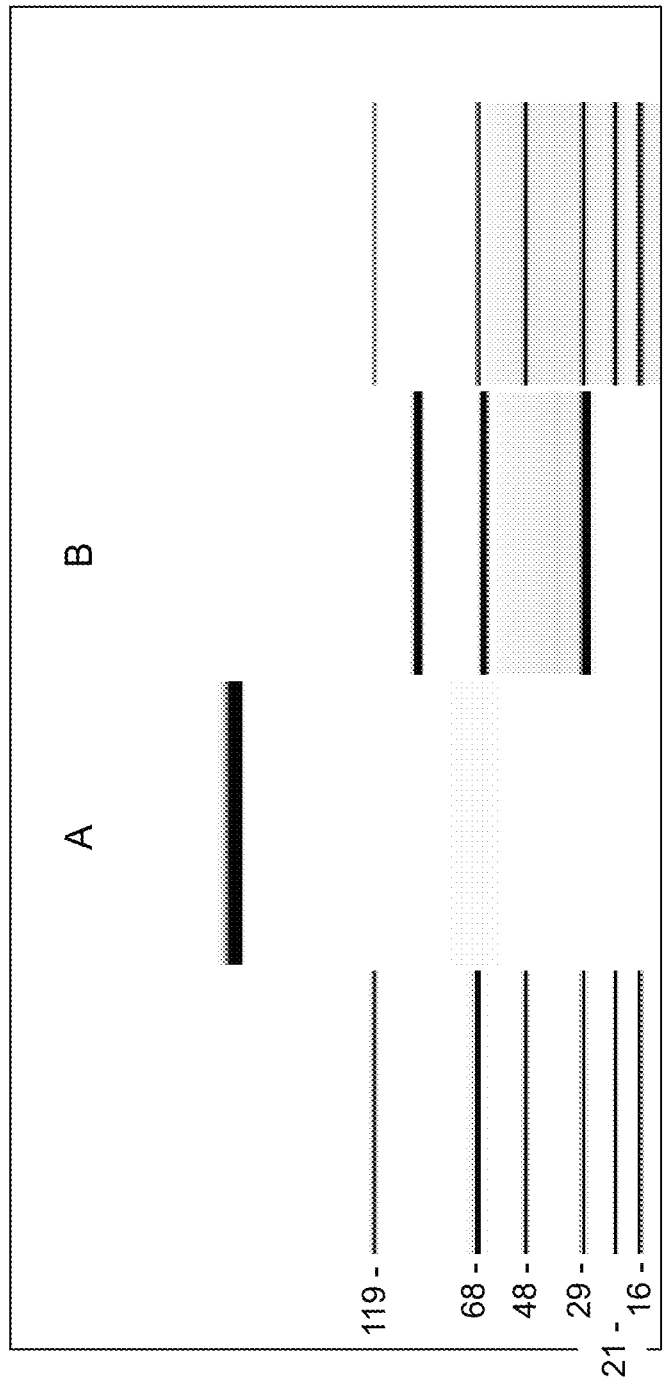
(FIG. 28A) Electropherogram of Her2 TCB, shown in FIG. 27A, (FIG. 28B) electropherogram of Her3 TCB, shown in FIG. 27B. Lane A=non-reduced, lane B=reduced.
Figure 28B:
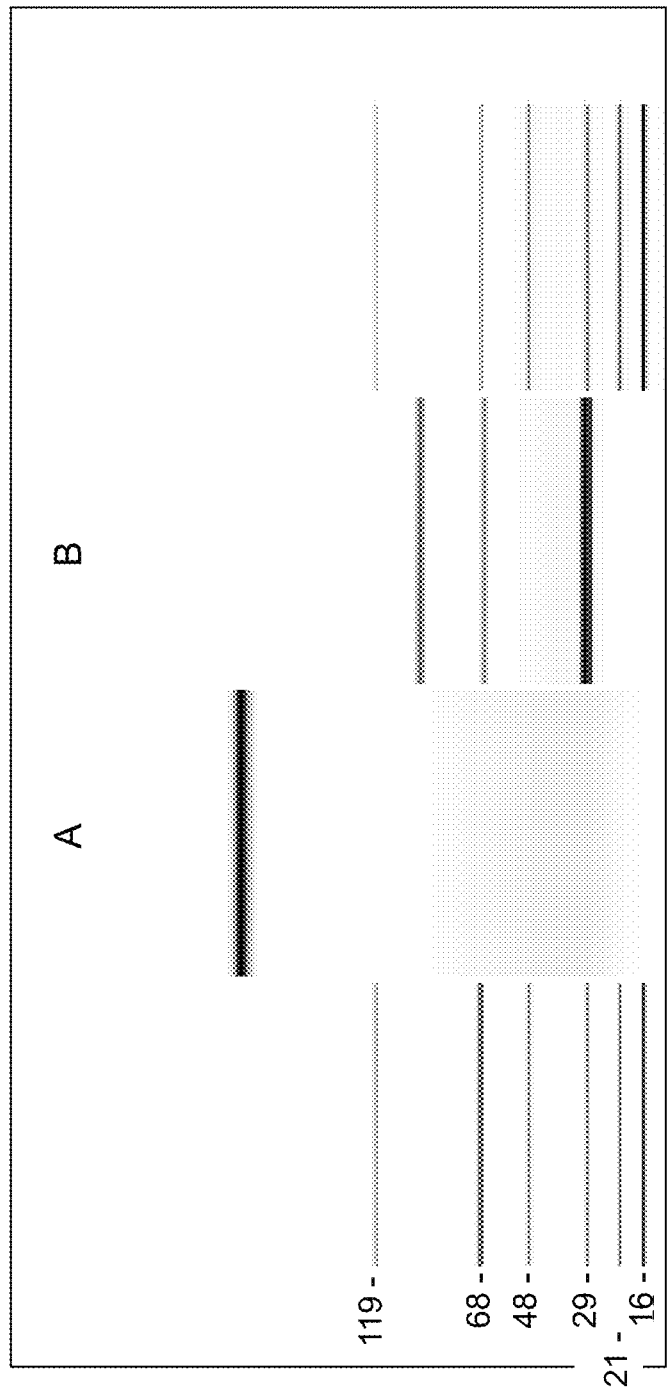
FIG. 28. CE-SDS analysis of the TCBs prepared in Example 3 (final purified preparation).

A schematic illustration of the molecules prepared in this example is shown in FIGS. 27A-27B. The anti-Her2/anti-CD3 "2+1 IgG CrossFab, inverted" molecule with charge modifications (referred to in this example as "Her2 TCB") comprises the amino acid sequences of SEQ ID NOs 21, 52, 53 and 54. The anti-Her3/anti-CD3 "2+1 IgG CrossFab" molecule with charge modifications (referred to in this example as "Her3 TCB") comprises the amino acid sequences of SEQ ID NOs 21, 55, 56 and 57.

The molecules were prepared, purified and analyzed as described in Example 1 above (with a single preparative SEC step).

Both molecules could be purified with high final quality shown by analytical size exclusion chromatography and CE-SDS (Tables 16 and 17). Although recovery of the Her2 TCB in this preparation was lower compared to the Her3 TCB, the protein was almost pure after the two purification steps (Protein A and SEC). CE-SDS analysis shows only 1.18% low molecular weight impurity at approximately 164 kDa (Table 17). The species detected at 187.28 kDa corresponds to the target molecule without N-linked glycosylation on the Fc domain (this species is commonly detected by CE-SDS for human IgG$_1$ after production in eukaryotic cells).

Her3 TCB could be purified with good recovery. The final quality was superior to the Her2 TCB comparing the final monomer content. Also the CE-SDS shows 100% target monomer protein, assuming the peak detected at 192.05 kDa corresponds to the non-glycosylated Fc-species.

For both preparations no product-related low molecular weight impurities such as free light chains (expected molecular weight at 25 kDa), dimerized light chains as it can occur by introducing only a CH1-CL exchange on one light chain (expected molecular weight at 50 kDa) or molecules with missing or non-covalently linked light chains (expected molecular weight at 125 kDa, 150 kDa or 175 kDa) have been detected by CE-SDS or analytical size exclusion chromatography.

TABLE 16

Summary of production and purification of anti-Her2/anti-CD3 and anti-Her3/anti-CD3 TCB molecules with charge modifications.

| Molecule | Titer [mg/l] | Recovery [%] | Yield [mg/l] | Analytical SEC (HMW/Monomer/LMW) [%] |
|---|---|---|---|---|
| Her2 TCB | 45 | 1.8 | 1 | 3.3/96.7/0 |
| Her3 TCB | 72 | 12.7 | 11.42 | 0/100/0 |

TABLE 17

CE-SDS analyses (non-reduced) of anti-Her2/anti-CD3 and anti-Her3/anti-CD3 TCB molecules with charge modifications.

| Molecule | Peak # | Size [kDa] | Purity [%] |
|---|---|---|---|
| Her2 TCB | 1 | 163.99 | 1.18 |
|  | 2 | 187.28 | 1.30 |
|  | 3 | 200.81 | 97.52 |
| Her3 TCB | 1 | 192.05 | 19.36 |
|  | 2 | 198.57 | 80.64 |

Binding of Her2 TCB and Her3 TCB to Cells

Jurkat suspension cells were harvested, washed with FACS buffer (PBS+0.1% BSA) once and viability was determined by ViCell.

Adherent KPL-4 tumor cells (kindly provided by J. Kurebayashi, Kawasaki Medical School, Japan) were harvested with Cell Dissociation Buffer (Gibco Invitrogen) and washed with FACS buffer once, before viability was determined by ViCell.

0.2 million cells were plated per well of a round-bottom 96-well plate and the plates were centrifuged for 4 min at 400 g. Then 25 μl per well of the TCB dilutions in FACS buffer was added to the cells. The cells were incubated for 30 min in the fridge. Afterwards the cells were washed twice with 150 μl FACS buffer per well.

25 μl of appropriately diluted secondary antibody (FITC conjugated AffiniPure F(ab')$_2$ Fragment, Goat Anti-Human IgG, F(ab')$_2$ fragment specific, Jackson ImmunoResearch) were added per well and the plates were stained for further 30 min at 4° C. in the dark.

The plates were washed twice with 150 μl FACS buffer per well and resuspended in 150 μl FACS buffer. The analysis was performed using a BD FACS CantoII, equipped with FACS Diva Software. Median fluorescence values (MFI) were plotted against the concentration of the TCB molecules.

Figure 29A:
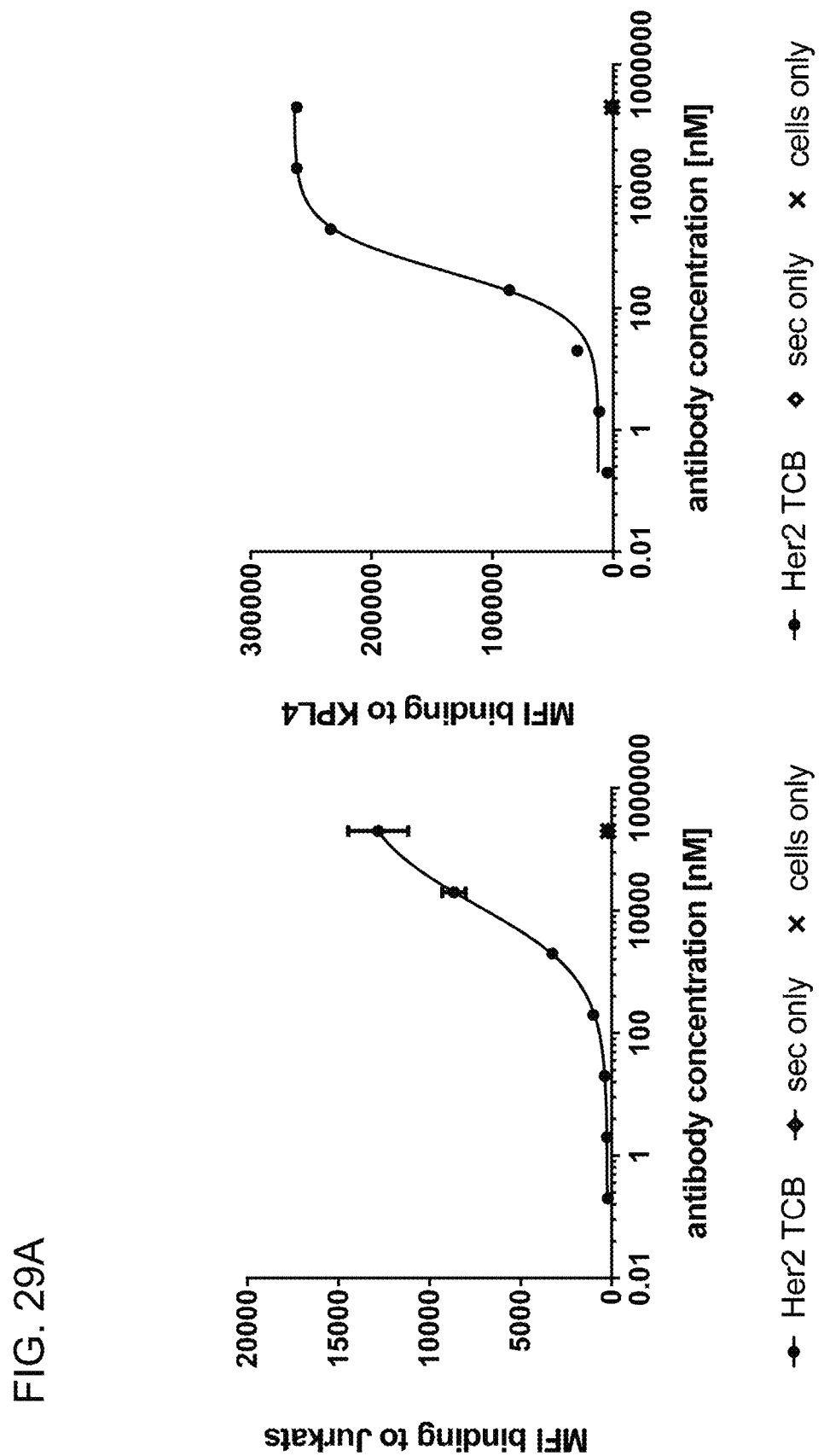
FIG. 29. Binding of Her2 TCB (FIG. 29A) and Her3 TCB (FIG. 29B) to cells, as determined by FACS. Median fluorescence intensities for binding of the Her2 TCB molecule to human CD3 on Jurkat cells (left) or to human Her2 (FIG. 29A) or Her3 (FIG. 29B) on KPL-4 cells (right), as measured by flow cytometry. Depicted are median fluorescence values, based on triplicates, including SD.
Figure 29B:
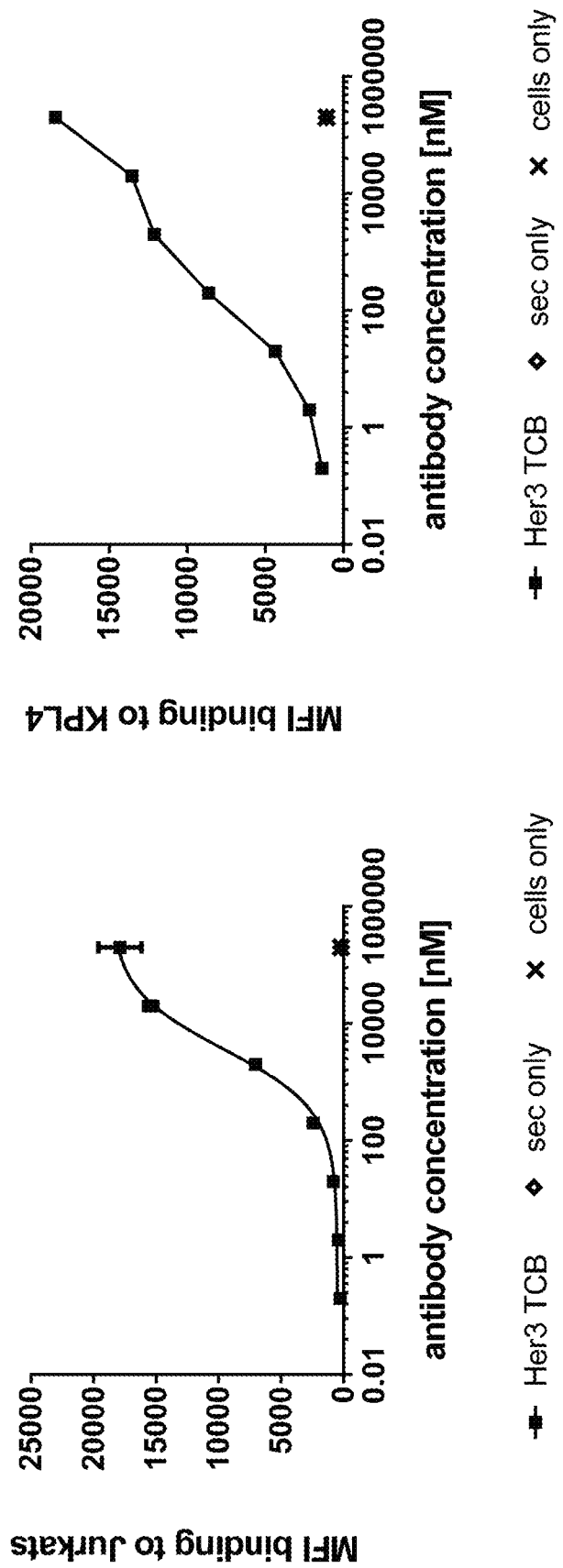

As shown in FIGS. 29A-29B, both TCBs show concentration-dependent good binding to their respective target antigens on cells.

Activation of Human CD8$^+$ T Effector Cells, after T Cell-Mediated Lysis of Human Tumor Cells, Induced by the Her3 TCB CD8$^+$ T effector cells of a classical tumor cell lysis experiment (as described below) with Her3 TCB using an effector-to-target ratio (E:T) of 10:1 and an incubation time of 48h were evaluated for the percentage of CD69-positive cells.

Briefly, after incubation, PBMCs were transferred to a round-bottom 96-well plate, centrifuged at 350×g for 5 min and washed twice with PBS containing 0.1% BSA. Surface staining for CD8 (Biolegend #300908) and CD69 (BioLegend #310904) was performed according to the suppliers' indications. Cells were washed twice with 150 μl/well PBS containing 0.1% BSA and fixed for 20 min at 4° C. using 100 μl/well 1% PFA. After centrifugation, the samples were resuspended in 200 μl/well PBS 0.1% BSA and analyzed at FACS CantoII (Software FACS Diva).

Figure 30:
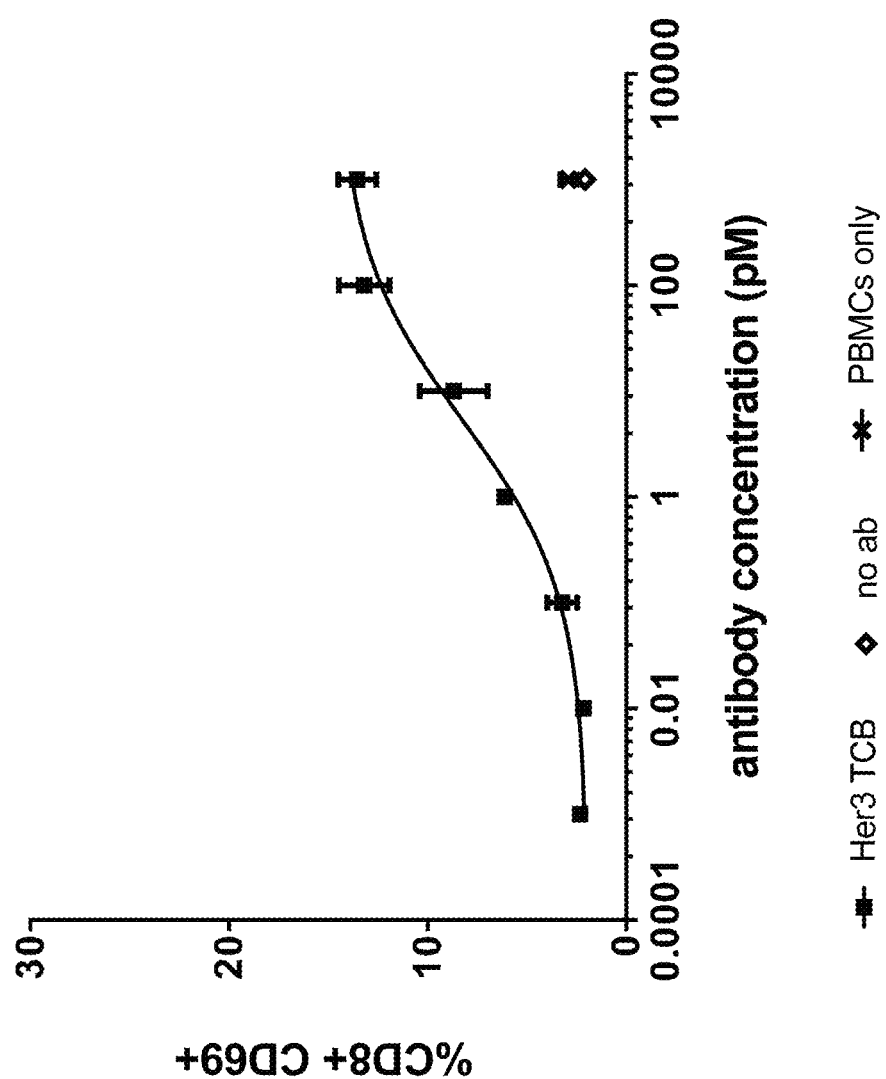
FIG. 30. T cell activation by Her3 TCB. Upon co-incubation of human PBMC effector cells, KPL-4 target cells and increasing concentrations of the Her3 TCB, the percentage of CD69 positive CD8 T cells was measured by FACS after 48h. Shown are triplicates with SD.

As shown in FIG. 30, the Her3 TCB induces cross-linkage of T cells and tumor cells (KPL-4) via its respective targeting moieties and induces activation of T cells in a concentration-dependent manner.

Jurkat-NFAT Activation Assay

The capacity of the Her2 TCB and the Her3 TCB to induce T cell cross-linking and subsequently T cell activation, was assessed using co-cultures of tumor antigen positive target cells (KPL-4) and Jurkat-NFAT reporter cells (a CD3-expressing human acute lymphatic leukemia reporter cell line with a NFAT promoter, GloResponse Jurkat NFAT-RE-luc2P, Promega # CS176501). Upon simultaneous binding of the TCB molecule to human Her2, respectively human Her3, antigen (expressed on tumor cells) and CD3 antigen (expressed on Jurkat-NFAT reporter cells), the NFAT promoter is activated and leads to expression of active firefly luciferase. The intensity of luminescence signal (obtained upon addition of luciferase substrate) is proportional to the intensity of CD3 activation and signaling. For the assay, KPL-4 human tumor cells were harvested with Cell Dissociation Buffer (Gibco Invitrogen) and viability was determined using ViCell. 20 000 cells/well were plated in a flat-bottom, white-walled 96-well-plate (Greiner bio-one) and diluted TCBs or medium (for controls) was added. Subsequently, Jurkat-NFAT reporter cells were harvested and viability assessed using ViCell. Cells were resuspended in cell culture medium and added to tumor cells to obtain a final E:T of 2.5:1 (for Her2 TCB) or 5:1 (for Her3 TCB) as indicated, and a final volume of 100 µl per well. Cells were incubated for 5 h at 37° C. in a humidified incubator. At the end of the incubation time, 100 µl/well of ONE-Glo solution (Promega, # E6120) (1:1 ONE-Glo and assay medium volume per well) were added to wells and incubated for 10 min at room temperature in the dark. Luminescence was detected using WALLAC Victor3 ELISA reader (PerkinElmer2030), 5 sec/well as detection time.

Figure 31A:
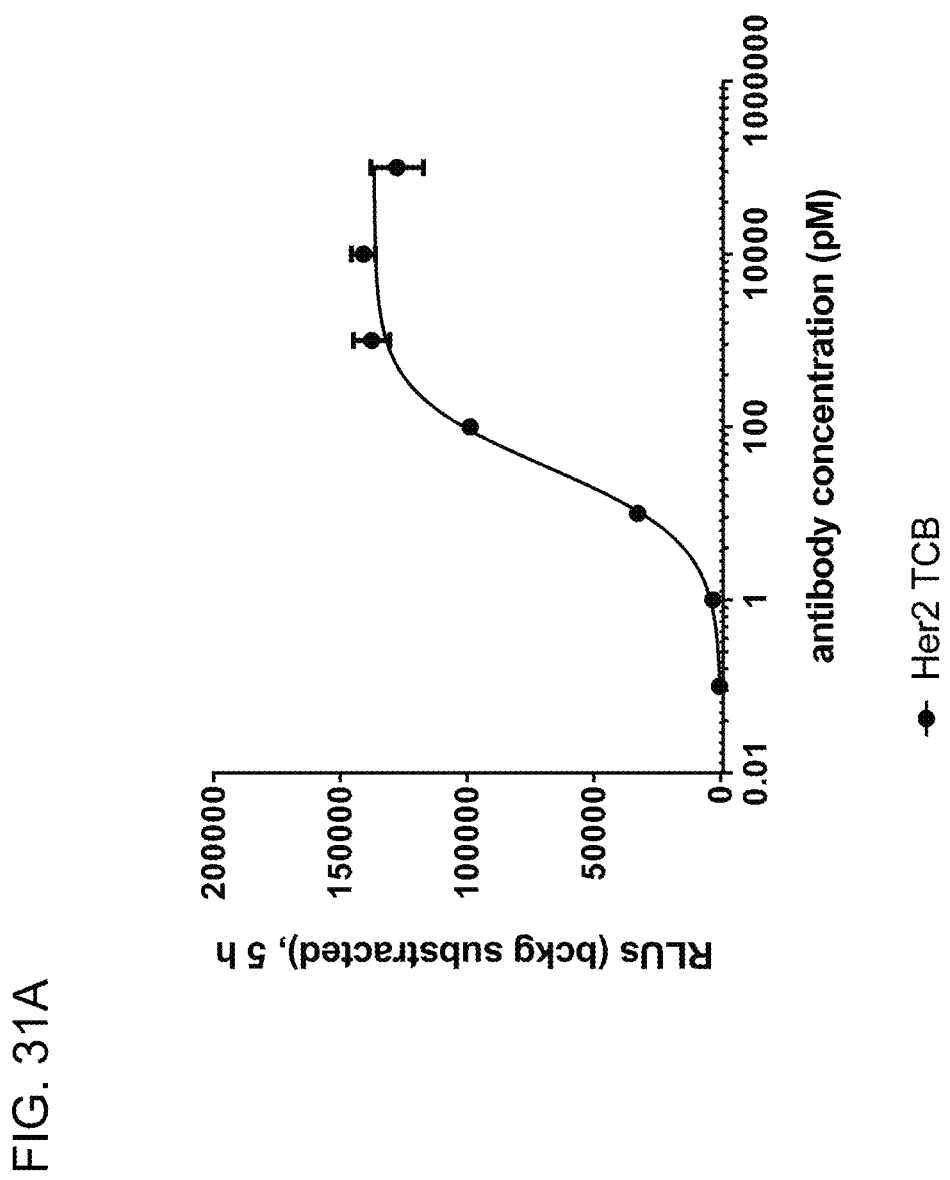
FIG. 31. Activation of Jurkat cells via CD3 after 5h, as determined by luminescence. Upon incubation of KPL4 tumor cells with Jurkat-NFAT reporter cells (E:T 5:1 (FIG. 31A) or 2.5:1 (FIG. 31B)) and increasing concentrations of the Her2 TCB (FIG. 31A) or the Her3 TCB (FIG. 31B), activation of Jurkats was determined by relative luminescent signals (RLUS) after 5h. EC50 values were calculated by Graph Pad Prism (34.4 pM (FIG. 31A) and 22 pM (FIG. 31B)). Depicted are average values from triplicates, error bars indicate SD.
Figure 31B:
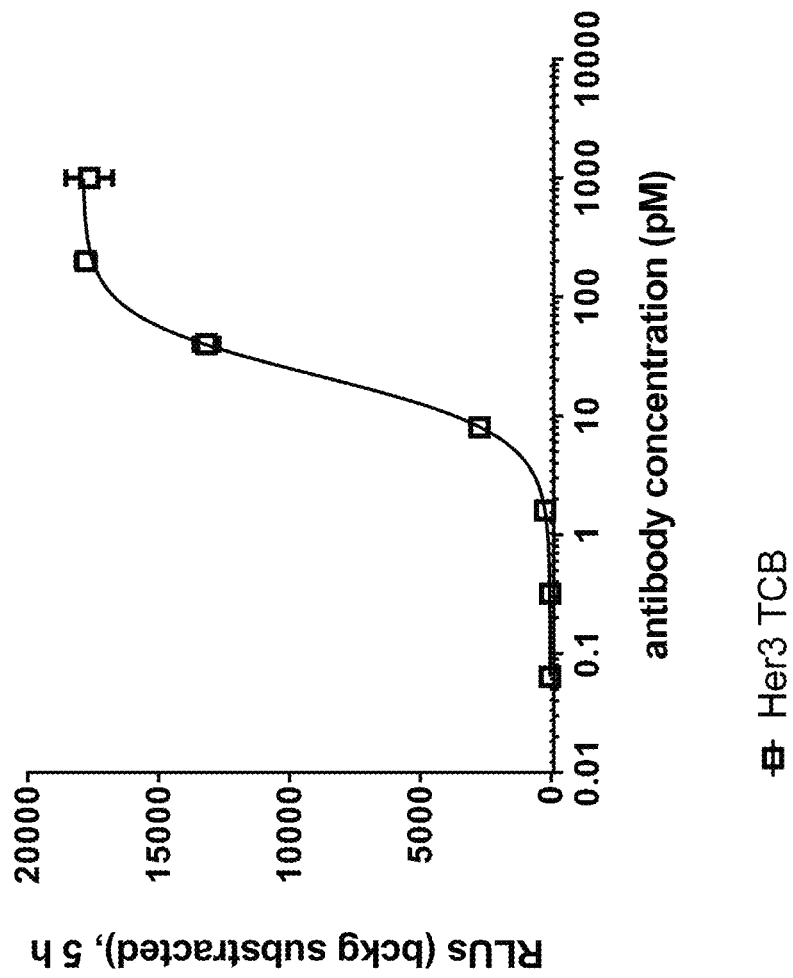

As depicted in FIGS. 31A and 31B, both TCB molecules induce T cell cross-linking via CD3 and subsequently T cell activation. The Her3 TCB is slightly more potent on KPL-4 cells, which might be explained by a higher level of Her3 over Her2 on these target cells.

Tumor Cell Lysis Induced by Her2 TCB and Her3 TCB

Tumor cell lysis of Her2- or Her3-expressing tumor target cells induced by the respective TCB molecules was assessed, using human peripheral blood mononuclear cells (PBMCs) as effectors, at an E:T of 10:1. Tumor cell lysis was determined by measurement of released LDH into the supernatants after 24 h and 48 h upon incubation with the TCBs, as indicated.

Human PBMCs were isolated from fresh blood or from a buffy coat. Briefly, blood was diluted 2:1 (fresh blood) or 3:1 (buffy coat) with PBS. About 30 ml of the blood/PBS mixture was layered on 15 ml of Histopaque (Sigma) and centrifuged for 30 min at 450×g without brake at RT. The lymphocytes were collected with a 10 ml pipette into 50 ml tubes containing PBS. The tubes were filled up to 50 ml with PBS and centrifuged 10 min at 350 g. The supernatant was discarded, the pellet re-suspended in 50 ml PBS and centrifuged for 10 min at 300×g. The washing step was repeated once. The cells were re-suspended in RPMI containing 10% FCS and 1% GlutaMax (Life Technologies) and stored at 37° C., 5% $CO_2$ in the incubator until assay start (not longer than 24h).

Target cells were harvested with Trypsin/EDTA, washed, and plated at density of 30 000 cells/well using flat-bottom 96-well plates. Cells were left to adhere overnight in a humidified incubator. On the day of the assay, the assay plates were centrifuged at 350×g for 5 min and the medium was aspirated. 100 µl per well of assay medium were added.

The TCBs were added at indicated concentrations (range of 0.001 pM-1 nM for the Her3 TCB, and 0.01 pM-100 nM for the Her2 TCB, in triplicates). PBMCs were added to target cells at the final E:T ratio of 10:1. Target cell killing was assessed after 24 h and 48 h of incubation by quantification of LDH (lactate dehydrogenase) released into cell supernatants by apoptotic/necrotic cells (LDH detection kit, Roche Applied Science, #11 644 793 001). Maximal lysis of the target cells (=100%) was achieved by incubation of target cells with 1% Triton X-100. Minimal lysis (=0%) refers to target cells co-incubated with effector cells without bispecific antibody. The EC50 values were calculated using GraphPadPrism5.

In another experiment, tumor cell lysis was determined by Caspase 3/7 activity after 6.5h by measuring luminescence in a microplate reader (5 s reading time per wells).

For the determination of Caspase 3/7 activity, KPL-4-Caspase-3/7 GloSensor target cells (KPL-4 cells stably transfected with GloSensor plasmid) were harvested as described above. After one wash with PBS the concentration was adjusted to $0.3 \times 10^6$ cells/ml in the assay medium (RPMI1640, 2% FCS, 1% Glutamax) and mixed with 2% v/v GloSensor cAMP Reagent (Promega). 100 µl (=30 000 cells) of this target cell suspension was transferred into each well of a 96-flat bottom plate with white walls. Peripheral blood mononuclear cells (PBMCs) were prepared by Histopaque density centrifugation of enriched lymphocyte preparations (buffy coats) obtained from healthy human donors, as described above. The tumor cell lysis assay was performed essentially as described above.

Figure 32A:
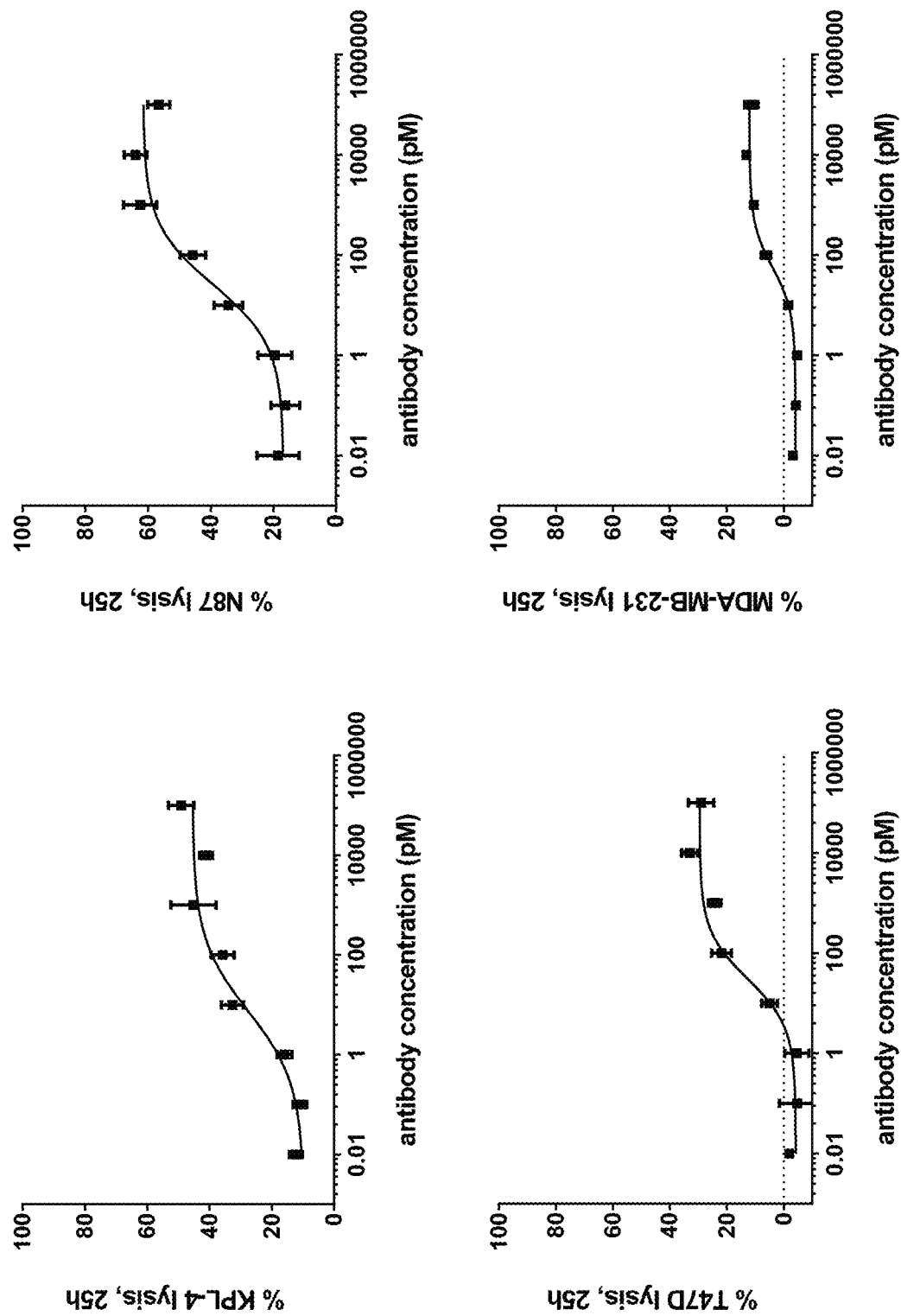
(FIG. 32A, FIG. 32B) Tumor cell lysis, as measured by LDH release, upon incubation of Her2-positive KPL4, N87, T47D or MDA-MB-231 target cells with human PBMC effector cells (E:T 10:1) and increasing concentrations of the Her 2 TCB molecule for 25 h (FIG. 32A) or 46 h (FIG. 32B). Depicted are average values from triplicates, error bars indicate SD. EC50 values were calculated by GraphPadPrism: 7.5 pM (KPL4 cells), 25.6 pM (N87 cells), 30.6 pM (T47D cells), and 59.9 pM (MDA-MB-231 cells).
Figure 32B:
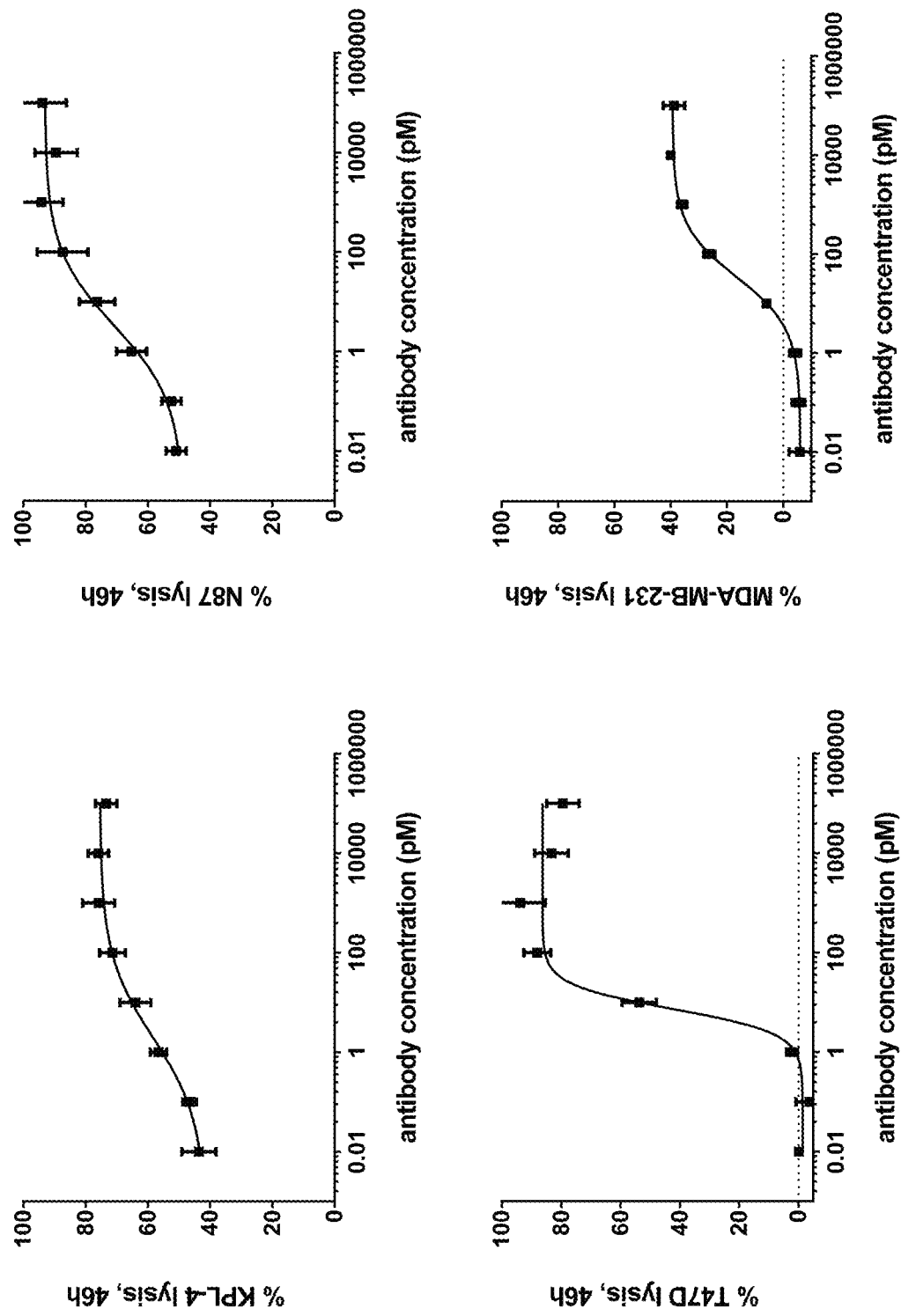
Figure 32C:
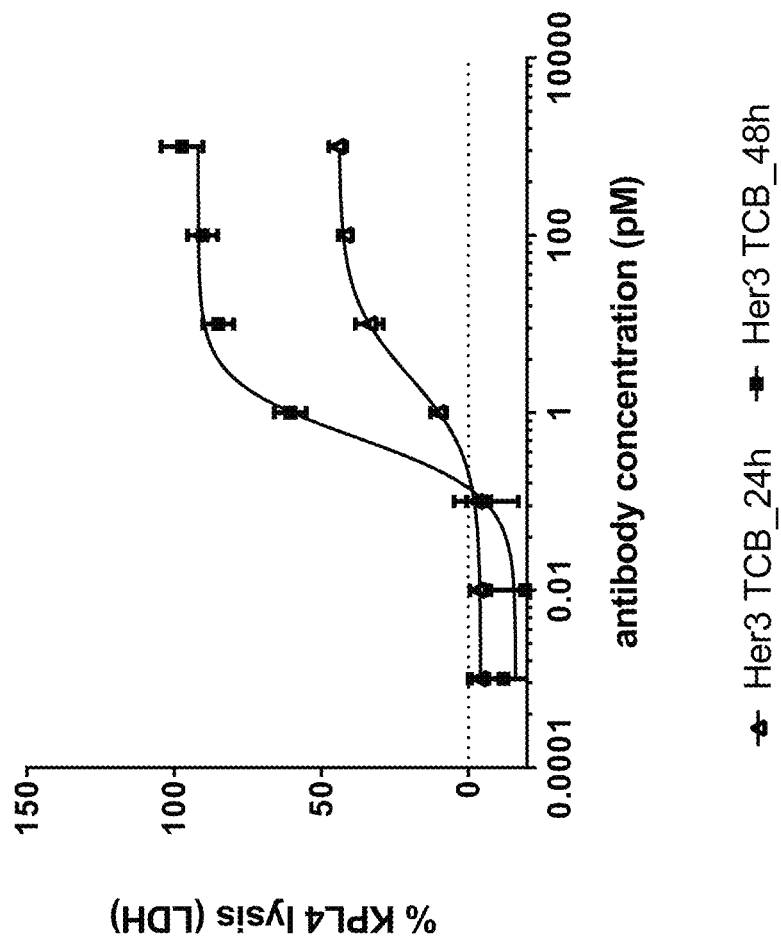
(FIG. 32C) Tumor cell lysis, as measured by LDH release, upon incubation of Her3-positive KPL4 target cells with human PBMC effector cells (E:T 10:1) and increasing concentrations of the Her 3 TCB molecule for 24 h or 48 h, as indicated. Depicted are average values from triplicates, error bars indicate SD. EC50 values were calculated by GraphPadPrism: 2.54 pM (24 h) and 0.53 pM (48 h).
Figure 33:
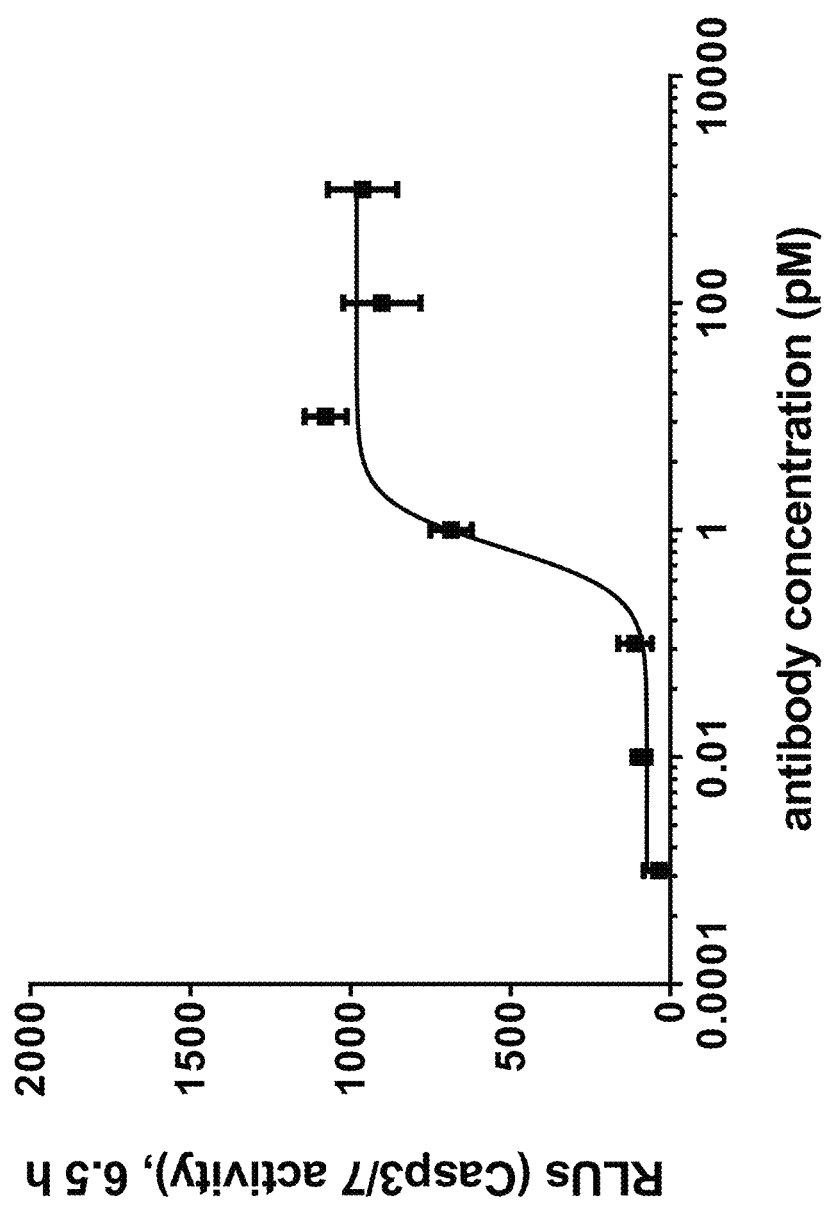
FIG. 33. Tumor cell lysis, induced by Her3 TCB, as determined by Caspase 3/7 activity (luminescence). Shown is the relative luminescent signal, that was measured as a consequence of Caspase 3/7 activity in KPL-4-Caspase-3/7 GloSensor target cells after 6.5 h co-incubation with PBMCs (E:T=10:1) and different concentrations of Her3 TCB, as indicated. Shown are triplicates with SD. EC50 value was calculated by GraphPadPrism: 0.7 pM.
Figure 35:
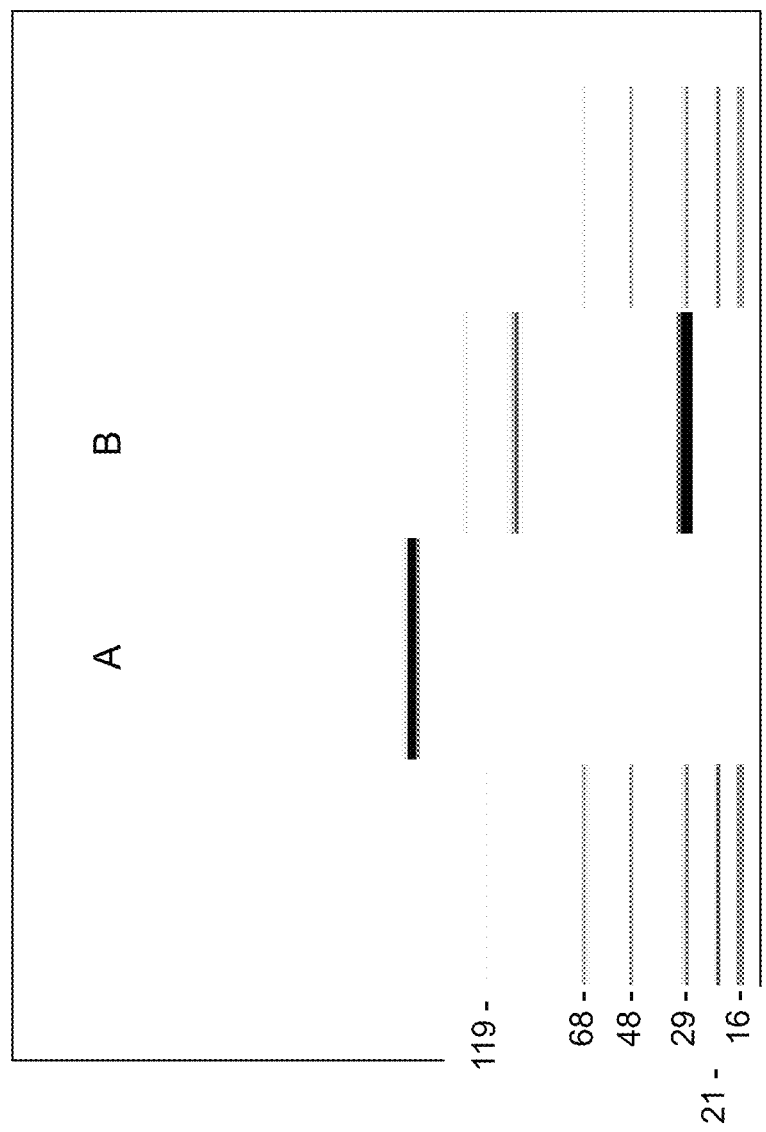
FIG. 35. CE-SDS analysis of the TCB with charge modifications prepared in Example 4 (final purified preparation): Electropherogram of (Fab)$_2$-XFab-LC007cv, shown in FIG. 34A. Lane A=non-reduced, lane B=reduced.

The results depicted in FIG. 32C and FIG. 33 illustrate that the Her3 TCB molecule induces potent and concentration-dependent apoptosis and lysis of KPL-4 tumor cells.

The same is true for the Her2 TCB that is depicted FIGS. 32A and 32B and shows significant, concentration-dependent lysis of tumor cells over time. Thereby, the EC50 of killing seems to depend on the expression level of Her2 on the respective target cell. The higher the expression level, the better the tumor cell killing by the Her2 TCB.

Example 4

Preparation of "(Fab)$_2$-CrossFab" T-Cell Bispecific Antibodies with and without Charge Modifications (Anti-MCSP/Anti-CD3)

A schematic illustration of the molecules prepared in this example is shown in FIGS. 34A-34B. The anti-MCSP/anti-CD3 "(Fab)$_2$-CrossFab" molecule with charge modifications in the MCSP binders (referred to as "(Fab)2-XFab-LC007cv" in this example) comprises the amino acid sequences of SEQ ID NOs 58, 59 and 60. The anti-MCSP/anti-CD3 "(Fab)$_2$-CrossFab" molecule without charge modifications (referred to as "(Fab)2-XFab" in this example) comprises the corresponding amino acid sequences without the charge modifications.

The molecules were prepared, purified and analyzed essentially as described in Example 1 above, with the following adaptations.

For the production of these molecules, the HEK293-EBNA cells were transfected with the corresponding expression vectors in a 1:2:1 ratio ("vector heavy chain":"vector light chain anti-MSCP Fab":"vector light chain anti-CD3 Fab").

Concentration of the constructs in the culture medium was determined by ProteinA-HPLC, based on binding of parts of the CH1 domain to ProteinA at pH8.0 and step elution from pH2.5 as described in Example 1.

The secreted proteins were purified from cell culture supernatants by affinity chromatography using affinity chromatography binding to CH1, followed by a size exclusion chromatographic step.

For affinity chromatography, supernatant was loaded on a HiTrap KappaSelect column (CV=5 mL, GE Healthcare)

equilibrated with 5 ml 50 mM Tris, 100 mM glycine, 150 mM NaCl pH 8.0. Unbound protein was removed by washing with at least 10 column volumes 50 mM Tris, 100 mM glycine, 150 mM NaCl pH 8.0. The target protein was eluted in 10 column volumes gradient to 50 mM Tris, 100 mM glycine, 150 mM NaCl pH 2.0. Protein solution was neutralized by adding 1/40 of 2 M Tris pH 8.0. Target protein is concentrated and filtered prior loading on a HiLoad Superdex 200 column (GE Healthcare) equilibrated with 20 mM histidine, 140 mM sodium chloride, 0.01% Tween-20, pH 6.0. Both molecules were produced and purified following the same method Compared to the molecule without charge modifications ("(Fab)2-XFab") the titer of the molecule with charges was 10 fold lower. Nevertheless the final recovery was approximately two times higher for the molecule with the charge modifications in the two anti-MCSP Fabs ("(Fab)2-XFab-LC007cv") (Table 18). The (Fab)2-XFab-LC007cv molecule could be purified to a final monomer content of 95.8% shown by size exclusion chromatography and a final purity proven by CE-SDS analyses of 94.33%.

TABLE 18

Summary of production and purification of anti-MCSP/anti-CD3 TCB molecules with and without charge modifications.

| Molecule | Titer [mg/l] | Recovery [%] | Yield [mg/l] | Analytical SEC (HMW/Monomer/LMW) [%] |
|---|---|---|---|---|
| (Fab)2-XFab | 25 | 6.24 | 7.8 | 0/100/0 |
| (Fab)2-XFab-LC007cv | 2.32 | 10.5 | 0.24 | 3.2/95.8/1 |

TABLE 19

CE-SDS analyses (non-reduced) of the anti-MCSP/anti-CD3 TCB molecule with charge modifications.

| Molecule | Peak # | Size [kDa] | Purity [%] |
|---|---|---|---|
| (Fab)2-XFab-LC007cv | 1 | 162.67 | 94.33 |
| | 2 | 170.59 | 5.67 |

Cell Binding of "(Fab)$_2$-CrossFab" T-Cell Bispecific Antibodies with and without Charge Modifications (Anti-MCSP/Anti-CD3)

Jurkat-NFAT suspension cells were harvested, washed with FACS buffer (PBS+0.1% BSA) once and viability was determined by ViCell.

Adherent MV-3 tumor cells were harvested with Cell Dissociation Buffer (Gibco Invitrogen) and washed with FACS buffer once, before viability was determined by ViCell.

0.2 million cells were plated per well of a round-bottom 96-well plate and the plates were centrifuged for 4 min at 400×g. Then 25 µl per well of the primary antibody dilutions in FACS buffer was added to the cells. The cells were incubated for 30 min in the fridge. Afterwards the cells were washed twice with 150 µl FACS buffer per well.

25 µl of the diluted secondary antibody (FITC conjugated AffiniPure F(ab')$_2$ Fragment, Goat Anti-Human IgG, F(ab')$_2$ fragment specific, Jackson ImmunoResearch) were added per well and the plates were stained for further 30 min at 4° C. in the dark.

The plates were washed twice with 150 µl FACS buffer per well and resuspended in 150 µl FACS buffer. The analysis was performed using a BD FACS Cantoll, equipped with FACS Diva Software. Median fluorescence values (MFI) were plotted against the concentration of the MCSP TCB molecules.

Figure 36:
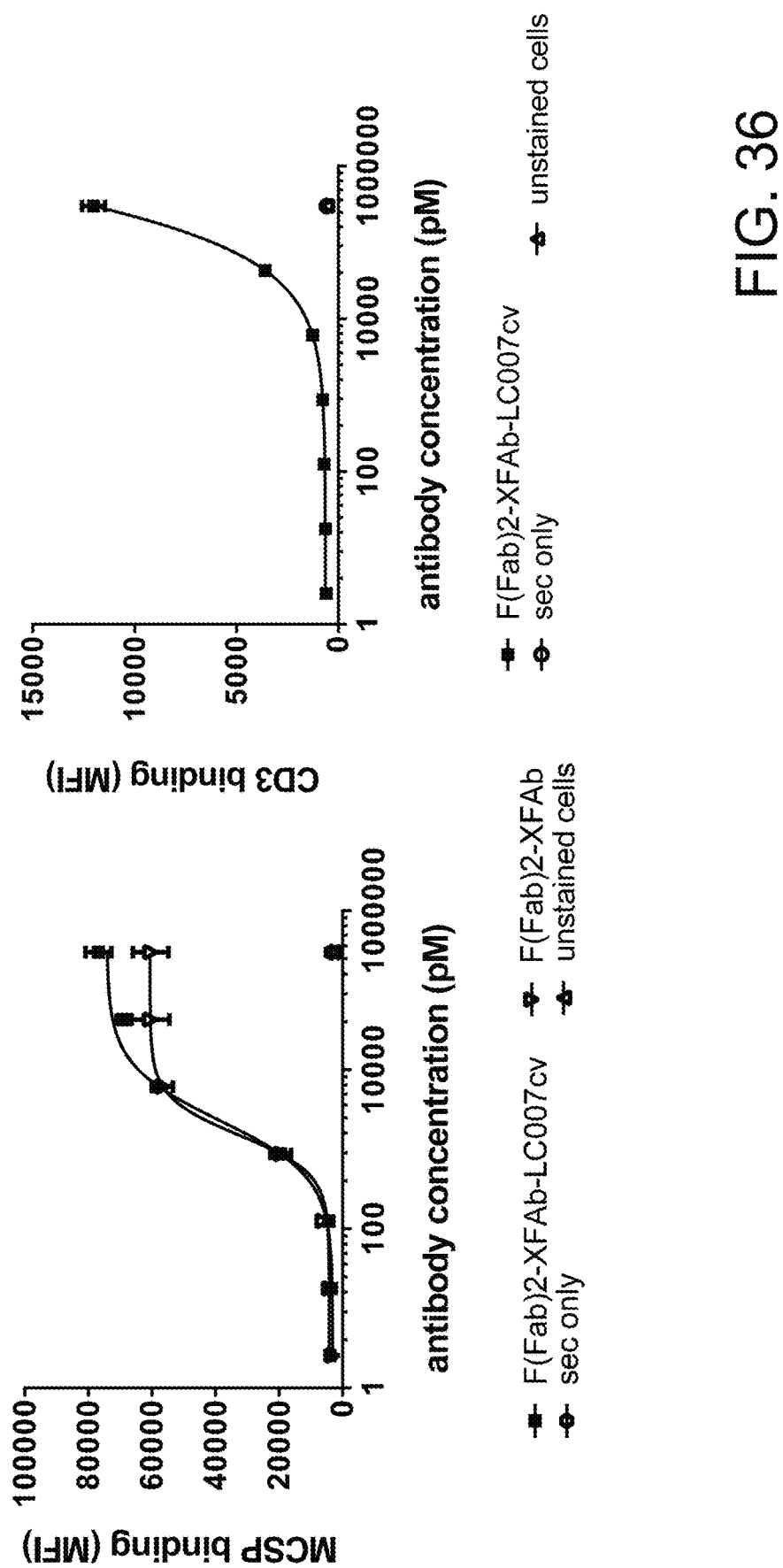
FIG. 36. Median fluorescence intensities for binding of the TCB molecules to human MCSP on MV-3 cells (left) or to human CD3 on Jurkat cells (right), as measured by flow cytometry. Depicted are median fluorescence values, based on triplicates, including SD.

As shown in FIG. 36, the (Fab)2-XFAb-LC007cv molecule shows concentration-dependent binding to human MCSP on MV-3 and to human CD3 on Jurkat cells. The (Fab)2-XFab molecule without charge modifications shows comparable binding to human MCSP as (Fab)2-XFAb-LC007cv (EC50 binding of 2.3 nM for the (Fab)2-XFAb-LC007cv versus EC 50 1.5 nM for the (Fab)2-XFab).

Tumor Cell Lysis Mediated by "(Fab)$_2$-CrossFab" T-Cell Bispecific Antibodies with and without Charge Modifications (Anti-MCSP/Anti-CD3)

Tumor cell lysis of MCSP-expressing MV-3 tumor target cells induced by the MCSP TCB molecules was using human PBMCs as effectors, at an E:T of 10:1. Tumor cell lysis was determined by measurement of released LDH into the supernatants after 24 h and 48 h upon incubation with the TCBs.

Briefly, target cells were harvested with Trypsin/EDTA, washed, and plated at density of 25 000 cells/well using flat-bottom 96-well plates. Cells were left to adhere overnight in a humidified incubator. On the day of the assay, the assay plates were centrifuged at 350×g for 5 min and the medium was aspirated. 100 µl per well of assay medium were added.

Peripheral blood mononuclear cells (PBMCs) were isolated from fresh blood. Briefly, blood was diluted 2:1 with PBS. About 30 ml of the blood/PBS mixture was layered on 15 ml of Histopaque (Sigma) and centrifuged for 30 min at 450×g without brake. The lymphocytes were collected with a 10 ml pipette into 50 ml tubes containing PBS. The tubes were filled up to 50 ml with PBS and centrifuged 10 min at 350×g. The supernatant was discarded, the pellet re-suspended in 50 ml PBS and centrifuged for 10 min at 300×g. The washing step was repeated once. The cells were re-suspended in RPMI containing 10% FCS and 1% GlutaMax (Life Technologies) and stored at 37° C., 5% CO$_2$ in the incubator until assay start (not longer than 24 h).

For the killing assay, the TCB molecules were added at indicated concentrations (range of 0.04 pM-10 nM in triplicates). PBMCs were added to target cells at the final E:T ratio of 10:1. Target cell killing was assessed after 24 h and 48 h of incubation by quantification of LDH (lactate dehydrogenase) released into cell supernatants by apoptotic/necrotic cells (LDH detection kit, Roche Applied Science, #11 644 793 001). Maximal lysis of the target cells (=100%) was achieved by incubation of target cells with 1% Triton X-100. Minimal lysis (=0%) refers to target cells co-incubated with effector cells without bispecific antibody. The EC50 values were calculated using GraphPadPrism5.

Figure 37:
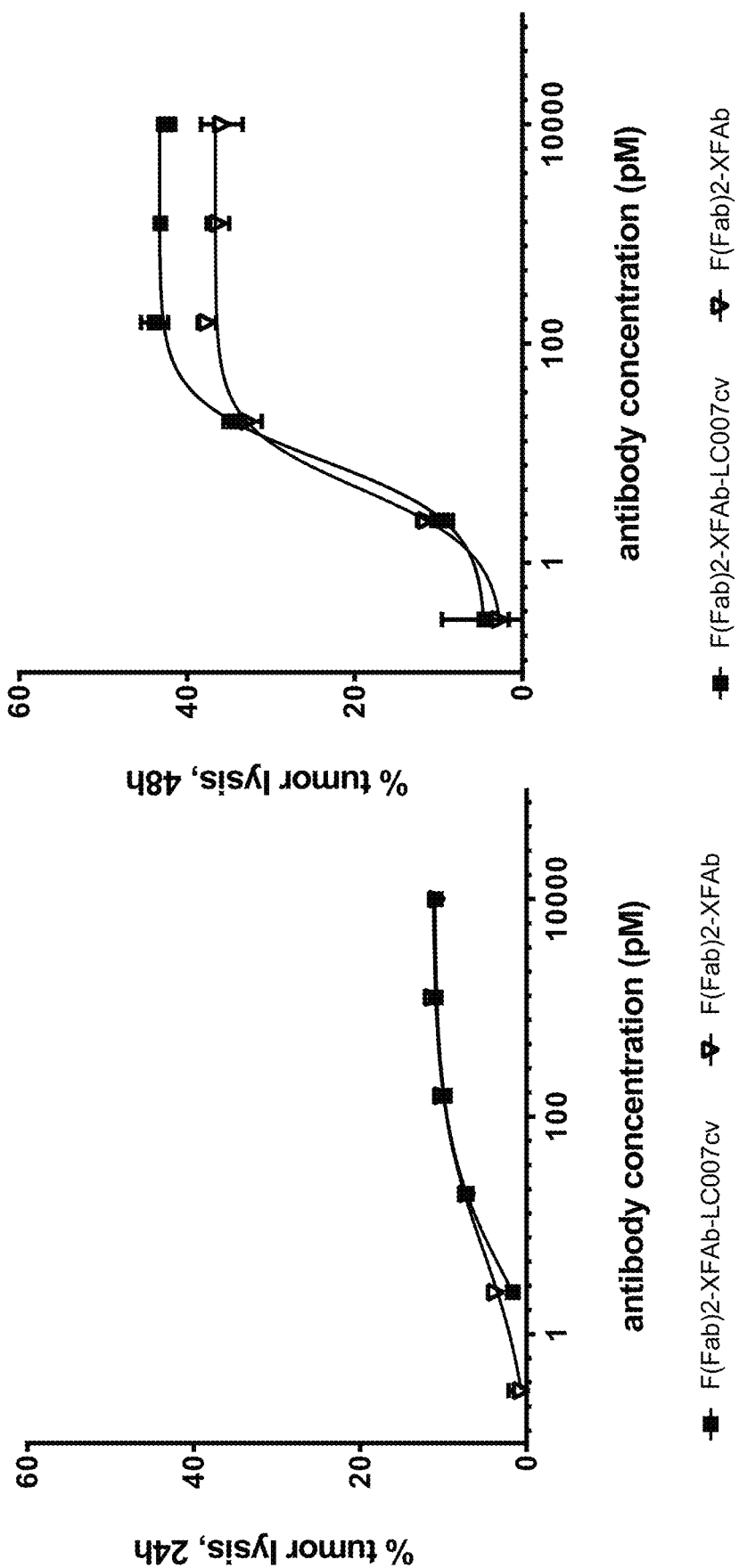
FIG. 37. Tumor cell lysis, as measured by LDH release, upon incubation of human MCSP-positive MV-3 cells with human PBMC effector cells (E:T 10:1) and increasing concentrations of the TCB molecules for 24h (left) or 48h (right). Depicted are average values from triplicates, error bars indicate SD.

As depicted in FIG. 37, both molecules show concentration-dependent lysis of hMCSP-expressing target cells. The potency of the (Fab)2-XFAb-LC007cv molecule (EC50 2.8 pM after 24 h, and 8.6 pM after 48 h) is comparable to the potency of the (Fab)2-XFab molecule without charge modifications (EC50 5.9 pM after 24 h, and 4.8 pM after 48 h).

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A method of treating a CD20-expressing cancer in an individual, comprising administering to said individual a therapeutically effective amount of a composition comprising a T cell activating bispecific antigen-binding molecule in a pharmaceutically acceptable form, the T cell activating bispecific antigen-binding molecule comprising:
    (a) a first Fab molecule which specifically binds to CD20, wherein the first Fab molecule comprises a heavy chain complementarity determining region (CDR) 1 comprising the amino acid sequence of SEQ ID NO: 46, a heavy chain CDR 2 comprising the amino acid sequence of SEQ ID NO: 47, a heavy chain CDR 3 comprising the amino acid sequence of SEQ ID NO: 48, a light chain CDR 1 comprising the amino acid sequence of SEQ ID NO: 49, a light chain CDR 2 comprising the amino acid sequence of SEQ ID NO: 50, and a light chain CDR 3 comprising the amino acid sequence of SEQ ID NO: 51; and
    (b) a second Fab molecule which specifically binds to CD3, wherein the variable domains VL and VH of the Fab light chain and the Fab heavy chain are replaced by each other, wherein the second Fab molecule comprises a heavy chain CDR 1 comprising the amino acid sequence of SEQ ID NO: 4, a heavy chain CDR 2 comprising the amino acid sequence of SEQ ID NO: 5, a heavy chain CDR 3 comprising the amino acid sequence of SEQ ID NO: 6, a light chain CDR 1 comprising the amino acid sequence of SEQ ID NO: 8, a light chain CDR 2 comprising the amino acid sequence of SEQ ID NO: 9, and a light chain CDR 3 comprising the amino acid sequence of SEQ ID NO: 10; and wherein:
    (i) in the constant domain CL of the first Fab molecule, the amino acid at position 124, according to Kabat, is substituted independently by lysine (K), arginine (R), or histidine (H), and wherein in the constant domain CH1 of the first Fab molecule, the amino acid at position 147 or the amino acid at position 213, according to the Kabat EU index, is substituted independently by glutamic acid (E), or aspartic acid (D); or
    (ii) in the constant domain CL of the second Fab molecule, the amino acid at position 124, according to Kabat, is substituted independently by lysine (K), arginine (R) or histidine (H), and wherein in the constant domain CH1 of the second Fab molecule, the amino acid at position 147 or the amino acid at position 213, according to the Kabat EU index, is substituted independently by glutamic acid (E) or aspartic acid (D).

2. A method of treating a CD20-expressing cancer in an individual, comprising administering to said individual a therapeutically effective amount of a composition comprising a T cell activating bispecific antigen-binding molecule in a pharmaceutically acceptable form, the T cell activating bispecific antigen-binding molecule comprising:
    (a) a first Fab molecule which specifically binds to CD20, wherein the first Fab molecule comprises a heavy chain complementarity determining region (CDR) 1 comprising the amino acid sequence of SEQ ID NO: 46, a heavy chain CDR 2 comprising the amino acid sequence of SEQ ID NO: 47, a heavy chain CDR 3 comprising the amino acid sequence of SEQ ID NO: 48, a light chain CDR 1 comprising the amino acid sequence of SEQ ID NO: 49, a light chain CDR 2 comprising the amino acid sequence of SEQ ID NO: 50, and a light chain CDR 3 comprising the amino acid sequence of SEQ ID NO: 51;

(b) a second Fab molecule which specifically binds to CD3, wherein the second Fab molecule comprises a heavy chain CDR 1 comprising the amino acid sequence of SEQ ID NO: 4, a heavy chain CDR 2 comprising the amino acid sequence of SEQ ID NO: 5, a heavy chain CDR 3 comprising the amino acid sequence of SEQ ID NO: 6, a light chain CDR 1 comprising the amino acid sequence of SEQ ID NO: 8, a light chain CDR 2 comprising the amino acid sequence of SEQ ID NO: 9, and a light chain CDR 3 comprising the amino acid sequence of SEQ ID NO: 10, wherein the variable domains VL and VH of the Fab light chain and the Fab heavy chain of the second Fab molecule, respectively, are replaced by each other;

(c) a third Fab molecule which specifically binds to CD20, wherein the third Fab molecule comprises a heavy chain CDR 1 comprising the amino acid sequence of SEQ ID NO: 46, a heavy chain CDR 2 comprising the amino acid sequence of SEQ ID NO: 47, a heavy chain CDR 3 comprising the amino acid sequence of SEQ ID NO: 48, a light chain CDR 1 comprising the amino acid sequence of SEQ ID NO: 49, a light chain CDR 2 comprising the amino acid sequence of SEQ ID NO: 50, and a light chain CDR 3 comprising the amino acid sequence of SEQ ID NO: 51; and (d) an Fc domain composed of a first and a second subunit capable of stable association, wherein:
(i) in the constant domain CL of the first Fab molecule and the third Fab molecule, the amino acid at position 124, according to Kabat, is substituted by lysine (K) and the amino acid at position 123, according to Kabat, is substituted by lysine (K) or arginine (R), and wherein in the constant domain CH1 of the first Fab molecule, and the third Fab molecule, the amino acid at position 147, according to the Kabat EU index, is substituted by glutamic acid (E) and the amino acid at position 213, according to the Kabat EU index, is substituted by glutamic acid (E); and
(ii) the first Fab molecule is fused at the C-terminus of the Fab heavy chain to the N-terminus of the Fab heavy chain of the second Fab molecule, and the second Fab molecule and the third Fab molecule are each fused at the C-terminus of the Fab heavy chain to the N-terminus of one of the subunits of the Fc domain.

3. A method of inducing lysis of a human CD20-expressing tumor target cell, comprising contacting the target cell with a T cell activating bispecific antigen-binding molecule in the presence of a T cell, the T cell activating bispecific antigen-binding molecule comprising:

(a) a first Fab molecule which specifically binds to CD20, wherein the first Fab molecule comprises a heavy chain CDR 1 comprising the amino acid sequence of SEQ ID NO: 46, a heavy chain CDR 2 comprising the amino acid sequence of SEQ ID NO: 47, a heavy chain CDR 3 comprising the amino acid sequence of SEQ ID NO: 48, a light chain CDR 1 comprising the amino acid sequence of SEQ ID NO: 49, a light chain CDR 2 comprising the amino acid sequence of SEQ ID NO: 50, and a light chain CDR 3 comprising the amino acid sequence of SEQ ID NO: 51; and (b) a second Fab molecule which specifically binds to CD3, wherein the variable domains VL and VH of the Fab light chain and the Fab heavy chain are replaced by each other, wherein the second Fab molecule comprises a heavy chain CDR 1 comprising the amino acid sequence of SEQ ID NO: 4, a heavy chain CDR 2 comprising the amino acid sequence of SEQ ID NO: 5, a heavy chain CDR 3 comprising the amino acid sequence of SEQ ID NO: 6, a light chain CDR 1 comprising the amino acid sequence of SEQ ID NO: 8, a light chain CDR 2 comprising the amino acid sequence of SEQ ID NO: 9, and a light chain CDR 3 comprising the amino acid sequence of SEQ ID NO: 10; and wherein:
(i) in the constant domain CL of the first Fab molecule, the amino acid at position 124 according to Kabat, is substituted independently by lysine (K), arginine (R), or histidine (H), and wherein in the constant domain CH1 of the first Fab molecule, the amino acid at position 147 or the amino acid at position 213, according to the Kabat EU index, is substituted independently by glutamic acid (E), or aspartic acid (D); or
(ii) in the constant domain CL of the second Fab molecule the amino acid at position 124, according to Kabat, is substituted independently by lysine (K), arginine (R) or histidine (H), and wherein in the constant domain CH1 of the second Fab molecule, the amino acid at position 147 or the amino acid at position 213, according to the Kabat EU index, is substituted independently by glutamic acid (E) or aspartic acid (D).

4. A method of inducing lysis of a human CD20-expressing tumor target cell, comprising contacting the target cell with a T cell activating bispecific antigen-binding molecule in the presence of a T cell, the T cell activating bispecific antigen-binding molecule comprising:

(a) a first Fab molecule which specifically binds to CD20, wherein the first Fab molecule comprises a heavy chain CDR 1 comprising the amino acid sequence of SEQ ID NO: 46, a heavy chain CDR 2 comprising the amino acid sequence of SEQ ID NO: 47, a heavy chain CDR 3 comprising the amino acid sequence of SEQ ID NO: 48, a light chain CDR 1 comprising the amino acid sequence of SEQ ID NO: 49, a light chain CDR 2 comprising the amino acid sequence of SEQ ID NO: 50, and a light chain CDR 3 comprising the amino acid sequence of SEQ ID NO: 51;

(b) a second Fab molecule which specifically binds to CD3, wherein the second Fab molecule comprises a heavy chain CDR 1 comprising the amino acid sequence of SEQ ID NO: 4, a heavy chain CDR 2 comprising the amino acid sequence of SEQ ID NO: 5, a heavy chain CDR 3 comprising the amino acid sequence of SEQ ID NO: 6, a light chain CDR 1 comprising the amino acid sequence of SEQ ID NO: 8, a light chain CDR 2 comprising the amino acid sequence of SEQ ID NO: 9, and a light chain CDR 3 comprising the amino acid sequence of SEQ ID NO: 10, wherein the variable domains VL and VH of the Fab light chain and the Fab heavy chain of the second Fab molecule are replaced by each other;

(c) a third Fab molecule which specifically binds to CD20, wherein the third Fab molecule comprises a heavy chain CDR 1 comprising the amino acid sequence of SEQ ID NO: 46, a heavy chain CDR 2 comprising the amino acid sequence of SEQ ID NO: 47, a heavy chain CDR 3 comprising the amino acid sequence of SEQ ID NO: 48, a light chain CDR 1 comprising the amino acid sequence of SEQ ID NO: 49, a light chain CDR 2 comprising the amino acid sequence of SEQ ID NO: 50, and a light chain CDR 3 comprising the amino acid sequence of SEQ ID NO: 51; and (d) an Fc domain composed of a first and a second subunit capable of stable association, wherein:
 (i) in the constant domain CL of the first Fab molecule and the third Fab molecule, the amino acid at position 124, according to Kabat, is substituted by lysine (K) and the amino acid at position 123, according to Kabat, is substituted by lysine (K) or arginine (R), and wherein in the constant domain CH1 of the first Fab molecule and the third Fab molecule, the amino acid at position 147, according to the Kabat EU index, is substituted by glutamic acid (E) and the amino acid at position 213, according to the Kabat EU index, is substituted by glutamic acid (E); and
 (ii) the first Fab molecule is fused at the C-terminus of the Fab heavy chain to the N-terminus of the Fab heavy chain of the second Fab molecule, and the second Fab molecule and the third Fab molecule are each fused at the C-terminus of the Fab heavy chain to the N-terminus of one of the subunits of the Fc domain.

5. The method of claim 1, wherein:
(a) the VH of the second Fab molecule comprises the amino acid sequence of SEQ ID NO: 3, and the VL of the second Fab molecule comprises the amino acid sequence of SEQ ID NO: 7; and/or
(b) the VH of the first Fab molecule comprises the amino acid sequence of SEQ ID NO: 30, and the VL of the first Fab molecule comprises the amino acid sequence of SEQ ID NO: 31.

6. The method of claim 2, wherein the CD3 is CD3 epsilon.

7. The method of claim 2, wherein, in the constant domain CL of the first Fab molecule and the third Fab molecule, and the amino acid at position 123, according to Kabat, is substituted by arginine (R).

8. The method of claim 2, wherein:
(a) the VH of the second Fab molecule comprises the amino acid sequence of SEQ ID NO: 3, and the VL of the second Fab molecule comprises the amino acid sequence of SEQ ID NO: 7; and/or
(b) the VH of the first Fab molecule and the VH of the third Fab molecule each comprises the amino acid sequence of SEQ ID NO: 30, and the VL of the first Fab molecule and the VL of the third Fab molecule each comprises the amino acid sequence of SEQ ID NO: 31.

9. The method of claim 2, wherein the Fc domain is an IgG Fc domain.

10. The method of claim 2, wherein the Fc domain comprises a modification promoting the association of the first and second subunit of the Fc domain.

11. The method of claim 9, wherein, in the CH3 domain of the first subunit of the Fc domain, an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

12. The method of claim 11, wherein the amino acid residue having a larger side chain volume is selected from the group consisting of arginine (R), phenylalanine (F), tyrosine (Y), and tryptophan (W), and the amino acid residue having a smaller side chain volume is selected from the group consisting of alanine (A), serine (S), threonine (T), and valine (V).

13. The method of claim 9, wherein, in the CH3 domain of the first subunit of the Fc domain, the threonine residue at position 366, according to the Kabat EU index, is replaced with a tryptophan residue (T366W), and in the CH3 domain of the second subunit of the Fc domain, the tyrosine residue at position 407, according to the Kabat EU index, is replaced with a valine residue (Y407V).

14. The method of claim 9, wherein, in the first subunit of the Fc domain, the serine residue at position 354, according to the Kabat EU index, is replaced with a cysteine residue (S354C), or the glutamic acid residue at position 356, according to the Kabat EU index, is replaced with a cysteine residue (E356C), and, in the second subunit of the Fc domain, the tyrosine residue at position 349, according to the Kabat EU index, is replaced by a cysteine residue (Y349C).

15. The method of claim 14, wherein the first subunit of the Fc domain comprises amino acid substitutions S354C and T366W, according to the Kabat EU index, and the second subunit of the Fc domain comprises amino acid substitutions Y349O, T366S, L368A, and Y407V, according to the Kabat EU index.

16. The method of claim 2, wherein the Fc domain exhibits reduced binding affinity to an Fc receptor and/or reduced effector function, as compared to a native IgG$_1$ Fc domain.

17. The method of claim 2, wherein the Fc domain comprises one or more amino acid substitution that reduces binding to an Fc receptor and/or effector function.

18. The method of claim 17, wherein the one or more amino acid substitution is at one or more position selected from the group of L234, L235, and P329, according to the Kabat EU index.

19. The method of claim 18, wherein each subunit of the Fc domain comprises three amino acid substitutions that reduce binding to an activating Fc receptor and/or reduce effector function, wherein the amino acid substitutions are L234A, L235A, and P329G, according to the Kabat EU index.

20. The method of claim 16, wherein the Fc receptor is an Fcγ receptor.

21. The method of claim 16, wherein the Fc receptor is a human Fc receptor.

22. The method of claim 16, wherein the effector function is antibody-dependent cell-mediated cytotoxicity (ADCC).

23. The method of claim 2, wherein the individual is a human.

24. The method of claim 3, wherein:
(a) the VH of the second Fab molecule comprises the amino acid sequence of SEQ ID NO: 3, and the VL of the second Fab molecule comprises the amino acid sequence of SEQ ID NO: 7; and/or
(b) the VH of the first Fab molecule and the VH of the third Fab molecule each comprises the amino acid sequence of SEQ ID NO: 30, and the VL of the first Fab molecule and the VL of the third Fab molecule each comprises the amino acid sequence of SEQ ID NO: 31.

25. The method of claim 4, wherein the CD3 is CD3 epsilon.

26. The method of claim 4, wherein, in the constant domain CL of the first Fab molecule and the third Fab molecule, the amino acid at position 123, according to Kabat, is substituted by arginine (R).

27. The method of claim 4, wherein:
   (a) the VH of the second Fab molecule comprises the amino acid sequence of SEQ ID NO: 3, the VL of the second Fab molecule comprises the amino acid sequence of SEQ ID NO: 7; and/or
   (b) the VH of the first and third Fab molecules each comprises the amino acid sequence of SEQ ID NO: 30, and the VL of the first and third Fab molecules each comprises the amino acid sequence of SEQ ID NO: 31.

28. The method of claim 4, wherein the Fc domain is an IgG Fc domain.

29. The method of claim 4, wherein the Fc domain comprises a modification promoting the association of the first and second subunit of the Fc domain.

30. The method of claim 28, wherein, in the CH3 domain of the first subunit of the Fc domain, an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

31. The method of claim 30, wherein the amino acid residue having a larger side chain volume is selected from the group consisting of arginine (R), phenylalanine (F), tyrosine (Y), and tryptophan (W), and the amino acid residue having a smaller side chain volume is selected from the group consisting of alanine (A), serine (S), threonine (T), and valine (V).

32. The method of claim 28, wherein, in the CH3 domain of the first subunit of the Fc domain, the threonine residue at position 366, according to the Kabat EU index, is replaced with a tryptophan residue (T366W), and in the CH3 domain of the second subunit of the Fc domain, the tyrosine residue at position 407, according to the Kabat EU index, is replaced with a valine residue (Y407V).

33. The method of claim 28, wherein, in the first subunit of the Fc domain, the serine residue at position 354, according to the Kabat EU index, is replaced with a cysteine residue (S354C), or the glutamic acid residue at position 356, according to the Kabat EU index, is replaced with a cysteine residue (E356C), and, in the second subunit of the Fc domain, the tyrosine residue at position 349, according to the Kabat EU index, is replaced by a cysteine residue (Y349C).

34. The method of claim 33, wherein the first subunit of the Fc domain comprises amino acid substitutions S354C and T366W, according to the Kabat EU index, and the second subunit of the Fc domain comprises amino acid substitutions Y3490, T366S, L368A, and Y407V, according to the Kabat EU index.

35. The method of claim 4, wherein the Fc domain exhibits reduced binding affinity to an Fc receptor and/or reduced effector function, as compared to a native IgG$_1$ Fc domain.

36. The method of claim 4, wherein the Fc domain comprises one or more amino acid substitution that reduces binding to an Fc receptor and/or effector function.

37. The method of claim 36, wherein the one or more amino acid substitution is at one or more position selected from the group of L234, L235, and P329, according to the Kabat EU index.

38. The method of claim 37, wherein each subunit of the Fc domain comprises three amino acid substitutions that reduce binding to an activating Fc receptor and/or reduce effector function, wherein the amino acid substitutions are L234A, L235A, and P329G, according to the Kabat EU index.

39. The method of claim 35, wherein the Fc receptor is an Fcγ receptor.

40. The method of claim 35, wherein the Fc receptor is a human Fc receptor.

41. The method of claim 35, wherein the effector function is ADCC.

* * * * *